(12) United States Patent
Drutu et al.

(10) Patent No.: US 7,863,449 B2
(45) Date of Patent: Jan. 4, 2011

(54) MODULATORS OF MUSCARINIC RECEPTORS

(75) Inventors: Ioana Drutu, Watertown, MA (US);
Dennis J. Hurley, San Marcos, CA (US); Upul K. Bandarage, Lexington, MA (US); Daniele M. Bergeron, La Mesa, CA (US); Paul S. Charifson, Framingham, MA (US); Robert J. Davies, Watertown, MA (US); Miguel Garcia-Guzman Blanco, San Diego, CA (US); Lewis R. Makings, Encinitas, CA (US); Akiko Nakatani, San Diego, CA (US); Gabriel Raffai, Tucson, AZ (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 877 days.

(21) Appl. No.: 11/288,939

(22) Filed: Nov. 29, 2005

(65) Prior Publication Data
US 2006/0270653 A1   Nov. 30, 2006

Related U.S. Application Data

(60) Provisional application No. 60/631,403, filed on Nov. 29, 2004.

(51) Int. Cl.
*C07D 471/10* (2006.01)
*A61K 31/438* (2006.01)
(52) U.S. Cl. .................................. 546/18; 514/278
(58) Field of Classification Search ............... 514/278; 546/18
See application file for complete search history.

(56) References Cited

U.S. PATENT DOCUMENTS

| | | |
|---|---|---|
| 3,654,287 A | 4/1972 | Dykstra |
| 3,666,764 A | 5/1972 | Campbell et al. |
| 3,959,475 A | 5/1976 | Bauer et al. |
| 3,962,259 A | 6/1976 | Bauer et al. |
| 4,233,307 A | 11/1980 | Ono et al. |
| 4,349,549 A | 9/1982 | Roszkowski et al. |
| 4,558,049 A | 12/1985 | Bernardi |
| 4,612,121 A | 9/1986 | Hermansson |
| 5,091,387 A | 2/1992 | Evans et al. |
| 5,219,860 A | 6/1993 | Chambers et al. |
| 5,324,733 A | 6/1994 | Billington et al. |
| 5,457,207 A | 10/1995 | Efange et al. |
| 5,536,716 A | 7/1996 | Chen et al. |
| 5,576,321 A | 11/1996 | Krushinski, Jr. et al. |
| 5,578,593 A | 11/1996 | Chen et al. |
| 5,614,523 A | 3/1997 | Audia et al. |
| 5,627,196 A | 5/1997 | Audia et al. |
| 5,652,235 A | 7/1997 | Chen et al. |
| 5,658,921 A | 8/1997 | Perregaard et al. |
| 5,665,725 A | 9/1997 | Moltzen et al. |
| 5,693,643 A | 12/1997 | Gilbert et al. |
| 5,741,789 A | 4/1998 | Hibschman et al. |
| 5,789,402 A | 8/1998 | Audia et al. |
| 5,817,679 A | 10/1998 | Shen et al. |
| 5,885,999 A | 3/1999 | Elliott et al. |
| 6,013,652 A | 1/2000 | Maccoss et al. |
| 6,130,217 A | 10/2000 | Arnold et al. |
| 6,166,040 A | 12/2000 | Fairhurst et al. |
| 6,294,534 B1 | 9/2001 | Nargund et al. |
| 6,316,437 B1 | 11/2001 | Hoffman |
| 6,326,375 B1 | 12/2001 | Fukami et al. |
| 6,436,962 B1 | 8/2002 | Hoffman et al. |
| 6,566,367 B2 | 5/2003 | Bakthavatchalam et al. |
| 6,713,487 B2 | 3/2004 | Yu et al. |
| 6,720,324 B2 | 4/2004 | Marzabadi et al. |
| 6,828,440 B2 | 12/2004 | Goehring et al. |
| 6,869,960 B2 | 3/2005 | Ito et al. |
| 6,943,199 B2 | 9/2005 | De Lombaert et al. |
| 7,045,527 B2 | 5/2006 | Chen et al. |
| 7,205,417 B2 | 4/2007 | Fukami et al. |
| 7,279,471 B2 | 10/2007 | Mueller et al. |
| 7,351,706 B2 | 4/2008 | Bissantz et al. |
| 7,491,715 B2 | 2/2009 | Ek et al. |
| 2002/0188124 A1 | 12/2002 | Fukami et al. |
| 2003/0036652 A1 | 2/2003 | Bakthavatchalam et al. |
| 2003/0158219 A1 | 8/2003 | Ito et al. |
| 2004/0054177 A1 | 3/2004 | Otake et al. |
| 2004/0072847 A1 | 4/2004 | Bakthavatchalam et al. |
| 2004/0122074 A1 | 6/2004 | Dow et al. |
| 2004/0142956 A1 | 7/2004 | Chen et al. |
| 2004/0204397 A1 | 10/2004 | Chaturvedula et al. |

(Continued)

FOREIGN PATENT DOCUMENTS

| | | |
|---|---|---|
| CN | 1535967 | 10/2004 |
| EP | 0070171 | 1/1983 |
| EP | 0414289 | 2/1991 |
| EP | 0444945 | 9/1991 |
| EP | 0486280 A2 | 5/1992 |
| GB | 1575800 | 10/1980 |
| GB | 2308064 | 6/1997 |
| JP | 59059685 | 4/1984 |
| JP | 2001/278886 | 10/2001 |

(Continued)

OTHER PUBLICATIONS

International Search Report and Written Opinion of the International Searching Authority for International Application No. PCT/US2005/042967, filed Nov. 29, 2005. Forms PCT/ISA/210 & PCT/ISA/237.
Abdel-Magid, A.F. et al., "Reductive Amination of Aldehydes and Ketones with Sodium Triacetoxyborohydride. Studies on Direct and Indirect Reductive Amination Procedures," *J. Org. Chem.*, 61, pp. 3849-3862 (1996).

(Continued)

*Primary Examiner*—Charanjit S Aulakh
(74) *Attorney, Agent, or Firm*—Honigman Miller Schwartz and Cohn LLP; Jonathan P. O'Brien; Christopher C. Forbes

(57) ABSTRACT

The present invention relates to modulators of muscarinic receptors. The present invention also provides compositions comprising such modulators, and methods therewith for treating muscarinic receptor mediated diseases.

12 Claims, No Drawings

U.S. PATENT DOCUMENTS

| | | | |
|---|---|---|---|
| 2005/0033048 | A1 | 2/2005 | Bakthavatchalam et al. |
| 2005/0143372 | A1 | 6/2005 | Ghosh et al. |
| 2005/0153998 | A1 | 7/2005 | Ito et al. |
| 2005/0176703 | A1 | 8/2005 | Gabriel et al. |
| 2005/0215576 | A1 | 9/2005 | Degnan et al. |
| 2005/0261332 | A1 | 11/2005 | Distefano et al. |
| 2006/0019962 | A1 | 1/2006 | Makings et al. |
| 2006/0040964 | A1 | 2/2006 | Bakthavatchalam et al. |
| 2006/0058778 | A1 | 3/2006 | Arcusa Villacampa |
| 2006/0106045 | A1 | 5/2006 | Hughes et al. |
| 2006/0111380 | A1 | 5/2006 | Otake et al. |
| 2006/0173027 | A1 | 8/2006 | Marzabadi et al. |
| 2006/0183904 | A1 | 8/2006 | Guo et al. |
| 2006/0211722 | A1 | 9/2006 | Jiao et al. |
| 2006/0217372 | A1 | 9/2006 | Blanco-Pillado et al. |
| 2006/0270673 | A1 | 11/2006 | Duggan et al. |
| 2007/0043023 | A1 | 2/2007 | Makings et al. |
| 2007/0149502 | A1 | 6/2007 | Chaturvedula et al. |
| 2007/0254903 | A1 | 11/2007 | Boatman et al. |
| 2008/0171753 | A1 | 7/2008 | Jitsuoka et al. |

FOREIGN PATENT DOCUMENTS

| | | |
|---|---|---|
| JP | 2002/316987 | 10/2002 |
| WO | WO 94/22846 | 10/1994 |
| WO | WO 95/11029 | 4/1995 |
| WO | WO 95/14025 | 5/1995 |
| WO | WO 95/28389 | 10/1995 |
| WO | WO 97/41878 | 11/1997 |
| WO | WO 97/41879 | 11/1997 |
| WO | WO 99/06434 | 2/1999 |
| WO | WO 99/32489 | 7/1999 |
| WO | WO 00/06146 | 2/2000 |
| WO | WO 00/06545 | 2/2000 |
| WO | WO0006153 A1 | 2/2000 |
| WO | WO 00/38720 | 7/2000 |
| WO | WO 01/02386 | 1/2001 |
| WO | WO 01/22919 | 4/2001 |
| WO | WO 01/29027 | 4/2001 |
| WO | WO0145707 A1 | 6/2001 |
| WO | WO0164213 A1 | 9/2001 |
| WO | WO02094825 A1 | 11/2002 |
| WO | WO 03/095427 | 11/2003 |
| WO | WO2004004714 A1 | 1/2004 |
| WO | WO2004010942 A2 | 2/2004 |
| WO | WO2004010943 A2 | 2/2004 |
| WO | WO2004011427 A2 | 2/2004 |
| WO | WO 2005/063745 | 7/2005 |
| WO | WO 2005/065779 | 7/2005 |
| WO | WO 2006/001958 | 1/2006 |

OTHER PUBLICATIONS

Caulfield, M.P., et al., "Classification of Muscarinic Acetylcholine Receptors," *International Union of Pharmacology.* XVII. *Pharmacol. Rev.*, 50, pp. 279-290 (1998).

Caulfield, M.P., et al., "Muscarinic Receptors-Characterization, Coupling, and Function," *Pharmacol. Ther.*, 58, pp. 319-379 (1993).

Chiavarelli, S. et al., "Preparation of spirocyclic template 1,2,3,4-tetrahydro-spiro[isoquinoline-4,4'-piperidine] compounds," *Gazzetta Chimica Italiana* 1960, 90, 189; CN1535967.

Efange, Simon M., "Spirovesamicols: Conformationally Restricted Analogues of 2-4-phenylpiperidino cyclohexanol as potential Modulators of Presynaptic Cholinergic Function," *J. Med. Chem.* 1994, 37, 2574-2582.

Efange, Simon M., "Vesamicol Analogues as Sigma Ligands," *Biochemical Pharmacology*, vol. 49n No. 6, pp. 791-791 (1995).

Felder, Christian C., et al., "Therapeutic Opportunities for Muscarinic Receptors in the Central Nervous System," *J. Med. Chem.*, 43(23), pp. 4333-4353 (2000).

Freireich, et al., "Quantitative Comparison of Toxicity of Anticancer Agents in Mouse, Rat, Hamster, Dog, Monkey and Man," *Cancer Chemother. Rep.*, 50: 219 (1966).

Hulme, E. C. et al., "Muscarinic Receptor Subtypes," *Ann. Rev. Pharmacol. Toxicol.*, 30, pp. 633-673 (1990).

Bignan, G., "Preparation of 3-Spirocyclic Indolin-2-ones as Ligands for the ORL-1 Receptor", Bioorganic and Medicinal Chem. Lett, 15 (2005), pp. 5022-5026.

Butera, J.. "Recent Approaches to the Treatment of Urinary Incontinence: A Survey of Patent Activity from 1995 to 1998", Expert Opinion on Therapeutic Patents, 8(8) (1998), pp. 1017-1035.

Bymaster, F., "Xanomeline: A Selective Muscarinic Agonist for the Treatment of Alzheimer's Disease", Drug Development Research, 40 (1997), pp. 158-170.

Chambers, M., "Spiropiperidines as High-Affinity, Selective σ Ligands", J. Med. Chem., 35(11) (1992), pp. 2033-2039.

Cheng, Y., "Solid Phase Synthesis of Spiroindoline", Tet, Lett., 38 (1997), pp. 1497-1500.

Custers, F., "Vesamicol and Some of its Derivatives: Questionable Ligands for Selectively Labelling Acetylcholine Transporters in Rat Brain", Eur. Jour. of Pharm., 338 (1997), pp. 177-183.

deLaszlo, S., "A Nonpeptidic Agonist Ligand of the Human C5A Receptor: Synthesis, Binding Affinity Optimization and functional Characterization", Bioarganic and Medicinal Chem. Lett., 7(2) (1997), pp. 213-218.

Dhar, T,G., "Design and Synthesis of Novel α1a Adrenoceptor-Selective Antagonists. 2. Approaches to Eliminate Opioid Agonist Metabolites via Modification of Linker and 4-Methoxycarbonyl-4-phenylpiperidine Moiety1.2", J. Med. Chem, 42 (1999), pp. 4778-4793.

Efange, S., "(+)-p-([18F]Fluorobenzyl)Spirotrozamicol {(+)-[18]Spiro-FBT}: Synthesis and Biological Evaluation of a High-Affinity Ligand for the Vesicular Acetylcholine Transporter (VAChT)", Nuclear Medicine and Biology, vol. 26 (1999), pp. 189-192.

Efange, S., "Comparative Tissue Distribution of conformationally Restricted Radioiodinated Vesamicol Receptor Ligands", Nuclear Medicine and Biology, 22(4) (1995), pp. 437-444.

Efange, S., "Spirovesamicols: Conformationally Restricted Analogs of 2-(4-Phenylpiperidino)cyclohexanol (Vesamicol, AH5183) as Potential Modulators of Presynaptic Cholinergic Function", J, Med. Chem, 37 (1994), pp. 2574-2582.

Evans, B., "Orally Active, Nonpeptide Oxytocin Antagonists", J. Med. Chem., 35(21) (1992), pp. 3919-3927.

Kim, D., Dooseop, et el., "Discovery of Human CCR5 Antagonists Containing Hydantoins for the Treatment of HIV-1 infection", Bioorganic and Medicinal Chem. Lett., 11 (2001), pp. 3099-3102.

Maligres, P. E, "Synthesis of the Orally Actve Spiroindoline-Based Growth Hormone Secretagogue, MK-677", Tetrahedron, 53 (1997), pp. 10983-10992.

Malmstrom, R., "Pharmacology of H 394/84, a dihydropyridine neuropeptide Y Y1 Receptor Antagonist, in Vivo", Eur. Jour. of Pharm., 418 (2001), pp. 95-104.

Matier, W., "Novel Cyclizations and Ring-Opening Reactions of 3-Phenylindene Derivatives", J. Org. Chem., vol. 36, No. 5 (1971), pp. 650-654.

Moltzen, E., "σ Ligands with Subnanomolar Affinity and Preference for the σ2 Binding Site. 2. Spiro-Joined Benzofuran, Isobenzofuran and Benzopyran Piperidines", J. Med. Chem., 38 (1995), pp. 2009-2017.

Morrow, D., "Synthesis of Some New 17-Spiro-Substituted Steroids", J. Med. Chem., 10(2) (1967), pp. 133-138.

Nargund, R., "Peptidomimetic Growth Hormone Secretagogues: Synthesis and Biological Activities of Analogs Varied at the Indole Nucleus of the Prototypical Spiropiperidine L-162,752", Bioorganic and Medicinal Chem. Lett., vol. 6, No. 14 (1996), pp. 1731-1736.

Nargund, R., "Synthesis and Biological Activities of Camphor-Based Non-Peptide Growth Hormone Secretagogues", Bioorganic and Medicinal Chem. Lett., vol. 6, No. 11 (1996), pp. 1265-1270.

Oprea, T., "Is There a Difference between Leads and Drugs? A Historical Perspective", J. Chem. Inf. Comput. Sci., 41 (2001), pp. 1308-1315.

Pasternak, A., "Potent, Orally Bioavailable Somatostatin Agonists: Good Absorption Achieved by Urea Backbone Cyclization", Bioorganic and Medicinal Chem. Lett., 9 (1999), pp. 491-496.

Patchett, A.A., "The Synthesis of 17β-Amino-17 α-(2'-carboxyethyl)androstane Lacatama1", J. Org. Chem, 27 (1962), pp. 3822-3828.

Pettibone, D.J., "Identification of an Orally Active, Nonpetidyl Oxytocin Antagonist", Jounal of Pharm. and Experimental Therap., 264(1) (1993), pp. 308-314.

Reimann, E., "Synthese und pharmakologische Prüfung Homologer und hydroxylierter 3,4-Dihydro-1'-methylspiro [naphthalin-(2H),4'-piperidine]", Archiv. Der. Pharmazie, VCH Verlagsgesellschaft MBH, Weinheim, DE, 323 (1990), pp. 35-39.

Rubin et al., "Novel Medications for Asthma: A Look Into the Future", Exper Opinion on Investigational Drugs (2007), 16(6), 889-897.

Takemoto, T., "Asymmetric Synthesis of Enantiomerically Pure Spiro[((2S)-hydroxy)indane-1,4'-piperidine]", Tetrahedron Asymmetry, 10 (1999), pp. 1787-1793.

Tata, J., "The Synthesis and Activity of Spiroindane Growth Hormone Secretagogues", Bioorganic and Medicinal Chem. Lett, 7(6) (1997), pp. 663-668.

Williams, P., "1-(((7,7-Dimethyl-2(S)-(2(S)-amino-4-(methylsulfonyl)butyramido)bicyclo[2.2.1]-heptan-1(S)-yl)methyl) sulfonyl)-4-2(2-methylphenyl)piperazine (L-368,899): An Orally Bioavailable, Non-Peptide Oxytocin Antagonist with Potential Utility for Managing Preterm Labor", J. Med. Chem, 37 (1994), pp. 555-571.

Yang, L., "Potent 3-Spiropiperidine Growth Hormone Secretagogues", Bioorganic and Medicinal Chem. Lett, 8(1) (1998), pp. 107-112.

Yang, L., "The Design and Synthesis of Non-Peptide Somatostatin Receptor Agonists", Proceedings of the American Peptide Symposium, 16th Minneapolis, MN, Jun. 26-Jul. 1, 1999, (2000), meeting date 1999, 250-252.

MODULATORS OF MUSCARINIC RECEPTORS

CLAIM OF PRIORITY

This application claims the benefit of U.S. provisional application No. 60/631,403, filed on Nov. 29, 2004, which is hereby incorporated by reference.

TECHNICAL FIELD OF THE INVENTION

The present invention relates to modulators of muscarinic receptors. The present invention also provides compositions comprising such modulators, and methods therewith for treating muscarinic receptor mediated diseases.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," *J. Med. Chem.*, 43(23), pp. 4333-4353 (2000); Hulme, E. C. et al., "Muscarinic Receptor Subtypes," *Ann. Rev. Pharmacol. Toxicol.*, 30, pp. 633-673 (1990); Caulfield, M. P. et al., "Muscarinic Receptors-Characterization, Coupling, and Function," *Pharmacol. Ther.*, 58, pp. 319-379 (1993); Caulfield, M. P. et al., International Union of Pharmacology. XVII. Classification of Muscarinic Acetylcholine Receptors," *Pharmacol. Rev.*, 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors). Despite the large therapeutic value of this family, cholinergic drugs are limited by the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides methods of modulating the activity of a muscarinic receptor (e.g., $M_1$, $M_2$, $M_3$, $M_4$, $M_5$, or combinations thereof) using compounds of formula I:

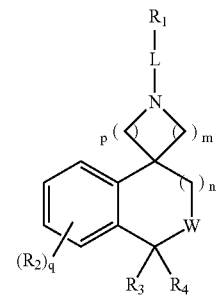

or a pharmaceutically acceptable salt thereof, wherein $R_1$, $R_2$, $R_3$, $R_4$, L, n, m, p, and q are described below.

DETAILED DESCRIPTION

I. Definitions:

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "muscarinic receptor," without a prefix specifying the receptor subtype, refers to one or more of the five receptor subtypes $M_1$-$M_5$.

The term "modulating" as used herein means increasing or decreasing, e.g. activity, by a measurable amount. Compounds that modulate muscarinic activity by increasing the activity of the muscarinic receptors are called agonists. Compounds that modulate muscarinic activity by decreasing the activity of the muscarinic receptors are called antagonists. An agonist interacts with a muscarinic receptor to increase the ability of the receptor to transduce an intracellular signal in response to endogenous ligand binding. An antagonist interacts with a muscarinic receptor and competes with the endogenous ligand(s) or substrate(s) for binding site(s) on the receptor to decrease the ability of the receptor to transduce an intracellular signal in response to endogenous ligand binding.

The phrase "treating or reducing the severity of a muscarinic receptor mediated disease" refers both to treatments for diseases that are directly caused by muscarinic activities and alleviation of symptoms of diseases not directly caused by muscarinic activities. Examples of diseases whose symptoms may be affected by muscarinic activity include, but are not limited to, CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradhycardia, gastric acid secretion, asthma, GI disturbances and wound healing.

As described herein, compounds of the invention may optionally be substituted with one or more substituents, such as are illustrated or as exemplified by particular classes, subclasses, and species of the invention described herein.

As used herein the term "aliphatic" encompasses the terms alkyl, alkenyl, alkynyl. An aliphatic group can be optionally substituted with one or more of halo, hydroxy, cyano, nitro, cycloaliphatic, heterocycloaliphatic, aryl, heteroaryl, alkylcarbonyl, alkoxy, alkylsulfonyl, alkylsulfanyl, alkylsulfinyl, amino, alkylamino, alkoxycarbonyl, alkylaminocarbonyl, combinations thereof, or the like.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, isobutyl, n-pentyl, n-heptyl, or 2-ethylhexyl. An alkyl group can be optionally substituted with one or more substituents as described above.

As used herein, an "alkenyl" group refers to an aliphatic carbon group that contains 2-10 (e.g., 2, 3, 4, 5, 6, 7, 8, 9 or 10) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents as described above.

As used herein, an "alkynyl" group refers to an aliphatic carbon group that contains 2-8 (e.g., 2-6 or 2-4) carbon atoms and at least one triple bond. Like an alkyl group, an alkynyl group can be straight or branched. An alkynyl group can be optionally substituted with one or more substituents as described above.

As used herein, an "amino" group refers to —$NR^XR^Y$ wherein each of $R^X$ and $R^Y$ is independently hydrogen, alkyl, cycloalkyl, sulfonyl, (cycloalkyl)alkyl, aryl, aralkyl, heterocycloalkyl, (heterocycloalkyl)alkyl, heteroaryl, or heteroaralkyl each of which are defined herein and are optionally substituted. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); tricyclic (e.g., fluorenyl, tetrahydrofluorenyl, anthracenyl, or tetrahydroanthracenyl); or a benzofused group having 3 rings. For example, a benzofused group includes phenyl fused with two or more $C_{4-8}$ carbocyclic moieties. An aryl can be optionally substituted with one or more substituents. Without limitation, an aryl can be optionally substituted with halo, hydroxy, cyano, nitro, aliphatic, cycloaliphatic, aryl, heterocycloaliphatic, heteroaryl, alkylsulfonyl, aliphaticaminocarbonyl, alkoxy, aminocarbonyl, alkoxycarbonyl, heteroarylcarbonyl, (heterocycloaliphatic)carbonyl, (heteroarylamino)carbonyl, cycloalkylcarbonyl, alkylcarbonylamino, cycloaliphaticsulfonyl, heterocycloaliphaticsulfonyl, alkylsulfanyl, alkylsulfonyl, (alkoxyalkyl)aminocarbony, combinations thereof, or the like.

As used herein, an "araliphatic" group refers to an aliphatic group (e.g., a $C_{1-4}$ alkyl group, a $C_{1-4}$ alkenyl group, or a $C_{1-4}$ alkynyl group) that is substituted with an aryl group. Both "aliphatic" and "aryl" have been defined above.

As used herein, an "aralkyl" group refers to an alkyl group (e.g., a $C_{1-4}$ alkyl group) that is substituted with an aryl group. Both "alkyl" and "aryl" are defined herein. An example of an aralkyl group is benzyl.

As used herein, a "bicyclic ring system" includes 5-12 (e.g., 7, 8, 9, 10, or 11) membered structures that form two rings, wherein the two rings have at least one atom in common (e.g., 2 atoms in common). Bicyclic ring structures include bicycloaliphatics (e.g., bicycloalkyl or bicycloalkenyl), bicycloheteroaliphatics (e.g., bicycloheteroalkyl or bicycloheteroalkenyl), bicyclic aryls, and bicyclic heteroaryls. Bicyclic ring systems also include bridged bicyclic rings and fused bicyclic rings (e.g., benzo fused).

The term "cycloaliphatic" means a saturated or partially unsaturated monocyclic, bicyclic, or tricyclic hydrocarbon ring that has a single point of attachment to the rest of the molecule. Cycloaliphatic rings are 3-8 membered monocyclic rings (e.g., 3-6 membered rings). Cycloaliphatic rings also include 5-12 membered bicyclic rings. Bicyclic cycloaliphatic (i.e., bicycloaliphatic rings) include bridged bicyclic cycloaliphatic rings and cycloaliphatic fused bicyclic rings. A cycloaliphatic group also encompasses a "cycloalkyl" group and a "cycloalkenyl" group.

Examples of substituents on a cycloaliphatic group include, without limitation, halo, hydroxy, cyano, nitro, aliphatic, alkoxy, alkoxyimino, alkoxyamino, oxo, aryloxyimmino, As used herein, a "cycloalkyl" group refers to a saturated carbocyclic mono-, bi-, or tri-, or multicyclic (fused or bridged) ring of 3-10 (e.g., 5-10) carbon atoms. Without limitation, examples of monocyclic cycloalkyl groups include cyclopropyl, cyclobutyl, cyclopentyl, cyclohexyl, cycloheptyl, or the like. Examples of bicyclic cycloalkyl groups include bridged bicyclic cycloalkyls and fused bicyclic cycloalkyls. Without limitation, bicyclic cycloalkyls include octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, bicycle[2.2.1]heptanyl, bicycle[3.1.1]heptanyl, or the like. Without limitation, multicyclic groups include adamantyl, cubyl, norbomyl, or the like. Cycloalkyl rings can be optionally substituted at any chemically viable ring position.

As used herein, a "cycloalkenyl" group refers to a partially unsaturated carbocyclic mono-, bi-, or tri-, or multicyclic (fused or bridged) ring of 3-10 (e.g., 5-10) carbon atoms. Without limitation, examples of monocyclic cycloalkenyl groups include cyclopropenyl, cyclobutenyl, cyclopentenyl, cyclohexenyl, cycloheptenyl, or the like. Without limitation, bicyclic cycloalkenyl groups include, for example, bicyclo[3.2.1]octenyl, bicyclo[2.2.2]octenyl, bicyclo[3.3.1]nonenyl, bicyclo[3.3.2.]decenyl, bicycle[2.2.1]heptenyl, or bicycle[3.1.1]heptenyl.

As used herein, the term "heterocycloaliphatic" and "heterocyclic" encompasses a heterocycloalkyl group and a heterocycloalkenyl group. Heterocycloaliphatic groups include 3-10 membered monocyclic ring structures having 1-3 heteroatoms. Heterocycloaliphatic groups also include 5-10 membered bicyclic heterocycloaliphatics (i.e., bicycloheterocycloaliphatics). Bicycloheteroaliphatic groups include bridged bicyclic structures, and fused bicyclic structures. Fused bicyclic structures can include a monocyclic heterocycloaliphatic fused to a monocyclic cycloaliphatic ring or a monocyclic heterocycloaliphatic ring.

As used herein, a "heterocycloalkyl" group refers to a 3-10 membered mono or bicyclic (fused or bridged) (e.g., 5 to 10 membered mono or bicyclic) saturated ring structure, in which one or more of the ring atoms is a heteroatom (e.g., N, O, S, or combinations thereof). Bicyclic heterocycloalkyls include bridged and fused bicyclic heterocycloalkyls. Non-limiting examples of heterocycloalkyls include optionally substituted piperidinyl, piperazinyl, tetrahydropyranyl, tetrahydrofuranyl, 1,4-dioxolanyl, 1,4-dithianyl, 1,3-dioxolanyl, oxazolidyl, isoxazolidyl, morpholinyl, thiomorpholinyl, octahydro-benzofuranyl, octahydro-chromenyl, octahydro-thiochromenyl, octahydro-indolyl, octahydro-pyrindinyl, decahydro-quinolinyl, octahydro-benzo[b]thiopheneyl, 2-oxa-bicyclo[2.2.2]octyl, 1-aza-bicyclo[2.2.2]octyl, 3-aza-bicyclo[3.2.1]octanyl, 2,6-dioxa-tricyclo[3.3.1.0$^{3,7}$]nonyl, or tropane. A monocyclic heterocycloalkyl group may be fused with a phenyl moiety such as tetrahydroisoquinoline. Heterocycloalkyl ring structures can be optionally substituted at any chemically viable position on the ring or rings.

A heterocycloalkyl group can be substituted at any chemically feasible position. Heterocycloalkyl substituents, without limitation, include halo, hydroxy, cyano, alkoxy, alkoxycarbonyl, aliphatic (e.g., alkyl, alkenyl, or alkynyl), cycloaliphatic, heterocycloaliphatic, aryl, heteroaryl, heterocycloaliphatic, arylcarbonyl, combinations thereof, or the like.

A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S). Bicyclic heterocycloalkenyls include bridged and fused bicyclic heterocycloalkenyls. Examples of heterocycloalkenyls include 2-pyrrolyl, 3-pyrrolyl, 2-imidazolyl, or 2-pyrazolyl. Monocyclic heterocycloaliphatics are numbered according to standard chemical nomenclature. Heterocycloalkenyl substituents, without limitation, include halo, hydroxy, cyano, alkoxy, alkoxycarbonyl, aliphatic (e.g., alkyl, alkenyl, or alkynyl), cycloaliphatic, heterocycloaliphatic, aryl, heteroaryl, heterocycloaliphatic, arylcarbonyl, combinations thereof, or the like.

A "heteroaryl" group, as used herein, refers to a monocyclic, bicyclic, or tricyclic ring systems having 4 to 15 ring atoms wherein one or more of the ring atoms is a heteroatom (e.g., N, O, S, or combinations thereof) and wherein one or more rings of the bicyclic or tricyclic ring structure is aromatic. A heteroaryl group includes a benzofused ring system having 2 to 3 rings. For example, a benzofused group includes benzo fused with one or two $C_{4-8}$ heterocyclic moieties (e.g., indolizyl, indolyl, isoindolyl, 3H-indolyl, indolinyl, benzo[b]furyl, benzo[b]thiopheneyl, quinolinyl, or isoquinolinyl). Some examples of heteroaryl are azetidinyl, pyridinyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiopheneyl, indazolyl, benzimidazolyl, benzthiazolyl, puryl, cinnolinyl, quinolinyl, cinnolinyl, phthalazyl, quinazolinyl, quinoxalinyl, isoquinolinyl, 4H-quinolizyl, benzo-1,2,5-thiadiazolyl, or 1,8-naphthyridyl. A heteroaryl can be optionally substituted at any chemically feasible position.

Without limitation, monocyclic heteroaryls include furyl, thiopheneyl, 2H-pyrrolyl, pyrrolyl, oxazolyl, thiazolyl, imidazolyl, pyrazolyl, isoxazolyl, isothiazolyl, 1,3,4-thiadiazolyl, 2H-pyranyl, 4-H-pyranyl, pyridinyl, pyridazinyl, pyrimidyl, pyrazolyl, pyrazyl, or 1,3,5-triazyl.

Without limitation, bicyclic heteroaryls include indolizyl, indolyl, isoindolyl, 3H-indolyl, indolinyl, benzo[b]furyl, benzo[b]thiopheneyl, quinolinyl, isoquinolinyl, indolizyl, isoindolyl, indazolyl, benzimidazolyl, benzthiazolyl, purinyl, 4H-quinolizyl, quinolinyl, isoquinolinyl, cinnolinyl, phthalazyl, quinazolinyl, quinoxalinyl, 1,8-naphthyridyl, or pteridyl.

Without limitation, a heteroaryl can be substituted with halo, hydroxy, cyano, aliphatic, cycloaliphatic, heterocycloaliphatic, aryl, heteroaryl, arylcarbonyl, arylcarbonylamino, aliphaticaminocarbonyl, alkoxy, combinations thereof, or the like.

A "heteroaraliphatic" group, as used herein, refers to an aliphatic group (e.g., $C_{1-4}$ alkyl group, $C_{1-4}$ alkenyl group, or $C_{1-4}$ alkynyl group) that is substituted with a heteroaryl group. Both "aliphatic" and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, "cyclic group" includes mono-, bi-, and tri-cyclic structures including cycloaliphatic, heterocycloaliphatic, aryl, or heteroaryl, each of which has been previously defined.

As used herein, an "acyl" group refers to a formyl group or alkyl-C(=O)— (also referred to as "alkylcarbonyl") where "alkyl" has been defined previously. Acetyl and pivaloyl are examples of acyl groups.

As used herein, a "carbonyl" group, when used alone or as part of another structure refers to the structure —C(O)—.

As used herein, a "carbamoyl" group refers to a group having the structure —O—CO—NR$^X$R$^Y$ or —NR$^X$—CO—O—R$^Z$ wherein R$^X$ and R$^Y$ have been defined above and R$^Z$ can be alkyl, aryl, aralkyl, heterocycloalkyl, heteroaryl, or heteroaralkyl.

As used herein, a "carboxy" and a "sulfo" group refer to —C(O)OH or —C(O)OR$^X$ and —SO$_3$H or —SO$_3$R$^X$, respectively.

As used herein, an "alkoxy" group refers to an alkyl-O— group where "alkyl" has been defined previously. Moreover an alkoxy group includes structures comprising two alkoxy groups on the same atom or adjacent atoms that form a ring together with the atom(s) to which they are bound.

As used herein, an "alkoxycarbonyl" group refers to the structure —C(O)O-alkyl.

As used herein, a "nitro" group refers to —N$^+$(O)O$^-$.

As used herein, a "sulfoxy" group refers to —O—SO—R$^X$ or —SO—O—R$^X$, where R$^X$ has been defined above.

As used herein, a "mercapto" group refers to —SH.

As used herein, a "sulfonyl" group refers to —S(O)$_2$—.

As used herein a "sulfinyl" group refers to —S(O)—.

As used herein a "sulfanyl" group refers to —S—.

As used herein, a "halogen" or "halo" group refers to fluorine, chlorine, bromine or iodine.

As used herein, a "haloaliphatic" group refers to an aliphatic group substituted with 1-3 halogen. For instance, the term haloalkyl includes the group —CF$_3$.

As used herein, a "sulfamoyl" group refers to the structure —S(O)$_2$—NR$^X$R$^Y$ or —NR$^X$—S(O)$_2$—R$^Z$ wherein R$^X$, R$^Y$, and R$^Z$ have been defined above.

As used herein, a "sulfamide" group refers to the structure —NR$^X$—S(O)$_2$—NR$^Y$R$^Z$ wherein R$^X$, R$^Y$, and R$^Z$ have been defined above.

As used herein, a "carbonylamino" group used alone or in connection with another group refers to an amido group such as R$^X$—C(O)—NR$^X$—. For instance an alkylcarbonylamino includes alkyl-C(O)—NR$^X$—, wherein R$^X$ has been defined above.

As used herein, a "aminocarbonyl" group used alone or in connection with another group refers to an amido group such as $N(R^X)_2$—C(O)—.

As used herein, an "alkoxycarbonyl" used alone or in connection with another group refers to a carbonyl group such as alkyl-O—C(O)—.

As used herein, an "alkoxyalkyl" refers to an alkyl group such as alkyl-O-alkyl-, wherein alkyl has been defined above.

As used herein, an "aminocarbonyl" refers to an amido group such as —$NR^X$—C(O)—, wherein $R^X$ has been defined above.

As used herein, an "aminosulfonyl" refers to the structure —$N(R^X)_2$—$S(O)_2$—, wherein $R^X$ has been defined above.

As used herein, an "oxo" refers to =O.

As used herein, an "aminoalkyl" refers to the structure $N(R^X)_2$-alkyl-.

As used herein, a "cyanoalkyl" refers to the structure (CN)-alkyl-.

As used herein, an "alkylsulfonyl" group refers to the structure alkyl-$S(O)_2$—.

As used herein, a "sulfonylamino" group refers to the structure $R^X$—$S(O)_2$—$N(R^X)_2$—, wherein $R^X$ has been defined above.

As used herein, an "imino" group refers to the functional group =N— and covers the structure =N—$R^X$ and oximes having the structure =N—$OR^X$ wherein $R^X$ is defined above.

As used herein, a "hydroxy" group refers to the structure —OH.

As used herein, a "guanidinyl" group refers to the structure $NH_2C(NH)NH$—.

As used herein, an "aliphatic chain" refers to a branched or straight aliphatic group (e.g., alkyl groups, alkenyl groups, or alkynyl groups). A straight aliphatic chain has the structure —$[CH_2]_p$—, where p is 1-6. A branched aliphatic chain is a straight aliphatic chain that is substituted with one or more aliphatic groups. A branched aliphatic chain has the structure —$[CHW]_p$— where W is hydrogen or an aliphatic group; however, W shall be an aliphatic group in at least one instance. The term aliphatic chain includes alkyl chains, alkenyl chains, and alkynyl chains, where alkyl, alkenyl, and alkynyl are defined above.

As used herein, a "urea" group refers to the structure —$NR^X$—CO—$NR^YR^Z$ and a "thiourea" group refers to the structure —$NR^X$—CS—$NR^YR^Z$. $R^X$, $R^Y$, and $R^Z$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group may have a substituent at each substitutable position of the group, and when more than one position in any given structure may be substituted with more than one substituent selected from a specified group, the substituent may be either the same or different at every position. A ring substituent, such as a heterocycloalkyl, may be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

II. Compounds:

A. Generic Compounds

The present invention provides methods of modulating the activity of a muscarinic receptor comprising the step of contacting said receptor with a compound of formula I:

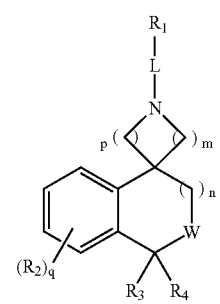

or a pharmaceutically acceptable salt thereof.

$R_1$ is cycloaliphatic, heterocycloaliphatic, aryl, or heteroaryl, each of which is optionally substituted with 1-3 of $R_5$, or $R_1$ is hydrogen.

Each $R_5$ is independently =O or $-Z^A R_6$, wherein each $Z^A$ is independently a bond or an optionally substituted branched or straight $C_{1-6}$ aliphatic chain wherein up to two carbon units of $Z^A$ are optionally and independently replaced by —CO—, —CS—, —CONR$^A$—, —CONR$^A$NR$^A$—, —CO$_2$—, —OCO—, —NR$^A$CO$_2$—, —O—, —NR$^A$CONR$^A$—, —OCONR$^A$—, —NR$^A$NR$^A$—, —NR$^A$CO—, —S—, —SO—, —SO$_2$—, —NR$^A$—, —SO$_2$NR$^A$—, —NR$^A$SO$_2$—, or —NR$^A$SO$_2$NR$^A$.

$R_6$ is independently $R^A$, halo, —OH, —NH$_2$, —NO$_2$, —CN, =NR$^A$, =NOR$^A$, or —OCF$_3$.

Each $R^A$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

Each $R_2$ is $-Z^B R_7$, wherein each $Z^B$ is independently a bond or an optionally substituted branched or straight $C_{1-4}$ aliphatic chain wherein up to two carbon units of $Z^B$ are optionally and independently replaced by —CO—, —CS—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$.

Each $R_7$ is independently $R^B$, halo, —OH, —CN, —NH$_2$, —NO$_2$, or —OCF$_3$.

Each $R^B$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

$R_3$ and $R_4$ are each independently $-Z^C R_8$, wherein each $Z^C$ is independently a bond or an optionally substituted branched or straight $C_{1-4}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —SO—, —SO$_2$—, —NR$^C$—, —SO$_2$NR$^C$—, —NR$^C$SO$_2$—, or —NR$^C$SO$_2$NR$^C$. Alternatively, $R_3$ and $R_4$ together form an oxo group.

Each $R_8$ is independently $R^C$, halo, —OH, —CN, or —OCF$_3$.

Each $R^C$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl.

W is —NR$_9$— or —O—.

$R_9$ is $-Z^D R_{10}$, wherein each $Z^D$ is independently a bond or an optionally substituted branched or straight $C_{1-4}$ aliphatic chain wherein up to two carbon units of $Z^D$ are optionally and independently replaced by —CO—, —CS—, —CONR$^D$—, —CONR$^D$NR$^D$—, —CO$_2$—, —OCO—, —NR$^D$CO$_2$—, —O—, —NR$^D$CONR$^D$—, —OCONR$^D$—, —NR$^D$NR$^D$—, —NR$^D$CO—, —S—, —SO—, —SO$_2$—, —NR$^D$—, —SO$_2$NR$^D$—, —NR$^D$SO$_2$—, or —NR$^D$SO$_2$NR$^D$.

Each $R_{10}$ is independently $R^D$, halo, —OH, —CN, or —OCF$_3$.

Each $R^D$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl.

m is 0-3, p is 0-3, and m+p is 3, 4, 5, or 6.

n is 0-2.

q is 0-4.

L is $Z^A$.

1. The -L-$R_1$ Group

1a. Substituent $R_1$:

$R_1$ is a cycloaliphatic, heterocycloaliphatic, aryl, or heteroaryl, each of which is optionally substituted with 1-3 of $R_5$, or $R_1$ is hydrogen. Each $R_5$ is =O or $-Z^A R_6$, wherein each $Z^A$ is independently a bond or an optionally substituted branched or straight $C_{1-6}$ aliphatic chain wherein up to two carbon units of $Z^A$ are optionally and independently replaced by —CO—, —CS—, —CONR$^A$—, —CONR$^A$NR$^A$—, —CO$_2$—, —OCO—, —NR$^A$CO$_2$—, —O—, —NR$^A$CONR$^A$—, —OCONR$^A$—, —NR$^A$NR$^A$—, —NR$^A$CO—, —S—, —SO—, —SO$_2$—, —NR$^A$—, —SO$_2$NR$^A$—, —NR$^A$SO$_2$—, or —NR$^A$SO$_2$NR$^A$. Each $R^6$ is independently $R^A$, halo, —OH, —NH$_2$, —NO$_2$, —CN, =NR$^A$, =NOR$^A$, or —OCF$_3$. Each $R^A$ is hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In several embodiments, $R_1$ is an optionally substituted cycloaliphatic. For example, $R_1$ is a monocyclic cycloaliphatic optionally substituted with 1-3 of $R_5$. In some instances, $R_1$ is a cyclopropyl, cyclobutyl, cyclopentyl, cyclohexyl, cycloheptyl, or cyclooctyl, each of which is optionally substituted with 1-3 of $R_5$. In other embodiments, $R_1$ is a cyclopropenyl, cyclobutenyl, cyclopentenyl, cyclohexenyl, cycloheptenyl, or cyclooctenyl, each of which is optionally substituted with 1-3 of $R_5$. In several embodiments, $R_1$ is optionally substituted with 1-3 of halo, hydroxy, cyano, nitro, oxo, or optionally substituted alkoxycarbonyl, optionally substituted alkoxyimino, optionally substituted alkylcarbonyl, optionally substituted aliphatic, optionally substituted cycloaliphatic, optionally substituted heterocycloaliphatic, optionally substituted aryl, optionally substituted heteroaryl, optionally substituted aralkyl, optionally substituted heteroaralkyl, optionally substituted aralkyloxyimino, optionally substituted aryloxyimino, optionally substituted arylcarbonyloxy, or combinations thereof.

In several embodiments, $R_1$ is a bicyclic (e.g., fused or bridged) cycloaliphatic that is optionally substituted with 1-3 of $R_5$. In several examples, $R_1$ is a bridged bicycloalkyl or a bridged bicycloalkenyl, each of which is optionally substituted with 1-3 of $R_5$. For example, $R_1$ is a bicyclo[1.1.1]pentyl, bicyclo[2.1.1]hexyl, bicyclo[2.2.1]heptyl, bicyclo[3.1.1]heptyl, bicyclo[2.2.2]octyl, bicyclo[3.2.1]octyl, bicyclo[3.3.1]nonyl, or bicyclo[3.3.3]undecyl, each of which is optionally substituted with 1-3 of halo, hydroxy, optionally substituted aliphatic, optionally substituted alkoxy, optionally substituted alkoxycarbonyl, or combinations thereof. In other examples, $R_1$ is a bicyclo[1.1.1]pentenyl, bicyclo[2.1.1]hexenyl, bicyclo[2.2.1]heptenyl, bicyclo[3.1.1]heptenyl, bicyclo[2.2.2]octenyl, bicyclo[3.2.1]octenyl, bicyclo[3.3.1]nonenyl, or bicyclo[3.3.3]undecenyl, each of which is optionally substituted with 1-3 of halo, hydroxy, optionally substituted aliphatic, optionally substituted alkoxy, optionally substituted alkoxycarbonyl, or combinations thereof.

In several examples, $R_1$ is an optionally substituted tricyclic cycloaliphatic. For example, $R_1$ is an optionally substituted adamantyl.

In several embodiments, $R_1$ is an optionally substituted heterocycloaliphatic. For example, $R_1$ is a monocyclic heterocycloaliphatic optionally substituted with 1-3 of $R_5$. In several embodiments, $R_1$ is tetrahydrofuranyl, tetrahydrothiopheneyl, 1,3-dioxolanyl, tetrahydrooxazolyl, pyrrolidinyl, imidazolidinyl, pyrazolidinyl, tetrahydropyran, piperidinyl, piperazinyl, tetrahydro-2H-thiopyranyl, piperazinyl, 1,2,3-triazolidinyl, dioxanyl, oxazolidinyl, morpholinyl, thiepanyl, dithianyl, octahydropyranyl, trithianyl, thiomorpholinyl, hexahydropyrimidinyl, hexahydropyridazinyl, or thiocanyl each of which is optionally substituted with 1-3 of halo, hydroxy, cyano, optionally substituted aliphatic, optionally substituted cycloaliphatic, optionally substituted heterocycloaliphatic, optionally substituted aryl, optionally substituted hetoaryl, optionally substituted alkoxycarbonyl, optionally substituted (cycloalkyl)oxycarbonyl, optionally substituted akylaminocarbonyl, optionally substituted (heterocycloalkyl)oxycarbonyl, optionally substituted arylcarbonyl, optionally substituted (alkoxy)alkoxycarbonyl, or combinations thereof.

In several examples, $R_1$ is a bicyclic (e.g., bridged or fused) heterocycloaliphatic that is optionally substituted with 1-3 of $R_5$. For example, $R_1$ is a bridged bicycloheteroaliphatic optionally substituted with 1-3 of $R_5$. For example, $R_1$ is a 2-azabicyclo[1.1.1]pentyl, 5-azabicyclo[2.1.1]hexyl, 7-azabicyclo[2.2.1]heptyl, 6-azabicyclo[3.1.1]heptyl, 2-azabicyclo[2.2.2]octyl, 8-azabicyclo[3.2.1]octyl, or 9-azabicyclo[3.3.1]nonyl, each of which is optionally substituted with 1-3 of hydrogen, halo, hydroxy, cyano, optionally substituted aliphatic, optionally substituted cycloaliphatic, optionally substituted heterocycloaliphatic, optionally substituted aryl, optionally substituted heteroaryl, optionally substituted alkoxycarbonyl, (cycloalkyloxy)carbonyl, (heterocycloalkyloxy)carbonyl, (alkoxy)alkoxycarbonyl, (alkynyloxy)carbonyl, or combinations thereof.

In several embodiments, $R_1$ is an aryl optionally substituted with 1-3 of $R_5$. For example, $R_1$ is phenyl or a bicyclic aryl, each of which is optionally substituted with 1-3 of $R_5$. For example, $R_1$ is phenyl that is optionally substituted with 1-3 of halo, hydroxy, cyano, nitro, optionally substituted aliphatic, optionally substituted cycloaliphatic, optionally substituted heterocycloaliphatic, optionally substituted aryl, optionally substituted heteroaryl, optionally substituted alkoxycarbonyl, (aliphatic)carbonyl, or combinations thereof. In other examples, $R_1$ is naphthylenyl, indenyl, 2,3-dihydro-1H-indenyl, 1,2,3,4-tetrahydronaphthalene, each of which is optionally substituted with 1-3 of halo, hydroxy, cyano, nitro, optionally substituted aliphatic, optionally substituted cycloaliphatic, optionally substituted heterocycloaliphatic, optionally substituted aryl, optionally substituted heteroaryl, optionally substituted alkoxycarbonyl, (aliphatic)carbonyl, or combinations thereof.

In several embodiments, $R_1$ is a heteroaryl optionally substituted with 1-3 of $R_5$. For example, $R_1$ is a monocyclic heteroaryl or a bicyclic heteroaryl, each of which is optionally substituted with 1-3 of $R_5$. In several examples, $R_1$ is furyl, thiopheneyl, 2H-pyrrolyl, 1H-pyrrolyl, oxazolyl, isoxazolyl, thiazolyl, imidazolyl, pyrazolyl, isoxazolyl, isothiazolyl, 1,3,4-thiadiazolyl, 2H-pyranyl, 4-H-pyranyl, pyridinyl, pyridazinyl, pyrimidyl, pyrazolyl, pyrazyl, 1,2,5-oxadiazolyl, 1,2,3-thiadiazolyl, or 1,3,5-triazinyl, each of which is optionally substituted with 1-3 of halo, hydroxy, cyano, nitro, optionally substituted aliphatic, optionally substituted alkoxy, optionally substituted (alkylcarbonyl)amino, or combinations thereof. In other examples, $R_1$ is benzo[b]thiopheneyl, benzofuranyl, indolyl, 3H-indolyl, isoindolyl, indolinyl, 1H-indazolyl, benzimidazolyl, benzthiazolyl, quinolinyl, cinnolinyl, phthalazinyl, or quinazolinyl, each of which is optionally substituted with 1-3 of halo, hydroxy, cyano, nitro, optionally substituted aliphatic, optionally substituted alkoxy, optionally substituted (alkylcarbonyl)amino, or combinations thereof.

In several embodiments, $R_1$ is hydrogen, optionally substituted aliphatic, optionally substituted (alkylsulfinyl)alkyl, optionally substituted alkoxyalkyl, or (alkylcarbonyl)alkyl.

1b. Linking Group L:

L is $Z^A$ wherein each $Z^A$ is independently a bond or an optionally substituted branched or straight $C_{1-6}$ aliphatic chain wherein up to two carbon units of $Z^A$ are optionally and independently replaced by —CO—, —CS—, —CONR$^A$—, —CONR$^A$NR$^A$—, —CO$_2$—, —OCO—, —NR$^A$CO$_2$—, —O—, —NR$^A$CONR$^A$—, —OCONR$^A$—, —NR$^A$NR$^A$—, —NR$^A$CO—, —S—, —SO—, —SO$_2$—, —NR$^A$—, —SO$_2$NR$^A$—, —NR$^A$SO$_2$—, or —NR$^A$SO$_2$NR$^A$. Each $R^A$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl. In several embodiments, L is a bond, an optionally substituted methylene group, or an optionally substituted ethylene group.

1c. -L-$R_1$ Group:

In several embodiments, -L-$R_1$ is one selected from: hydrogen; cyclohexylmethyl-; bicyclo[2.2.1]hept-2-yl-; (bicyclo[2.2.1]hept-2-yl)methyl-; bicyclo[3.2.1]octan-3-yl-; 8-aza-8-ethoxycarbonylbicyclo[3.2.1]octan-3-yl-; 4-propylcyclohexyl-; tetrahydropyran-4-yl-; 1-ethoxycarbonylpiperidin-4-yl-; benzofuran-2-yl-; (benzothiophene-2-yl) methyl-; 1,2-dihydroindan-2-yl-; cyclohexyl-; 8-aza-8-methoxycarbonylbicyclo[3.2.1]octan-3-yl-; 8-aza-8-(1-methylethoxy)carbonylbicyclo[3.2.1]octan-3-yl-; 8-aza-8-(tetrahydrofuran-3-yloxy)carbonylbicyclo[3.2.1]octan-3-yl-; (1-methoxycarbonylpiperidin-4-yl)methyl-; (1-ethoxycarbonylpiperidin-4-yl)methyl-; (1-(1-methyl)ethoxycarbonylpiperidin-4-yl)methyl-; (1-cyclobutoxycarbonylpiperidin-4-yl)methyl-; (1-cyclopentoxycarbonylpiperidin-4-yl)methyl-; (1-(tetrahydrofuran-3-yloxy)carbonylpiperidin-4-yl)methyl-; (1-(2-methoxy)ethoxycarbonylpiperidin-4-yl)methyl-; 8-aza-8-propoxycarbonylbicyclo[3.2.1]octan-3-yl-; 8-aza-8-butoxycarbonylbicyclo[3.2.1 ]octan-3-yl-; 8-aza-8-(2-methoxy)ethoxycarbonylbicyclo[3.2.1]octan-3-yl-; 8-aza-8-(1-methyl)ethoxycarbonylbicyclo[3.2.1]octan-3-yl-; 1-propoxycarbonypiperidin-4-yl-; 1-(tetrahydrofuran-3-yloxy)carbonylpiperidin-4-yl-; 1-(2-methoxy)ethoxycarbonylpiperidin-4-yl-; 1-(1,1-dimethyl)ethoxycarbonylpiperidin-4-yl-; (1-ethoxycarbonylpyrrolidin-3-yl)methyl-; (1-ethoxycarbonyl-4-methylpiperidin-4-yl)methyl-; 8-aza-8-(3-propargyloxy)carbonylbicyclo[3.2.1]octan-6-yl-; 8-azabicyclo[3.2.1]octan-3-yl-; (1-methoxycarbonylazetidin-3-yl)methyl-; 4-methoxybenzyl-; 3-methoxybenzyl-; 2-methoxybenzyl-; 4-ethoxybenzyl-; 1,2-dihydrobenzofuran-5-yl-; 3-fluoro-4-methoxybenzyl-; 4-fluorobenzyl-; 3-fluorobenzyl-; 2-fluorobenzyl-; 2,4-difluorobenzyl-; pyridine-4-ylmethyl-; pyridine-3-ylmethyl-; pyridine-2-ylmethyl-; 4-acetylbenzyl-; 1,4-dioxaspiro[4.5]decan-8-yl-; 4-oxocyclohexyl-; 4-carbethoxycyclohexyl-; 6-methoxypyridin-3-yl-; 3-acetoxybenzyl-; 4-propionoxybenzyl-; 4-acetoxybenzyl-; 4-(1-hydroxyethyl)benzyl-; bicyclo[2.2.2]octan-2-yl-; tetrahydrothiopyran-4-yl-; bicyclo[2.2.1]heptan-2-yl-; cycloheptyl-; bicyclo[3.3.1]nonan-9-yl-; 2-adamantyl-; 2-chlorobenzyl-; 2-cyanobenzyl-; 2-hydroxybenzyl-; 2-methoxycarbonylbenzyl-; 2-fluoro-5-methylbenzyl-; (6-methylpyridin-2-yl)methyl-; 2,6-dimethoxybenzyl-; 2-methoxyethyl-; 2-ethoxyethyl-; (tetrahydropyran-2-yl)methyl-; 2-oxobutyl-; 2-oxopropyl-; (tetrahydropyran-3-yl)methyl-; (thiazol-2-yl)methyl-; (3-methylthiophene-2-yl)methyl-; (4,5-dimethylfuran-2-yl)methyl-; (2,4-dimethylthiophene-5-yl)methyl-; furan-3-ylmethyl-; (3,6,6-trimethylcyclohexa-1,3-diene-2-yl)methyl-; (1,3- dimethylcyclohexene-4-yl)methyl-; (2,2-dimethylbicyclo[3.1.1]hept-5-ene-5-yl)methyl-; 4-ethoxyiminocyclohexyl-; 3,3-dimethylbutyl-; 1-benzoylpiperidin-4-yl-; 2-(tetrahydrothiopyran-4-yl)ethyl-; tetrahydrofuran-3-ylmethyl-; 1-(pyrazine-2-yl)piperidine-4-yl-; 1-(thiazole-2-yl)piperidine-4-yl-; 2-aza-3-methyl-1-oxaspiro[4.5]dec-2-ene-8-yl-; 1-(3-methyl-1,2,4-thiadiazole-5-yl)piperidine-4-yl-; 1-(3,6-dimethylpiperazine-2-yl)piperidine-4-yl-; 1-(2-fluorophenyl)piperidine-4-yl-; 1-(3-fluorophenyl)piperidine-4-yl-; 1-(4-fluorophenyl)piperidine-4-yl-; 1-(2-methoxyphenyl)piperidine-4-yl-; 1-(3-methpxyphenyl)piperidine-4-yl-; 1-(4-methoxyphenyl)piperidine-4-yl-; 1-(5-fluoro-2-methoxyphenyl)piperidine-4-yl-; 1-(pyrimidine-2-yl)piperidine-4-yl-; 1-(pyrimidine-5-yl)piperidine-4-yl-; (1-(pyrazine-2-yl)pyrrolidine-3-yl)methyl-; (1-(thiazole-2-yl)pyrrolidine-3-yl)methyl-; 1-(pyridine-2-yl)piperidine-4-yl-; 1-(pyridine-3-yl)piperidine-4-yl-; 1-(thiophene-3-yl)piperidine-4-yl-; and 3-methylsulfanylbutyl-.

2. Substituent $R_2$:

Each $R_2$ is -$Z^B R_7$, wherein each $Z^B$ is independently a bond or an optionally substituted branched or straight $C_{1-4}$ aliphatic chain wherein up to two carbon units of $Z^B$ are optionally and independently replaced by —CO—, —CS—, —CONR$^B$—, —CONR$^B$NR$^B$—, —CO$_2$—, —OCO—, —O—, —OCONR$^B$—, —S—, —SO—, —SO$_2$—, or —SO$_2$NR$^B$—. Each $R_7$ is independently $R^B$, halo, —OH, —CN, —NH$_2$, —NO$_2$, or —OCF$_3$. Each $R^B$ is hydrogen, an optionally substituted $C_{1-8}$ aliphatic group, an optionally substituted cycloaliphatic, an optionally substituted heterocycloaliphatic, an optionally substituted aryl, an optionally substituted heteroaryl.

In several embodiments, $R_2$ is an optionally substituted cycloaliphatic. For example, $R_2$ is a monocyclic cycloaliphatic optionally substituted with 1-3 of $R_7$. In some instances, $R_2$ is a cyclopropyl, cyclobutyl, cyclopentyl, cyclohexyl, cycloheptyl, or cyclooctyl, each of which is optionally substituted with 1-3 of $R_7$. In other embodiments, $R_2$ is a cyclopropenyl, cyclobutenyl, cyclopentenyl, cyclohexenyl, cycloheptenyl, or cyclooctenyl, each of which is optionally substituted with 1-3 of $R_7$. In several embodiments, $R_2$ is optionally substituted with 1-3 of halo, hydroxy, cyano, nitro, oxo, or optionally substituted alkoxycarbonyl, optionally substituted alkoxyimino, optionally substituted alkylcarbonyl, optionally substituted aliphatic, optionally substituted cycloaliphatic, optionally substituted heterocycloaliphatic, optionally substituted aryl, optionally substituted heteroaryl, optionally substituted aralkyl, optionally substituted heteroaralkyl, optionally substituted aralkyloxyimino, optionally substituted aryloxyimino, optionally substituted arylcarbonyloxy, or combinations thereof.

In several embodiments, $R_2$ is a bicyclic (e.g., fused or bridged) cycloaliphatic that is optionally substituted with 1-3 of $R_7$. In several examples, $R_2$ is a bridged bicycloalkyl or a bridged bicycloalkenyl, each of which is optionally substituted with 1-3 of $R_7$. For example, $R_2$ is a bicyclo[1.1.1]pentyl, bicyclo[2.1.1]hexyl, bicyclo[2.2.1]heptyl, bicyclo[3.1.1]heptyl, bicyclo[2.2.2]octyl, bicyclo[3.2.1]octyl, bicyclo[3.3.1]nonyl, or bicyclo[3.3.3]undecyl, each of which is optionally substituted with 1-3 of halo, hydroxy, or optionally substituted aliphatic, optionally substituted alkoxy, optionally substituted alkoxycarbonyl, or combinations thereof. In other examples, $R_2$ is a bicyclo[1.1.1]pentenyl, bicyclo[2.1.1]hexenyl, bicyclo[2.2.1]heptenyl, bicyclo[3.1.1]heptenyl, bicyclo[2.2.2]octenyl, bicyclo[3.2.1]octenyl, bicyclo[3.3.1]nonenyl, or bicyclo[3.3.3]undecenyl, each of which is optionally substituted with 1-3 of halo, hydroxy, or optionally substituted aliphatic, optionally substituted alkoxy, optionally substituted alkoxycarbonyl, or combinations thereof.

In several examples, $R_2$ is an optionally substituted tricyclic cycloaliphatic. For example, $R_2$ is an optionally substituted adamantyl.

In several embodiments, $R_2$ is an optionally substituted heterocycloaliphatic. For example, $R_2$ is a monocyclic heterocycloaliphatic optionally substituted with 1-3 of $R_7$. In several embodiments, $R_2$ is tetrahydrofuranyl, tetrahydrothipheneyl, 1,3-dioxolanyl, tetrahydrooxazolyl, pyrrolidinyl, imidazolidinyl, pyrazolidinyl, tetrahydropyran, piperidinyl, piperazinyl, tetrahydro-2H-thiopyranyl, piperazinyl, 1,2,3-triazolidinyl, dioxanyl, oxazolidinyl, morpholinyl, thiepanyl, dithianyl, octahydropyranyl, trithianyl, thiomorpholinyl, hexahydropyrimidinyl, hexahydropyridazinyl, or thiocaneyl each of which is optionally substituted with 1-3 of halo, hydroxy, cyano, optionally substituted aliphatic, optionally substituted cycloaliphatic, optionally substituted heterocycloaliphatic, optionally substituted aryl, optionally substituted heteroaryl, optionally substituted alkoxycarbonyl, optionally substituted (cycloalkyl)oxycarbonyl, optionally substituted akylaminocarbonyl, optionally substituted (heterocycloalkyl)oxycarbonyl, optionally substituted arylcarbonyl, optionally substituted (alkoxy)alkoxycarbonyl, or combinations thereof.

In several examples, $R_2$ is a bicyclic heterocycloaliphatic that is optionally substituted with 1-3 of $R_7$. For example, $R_2$ is a bridged bicycloheteroaliphatic optionally substituted with 1-3 of $R_7$. For example, $R_2$ is a 2-azabicyclo[1.1.1]pentyl, 5-azabicyclo[2.1.1]hexyl, 7-azabicyclo[2.2.1]heptyl, 6-azabicyclo[3.1.1]heptyl, 2-azabicyclo[2.2.2]octyl, 8-azabicyclo[3.2.1]octyl, or 9-azabicyclo[3.3.1]nonyl, each of which is optionally substituted with 1-3 of hydrogen, halo, hydroxy, cyano, optionally substituted aliphatic, optionally substituted cycloaliphatic, optionally substituted heterocycloaliphatic, optionally substituted aryl, optionally substituted heteroaryl, optionally substituted alkoxycarbonyl, (cycloalkyl)oxycarbonyl, (heterocycloalkyloxy)carbonyl, (alkoxy)alkoxycarbonyl, or combinations thereof.

In several embodiments, $R_2$ is an aryl optionally substituted with 1-3 of $R_7$. For example, $R_2$ is phenyl or a bicyclic aryl, each of which is optionally substituted with 1-3 of $R_7$. For example, $R_2$ is phenyl that is optionally substituted with 1-3 of halo, hydroxy, cyano, nitro, optionally substituted aliphatic, optionally substituted cycloaliphatic, optionally substituted heterocycloaliphatic, optionally substituted aryl, optionally substituted heteroaryl, optionally substituted alkoxycarbonyl, (aliphatic)carbonyl, or combinations thereof. In other examples, $R_2$ is naphthylenyl, indenyl, 2,3-dihydro-1H-indenyl, 1,2,3,4-tetrahydronaphthalene, each of which is optionally substituted with 1-3 of halo, hydroxy, cyano, nitro, optionally substituted aliphatic, optionally substituted cycloaliphatic, optionally substituted heterocycloaliphatic, optionally substituted aryl, optionally substituted heteroaryl, optionally substituted alkoxycarbonyl, (aliphatic)carbonyl, or combinations thereof.

In several embodiments, $R_2$ is a heteroaryl optionally substituted with 1-3 of $R_7$. For example, $R_2$ is a monocyclic heteroaryl or a bicyclic heteroaryl, each of which is optionally substituted with 1-3 of $R_7$. In several examples, $R_2$ is furyl, thiopheneyl, 2H-pyrrolyl, pyrrolyl, oxazolyl, isoxazolyl, thiazolyl, imidazolyl, pyrazolyl, isoxazolyl, isothiazolyl, 1,3,4-thiadiazolyl, 2H-pyranyl, 4-H-pyranyl, pyridinyl, pyridazinyl, pyrimidyl, pyrazolyl, pyrazyl, 1,2,5-oxadiazolyl, 1,2,3-thiadiazolyl, or 1,3,5-triazyl, each of which is optionally substituted with 1-3 of halo, hydroxy, cyano, nitro, optionally substituted aliphatic, optionally substituted alkoxy, optionally substituted (alkylcarbonyl)amino, or combinations thereof. In other examples, $R_2$ is benzo[b]thiopheneyl, benzofuranyl, indolyl, 3H-indolyl, isoindolyl, indolinyl, 1H-indazolyl, benzimidazolyl, benzthiazolyl, quinolinyl, cinnolinyl, phthalazinyl, or quinazolinyl, each of which is optionally substituted with 1-3 of halo, hydroxy, cyano, nitro, optionally substituted aliphatic, optionally substituted alkoxy, optionally substituted (alkylcarbonyl)amino, or combinations thereof.

In several embodiments, $R_2$ is hydrogen, optionally substituted aliphatic, optionally substituted (alkylsulfinyl)alkyl, optionally substituted alkoxyalkyl, or (alkylcarbonyl)alkyl. In several embodiments, $R_2$ is one selected from hydrogen, chloro, fluoro, methyl, and ethyl.

3. Substituents $R_3$ and $R_4$:

Each $R_3$ and $R_4$ is independently -$Z^C R_8$, wherein each $Z^C$ is independently a bond or an optionally substituted branched or straight $C_{1-4}$ aliphatic chain wherein up to two carbon units of $Z^C$ are optionally and independently replaced by —CO—, —CS—, —CONR$^C$—, —ONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —SO—, —SO$_2$—, —NR$^C$—, —SO$_2$NR$^C$—, —NR$^C$SO$_2$—, or —NR$^C$SO$_2$NR$^C$. Alternatively, $R_3$ and $R_4$ together form an oxo group. Each $R_8$ is independently $R^C$, halo, —OH, —CN, or —OCF$_3$. Each $R^C$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl.

In several embodiments, $R_3$ or $R_4$ is an optionally substituted cycloaliphatic. For example, $R_3$ or $R_4$ is a monocyclic cycloaliphatic optionally substituted with 1-3 of $R_8$. In some instances, $R_3$ or $R_4$ is a cyclopropyl, cyclobutyl, cyclopentyl, cyclohexyl, cycloheptyl, or cyclooctyl, each of which is optionally substituted with 1-3 of $R_8$. In other embodiments, $R_3$ or $R_4$ is a cyclopropenyl, cyclobutenyl, cyclopentenyl, cyclohexenyl, cycloheptenyl, or cyclooctenyl, each of which is optionally substituted with 1-3 of $R_8$. In several embodiments, $R_3$ or $R_4$ is optionally substituted with 1-3 of halo, hydroxy, cyano, nitro, oxo, or optionally substituted alkoxycarbonyl, optionally substituted alkoxyimino, optionally substituted alkylcarbonyl, optionally substituted aliphatic, optionally substituted cycloaliphatic, optionally substituted heterocycloaliphatic, optionally substituted aryl, optionally substituted heteroaryl, optionally substituted aralkyl, optionally substituted heteroaralkyl, optionally substituted aralkyloxyimino, optionally substituted aryloxyimino, optionally substituted arylcarbonyloxy, or combinations thereof.

In several embodiments, $R_3$ or $R_4$ is an optionally substituted heterocycloaliphatic. For example, $R_3$ or $R_4$ is a monocyclic heterocycloaliphatic optionally substituted with 1-3 of $R_8$. In several embodiments, $R_3$ or $R_4$ is tetrahydrofuranyl, tetrahydrothiopheneyl, 1,3-dioxolanyl, tetrahydrooxazolyl, pyrrolidinyl, imidazolidinyl, pyrazolidinyl, tetrahydropyran, piperidinyl, piperazinyl, tetrahydro-2H-thiopyranyl, piperazinyl, 1,2,3-triazolidinyl, dioxanyl, oxazolidinyl, morpholinyl, thiepanyl, dithianyl, octahydropyranyl, trithianyl, thiomorpholinyl, hexahydropyrimidinyl, hexahydropyridazinyl, or thiocaneyl each of which is optionally substituted with 1-3 of halo, hydroxy, cyano, optionally substituted aliphatic, optionally substituted cycloaliphatic, optionally substituted heterocycloaliphatic, optionally substituted aryl, optionally substituted heteroaryl, optionally substituted alkoxycarbonyl, optionally substituted (cycloalkyl)oxycarbonyl, optionally substituted akylaminocarbonyl, optionally substituted (heterocycloalkyl)oxycarbonyl, optionally substituted arylcarbonyl, optionally substituted (alkoxy)alkoxycarbonyl, or combinations thereof.

In several embodiments, $R_3$ or $R_4$ is an aryl optionally substituted with 1-3 of $R_8$. For example, $R_3$ or $R_4$ is phenyl or a bicyclic aryl, each of which is optionally substituted with 1-3 of $R_8$. For example, $R_3$ or $R_4$ is phenyl that is optionally substituted with 1-3 of halo, hydroxy, cyano, nitro, optionally substituted aliphatic, optionally substituted cycloaliphatic, optionally substituted heterocycloaliphatic, optionally substituted aryl, optionally substituted heteroaryl, optionally substituted alkoxycarbonyl, (aliphatic)carbonyl, or combinations thereof.

In several embodiments, $R_3$ or $R_4$ is a heteroaryl optionally substituted with 1-3 of $R_8$. For example, $R_3$ or $R_4$ is a monocyclic heteroaryl or a bicyclic heteroaryl, each of which is optionally substituted with 1-3 of $R_8$. In several examples, $R_3$ or $R_4$ is fuiryl, thiopheneyl, 2H-pyrrolyl, pyrrolyl, oxazolyl, isoxazolyl, thiazolyl, imidazolyl, pyrazolyl, isoxazolyl, isothiazolyl, 1,3,4-thiadiazolyl, 2H-pyranyl, 4-H-pyranyl, pyridinyl, pyridazinyl, pyrimidyl, pyrazolyl, pyrazyl, 1,2,5-oxadiazolyl, 1,2,3-thiadiazolyl, or 1,3,5-triazyl, each of which is optionally substituted with 1-3 of halo, hydroxy, cyano, nitro, optionally substituted aliphatic, optionally substituted alkoxy, optionally substituted (alkylcarbonyl)amino, or combinations thereof.

In several embodiments, $R_3$ or $R_4$ is hydrogen, hydroxy, cyano, or optionally substituted aliphatic. In several embodiments, $R_3$ or $R_4$ is selected from hydrogen, hydroxy, chloro, fluoro, methyl, and ethyl. In alternative embodiments, $R_3$ and $R_4$ together form an oxo group. In yet another embodiment, $R_3$ is H.

4. Group W:

W is —NR$_9$— or —O—. $R_9$ is -$Z^D R_{10}$, wherein each $Z^D$ is independently a bond or an optionally substituted branched or straight $C_{1-4}$ aliphatic chain wherein up to two carbon units of $Z^D$ are optionally and independently replaced by —CO—, —CS—, —CONR$^D$—, —CONR$^D$NR$^D$—, —CO$_2$—, —OCO—, —NR$^D$CO$_2$—, —O—, —NR$^D$CONR$^D$—, —OCONR$^D$—, —NR$^D$NR$^D$—, —NR$^D$CO—, —S—, —SO—, —SO$_2$—, —NR$^D$—, —SO$_2$NR$^D$—, —NR$^D$SO$_2$—, or —NR$^D$SO$_2$NR$^D$. Each $R_{10}$ is independently $R^D$, halo, —OH, —CN, or —OCF$_3$. Each $R^D$ is independently hydrogen, an optionally substituted $C_{1-8}$ aliphatic group; an optionally substituted cycloaliphatic, an optionally substited heterocycloaliphatic, an optionally substituted aryl, or an optionally substituted heteroaryl.

In several embodiments, W is —NR$_9$—; $R_9$ is $Z^D R_{10}$; $Z^D$ is —C(O)—, —SO$_2$—, —C(O)NR$^D$—, —SO$_2$NR$^D$—, —C(O)O—, or —OC(O)NR$^D$—; and $R_{10}$ is aliphatic, cycloaliphatic, heterocycloaliphatic, aryl, heteroaryl, alkoxy, (cycloaliphatic)oxy, or aryloxy, each of which is optionally substituted.

In several embodiments, W is —NR$_9$—; $R_9$ is $Z^D R_{10}$; $Z^D$ is —C(O)—, —SO$_2$—, —C(O)NR$^D$—, —SO$_2$NR$^D$—, —C(O)O—, or —OC(O)NR$^D$—; and $R_{10}$ is an optionally substituted cycloaliphatic. For example, $R_{10}$ is an optionally substituted monocyclic cycloaliphatic or an optionally substituted bicyclic cycloaliphatic. In several embodiments, $R_{10}$ is a monocyclic cycloalkyl or a monocyclic cycloalkenyl, each of which is optionally substituted. In several examples, $R_{10}$ is a cyclopropyl, cyclobutyl, cyclopentyl, cyclohexyl, cycloheptyl, or cyclooctyl, each of which is optionally substituted. In other examples, $R_{10}$ is a cyclopropenyl, cyclobutenyl, cyclopentenyl, cyclohexenyl, cycloheptenyl, or cyclooctenyl, each of which is optionally substituted. In several embodiments, $R_{10}$ is a bridged or fused bicycloaliphatic, each of which is optionally substituted. For example, $R_{10}$ is a bridged bicycloalkyl or a bridged bicycloalkenyl, each of which is optionally substituted. In several examples, $R_{10}$ is a 2-azabicyclo[1.1.1]pentyl, 5-azabicyclo[2.1.1]hexyl, 7-azabicyclo[2.2.1]heptyl, 6-azabicyclo[3.1.1]heptyl, 2-azabicyclo[2.2.2]octyl, 8-azabicyclo[3.2.1]octyl, or 9-azabicyclo[3.3.1]nonyl, each of which is optionally substituted. In several embodiments, $R_{10}$ is optionally substituted with 1-3 of halo, hydroxy, cyano, nitro, aryl, aliphatic, cycloaliphatic, heterocycloaliphatic, aryl, heteroaryl, alkoxy, alkoxycarbonyl, alkylcarbonyl, alkylaminocarbonyl, or combinations thereof.

In several embodiments, W is —$NR_9$—; $R_9$ is $Z^D R_{10}$; $Z^D$ is —C(O)—, —$SO_2$—, —C(O)$NR^D$—, —$SO_2 NR^D$—, —C(O)O—, or —OC(O)$NR^D$—; and $R_{10}$ is an optionally substituted heterocycloaliphatic. In several examples, $R_{10}$ is an optionally substituted monocyclic heterocycloaliphatic. In other embodiments, $R_{10}$ is tetrahydrofuranyl, tetrahydrothiopheneyl, 1,3-dioxolanyl, tetrahydrooxazolyl, pyrrolidinyl, imidazolidinyl, pyrazolidinyl, tetrahydropyran, piperidinyl, piperazinyl, tetrahydro-2H-thiopyranyl, piperazinyl, 1,2,3-triazolidinyl, dioxanyl, oxazolidinyl, morpholinyl, thiepanyl, dithianyl, octahydropyranyl, trithianyl, thiomorpholinyl, hexahydropyrimidinyl, hexahydropyridazinyl, or thiocanyl, each of which is optionally substituted.

In several embodiments, W is —$NR_9$—; $R_9$ is $Z^D R_{10}$; $Z^D$ is —C(O)—, —$SO_2$—, —C(O)$NR^D$—, —$SO_2 NR^D$—, —C(O)O—, or —OC(O)$NR^D$—; and $R_{10}$ is an optionally substituted aryl. In some examples, $R_{10}$ is an optionally substituted monocyclic aryl or an optionally substituted bicyclic aryl. For example, $R_{10}$ is phenyl that is optionally substituted with 1-3 of halo, hydroxy, cyano, optionally substituted aliphatic, optionally substituted aryl, optionally substituted alkoxy, or combinations thereof. In other examples, $R_{10}$ is a naphthylenyl, indenyl, 2,3-dihydro-1H-indenyl, 1,2,3,4-tetrahydronaphthalene, each of which is optionally substituted.

In several embodiments, W is —$NR_9$—; $R_9$ is $Z^D R_{10}$; $Z^D$ is —C(O)—, —$SO_2$—, —C(O)$NR^D$—, —$SO_2 NR^D$—, —C(O)O—, or —OC(O)$NR^D$—; and $R_{10}$ is an optionally substituted heteroaryl. In several examples, $R_{10}$ is a monocyclic heteroaryl or a bicyclic heteroaryl, each of which is optionally substituted. For example, $R_{10}$ is furyl, thiopheneyl, 2H-pyrrolyl, 1H-pyrrolyl, oxazolineyl, isoxazolyl, thiazolyl, imidazolyl, pyrazolyl, isoxazolyl, isothiazolyl, 1,3,4-thiadiazolyl, 2H-pyranyl, 4-H-pyranyl, pyridinyl, pyridazinyl, pyrimidyl, pyrazolyl, pyrazyl, 1,2,5-oxadiazolyl, 1,2,3-thiadiazolyl, or 1,3,5-triazyl, each of which is optionally substituted with 1-3 of halo, hydroxy, cyano, nitro, optionally substituted aliphatic, optionally substituted alkoxy, optionally substituted aryl, optionally substituted (alkylcarbonyl)amino, or combinations thereof. In other examples, $R_{10}$ is benzo[b]thiopheneyl, benzofuranyl, indolyl, 3H-indolyl, isoindolyl, indolinyl, 1H-indazolyl, benzimidazolyl, benzthiazolyl, quinolinyl, cinnolinyl, phthalazinyl, or quinazolinyl, each of which is optionally substituted with 1-3 of halo, hydroxy, cyano, nitro, optionally substituted aliphatic, optionally substituted alkoxy, optionally substituted (alkylcarbonyl)amino, or combinations thereof.

In several embodiments, $R_{10}$ is an optionally substituted alkoxy. For example, $R_{10}$ is an optionally substituted $C_{1-6}$ alkoxy. In other examples, $R_{10}$ is methoxy, ethoxy, propoxy, isopropoxy, butoxy, sec-butoxy, isobutoxy, or tert-butoxy, each of which is optionally substituted with 1-3 halo, alkoxy, or combinations thereof.

In several embodiments, $R_{10}$ is an optionally substituted (cycloaliphatic)oxy. For example, $R_{10}$ is an optionally substituted cycloalkyloxy. In other examples, $R_{10}$ is cyclopropyloxy, cyclopentyloxy, cyclohexyloxy, or cycloheptyloxy, each of which is optionally substituted with 1-3 of halo, hydroxy, aliphatic, or combinations thereof.

In several embodiments, $R_{10}$ is an optionally substituted aroyl. In several examples, $R_{10}$ is a monocyclic aroyl or a bicyclic aroyl, each of which is optionally substituted. For example, $R_{10}$ is a phenyloxy that is optionally substituted with 1-3 of halo, hydroxy, cyano, optionally substituted aliphatic, optionally substituted alkoxy, or combinations thereof.

In several alternative embodiments, W is —$NR_9$—; $R_9$ is -$Z^D R_{10}$; $Z^D$ is —C(O)$NR^D$— or —$SO_2 NR^D$—; and $R_{10}$ is hydrogen, optionally substituted aliphatic, optionally substituted cycloaliphatic, optionally substituted heterocycloaliphatic, optionally substituted aryl, or optionally substituted heteroaryl.

In several embodiments, W is —$NR_9$—, $R_9$ is -$Z^D R_{10}$, $Z^D$ is —C(O)$NR^D$— or —$SO_2 NR^D$—, and $R_{10}$ is an optionally substituted aliphatic. In many examples, $R_{10}$ is an optionally substituted $C_{1-6}$ aliphatic. For example, $R_{10}$ is methyl, ethyl, propyl, isopropyl, butyl, sec-butyl, isobutyl, or tert-butyl, each of which is optionally substituted with 1-3 halo, hydroxy, cyano, aryl, cycloaliphatic, or combinations thereof.

In several embodiments, W is —$NR_9$—, $R_9$ is -$Z^D R_{10}$, $Z^D$ is —C(O)$NR^D$— or —$SO_2 NR^D$—, and $R_{10}$ is an optionally substituted cycloaliphatic. For example, $R_{10}$ is a monocyclic cycloaliphatic or a bicyclic cycloaliphatic, each of which is optionally substituted. In some examples, $R_{10}$ is a monocyclic cycloalkyl or a monocyclic cycloalkenyl, each of which are optionally substituted. In other examples, $R_{10}$ is cyclopropyl, cyclopentyl, cyclohexyl, or cycloheptyl, each of which is optionally substituted with 1-3 of halo, hydroxy, aliphatic, or combinations thereof.

In several embodiments, W is —$NR_9$—, $R_9$ is -$Z^D R_{10}$, $Z^D$ is —C(O)$NR^D$— or —$SO_2 NR^D$—, and $R_{10}$ is an optionally substituted aryl. For example, $R_{10}$ is phenyl that is optionally substituted with 1-3 of halo, hydroxy, cyano, optionally substituted aliphatic, optionally substituted aryl, optionally substituted alkoxy, or combinations thereof.

In several embodiments, W is —$NR_9$—, $R_9$ is -$Z^D R_{10}$, $Z^D$ is —C(O)$NR^D$—, —$SO_2 NR^D$—, —C(O)O—, or —OC(O)$NR^D$—; and $R_{10}$ is an optionally substituted heteroaryl. In several examples, $R_{10}$ is a monocyclic heteroaryl or a bicyclic heteroaryl, each of which is optionally substituted. For example, $R_{10}$ is furyl, thiopheneyl, 2H-pyrrolyl, pyrrolyl, oxazolyl, isoxazolyl, thiazolyl, imidazolyl, pyrazolyl, isoxazolyl, isothiazolyl, 1,3,4-thiadiazolyl, 2H-pyranyl, 4-H-pyranyl, pyridinyl, pyridazinyl, pyrimidyl, pyrazolyl, pyrazyl, 1,2,5-oxadiazolyl, 1,2,3-thiadiazolyl, or 1,3,5-triazyl, each of which is optionally substituted with 1-3 of halo, hydroxy, cyano, optionally substituted aliphatic, optionally substituted alkoxy, optionally substituted aryl, or combinations thereof.

In other embodiments, W is —$NR_9$—; $R_9$ is one selected from hydrogen; acetyl-; 2-methylpropionyl-; cyclobutylcarbonyl-; 4-fluorobenzoyl-; (isoxazol-5-yl)carbonyl-; (1H-1,5-dimethylpyrazol-3-yl)carbonyl-; ethylaminocarbonyl-; 1-methylethylaminocarbonyl-; 4-fluorophenylcarbonyl-; ((3,5-dimethylisoxazol-4-yl)amino)carbonyl-; methoxycarbonyl-; 1-methylethoxycarbonyl-; methylsulfonyl-; propylsulfonyl-; 4-fluorophenylsulfonyl-; (3,5-dimethylisoxazol-4-yl)sulfonyl-; (1,2,5-oxadiazole-3-yl)carbonyl-; (2,5-dimethyloxazole-4-yl)carbonyl-; (1H-1-methylimidazole-4-yl)carbonyl-; (4-methyl-1,2,3-thiadiazole-5-yl)carbonyl-; (2,5-dimethylfuran-3-yl)carbonyl-; ((1H-1-(1,1-dimethylethyl)-3-methylpyrazole-5-yl)carbonyl-; cyclopropylcarbonyl-; cyclopentylcarbonyl-; cyclohexylcarbonyl-; ((2,2-dimethyl)propion-1-yl)carbonyl-; (pyridin-3-yl)carbonyl-; (pyridin-4-yl)carbonyl-; (thiophene-2-yl)carbonyl-; cyclobutyloxycarbonyl-; cyclopentyloxycarbonyl-; 2-methoxyethoxycarbonyl-; dimethylaminocarbonyl-; cyclopentylaminocarbonyl-; dimethylaminosulfonyl-; thiophene-2-sulfonyl-; (2-acetylamino-4-methylthiazole-5-yl)sulfonyl-; benzenesulfonyl-; 4-methylbenzenesulfonyl-; 4-trifluoromethylbenzenesulfonyl-; 4-chlorobenzenesulfonyl-; 4-trifluoromethoxybenzenesulfonyl-; 4-methoxybenzenesulfonyl-; 4-cyanobenzenesulfonyl-; 4-phenylbenzenesulfonyl-; 4-acetoxyaminobenzenesulfonyl-; 3,4-dichlorobenzenesulfonyl-; 3-methylbenzenesulfonyl-; 3-fluorobenzenesulfonyl-; 3-chlorobenzenesulfonyl-; 2-fluorobenzenesulfonyl-; 2-chlorobenzenesulfonyl-; benzylsulfonyl-; propionyl-; butanoyl-; benzoyl-; (thiophene-2-yl)carbonyl-; (benzthiophene-2-yl)carbonyl-; phenylaminocarbonyl-; 4-fluorophenoxycarbonyl-; 2,2,2-trifluoropropionyl-; 1-methylcyclopropylcarbonyl-; pentanoyl-; 3-methylbutanoyl-; 1-methylcyclohexanoyl-; (5-methylisoxazol-4-yl)carbonyl-; (3,5-dimethylisoxazol-4-yl)carbonyl-; (2-methylthiazol-4-yl)carbonyl-; (1H-1-phenyl-5-trifluoromethylpyrazol-4-yl)carbonyl-; cyclohexylaminocarbonyl-; propylaminocarbonyl-; butylaminocarbonyl-; cyclopentylaminocarbonyl-; diethylaminocarbonyl-; piperidinylcarbonyl-; ethoxycarbonyl-; propoxycarbonyl-; butoxycarbonyl-; (2-methyl-4-trifluoromethylthiazol-5-yl)carbonyl-; (4-(1-methylethyl)- 1,2,3-thiadiazole-5-yl)carbonyl-; 1,1-dimethylethylaminocarbonyl-; 1-trifluoromethylcyclopropylcarbonyl-; 1-trifluoromethylcyclobutylcarbonyl-; (1H-1,2-dimethylimidazol-4-yl)sulfonyl-; 2-hydroxy-2-methylpropionyl-; 2-ethyl-2-hydroxybutanoyl-; 3-fluorophenyl-; 2,3-difluorophenyl-; 3-methoxyphenyl-; 4-chlorophenyl-; 3-methyl-4-chlorophenyl-; 3-chlorophenyl-; 3-fluoro-4-methylphenyl-; 3,4,-dimethylphenyl-; 3-methylphenyl-; 3-methylbutyl-; cyclohexylmethyl-; 1-phenylpropyne-3-yl-; 2-methylcyclohexyl-; cycloheptyl-; bicyclo[2.2.1]-2-yl-; benzyl-; and ethyl-.

In other embodiments, W is —NR$_9$— and n is 0.

In some embodiments, W is oxygen and n is 0.

In some embodiments, $Z^D$ is a bond.

4. Variables n, m, p, and q:

m and p are each independently 0-3; however, m+p is 3, 4, 5, or 6. In several embodiments, m and p are both 2. In several embodiments, m is 1 and p is 3, or m is 3 and p is 1.

Each n is 0-2 (e.g., 0, 1, or 2)

Each q is 0-4 (e.g., 0, 1, 2, 3, or 4).

In several embodiments, m and p are each 0, 1, or 2. In other embodiments, n is 0 or 1. In several embodiments, q is 1 or 2.

B. Sub-Generic Compounds

Another aspect of the present invention provides additional methods of modulating the activity of a muscarinic receptor comprising the step of contacting said receptor with a compound of formula Ia:

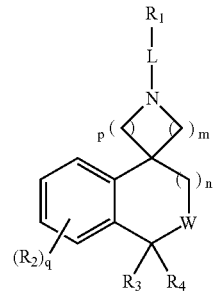

Ia or a pharmaceutically acceptable salt thereof.

$R_1$ is a cycloaliphatic or a heterocycloaliphatic, each of which is optionally substituted with 1-3 of $R_5$. Each $R_5$ is defined as -$Z^A R_6$, wherein each $Z^A$ is independently a bond or an optionally substituted branched or straight $C_{1-4}$ aliphatic chain wherein up to two carbon units of $Z^A$ are optionally and independently replaced by —CO—, —CS—, —CONR$^A$—, —CONR$^A$NR$^A$—, —CO$_2$—, —OCO—, —NR$^A$CO$_2$—, —O—, —NR$^A$CONR$^A$—, —OCONR$^A$—, —NR$^A$NR$^A$, NR$^A$CO—, —S—, —SO—, —SO$_2$—, —NR$^A$—, —SO$_2$NR$^A$—, —NR$^A$SO$_2$—, or —NR$^A$SO$_2$NR$^A$. Each $R_6$ is independently R$^A$, halo, =O, —OH, —NH$_2$, —NO$_2$, —CN, —CF$_3$, or —OCF$_3$. Each R$^A$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl.

Each L is a bond, a methylene group, or an ethylene group.

Each $R_2$, $R_3$, $R_4$, W, m, n, p, and q is as defined in formula I.

Another aspect of the present invention provides additional methods of modulating the activity of a muscarinic receptor comprising the step of contacting said receptor with a compound of formula Ib:

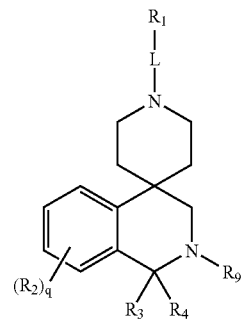

Ib or a pharmaceutically acceptable salt thereof wherein:

Each $R_1$, $R_2$, $R_3$, $R_4$, $R_9$, and q is as defined in formula I.

An additional aspect of the present invention provides compounds of formula Ic that are useful for modulating the activity of muscarinic receptors:

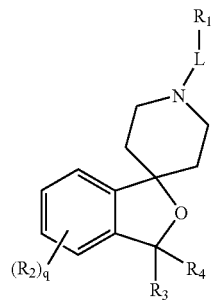

Ic or a pharmaceutically acceptable salt thereof.

Each $R_1$, $R_2$, $R_3$, $R_4$, L and q are as defined in formula I.

An additional aspect of the present invention provides compounds of formula Id that are useful for modulating the activity of muscarinic receptors:

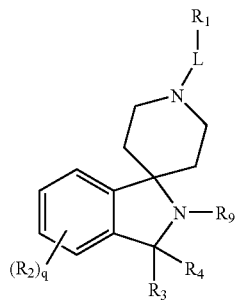

Id or a pharmaceutically acceptable salt thereof, wherein:

Each $R_1$, $R_2$, $R_3$, $R_4$, $R_9$, L, and q is as defined above in formula I.

C. Exemplary Compounds

Exemplary compounds of the present invention include, but are not limited to, those illustrated in Table 1 below.

TABLE 1

Exemplary compounds of formulae (I, Ia, Ib, Ic, and Id)

| 1 | 2 |
|---|---|
| 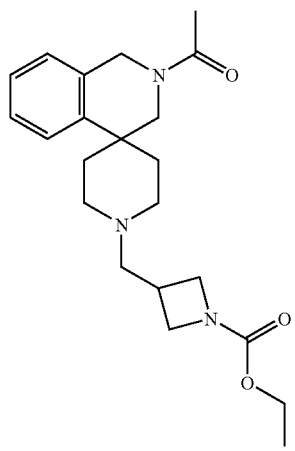 | 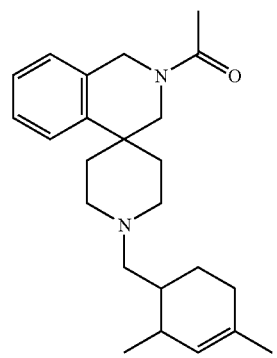 |
| 3 | 4 |
| 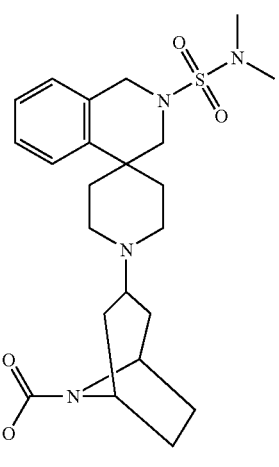 | 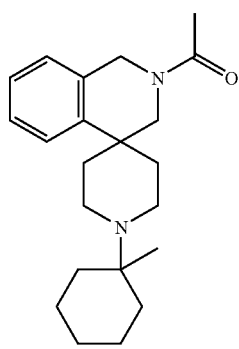 |

TABLE 1-continued
Exemplary compounds of formulae (I, Ia, Ib, Ic, and Id)
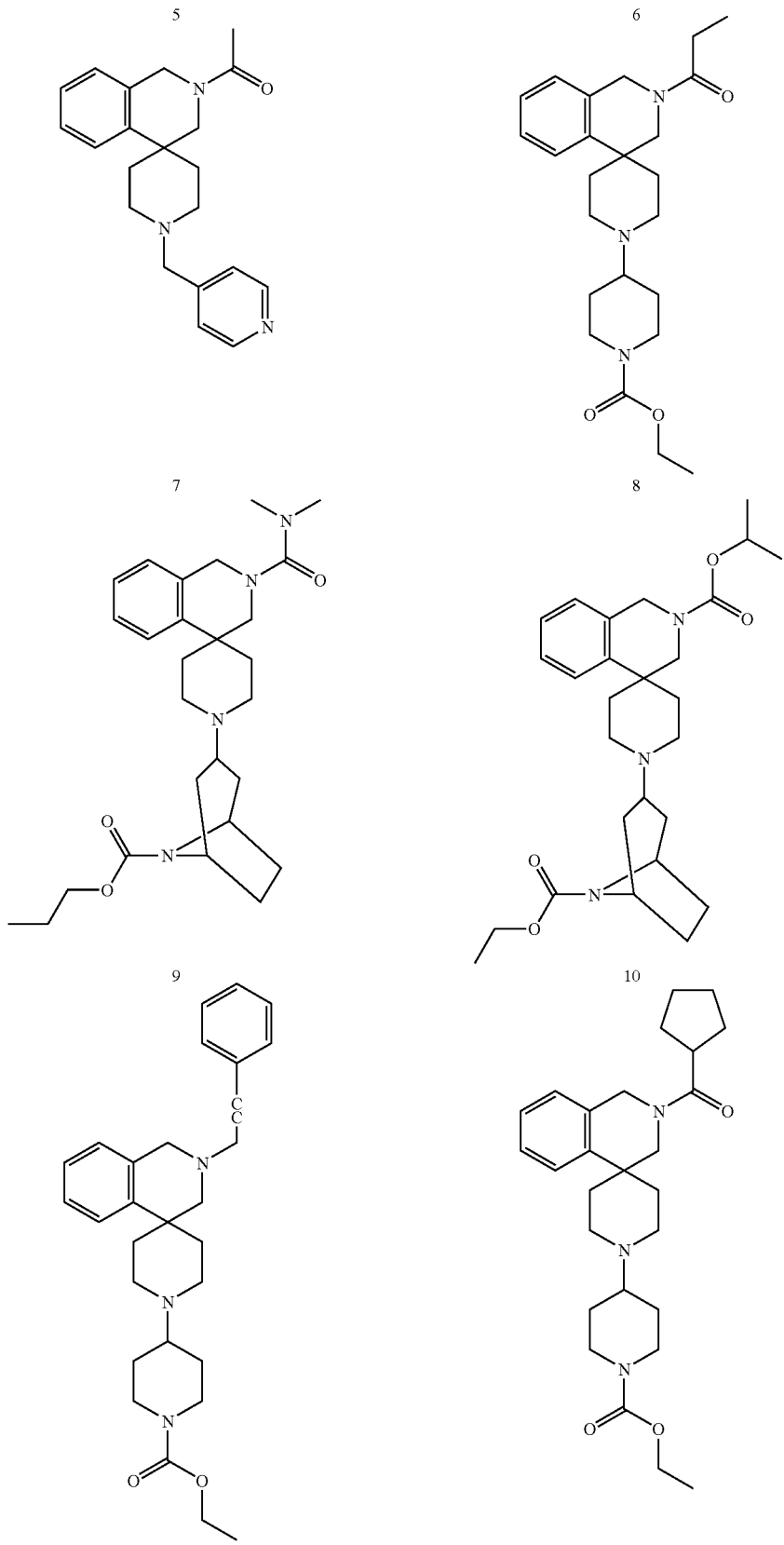

TABLE 1-continued

Exemplary compounds of formulae (I, Ia, Ib, Ic, and Id)

TABLE 1-continued
Exemplary compounds of formulae (I, Ia, Ib, Ic, and Id)
17
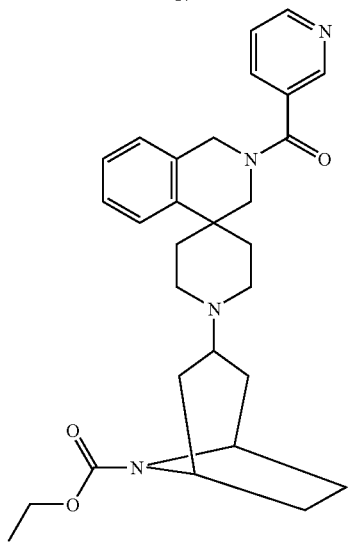
18
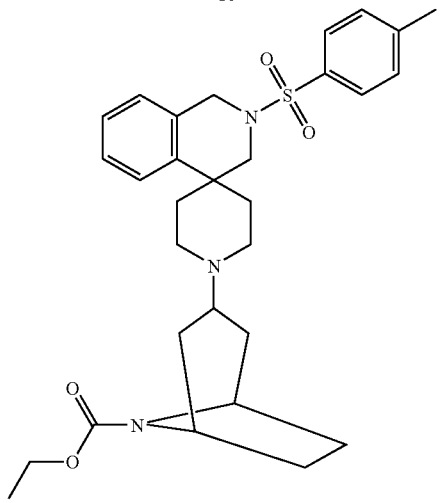
19
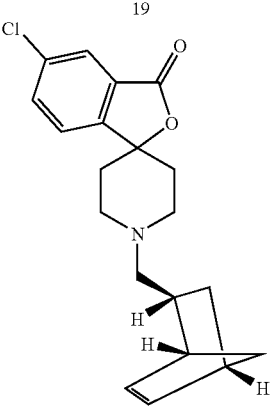
20
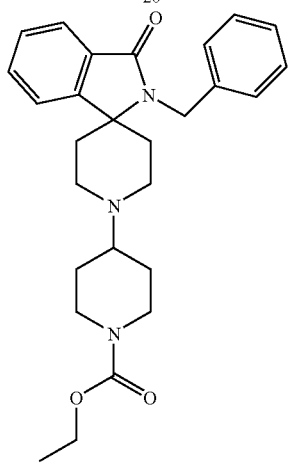
21
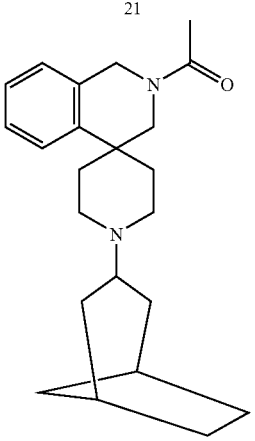
22
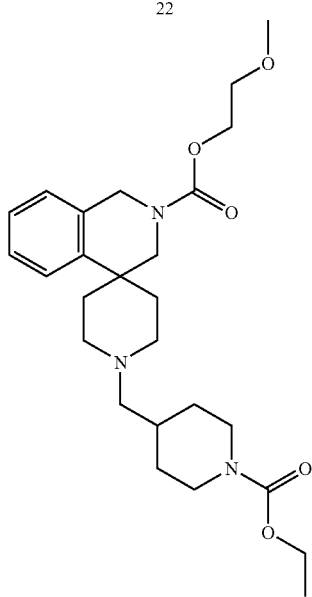

TABLE 1-continued

Exemplary compounds of formulae (I, Ia, Ib, Ic, and Id)

TABLE 1-continued
Exemplary compounds of formulae (I, Ia, Ib, Ic, and Id)
29
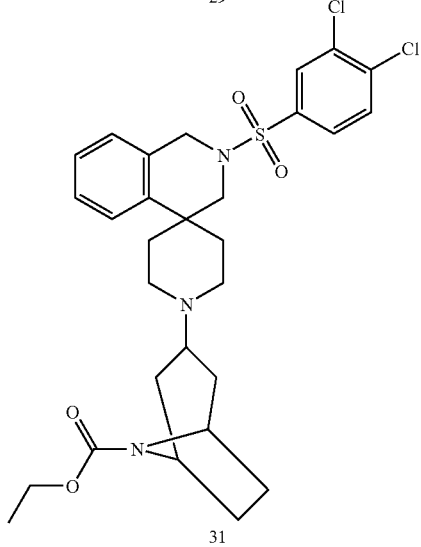
30
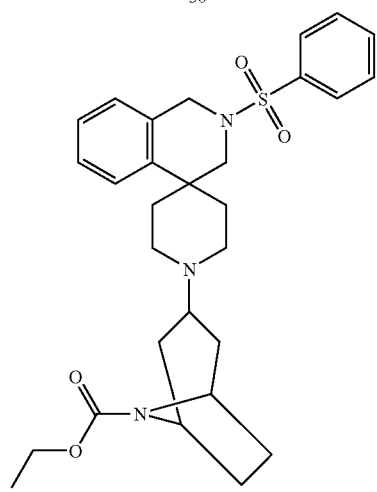
31
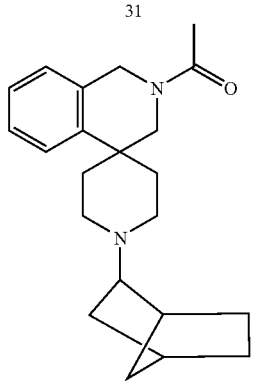
32
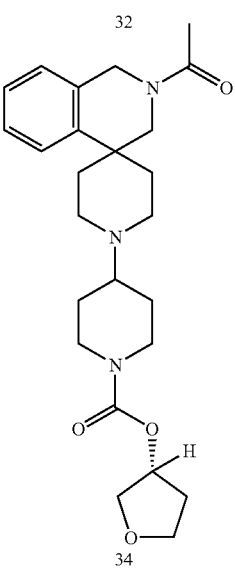
33
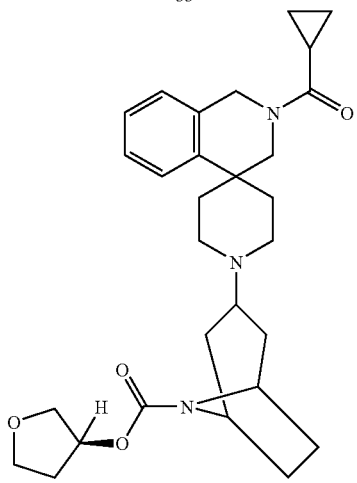
34
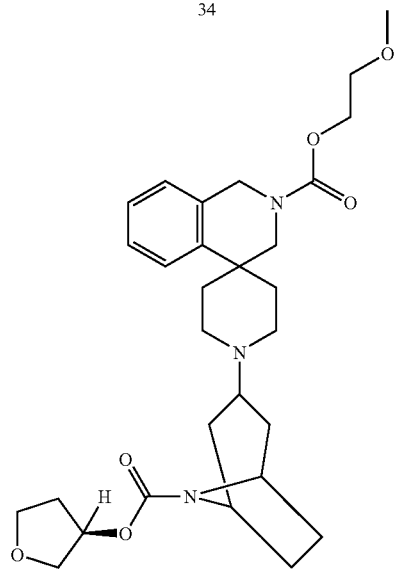

TABLE 1-continued
Exemplary compounds of formulae (I, Ia, Ib, Ic, and Id)
35
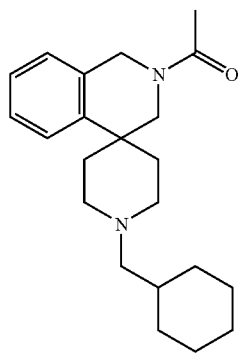
36
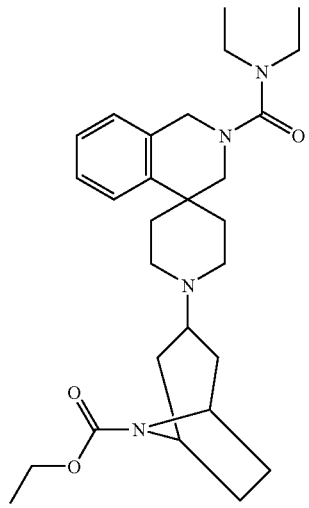
37
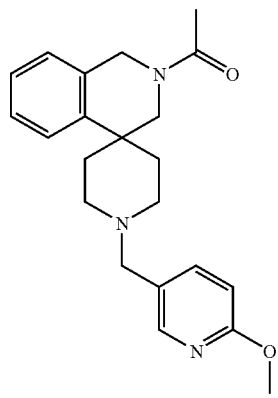
38
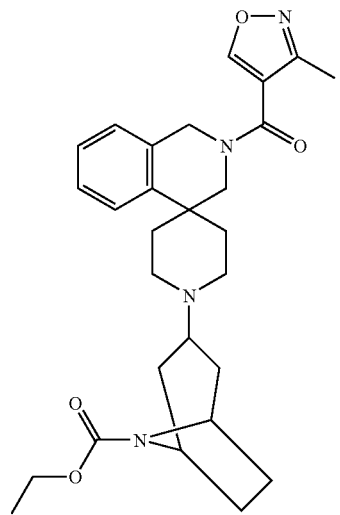
39
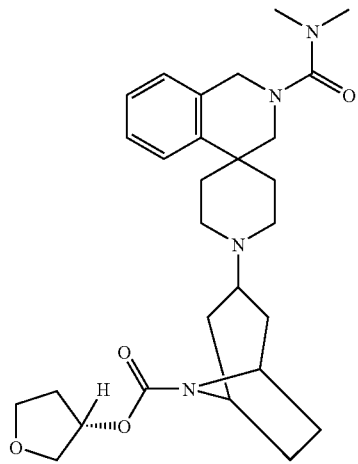
40
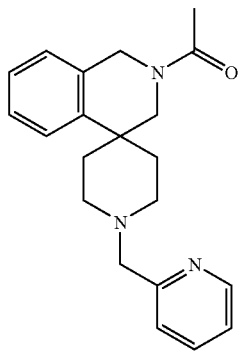

TABLE 1-continued
Exemplary compounds of formulae (I, Ia, Ib, Ic, and Id)
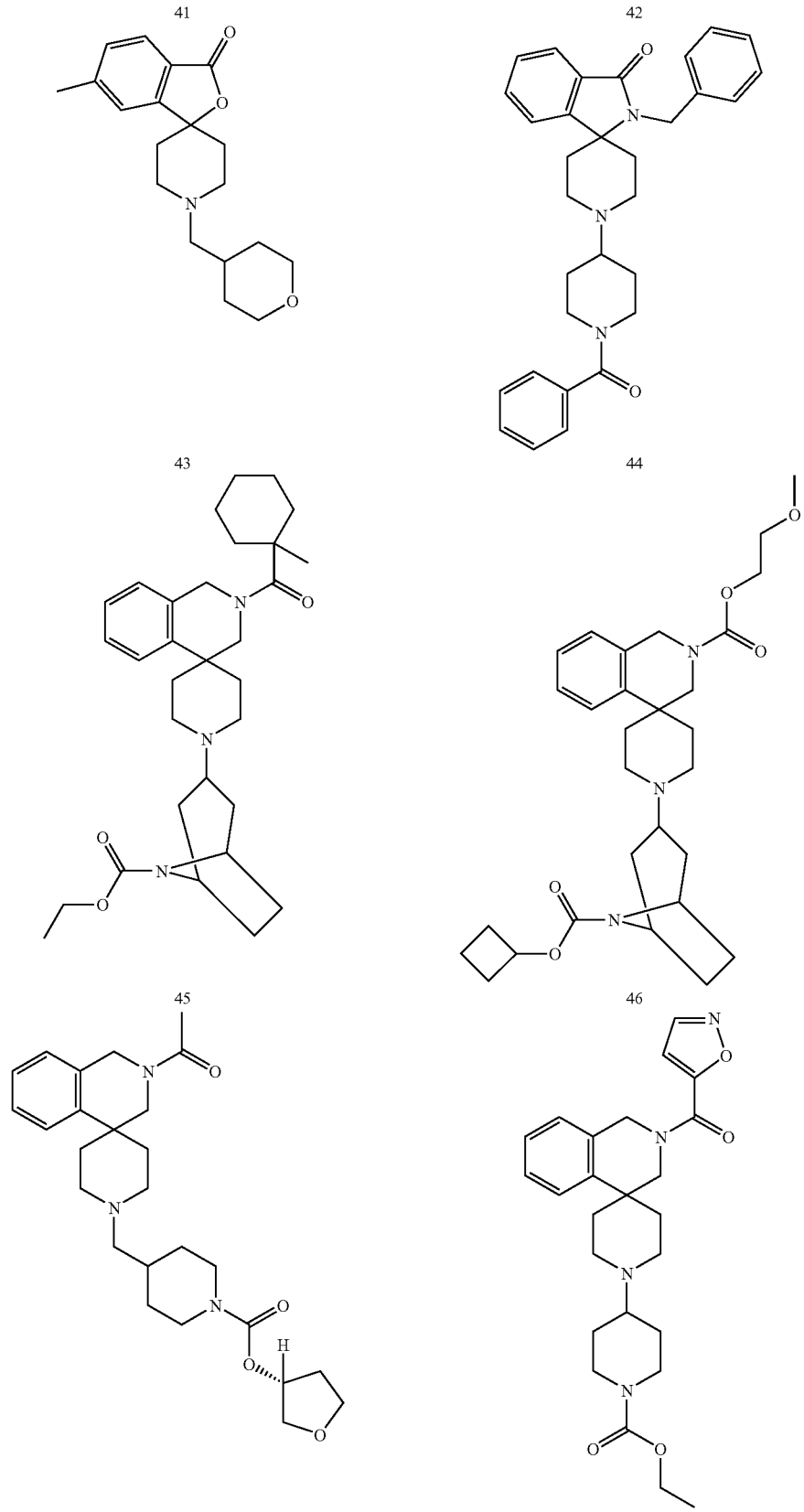

TABLE 1-continued
Exemplary compounds of formulae (I, Ia, Ib, Ic, and Id)
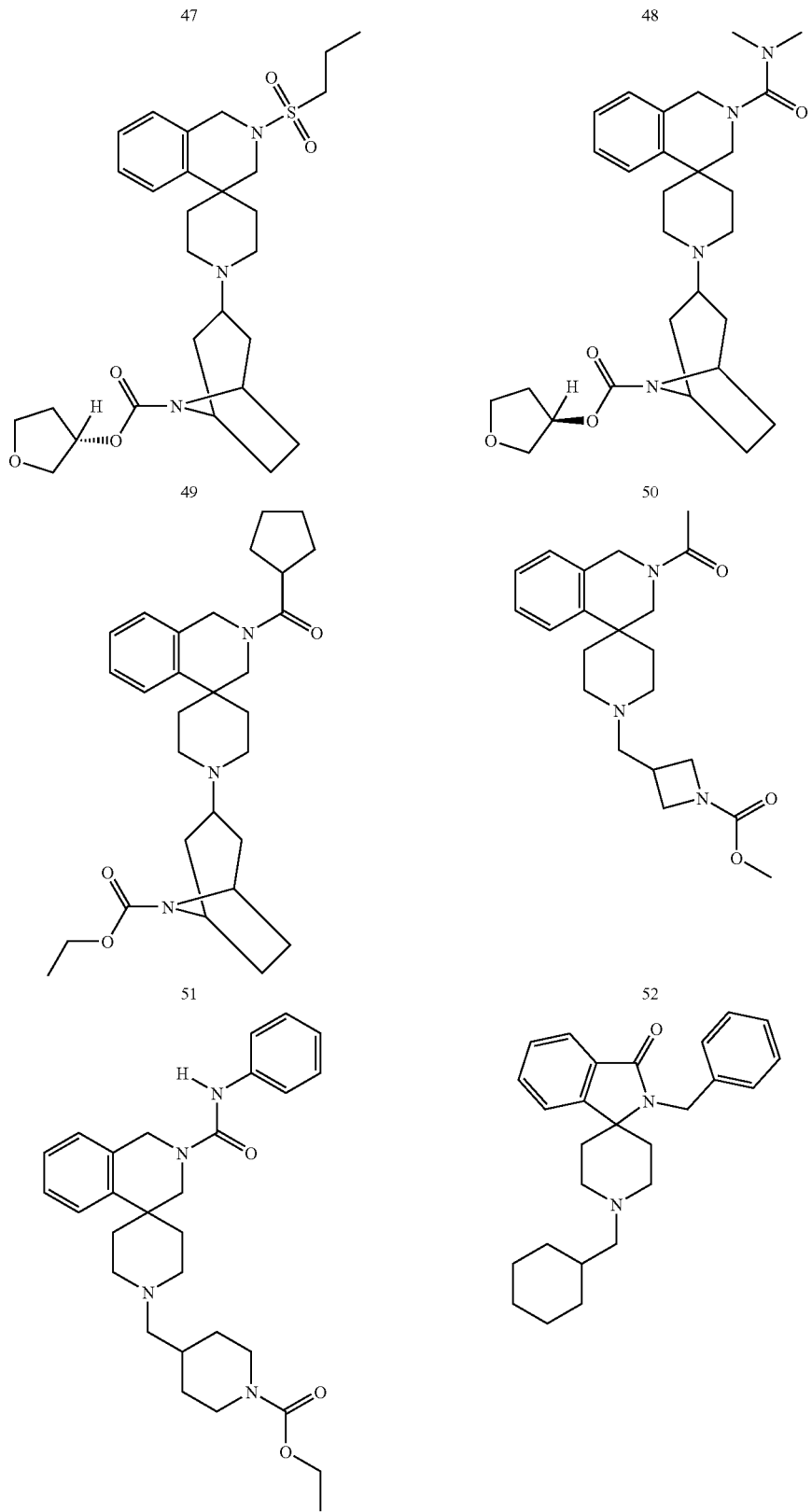

TABLE 1-continued
Exemplary compounds of formulae (I, Ia, Ib, Ic, and Id)
53
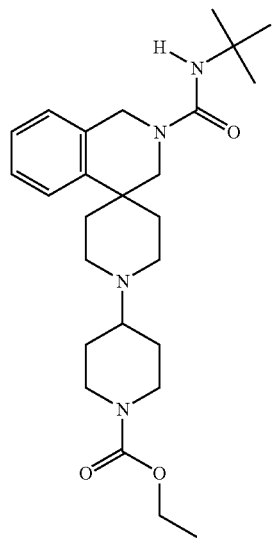
54
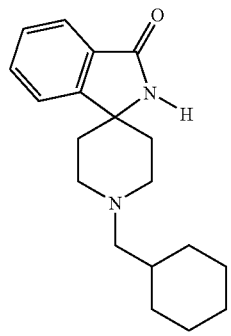
55
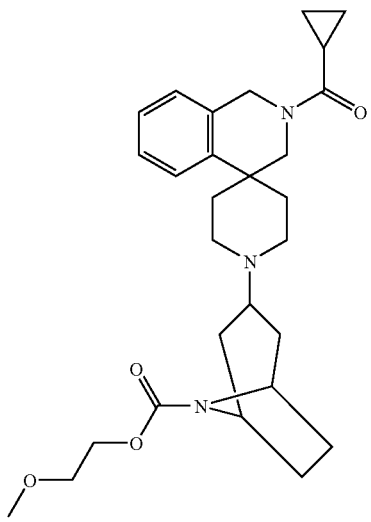
56
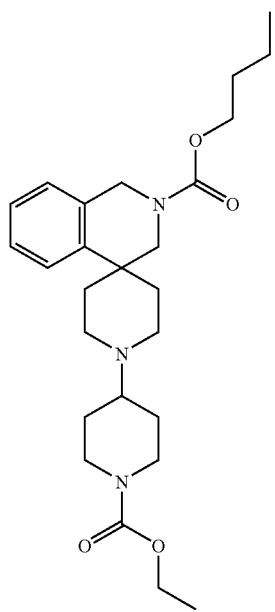
57
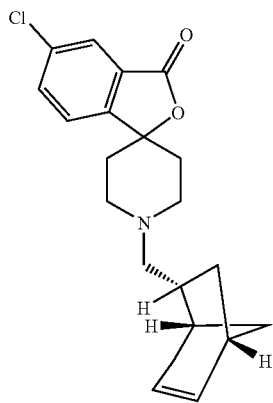
58
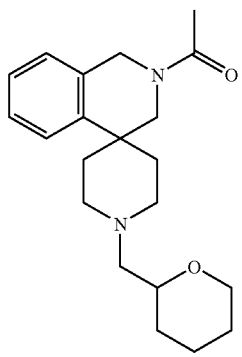

TABLE 1-continued
Exemplary compounds of formulae (I, Ia, Ib, Ic, and Id)
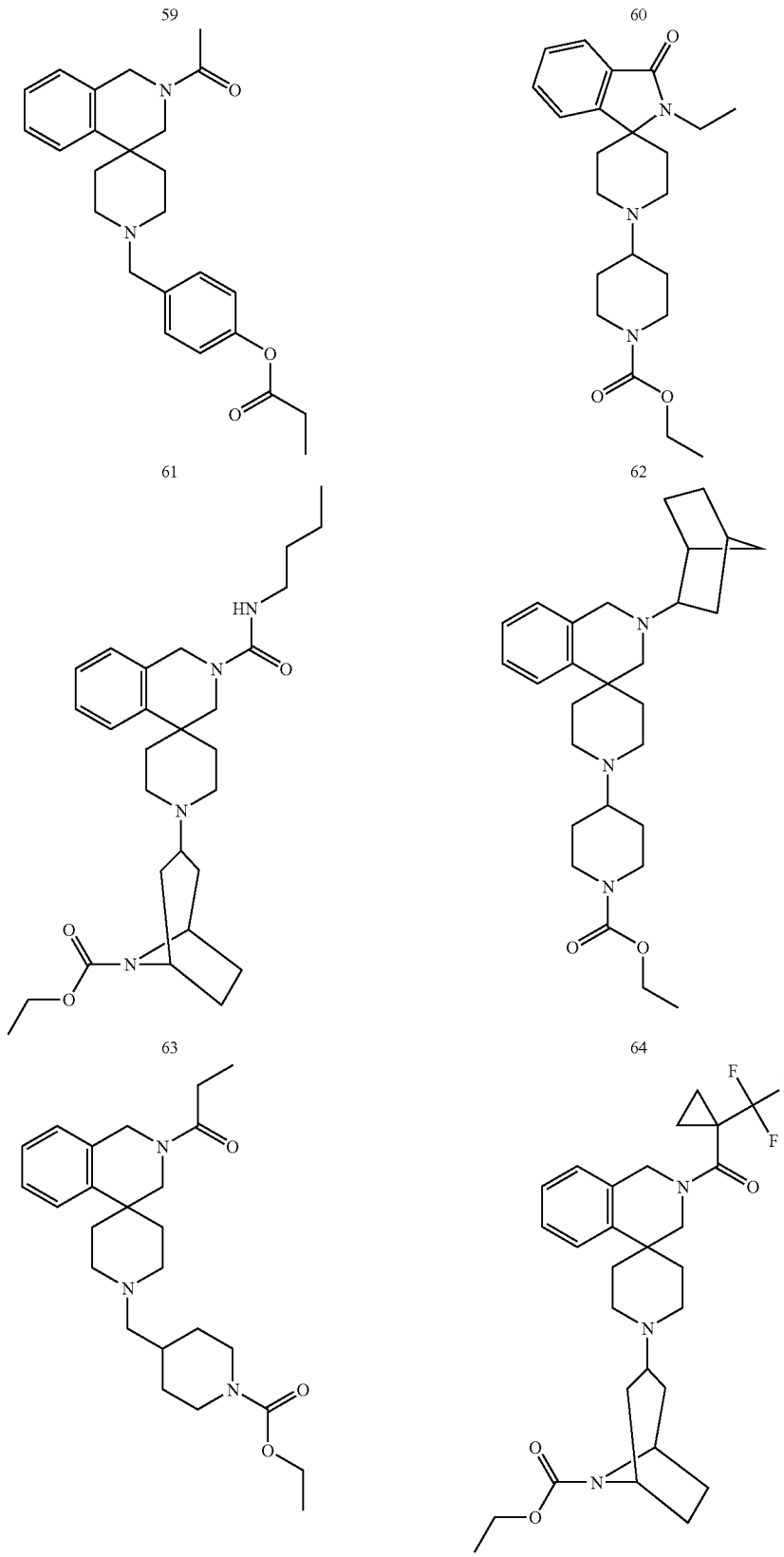

TABLE 1-continued
Exemplary compounds of formulae (I, Ia, Ib, Ic, and Id)
65
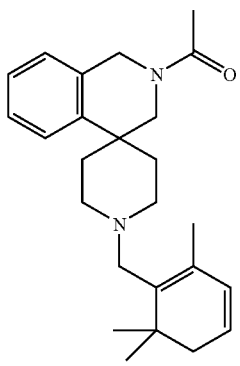
66
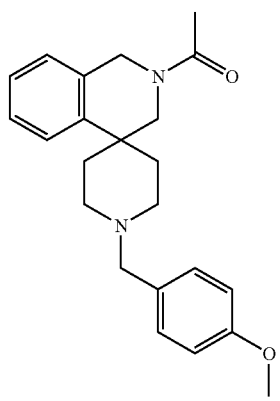
67
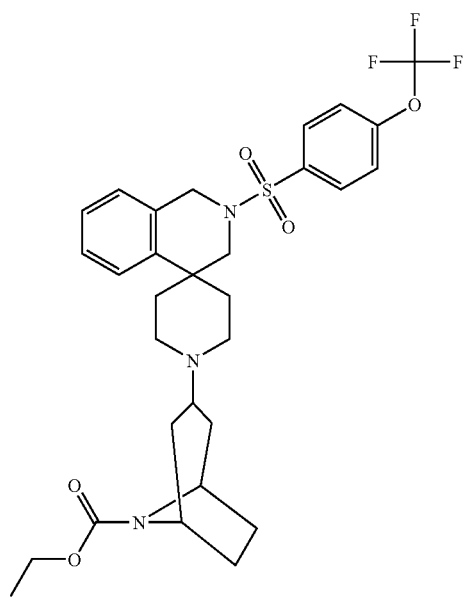
68
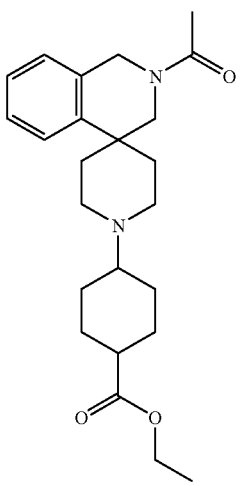
69
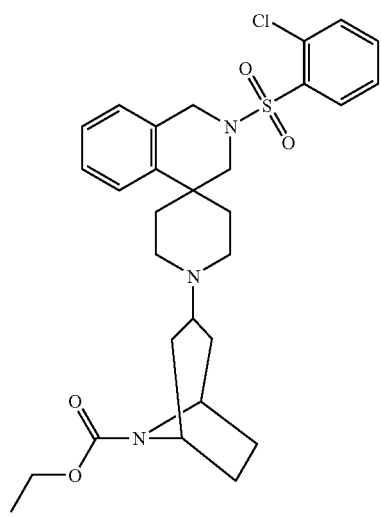
70
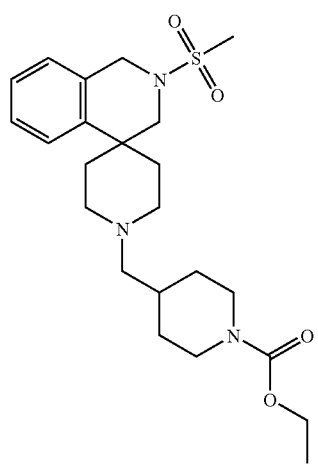

TABLE 1-continued

Exemplary compounds of formulae (I, Ia, Ib, Ic, and Id)

TABLE 1-continued
Exemplary compounds of formulae (I, Ia, Ib, Ic, and Id)
77
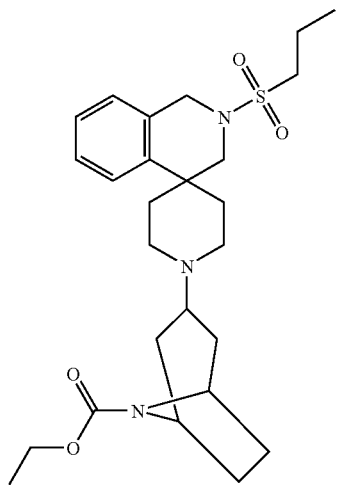
78
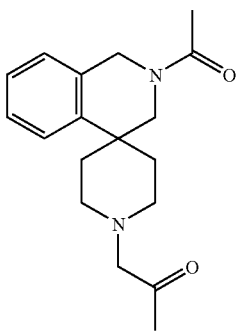
79
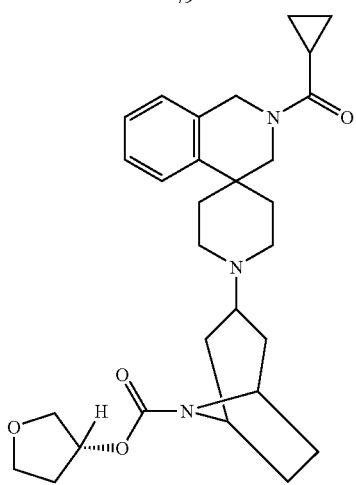
80
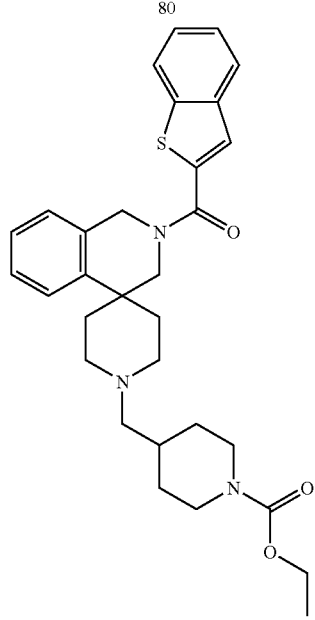
81
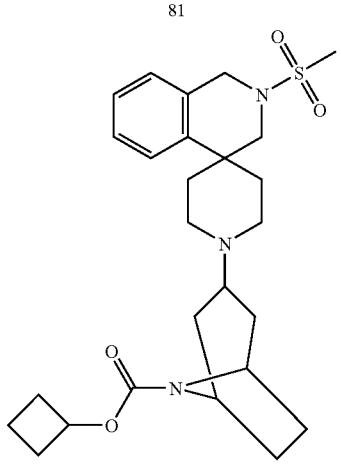
82
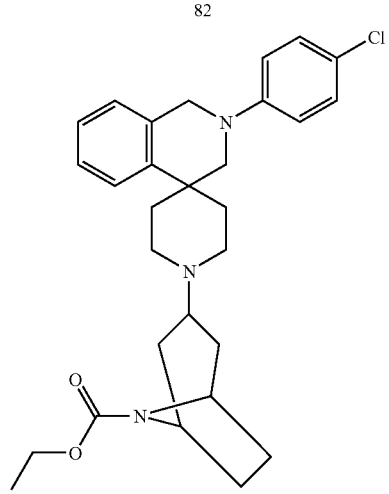

TABLE 1-continued
Exemplary compounds of formulae (I, Ia, Ib, Ic, and Id)
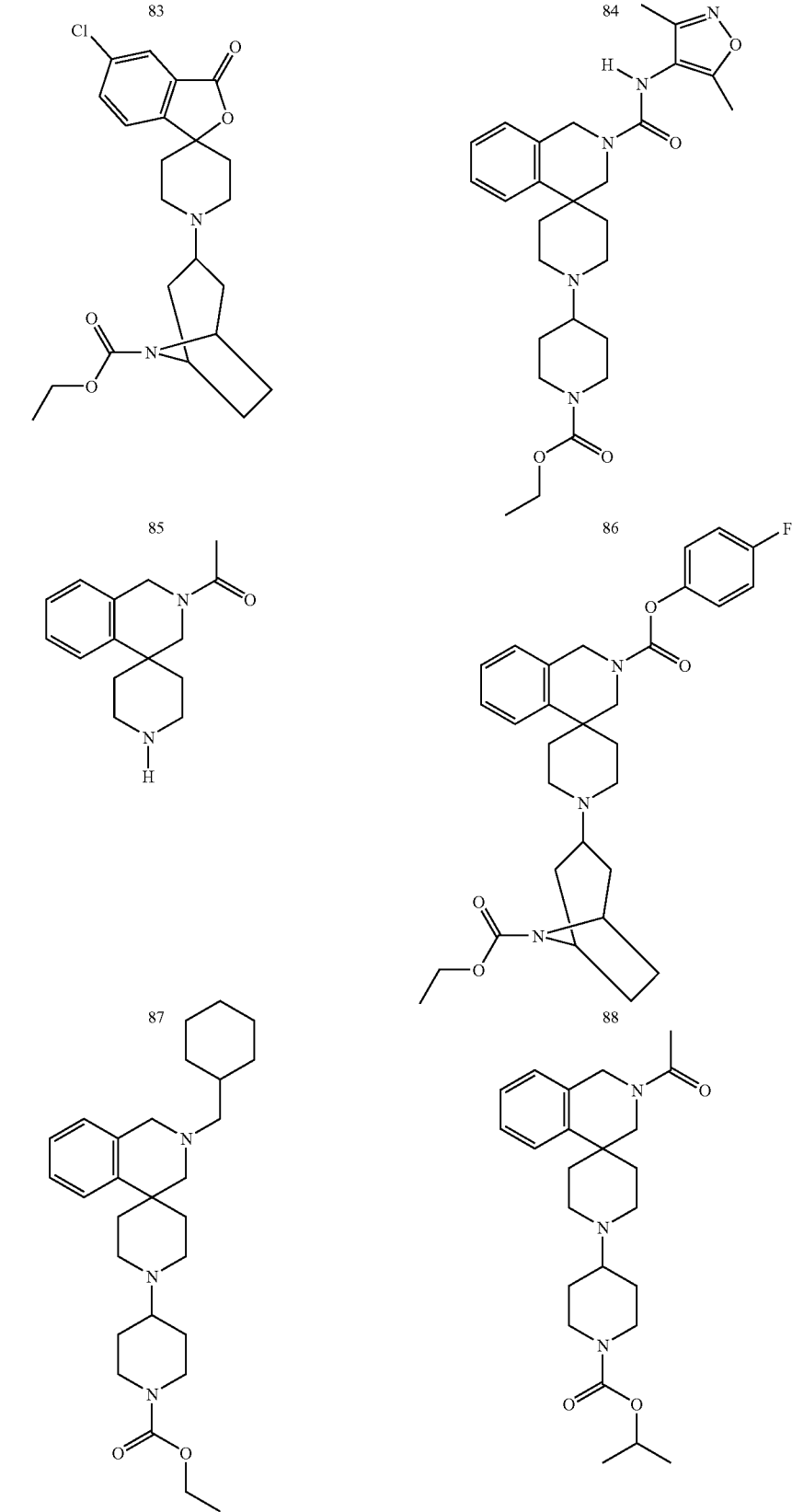

TABLE 1-continued
Exemplary compounds of formulae (I, Ia, Ib, Ic, and Id)
89
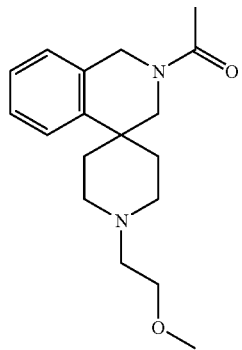
90
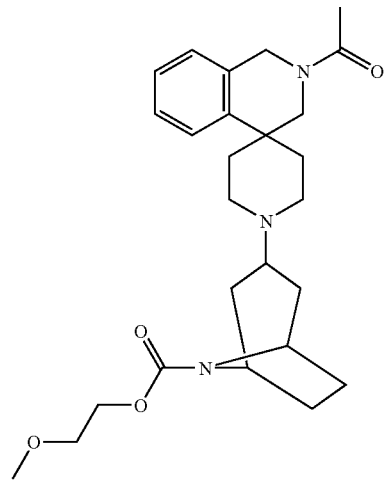
91
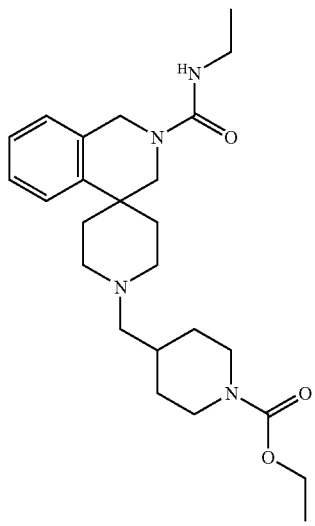
92
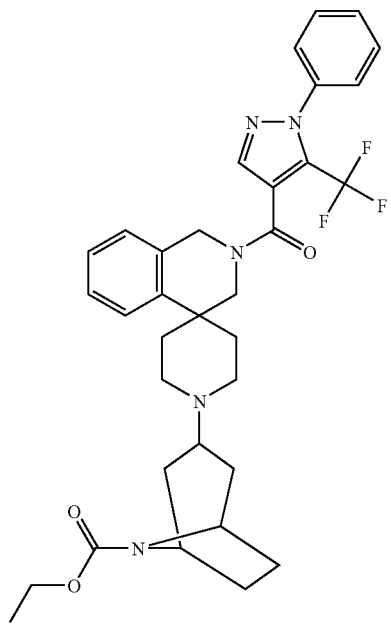
93
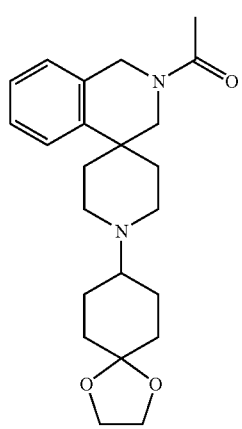
94
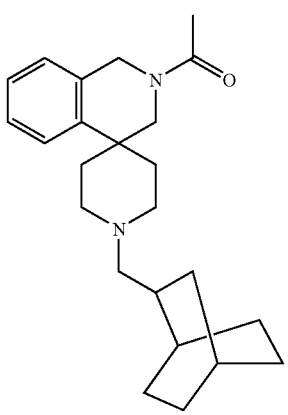

TABLE 1-continued
Exemplary compounds of formulae (I, Ia, Ib, Ic, and Id)
95
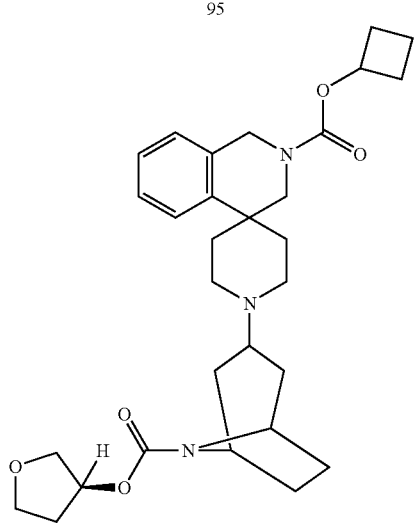
96
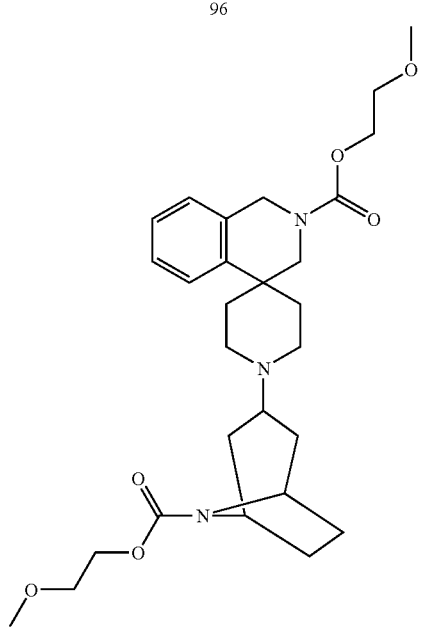
97
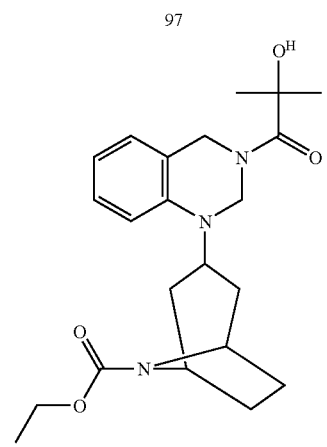
98
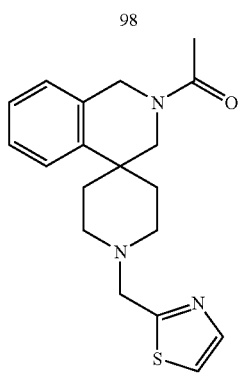
99
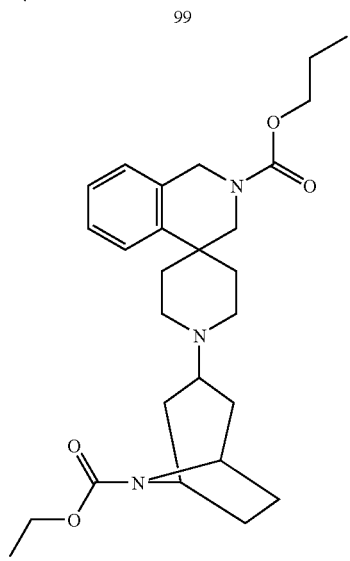
100
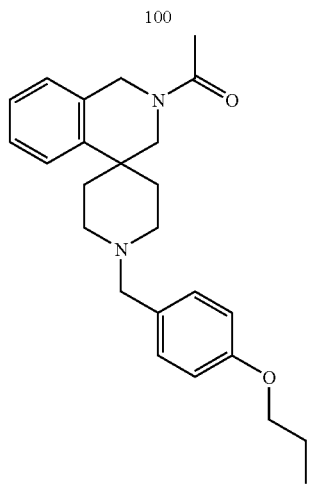

TABLE 1-continued
Exemplary compounds of formulae (I, Ia, Ib, Ic, and Id)
101
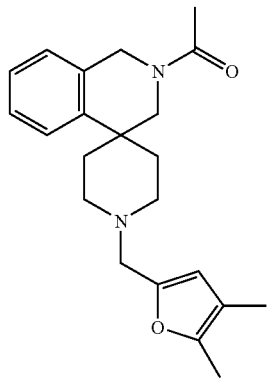
102
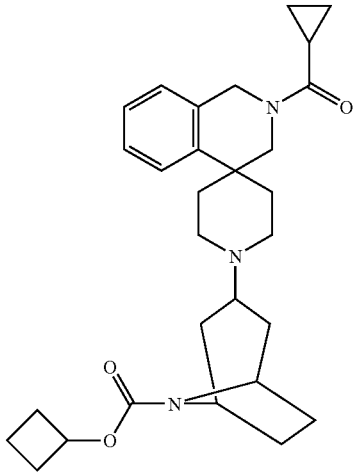
103
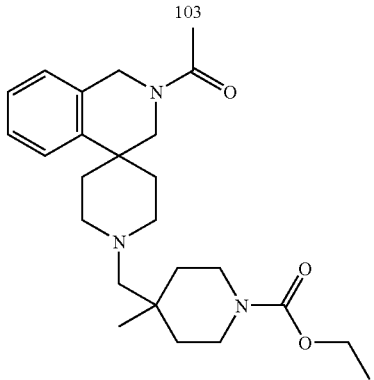
104
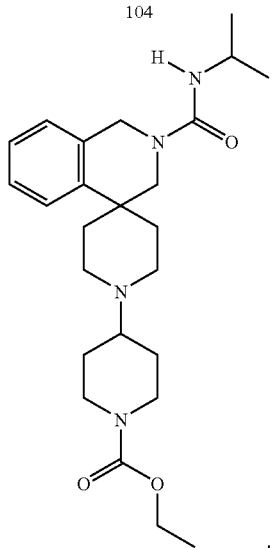
105
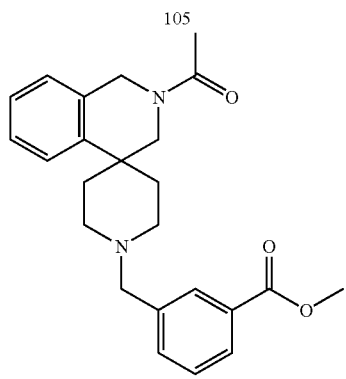
106
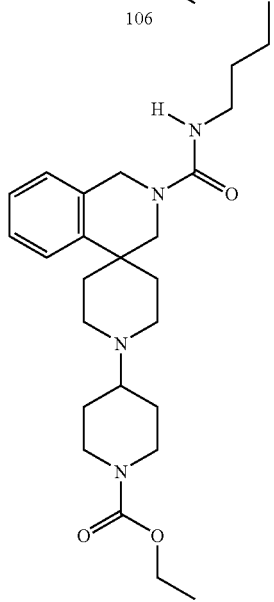

TABLE 1-continued
Exemplary compounds of formulae (I, Ia, Ib, Ic, and Id)
107
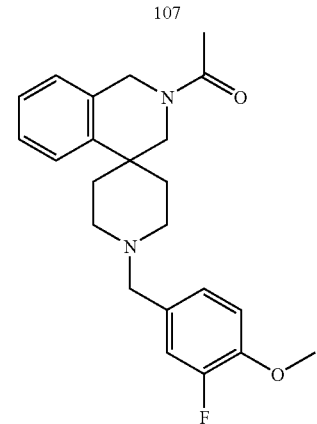
108
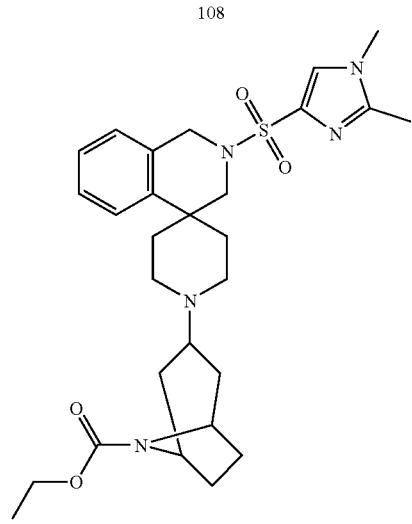
109
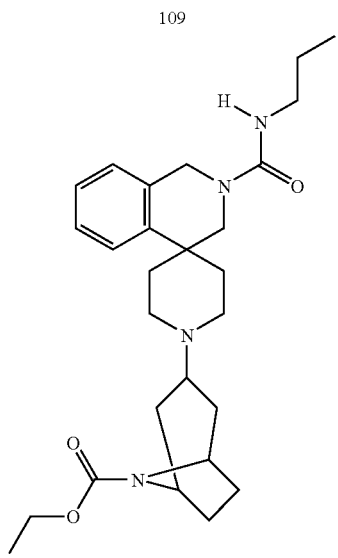
110
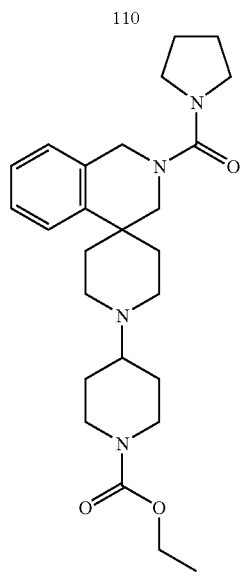
111
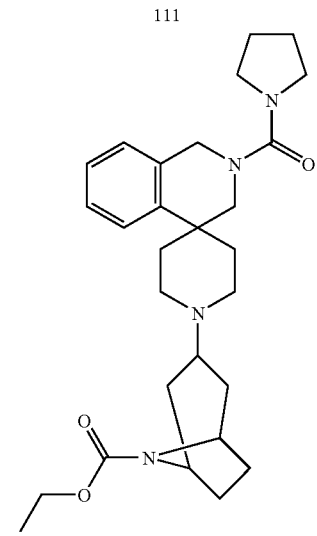
112
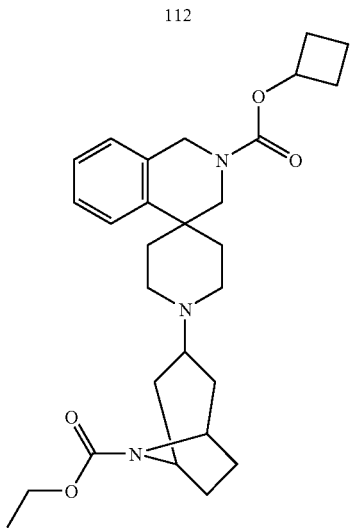

TABLE 1-continued
Exemplary compounds of formulae (I, Ia, Ib, Ic, and Id)
113
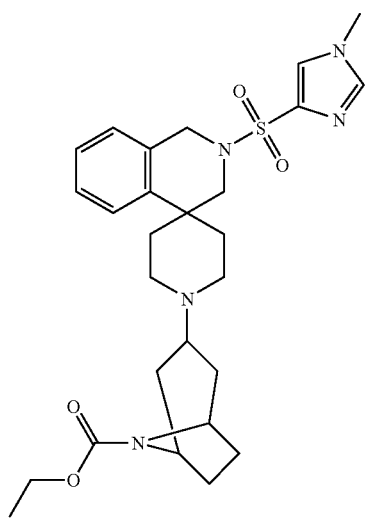
114
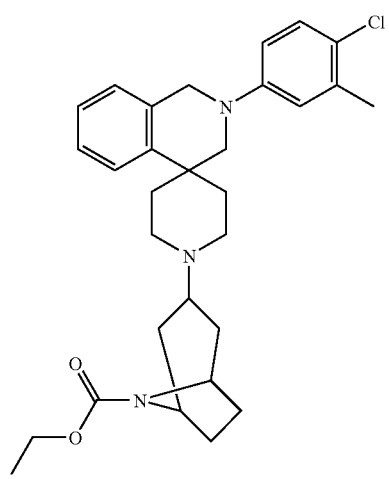
115
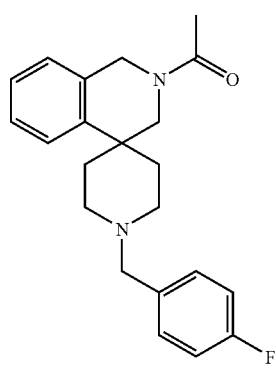
116
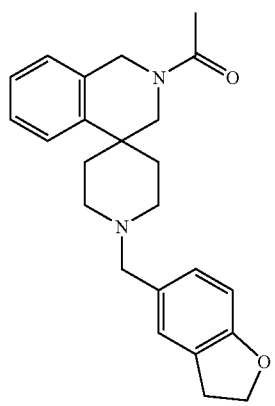
117
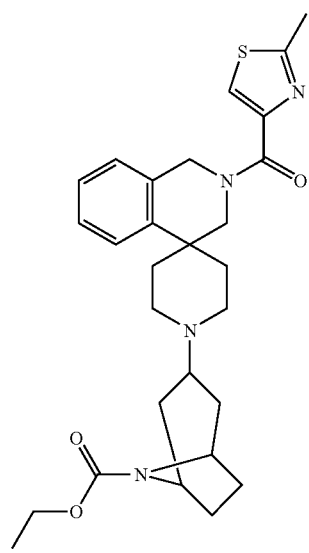
118
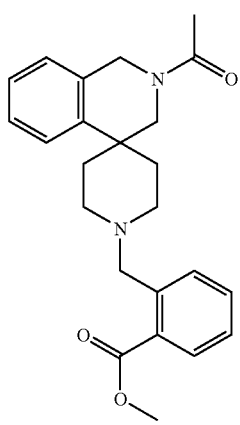

TABLE 1-continued
Exemplary compounds of formulae (I, Ia, Ib, Ic, and Id)
119
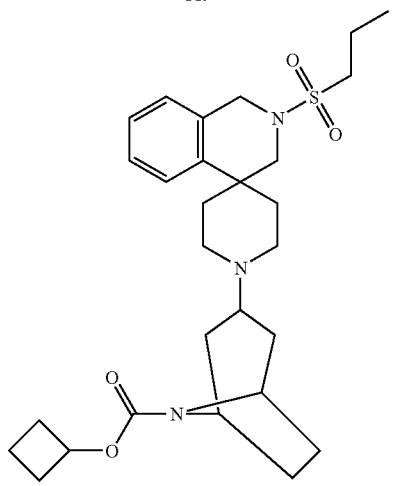
120
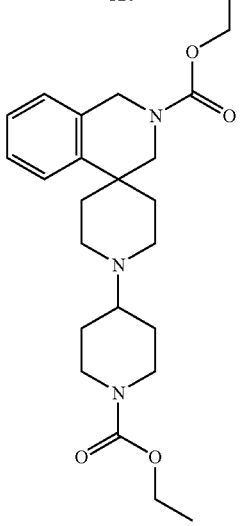
121
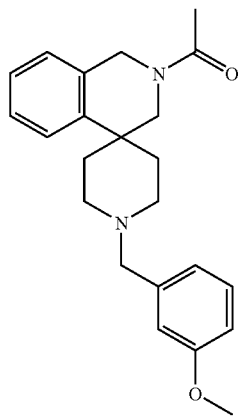
122
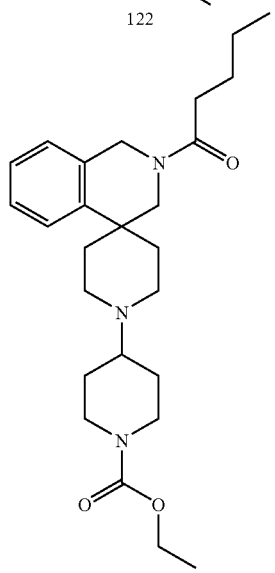
123
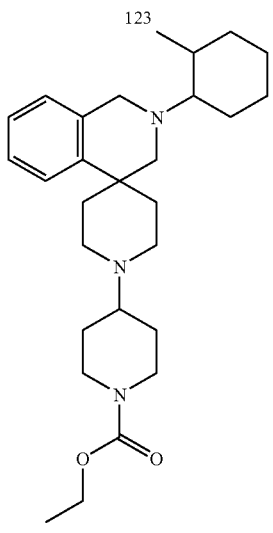
124
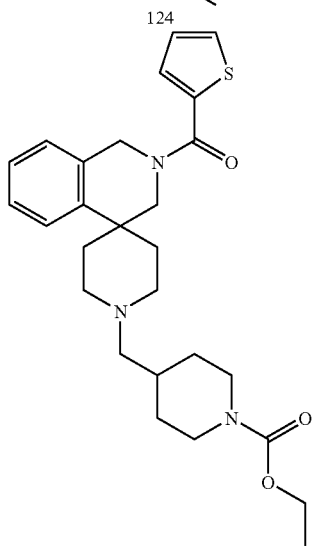

TABLE 1-continued
Exemplary compounds of formulae (I, Ia, Ib, Ic, and Id)
125
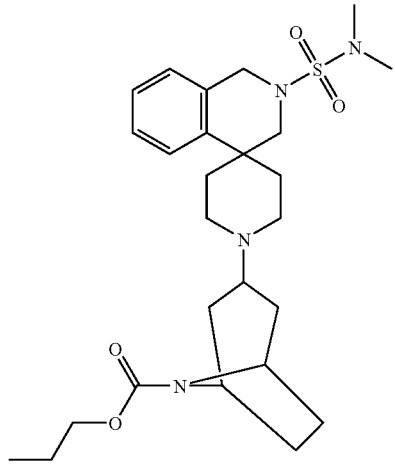
126
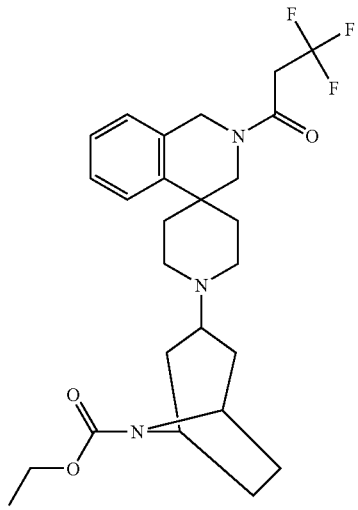
127
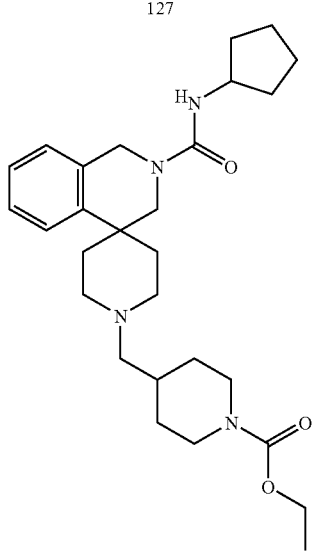
128
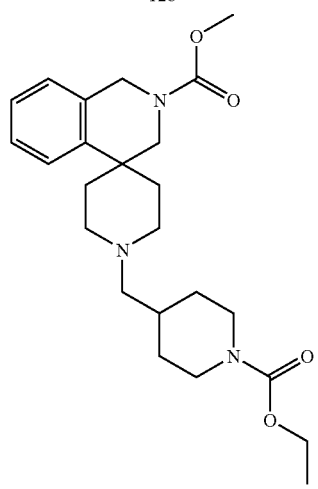
129
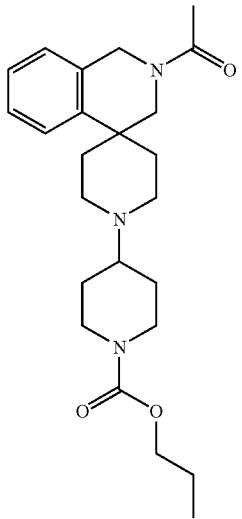
130
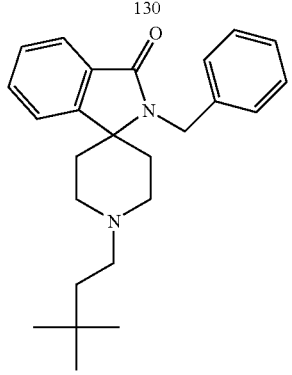

TABLE 1-continued
Exemplary compounds of formulae (I, Ia, Ib, Ic, and Id)
131
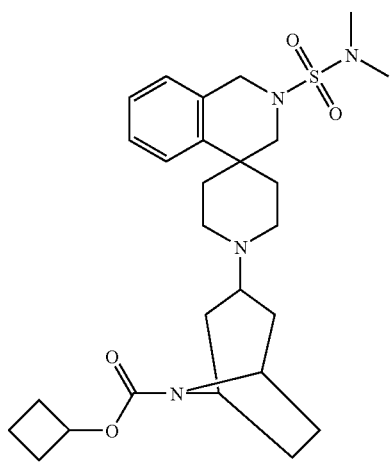
132
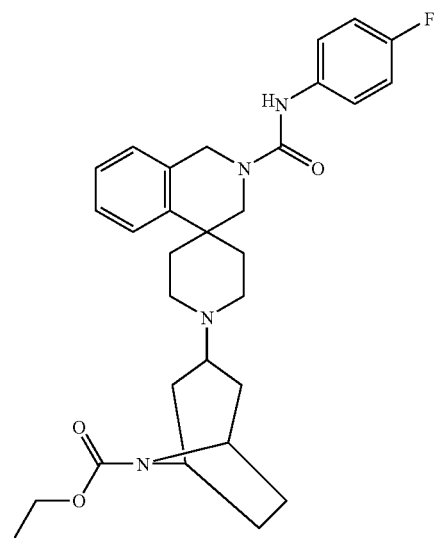
133
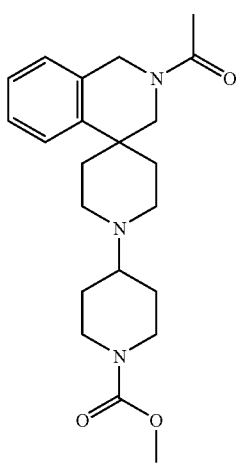
134
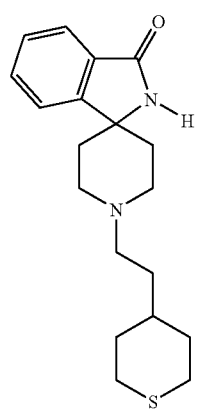
135
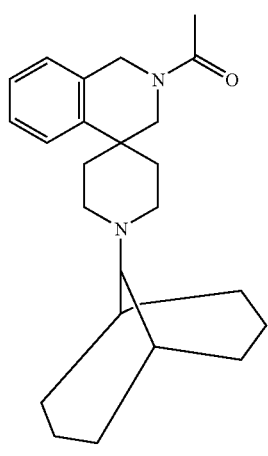
136
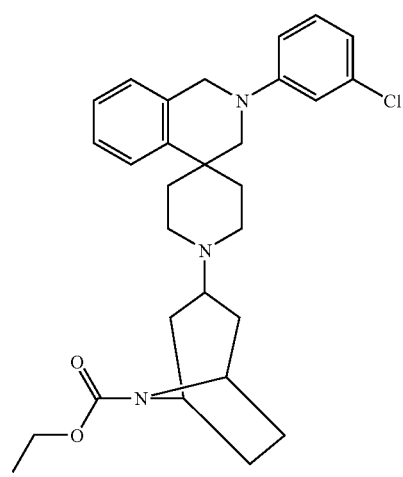

TABLE 1-continued
Exemplary compounds of formulae (I, Ia, Ib, Ic, and Id)
137
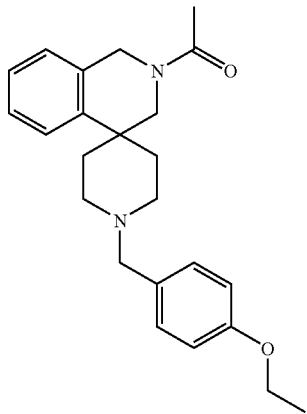
138
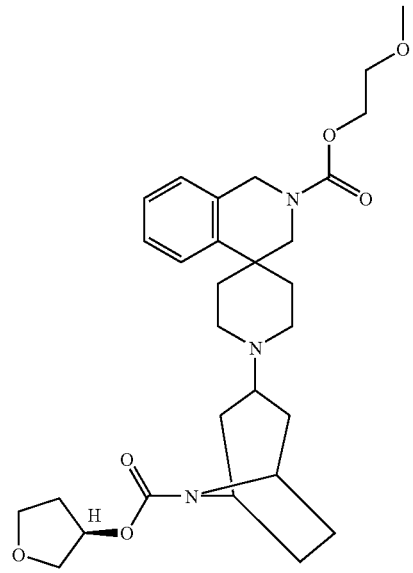
139
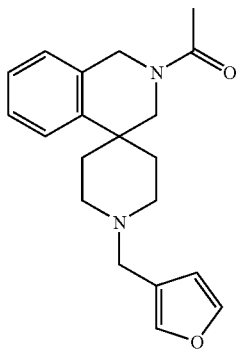
140
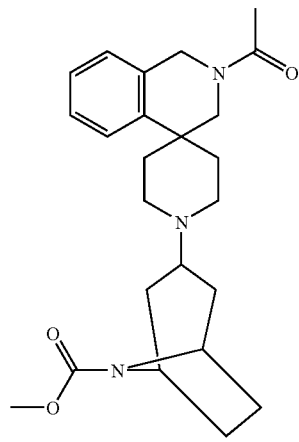
141
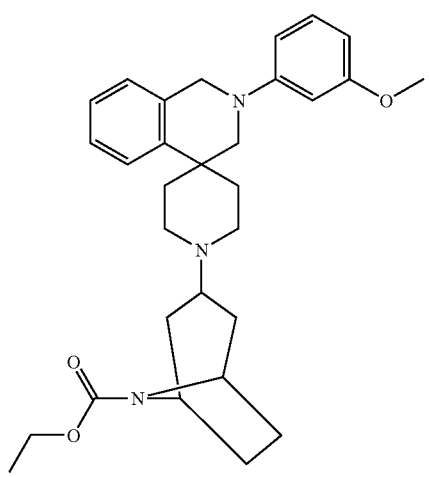
142
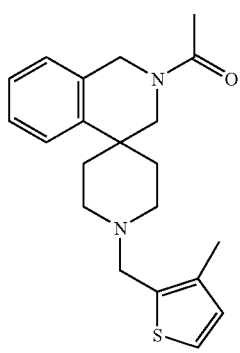

TABLE 1-continued
Exemplary compounds of formulae (I, Ia, Ib, Ic, and Id)
143
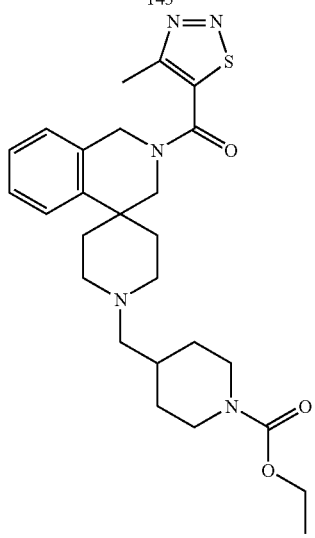
144
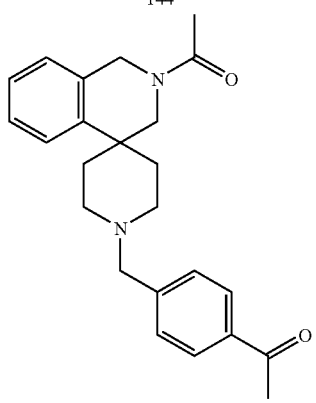
145
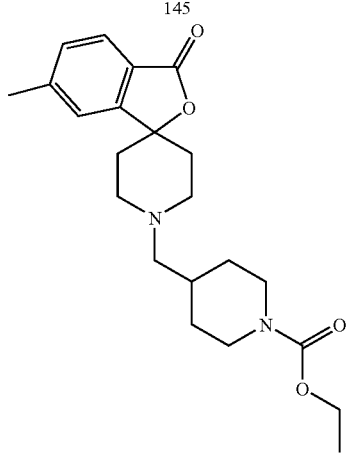
146
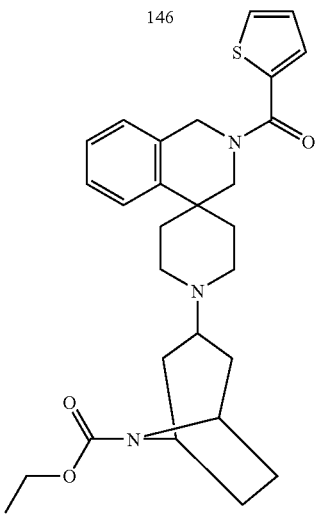
147
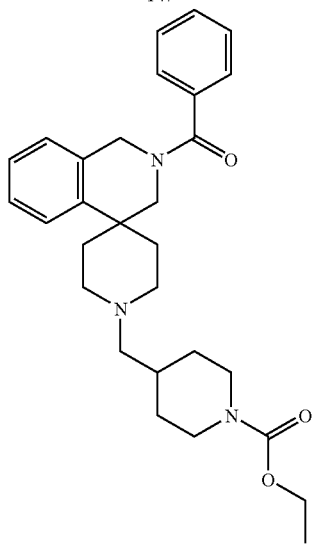
148
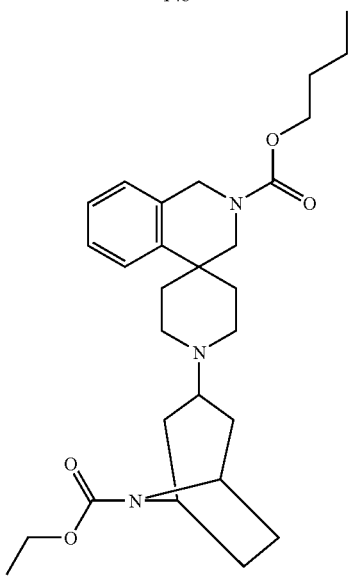

US 7,863,449 B2
TABLE 1-continued
Exemplary compounds of formulae (I, Ia, Ib, Ic, and Id)
149
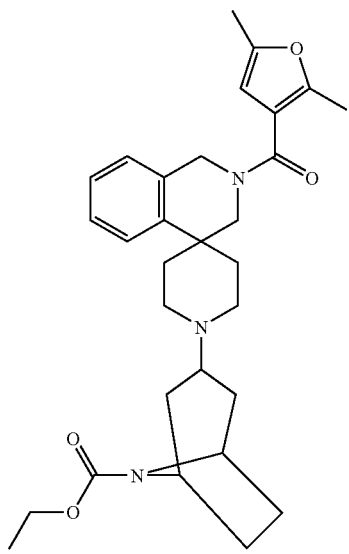
150
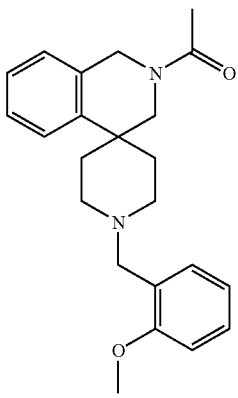
151
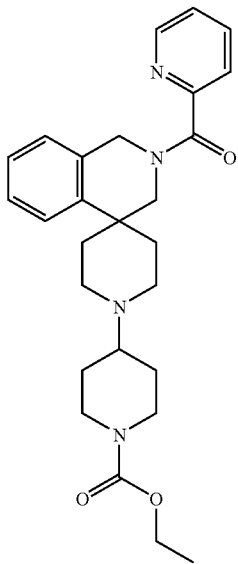
152
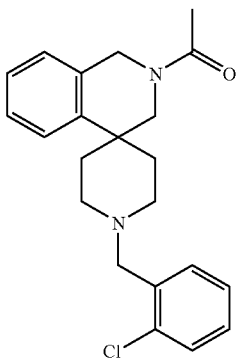
153
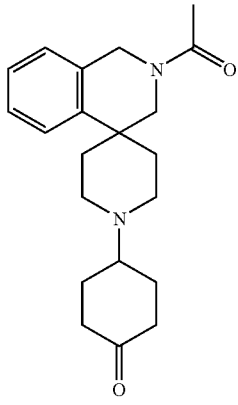
154
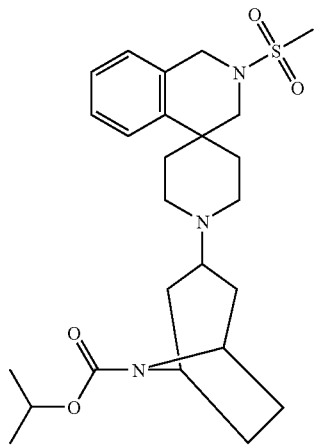

TABLE 1-continued
Exemplary compounds of formulae (I, Ia, Ib, Ic, and Id)
155
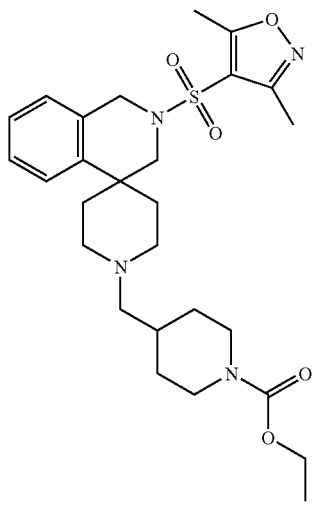
156
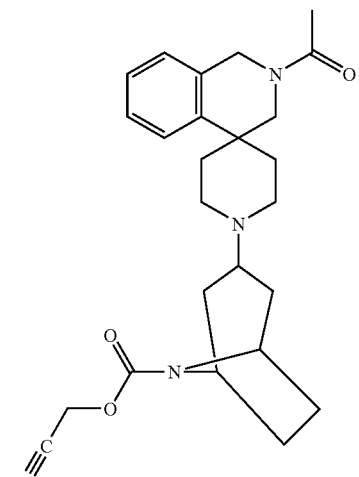
157
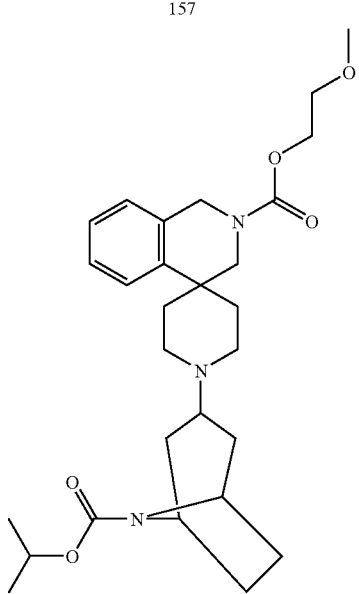
158
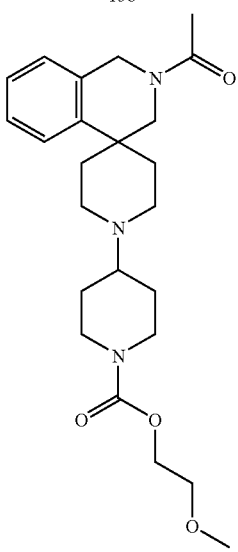
159
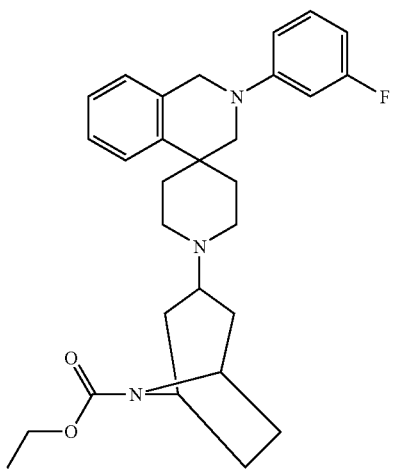
160
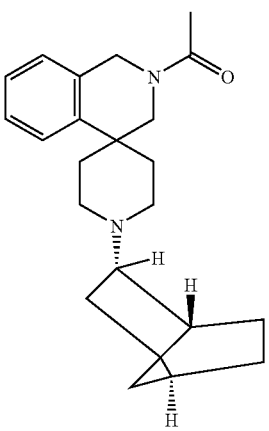

TABLE 1-continued
Exemplary compounds of formulae (I, Ia, Ib, Ic, and Id)
161
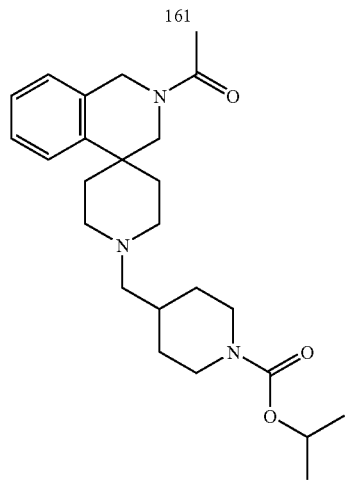
162
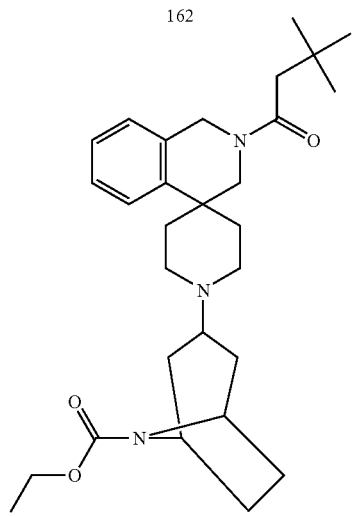
163
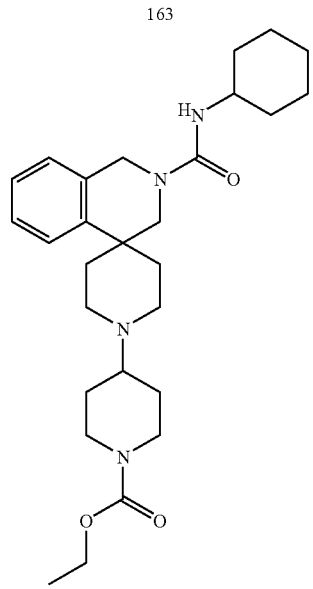
164
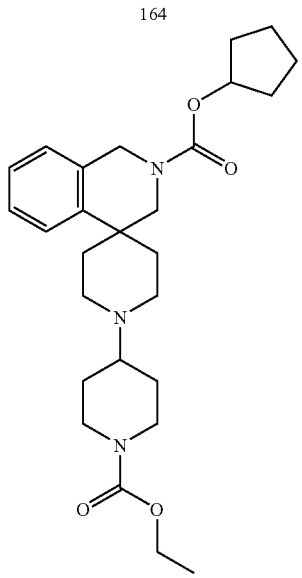
165
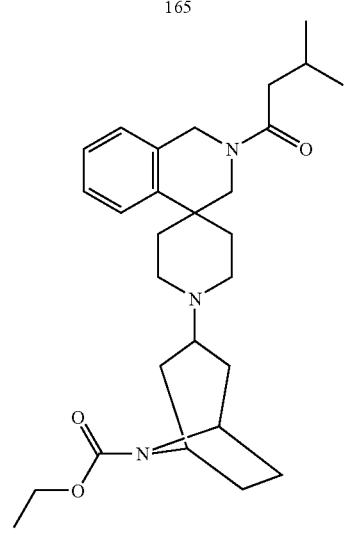
166
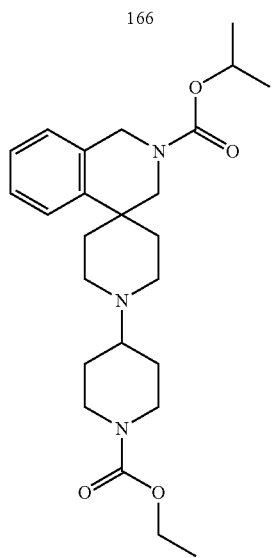

TABLE 1-continued
Exemplary compounds of formulae (I, Ia, Ib, Ic, and Id)
167
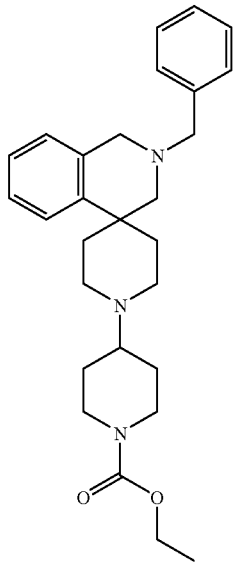
168
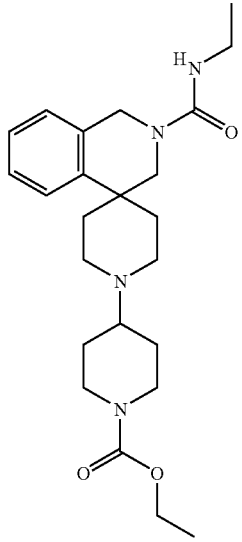
169
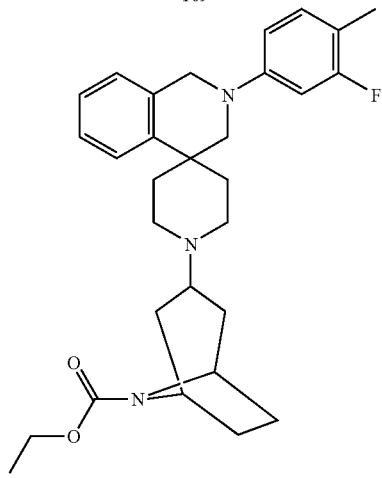
170
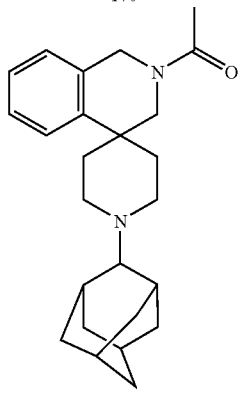
171
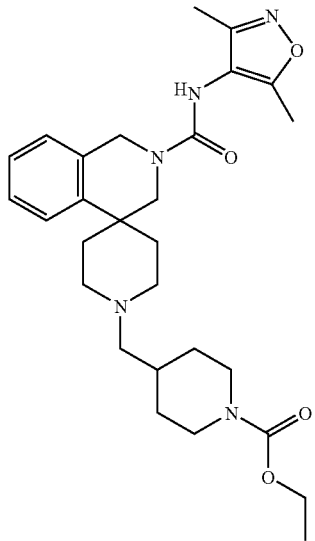
172
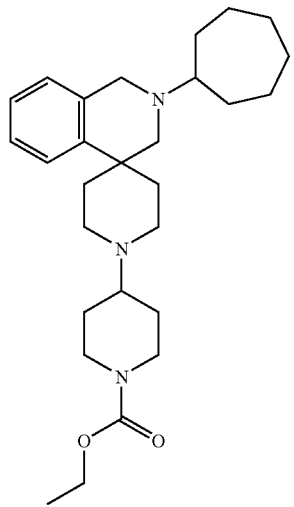

TABLE 1-continued
Exemplary compounds of formulae (I, Ia, Ib, Ic, and Id)
173
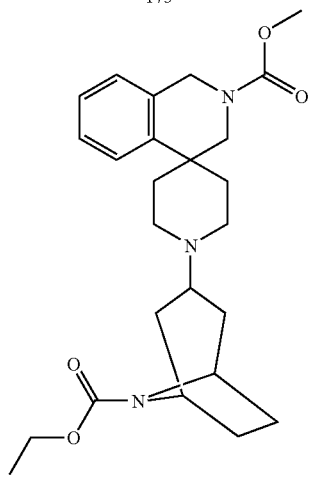
174
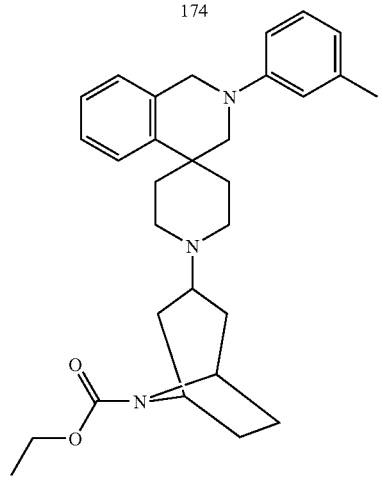
175
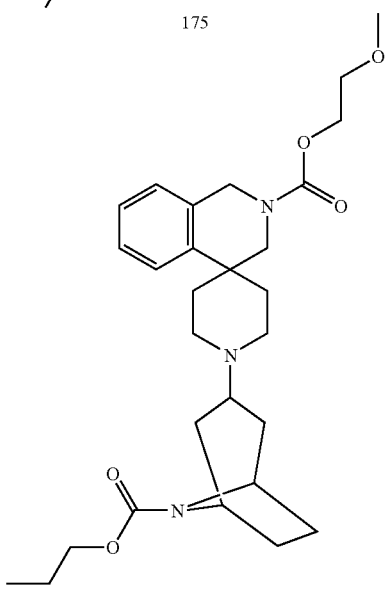
176
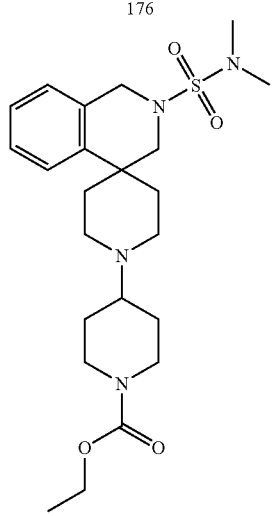
177
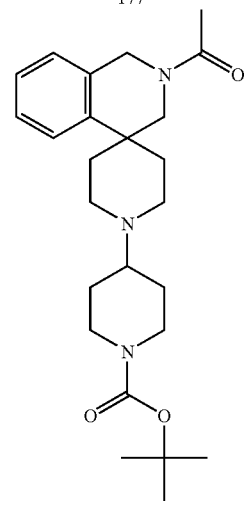
178
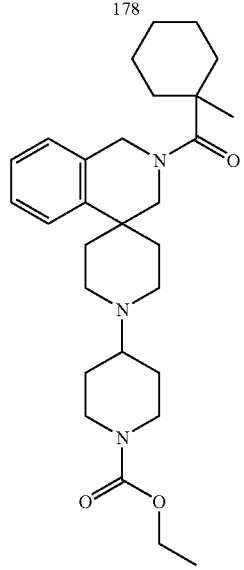

TABLE 1-continued
Exemplary compounds of formulae (I, Ia, Ib, Ic, and Id)
179
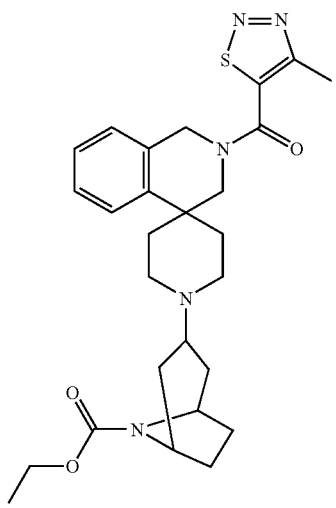
180
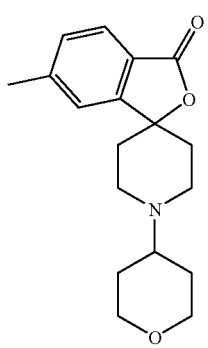
181
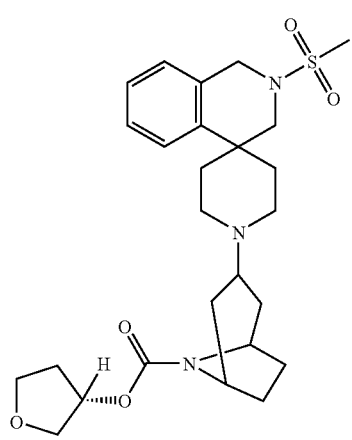
182
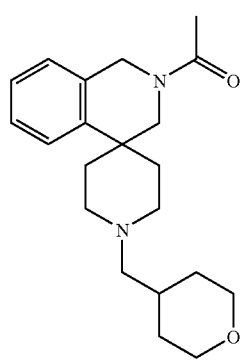
183
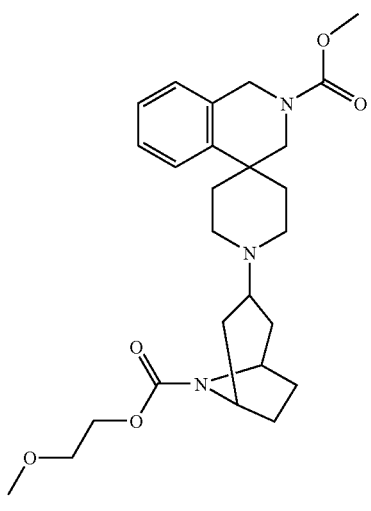
184
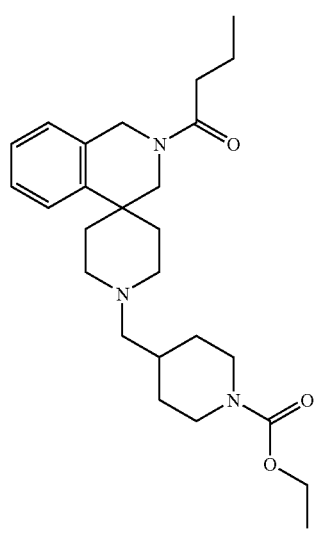

TABLE 1-continued
Exemplary compounds of formulae (I, Ia, Ib, Ic, and Id)
185
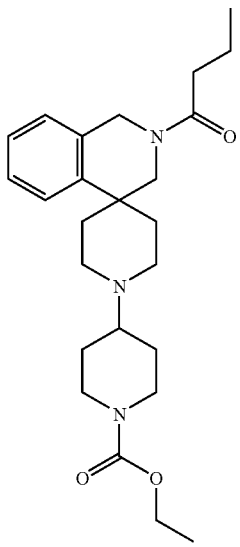
186
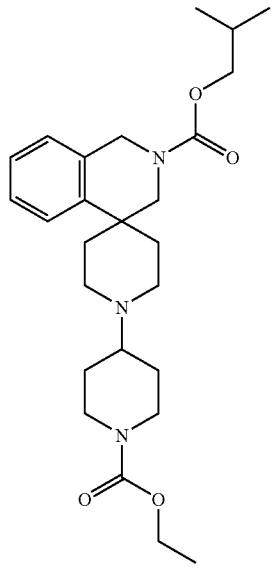
187
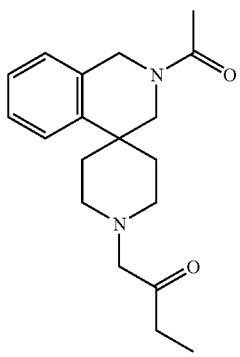
188
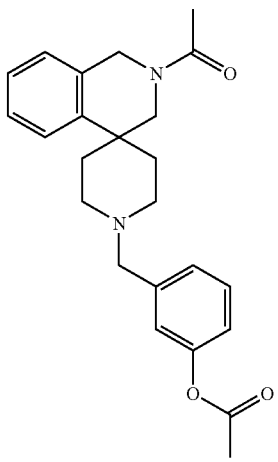
189
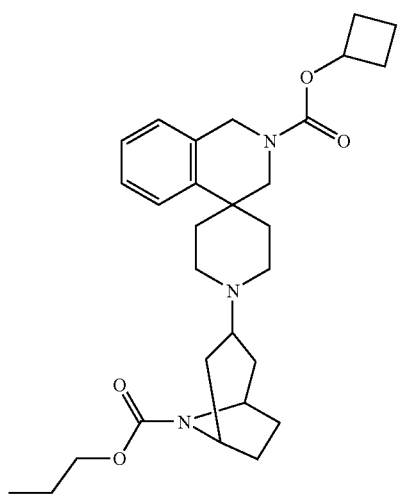
190
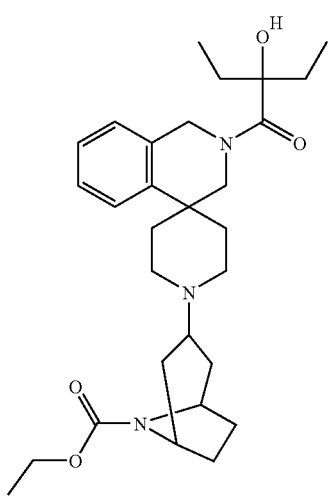

TABLE 1-continued
Exemplary compounds of formulae (I, Ia, Ib, Ic, and Id)
191
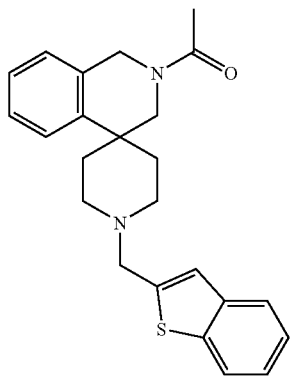
192
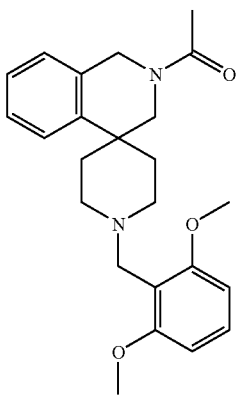
193
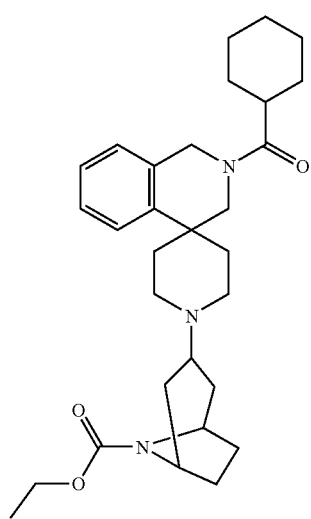
194
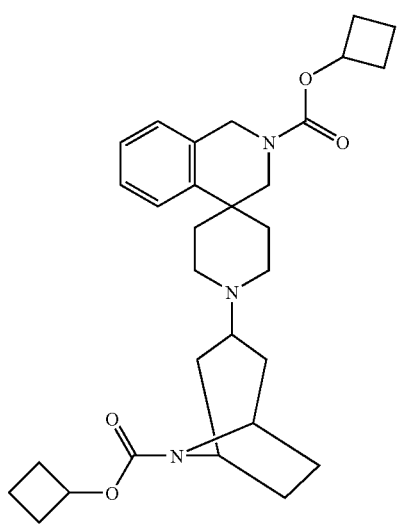
195
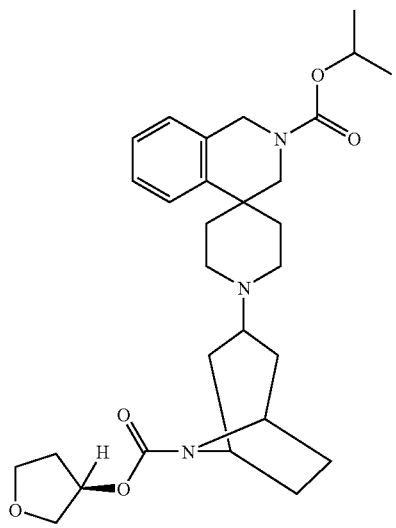
196
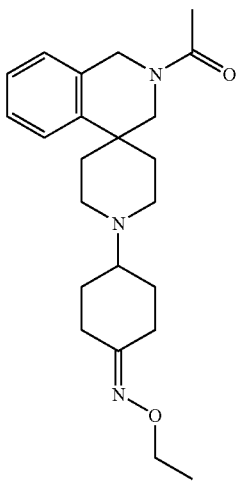

TABLE 1-continued
Exemplary compounds of formulae (I, Ia, Ib, Ic, and Id)
197
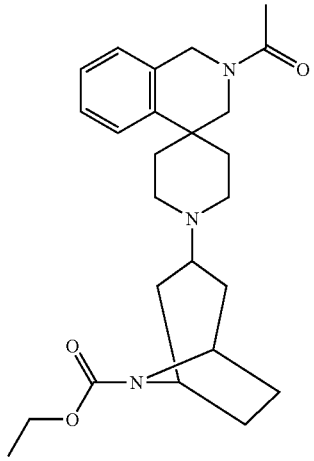
198
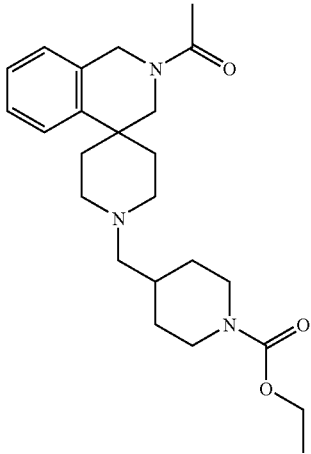
199
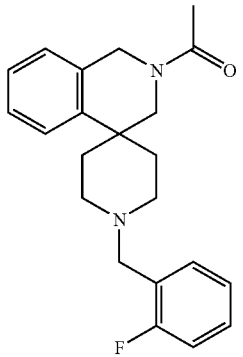
200
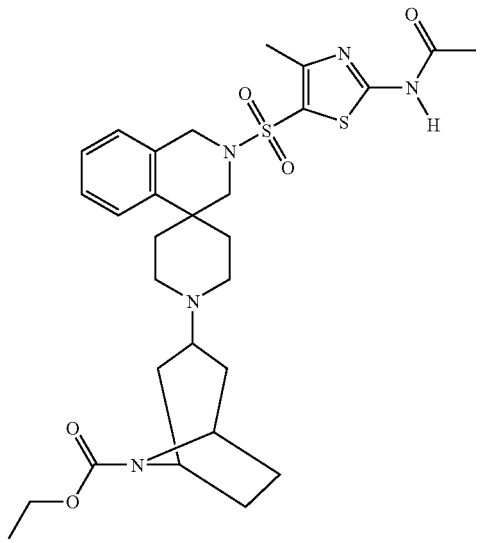
201
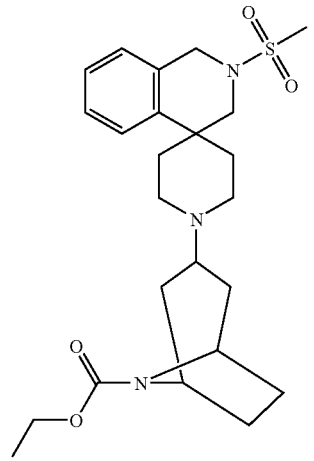
202
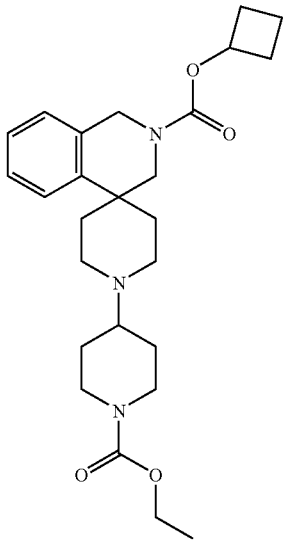

TABLE 1-continued
Exemplary compounds of formulae (I, Ia, Ib, Ic, and Id)
203
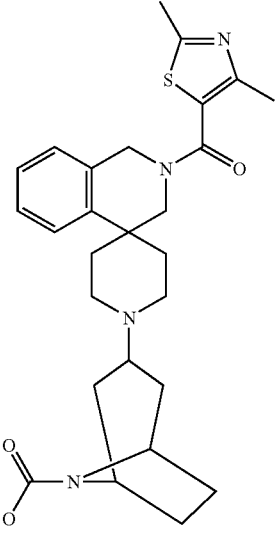
204
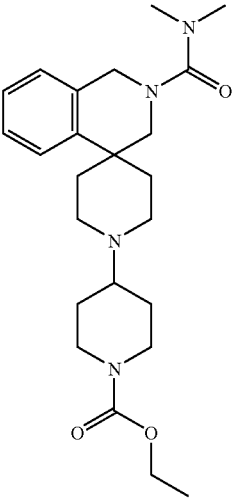
205
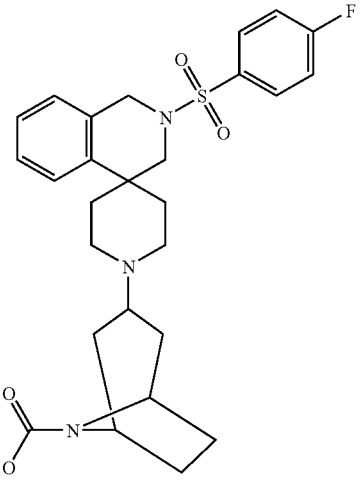
206
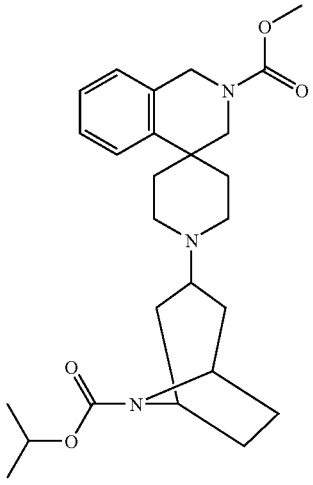
207
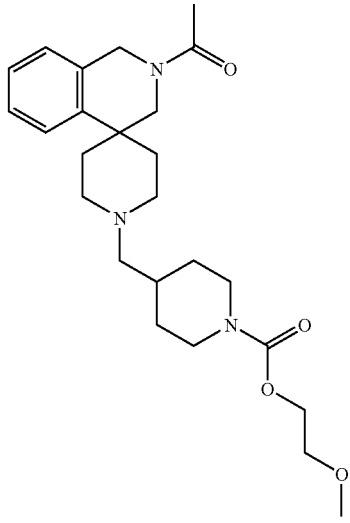
208
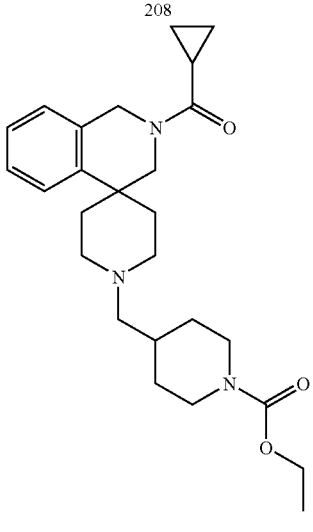

TABLE 1-continued

Exemplary compounds of formulae (I, Ia, Ib, Ic, and Id)

TABLE 1-continued
Exemplary compounds of formulae (I, Ia, Ib, Ic, and Id)
215
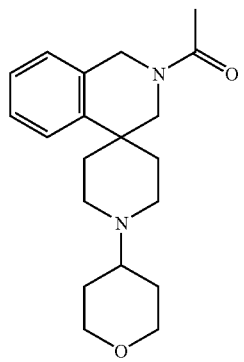
216
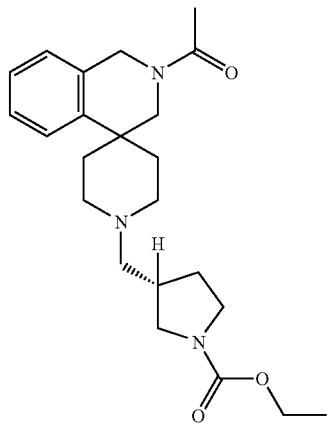
217
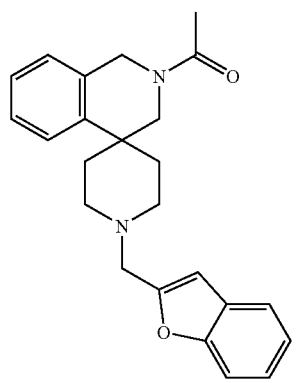
218
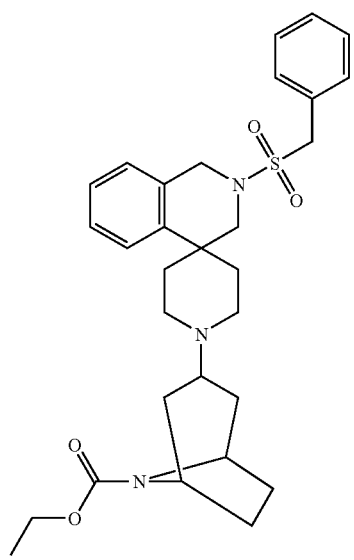
219
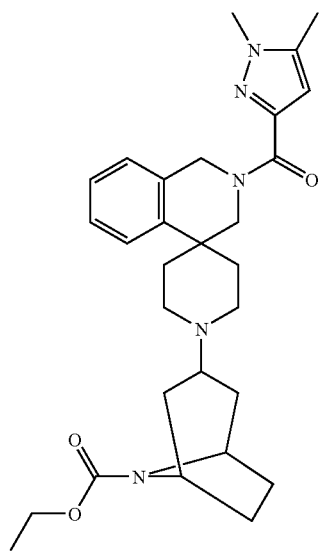
220
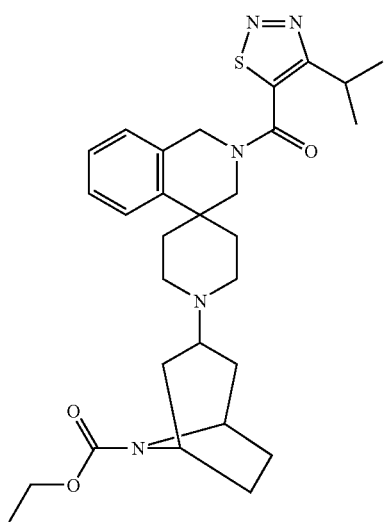

TABLE 1-continued
Exemplary compounds of formulae (I, Ia, Ib, Ic, and Id)
221
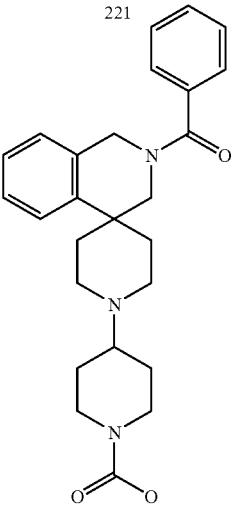
222
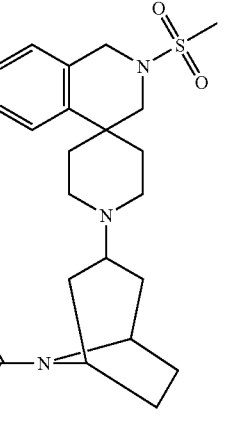
223
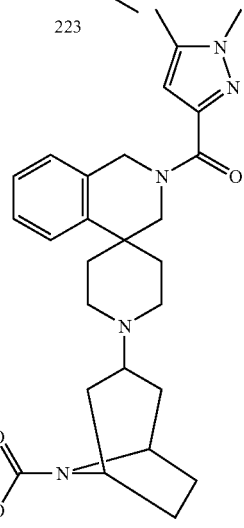
224
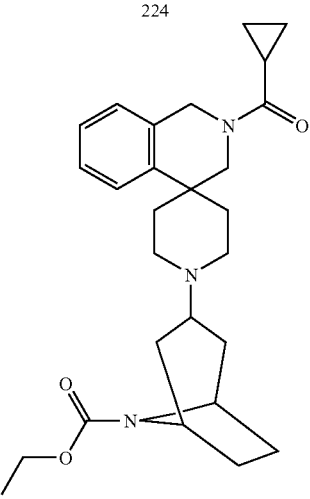
225
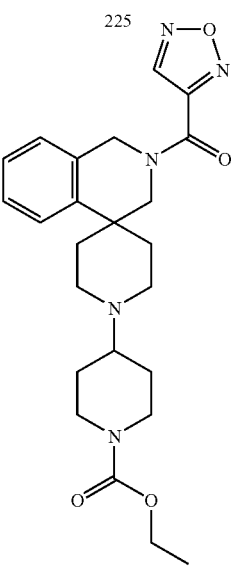
226
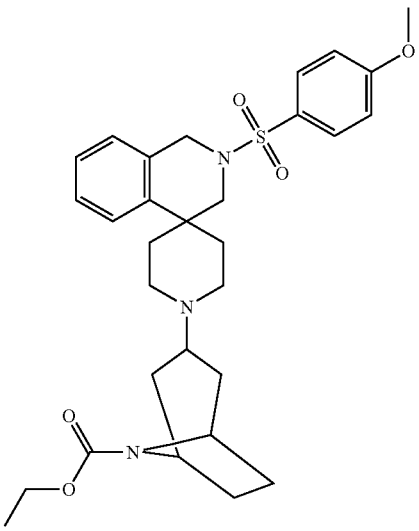

TABLE 1-continued
Exemplary compounds of formulae (I, Ia, Ib, Ic, and Id)
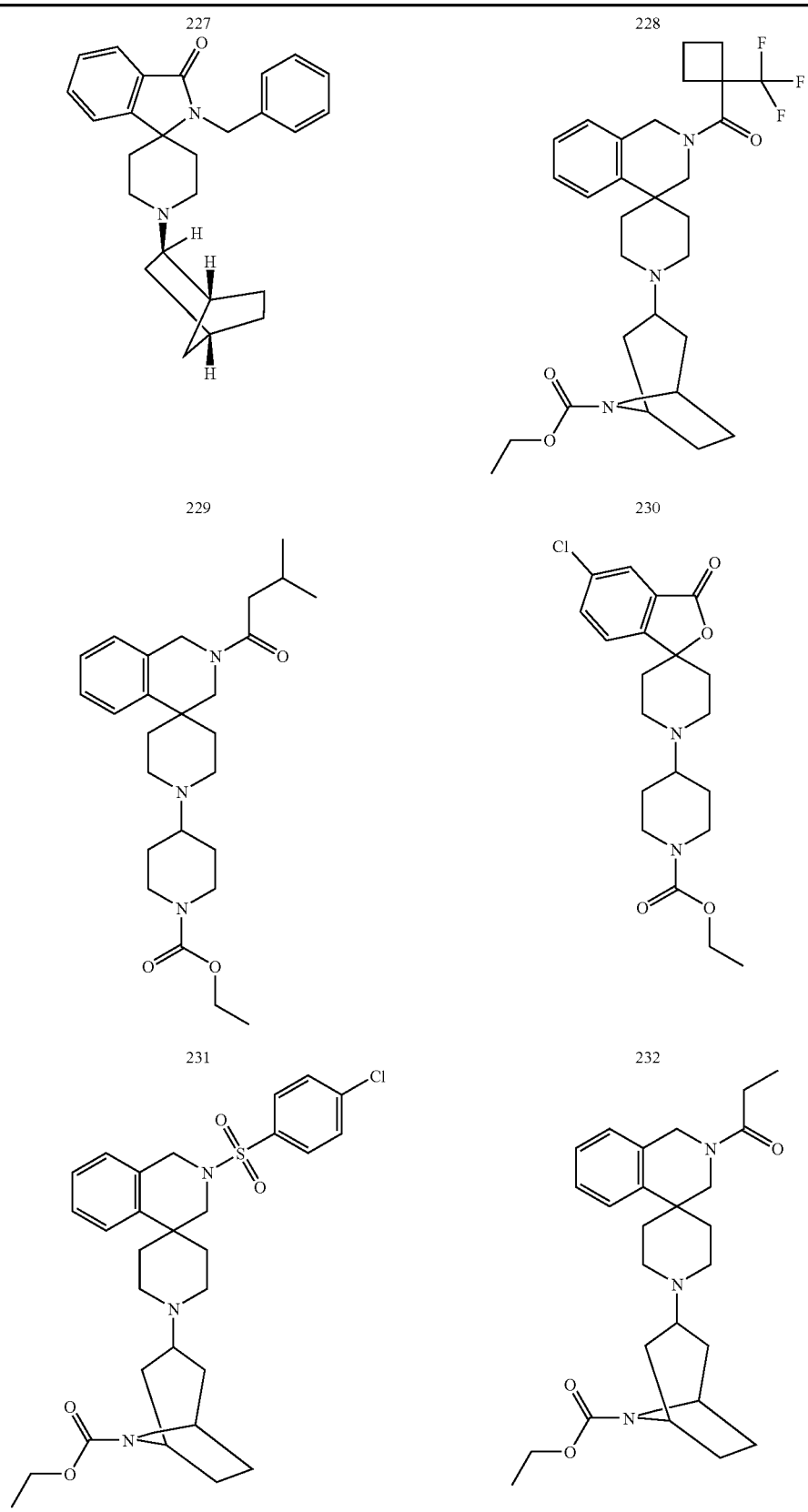

TABLE 1-continued
Exemplary compounds of formulae (I, Ia, Ib, Ic, and Id)
233
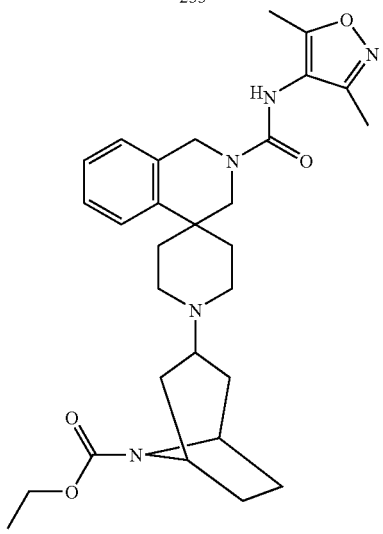
234
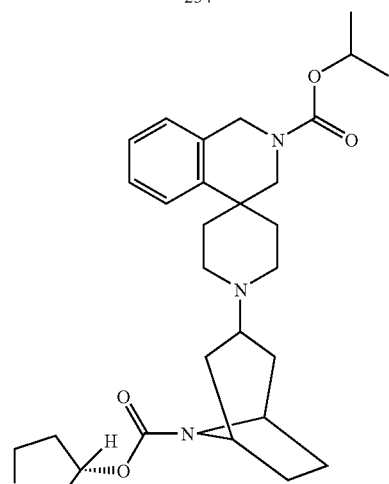
235
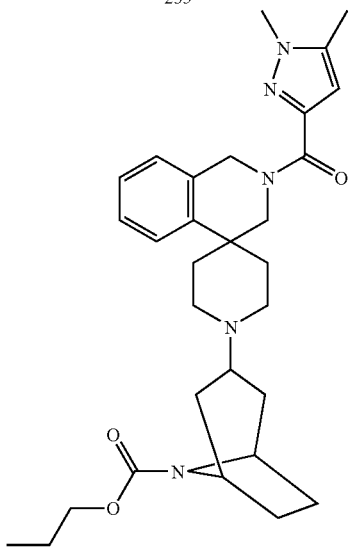
236
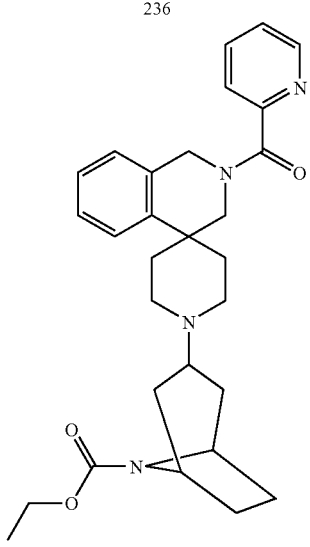
237
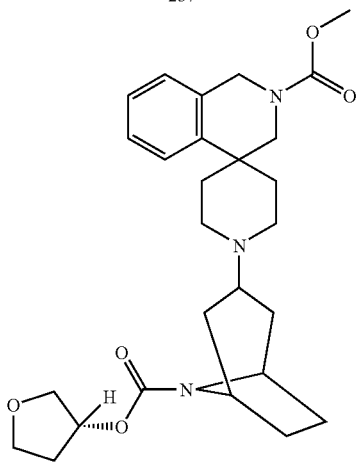
238
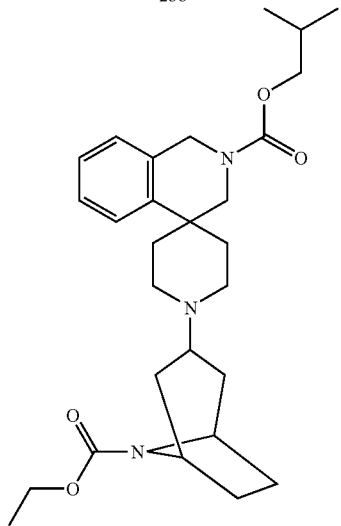

TABLE 1-continued
Exemplary compounds of formulae (I, Ia, Ib, Ic, and Id)
239
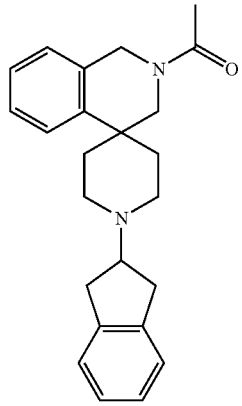
240
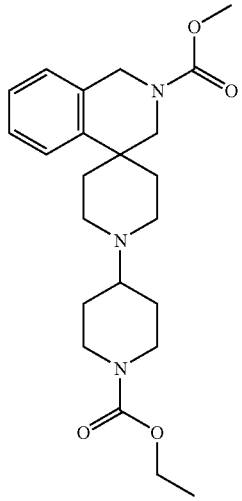
241
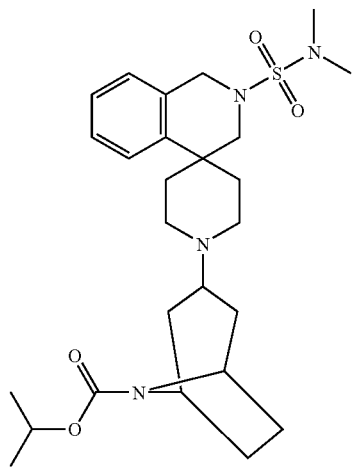
242
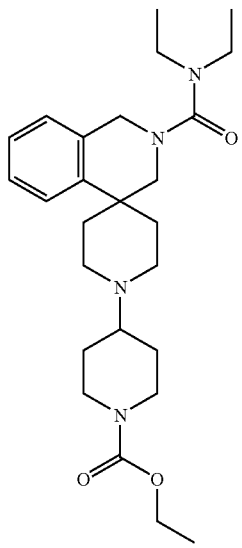
243
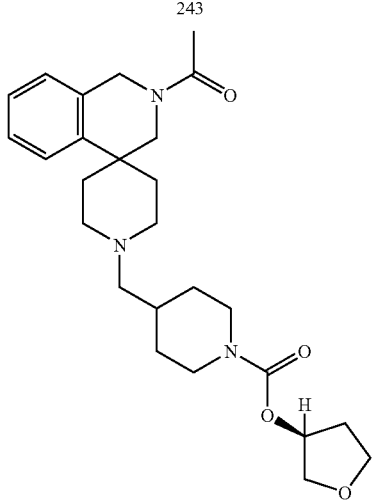
244
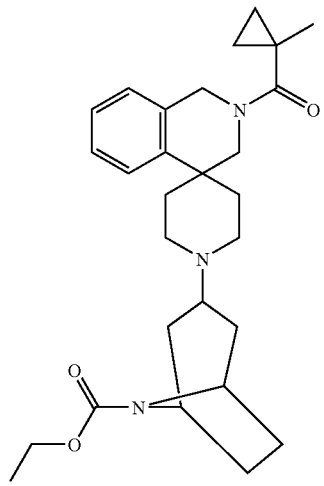

TABLE 1-continued
Exemplary compounds of formulae (I, Ia, Ib, Ic, and Id)
245
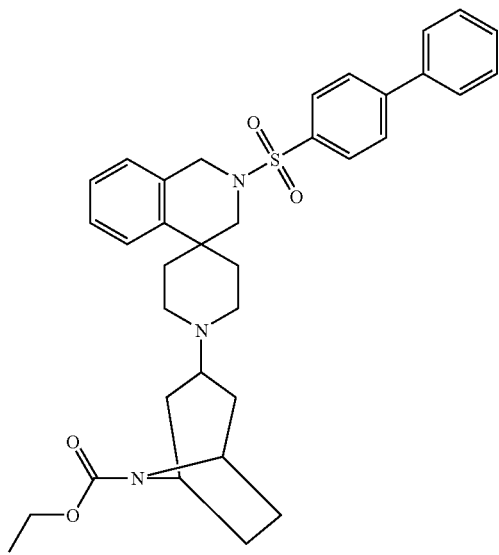
246
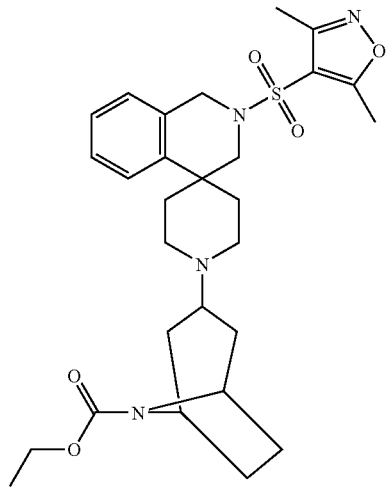
247
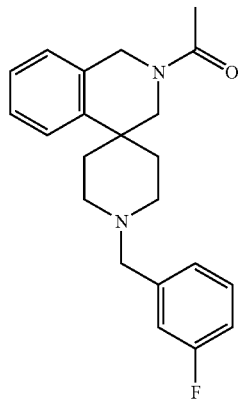
248
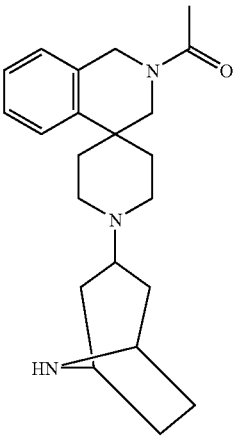
249
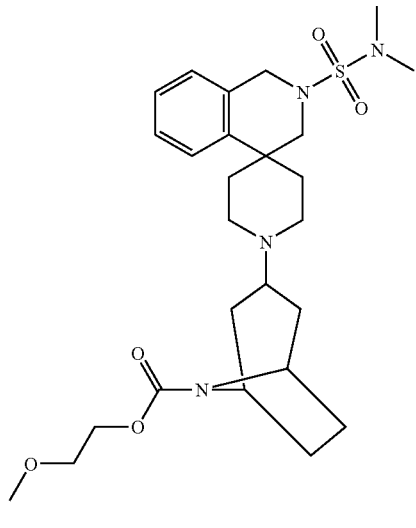
250
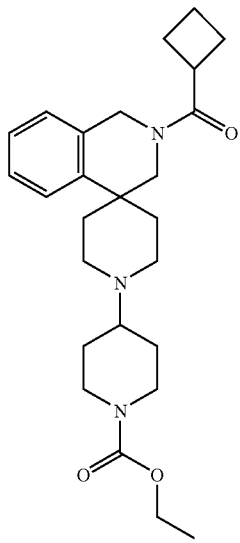

TABLE 1-continued
Exemplary compounds of formulae (I, Ia, Ib, Ic, and Id)
251
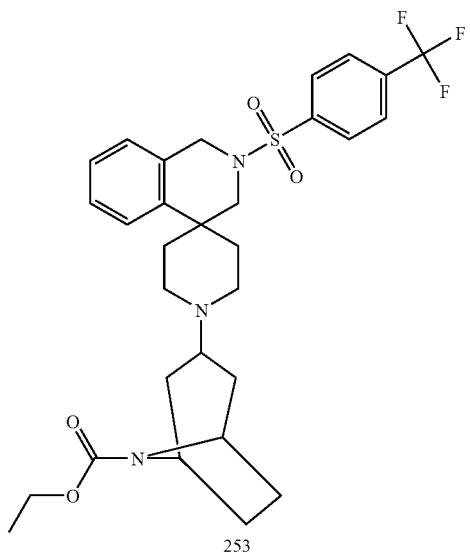
252
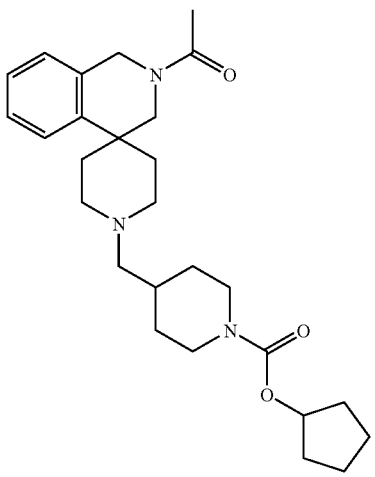
253
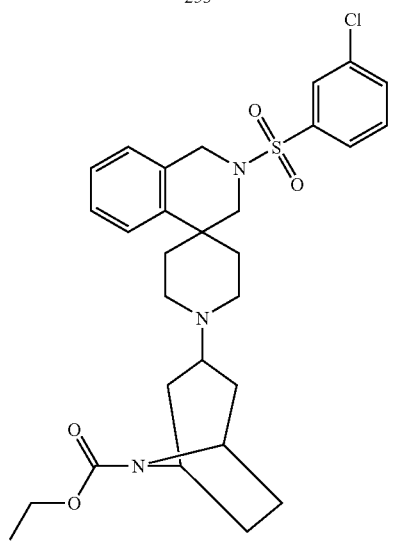
254
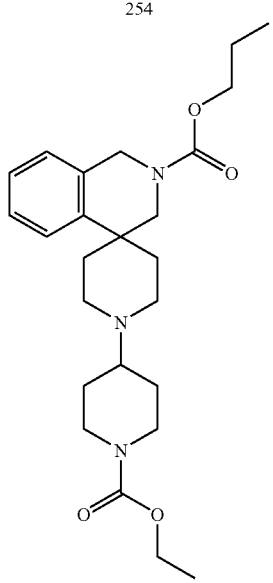
255
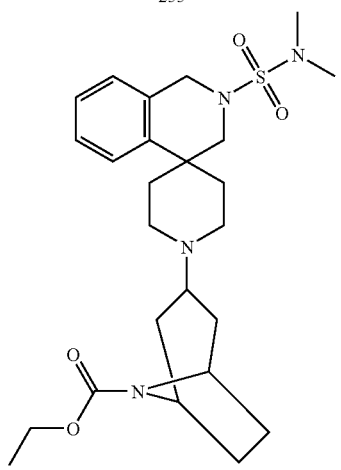
256
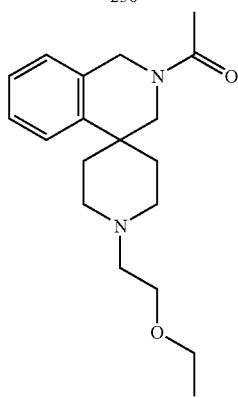

TABLE 1-continued
Exemplary compounds of formulae (I, Ia, Ib, Ic, and Id)
257
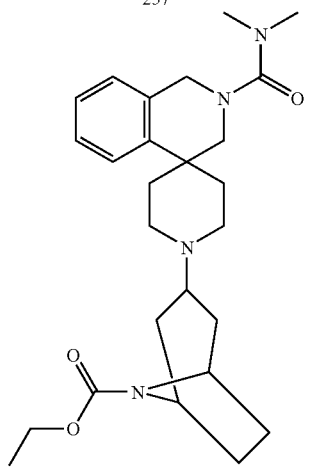
258
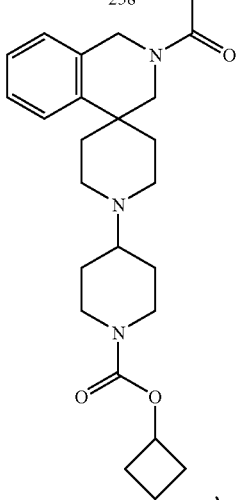
259
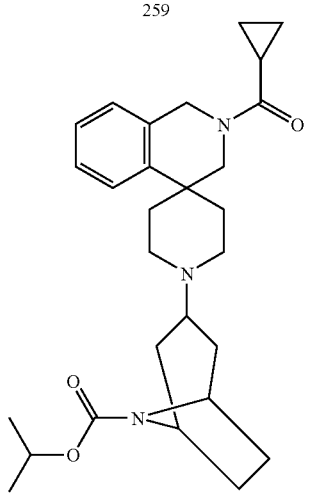
260
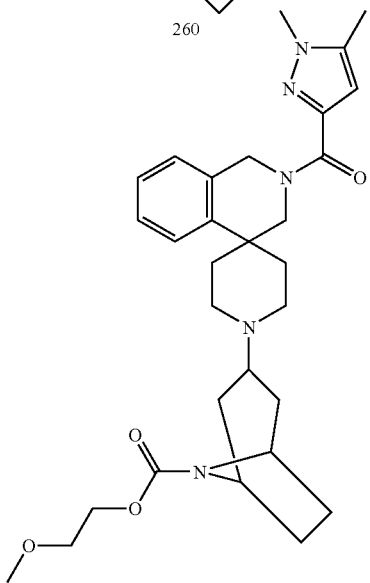
261
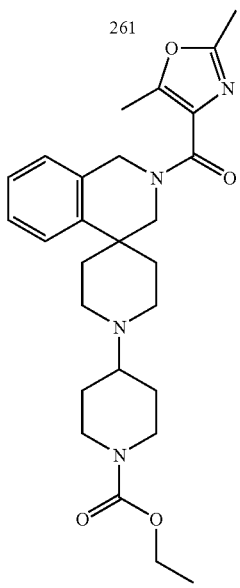
262
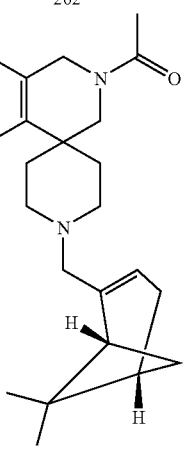

TABLE 1-continued
Exemplary compounds of formulae (I, Ia, Ib, Ic, and Id)
263
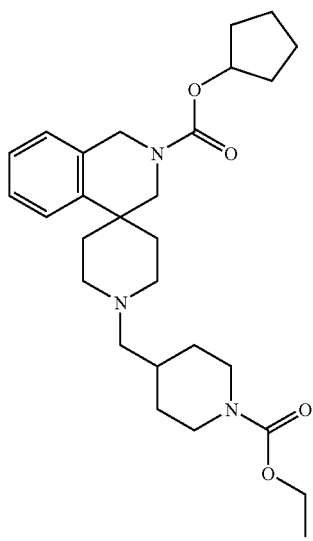
264
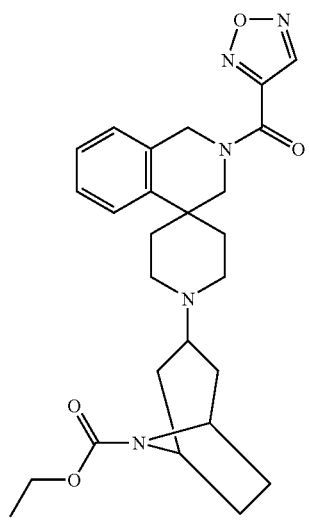
265
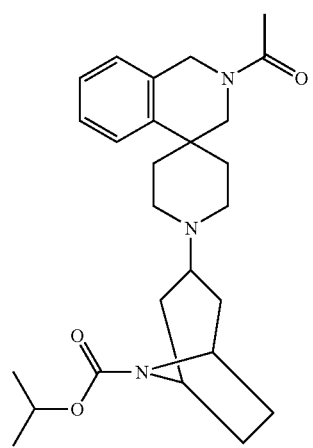
266
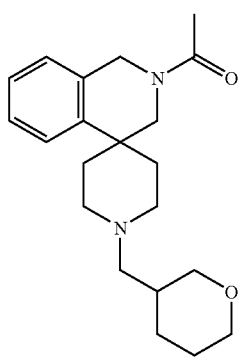
267
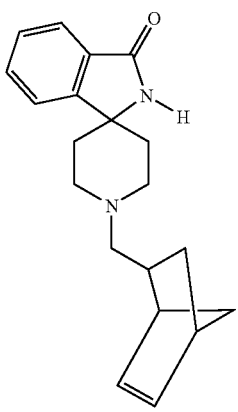
268
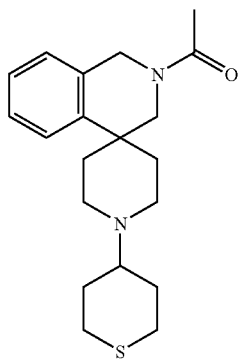

TABLE 1-continued
Exemplary compounds of formulae (I, Ia, Ib, Ic, and Id)
269
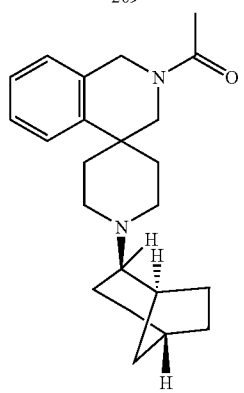
270
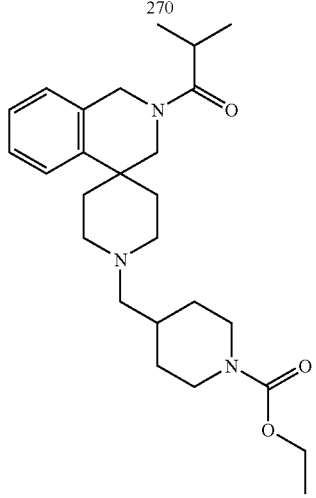
271
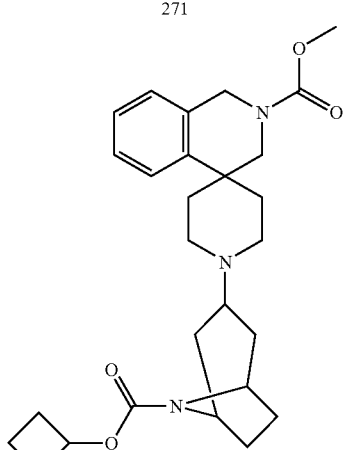
272
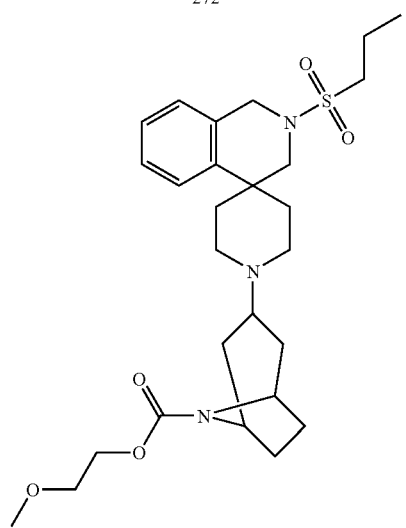
273
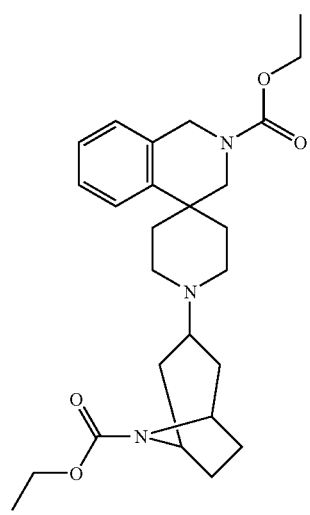
274
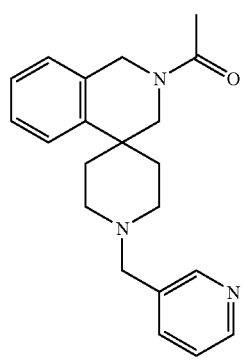

TABLE 1-continued
Exemplary compounds of formulae (I, Ia, Ib, Ic, and Id)
275
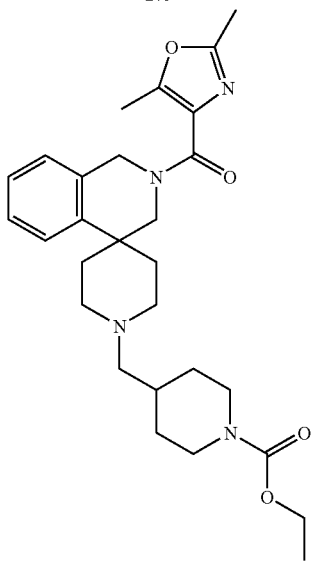
276
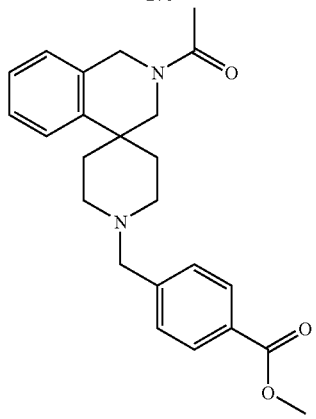
277
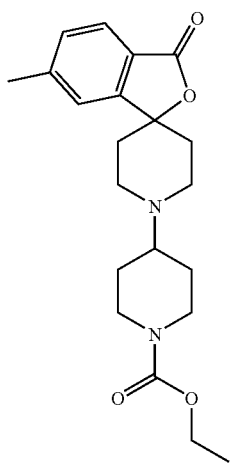
278
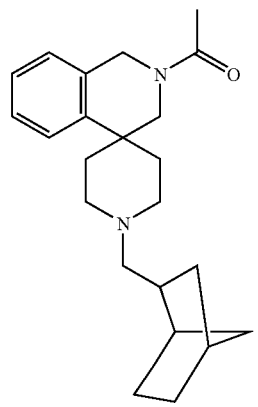
279
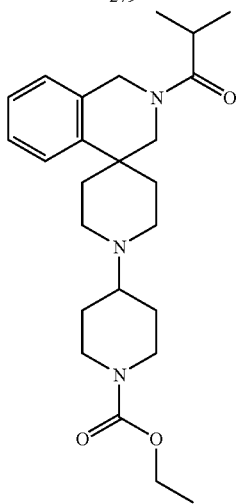
280
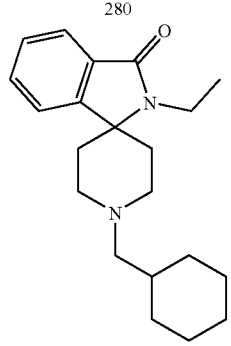

TABLE 1-continued
Exemplary compounds of formulae (I, Ia, Ib, Ic, and Id)
281
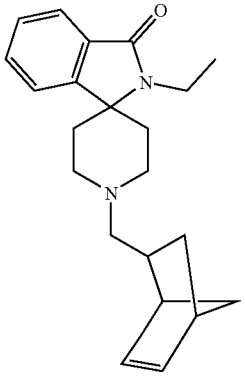
282
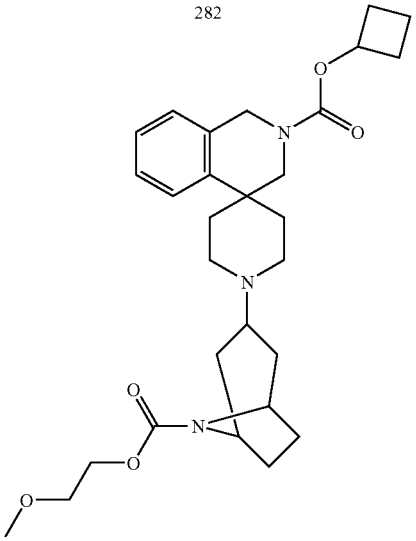
283
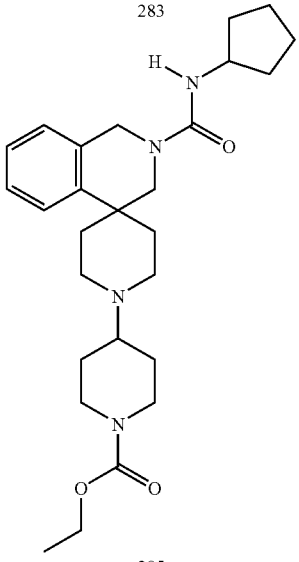
284
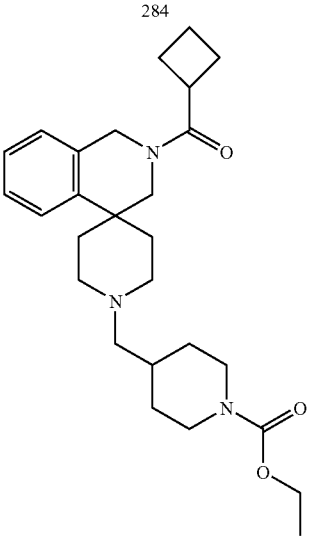
285
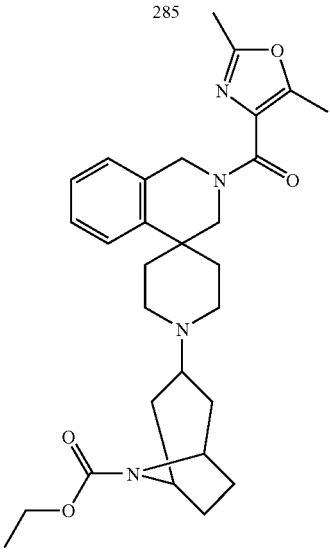
286
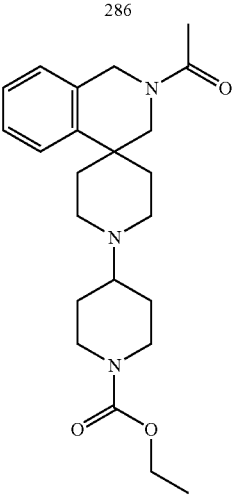

TABLE 1-continued
Exemplary compounds of formulae (I, Ia, Ib, Ic, and Id)
287
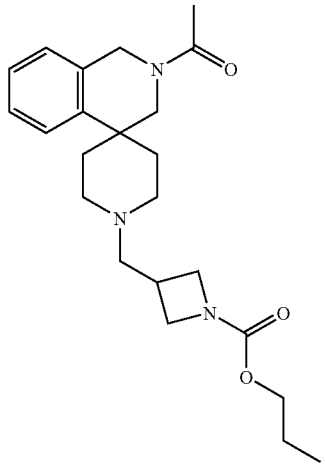
288
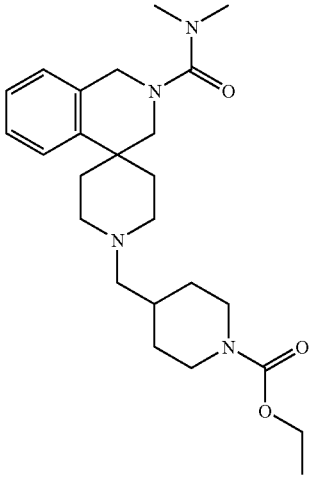
289
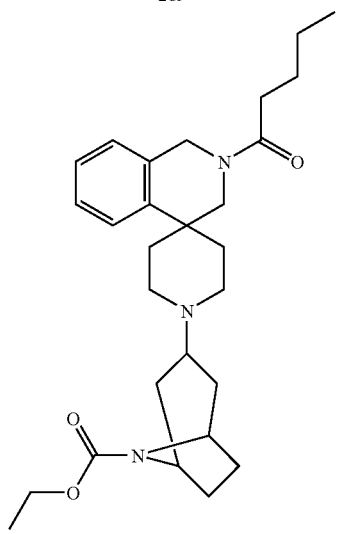
290
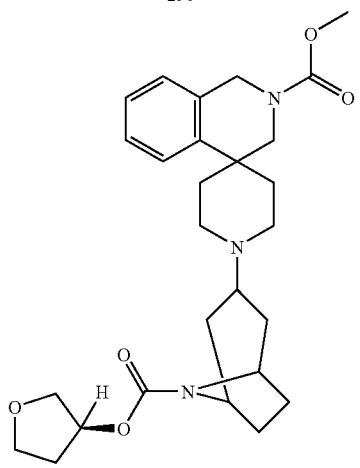
291
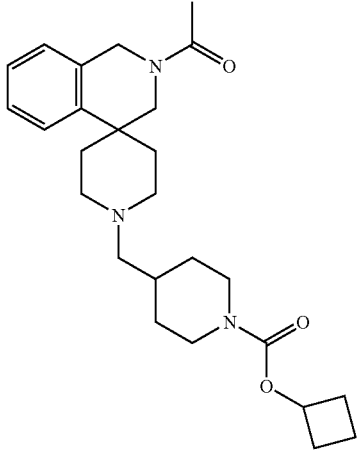
292
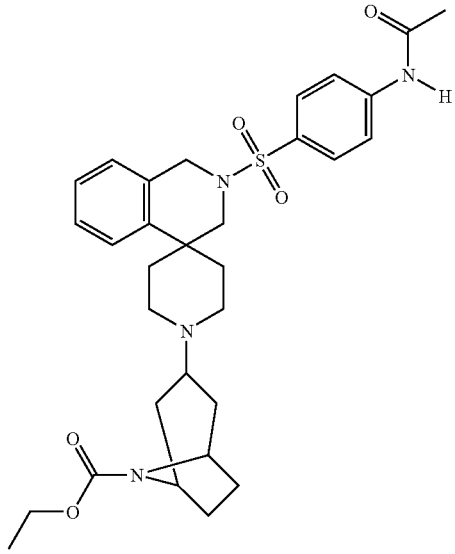

TABLE 1-continued
Exemplary compounds of formulae (I, Ia, Ib, Ic, and Id)
293
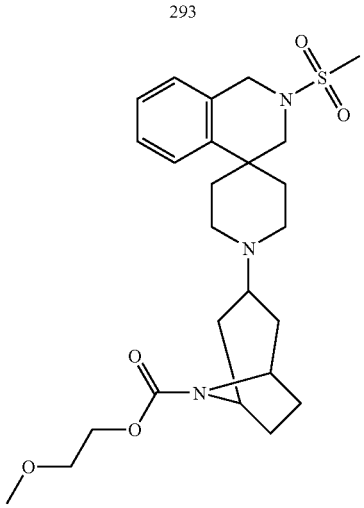
294
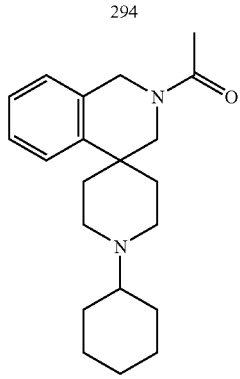
295
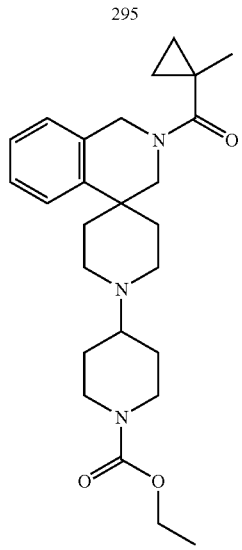
296
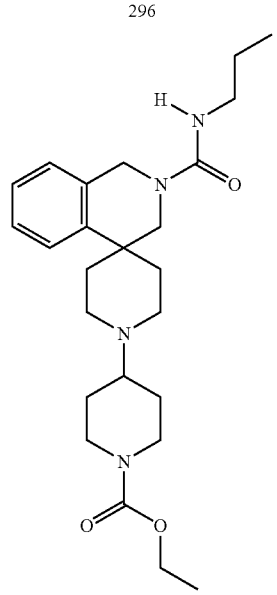
297
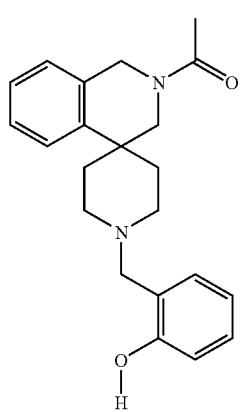
298
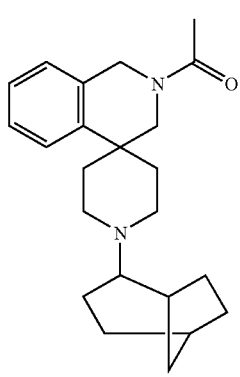

TABLE 1-continued
Exemplary compounds of formulae (I, Ia, Ib, Ic, and Id)
299
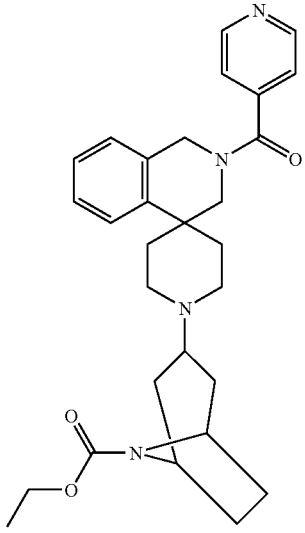
300
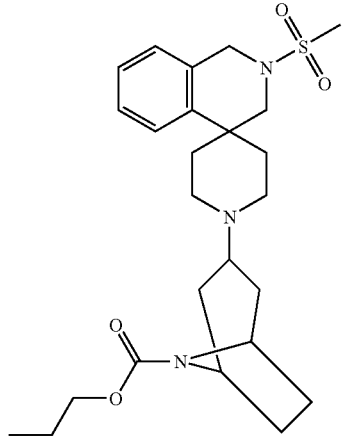
301
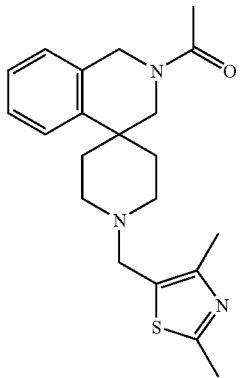
302
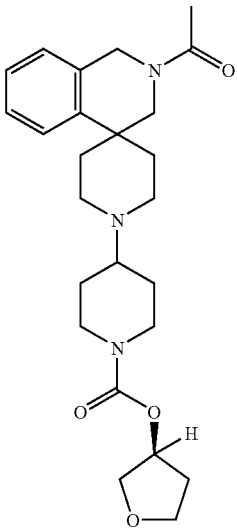
303
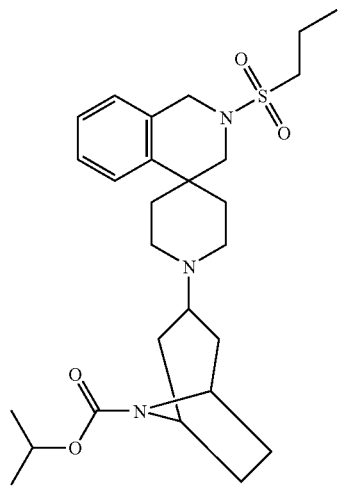
304
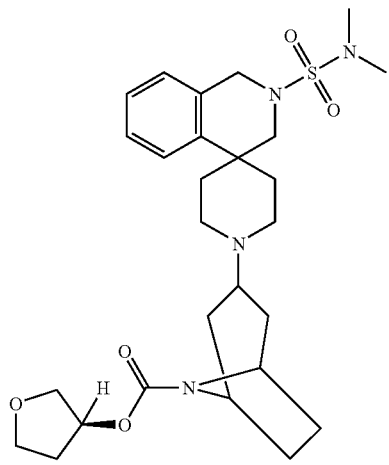

TABLE 1-continued
Exemplary compounds of formulae (I, Ia, Ib, Ic, and Id)
305
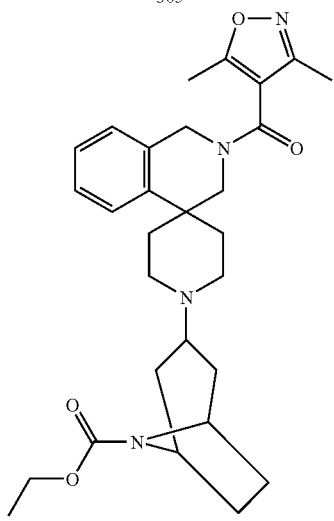
306
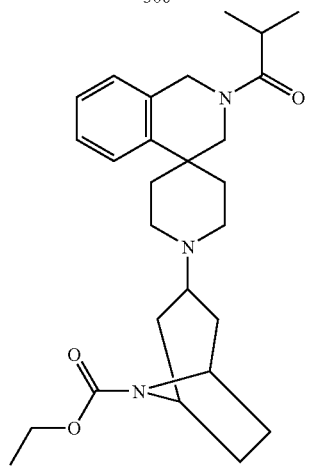
307
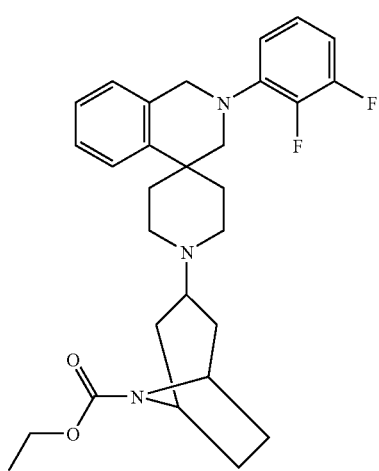
308
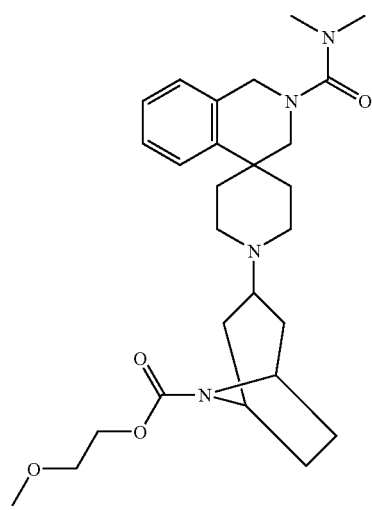
309
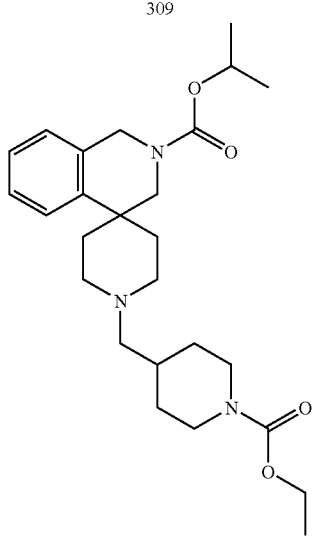
310
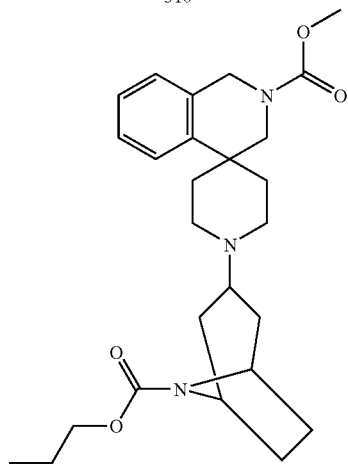

TABLE 1-continued
Exemplary compounds of formulae (I, Ia, Ib, Ic, and Id)
311
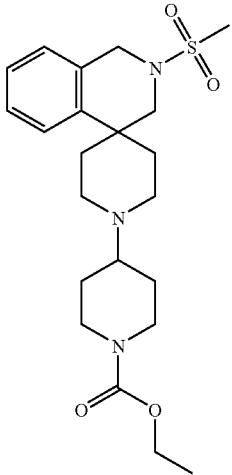
312
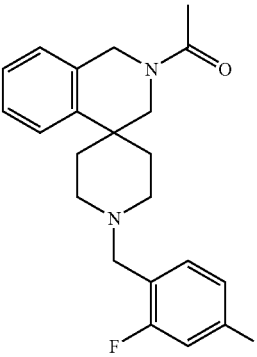
313
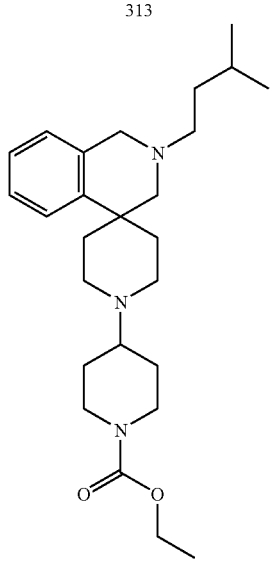
314
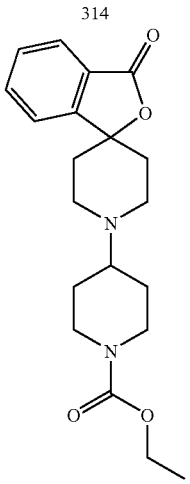
315
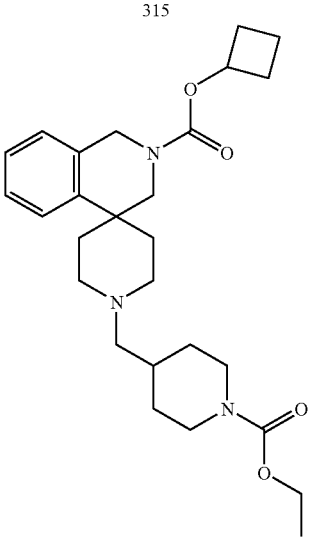
316
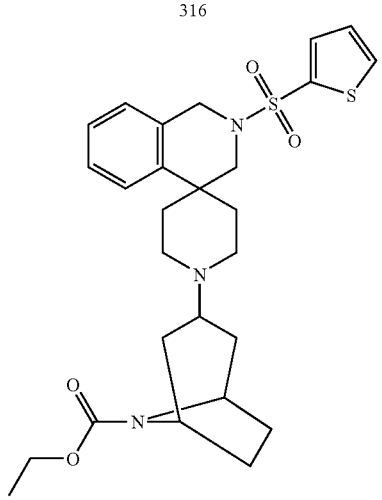

TABLE 1-continued
Exemplary compounds of formulae (I, Ia, Ib, Ic, and Id)
317
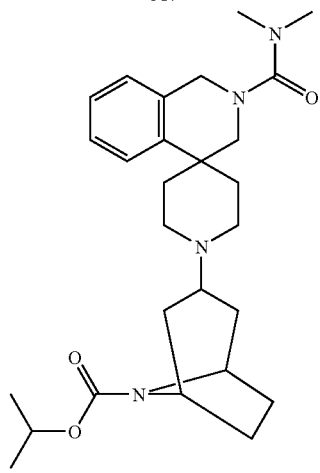
318
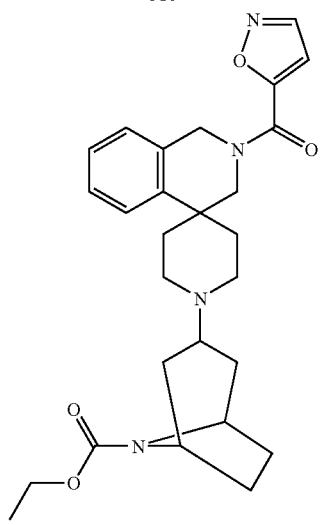
319
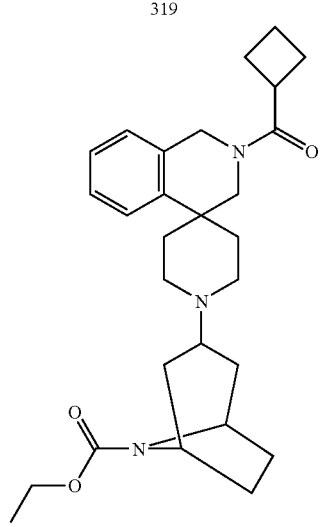
320
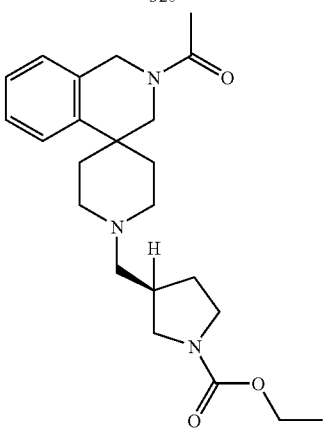
321
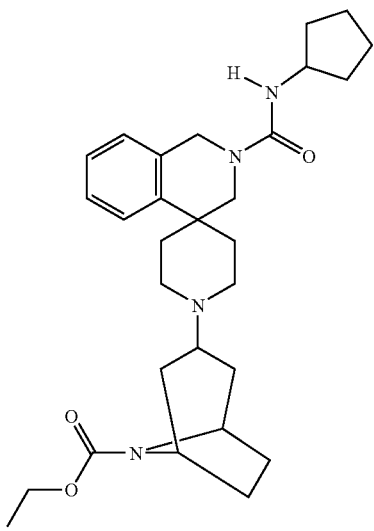
322
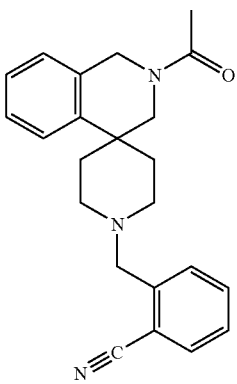

TABLE 1-continued
Exemplary compounds of formulae (I, Ia, Ib, Ic, and Id)
323
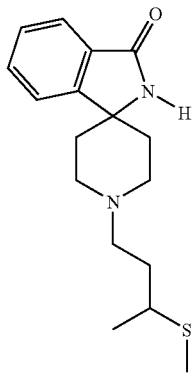
324
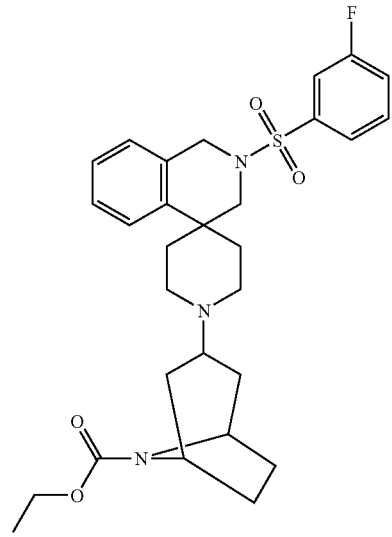
325
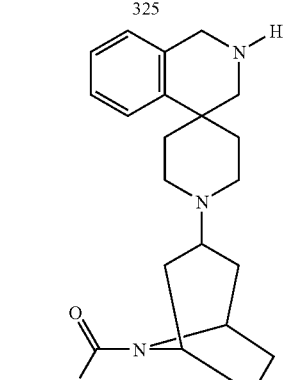
326
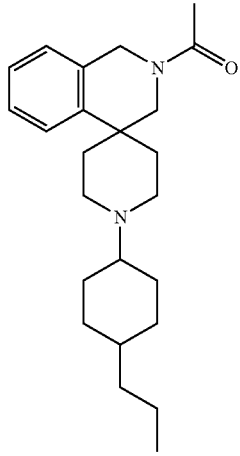
327
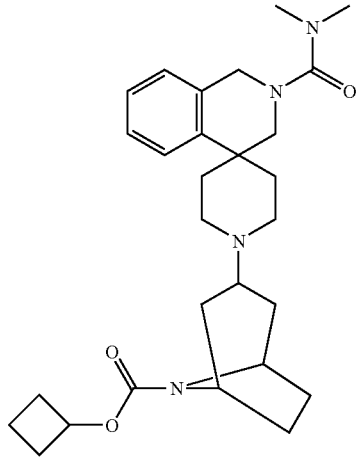
328
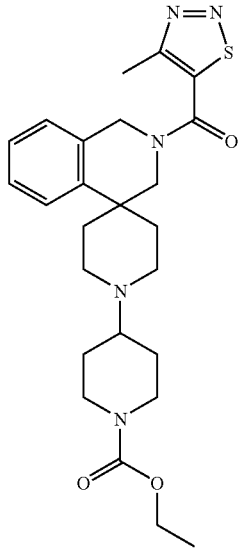

TABLE 1-continued
Exemplary compounds of formulae (I, Ia, Ib, Ic, and Id)
329
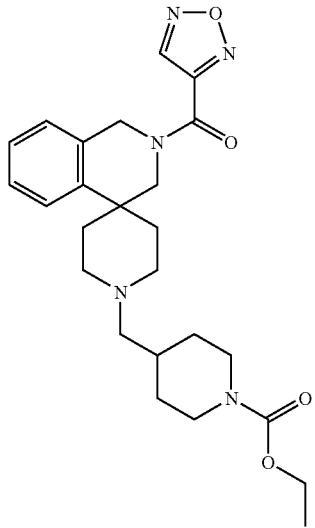
330
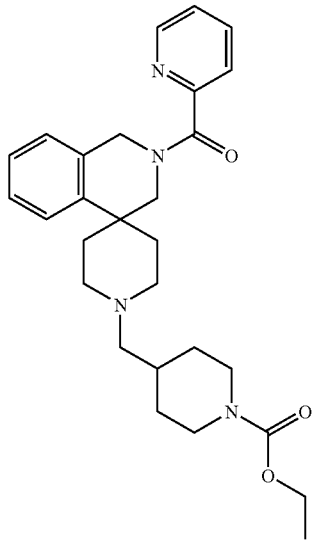
331
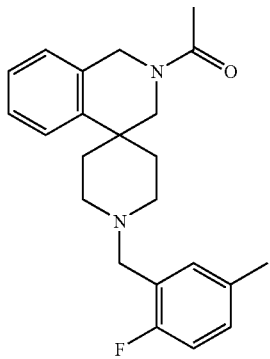
332
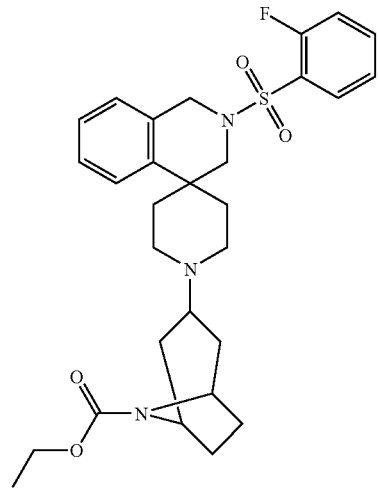
333
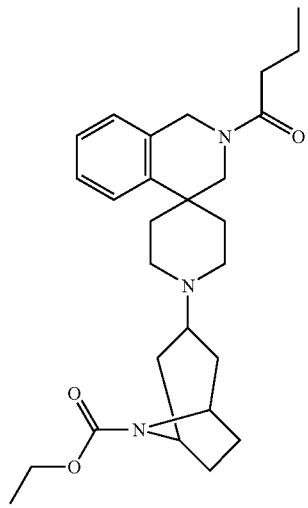
334
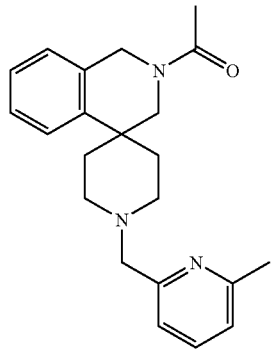

TABLE 1-continued
Exemplary compounds of formulae (I, Ia, Ib, Ic, and Id)
335
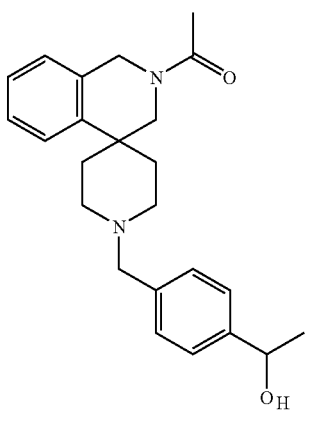
336
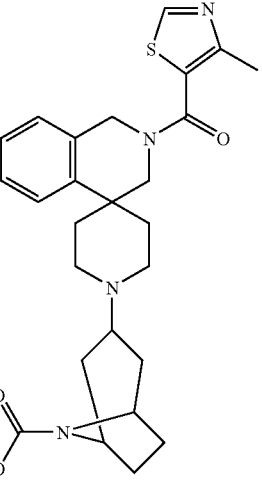
337
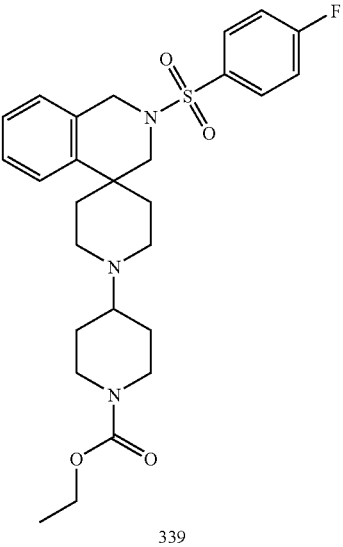
338
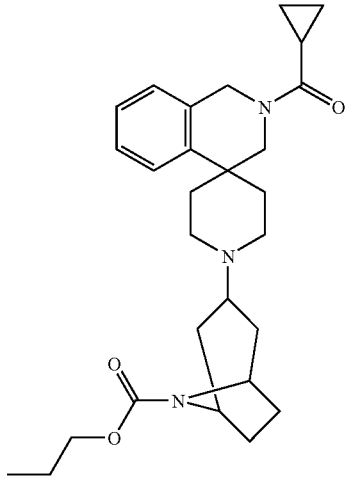
339
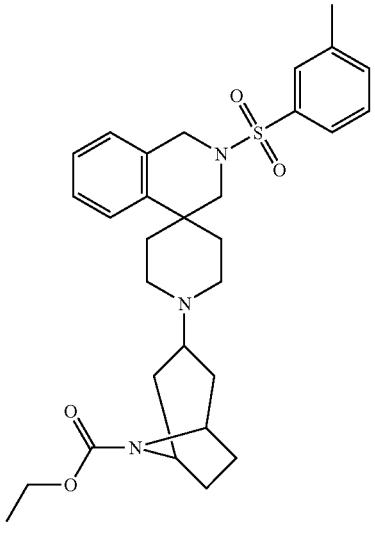
340
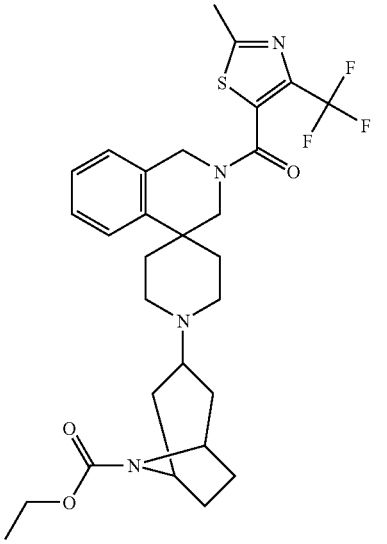

US 7,863,449 B2
TABLE 1-continued
Exemplary compounds of formulae (I, Ia, Ib, Ic, and Id)
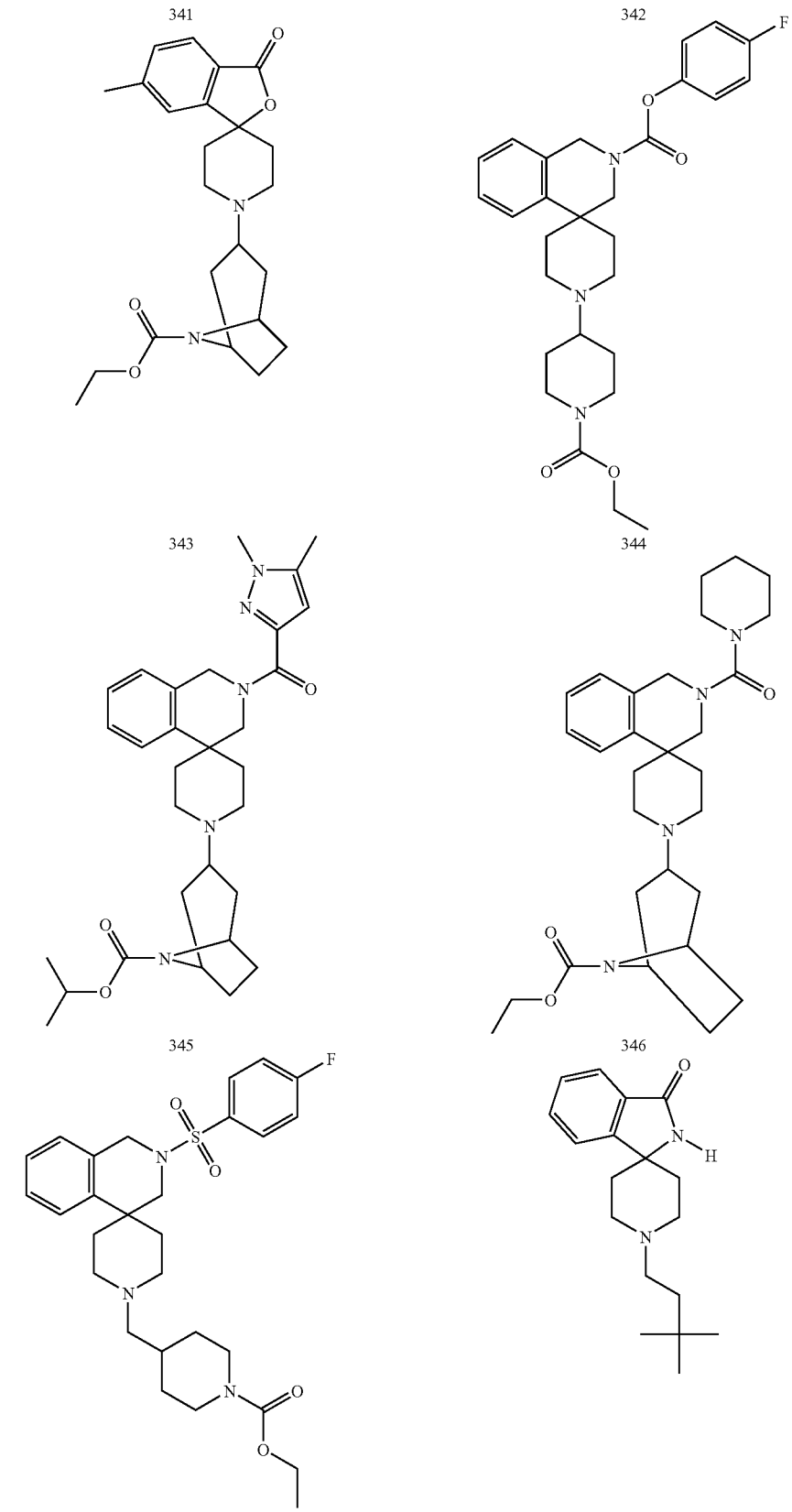

TABLE 1-continued
Exemplary compounds of formulae (I, Ia, Ib, Ic, and Id)
347
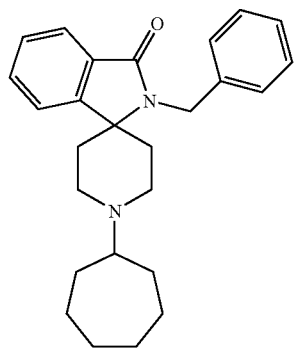
348
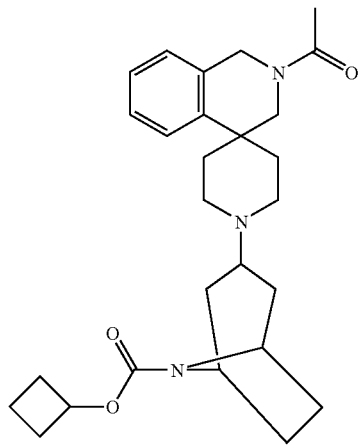
349
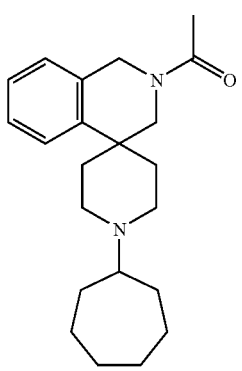
350
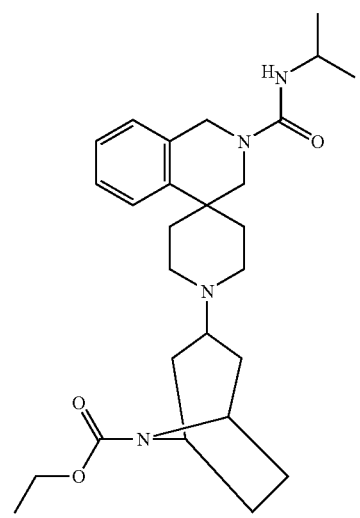
351
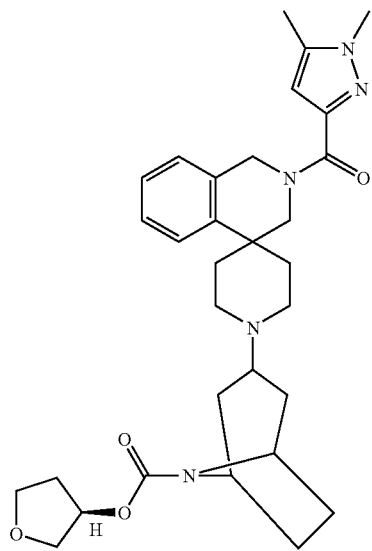
352
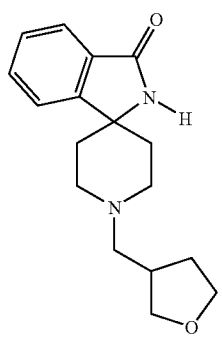

TABLE 1-continued
Exemplary compounds of formulae (I, Ia, Ib, Ic, and Id)
353
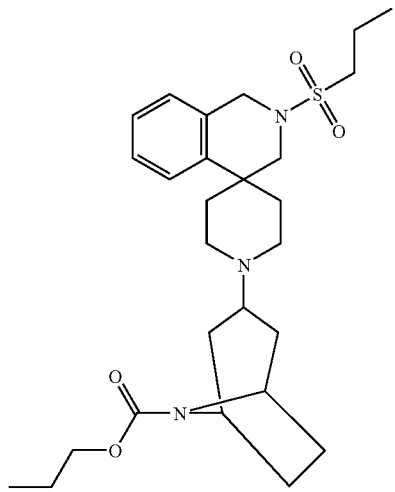
354
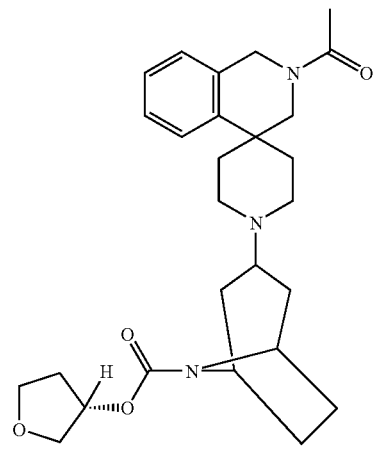
355
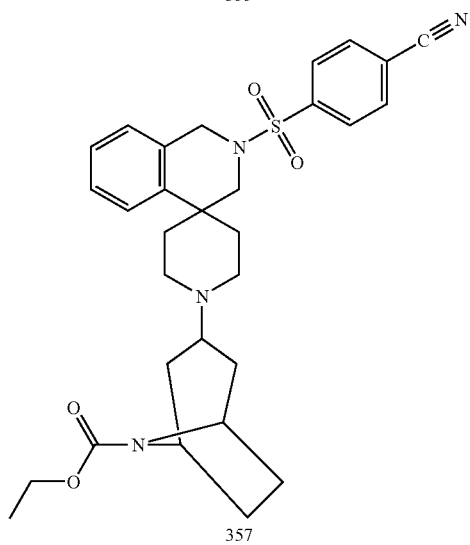
356
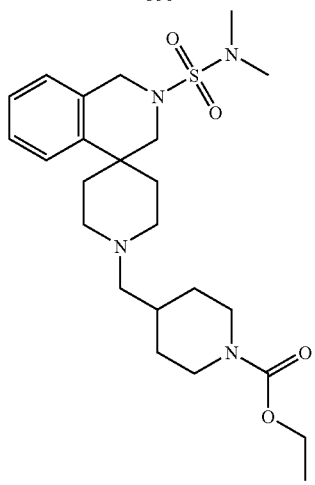
357
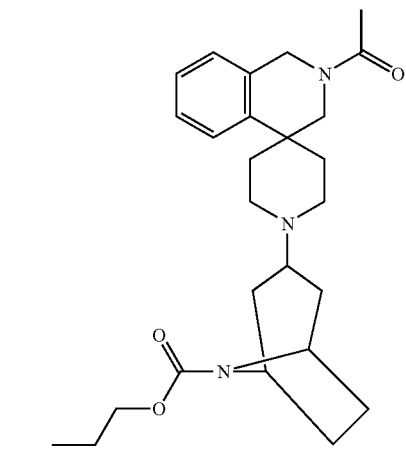
358
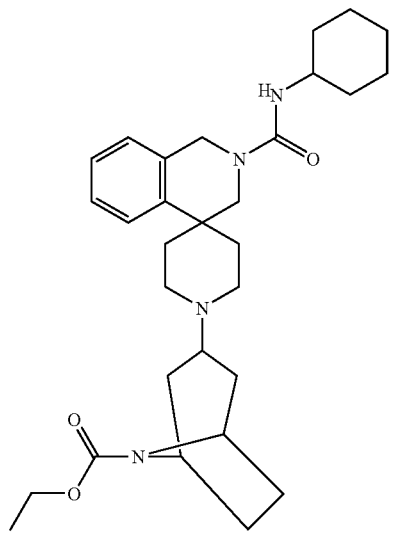

III. Synthetic Schemes:

The compounds of formulae (I, Ia, Ib, Ic, and Id) may be readily synthesized from commercially available or known starting materials using known methods. Exemplary synthetic routes to produce compounds of formulae (I, Ia, Ib, Ic, and Id) are provided in Preparations A-C and Schemes 1-5 below. For simplicity of illustration, schemes 1-5 depict only a single $R_2$ substituent on the fused phenyl ring of formulae (I, Ia, Ib, Ic, and Id); however, the compounds of this invention may include 1 to 4 $R_2$ substituents on the fused phenyl ring.

Scheme 1 below depicts general conditions for the synthesis of compounds of formula I.

Scheme 1:

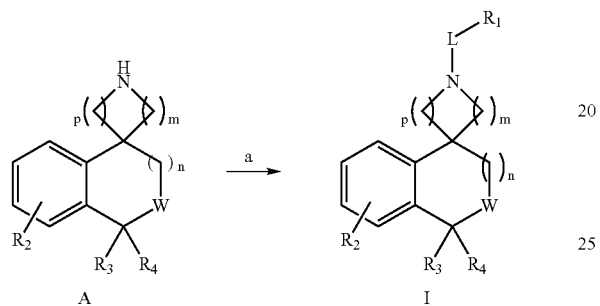

The reaction of amine (A) with an appropriate aldehyde or ketone under reductive amination conditions (step a), typically using NaBH(OAc)$_3$ in DCE/AcOH/TEA at room temperature, may be used to provide the desired compounds of formulae (I, Ia, Ib, Ic, and Id). For less reactive ketones, alternative conditions may be used. For example, the treatment of the amine (A) and the ketone in a neat solution of Ti(OiPr)$_4$, followed by treatment with NaBH$_4$ in MeOH, may be used to provide the desired compounds of formulae (I, Ia, Ib, Ic, and Id). See Abdel-Magid, A. F. et al., "Reductive Amination of Aldehydes and Ketones with Sodium Triacetoxyborohydride. Studies on Direct and Indirect Reductive Amination Procedures," *J. Org. Chem.*, 61, pp. 3849-3862 (1996) and the references cited therein.

Alternatively, the nitrogen of (A) may be alkylated with an alkyl halide in the presence of an appropriate base to provide the desired compounds of formulae (I, Ia, Ib, Ic, and Id). Typically, the amine (A) is reacted with an alkyl iodide, bromide, or chloride in the presence of an appropriate base to yield compounds of formulae (I, Ia, Ib, Ic, and Id). Bases may be organic such as triethylamine, or inorganic such as Na$_2$CO$_3$ or Cs$_2$CO$_3$. Typical reaction solvents include but are not limited to DMF, acetone, and acetonitrile.

Scheme 2 illustrates conditions for the synthesis of compounds of formulae (I and Ic) in which n is 0, p is 2, m is 2, W is —O— and $R_3$ and $R_4$ together form an oxo.

Scheme 2:

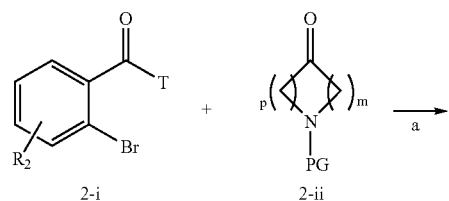

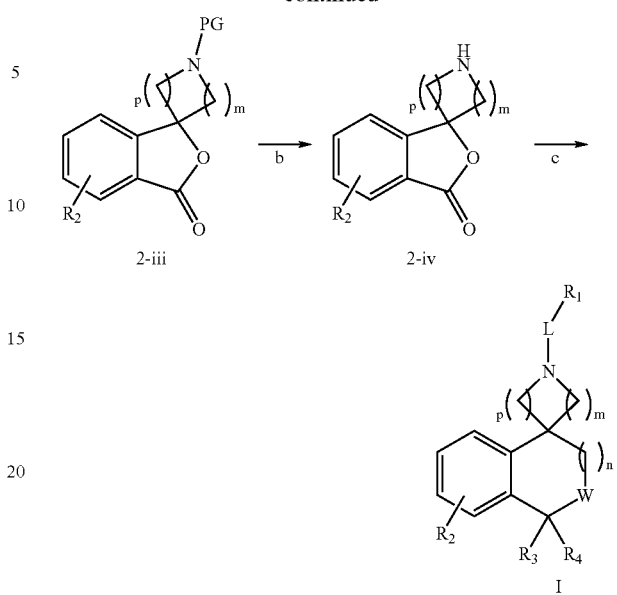

Compounds of type 2-iv in Scheme 2 may be prepared from compounds of type 2-i, where T can be —OH or —NHPh using procedures analogous to those found in WO 200310191 "Method of substituent introduction through halogen-metal exchange reaction". For example, in step a the bromoaryl compound 1-i is transmetalated with, for example, butyl lithium followed by reaction with the ketone 2-ii to give the isobenzofuranone 2-iii. Deprotection of 2-iii is achieved using known conditions dependent upon the particular protecting group. For example, 2-iii is reacted with 1-chloroethylchloroformate when the PG is benzyl. Reductive amination of 2iv, as described previously for Scheme 1, provides the compounds of the invention.

Scheme 3 illustrates alternative conditions for the synthesis of compounds of formulae (I and Id) in which n is 0, p is 2, m is 2, W is —N(R$_9$)—, and $R_3$ and $R_4$ together form oxo.

Scheme 3:

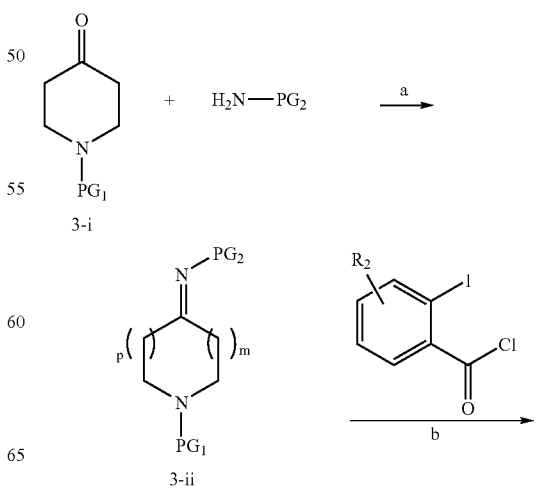

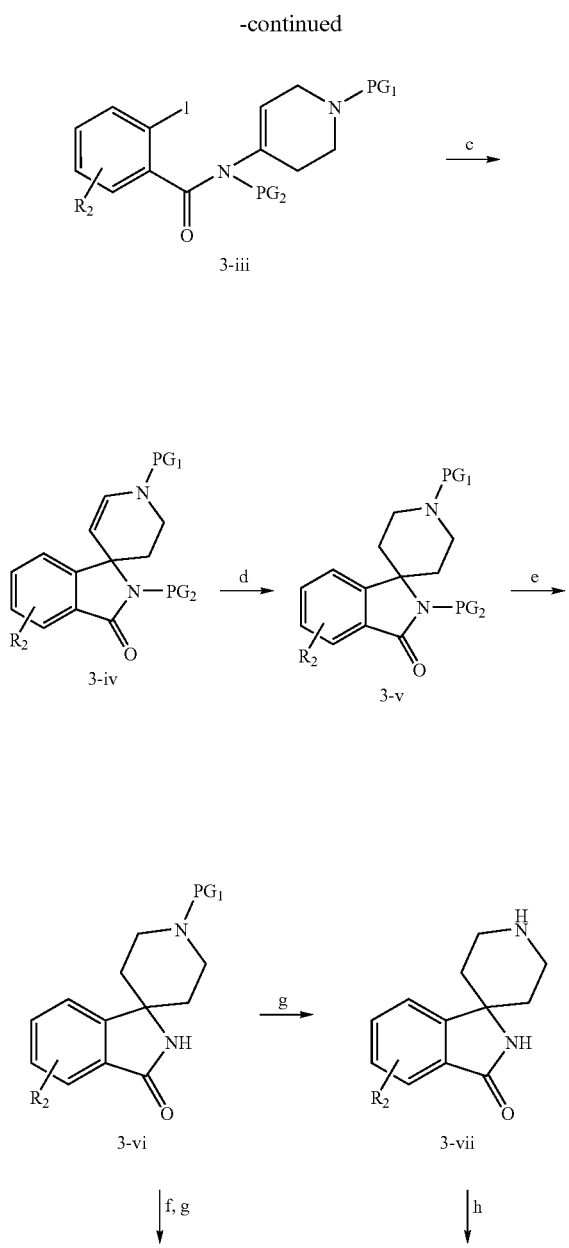

Amines of type 3-vi in Scheme 3, where n is 0, were prepared using procedures described in US 2002188124 "Preparation of spiroisoindolinepiperidinecarboxamides, spirocyclohexaneisobenzofurancarboxamides, spiroazaisobenzofurancyclohexanecarboxamides, and related compounds as neuropeptide Y antagonists". Referring to Scheme 3, reaction of the ketone 3-i with $H_2N$—$PG_2$ where $PG_2$ is, for example, benzyl, in the presence of a catalyst, for example, borontrifluoride etherate, provides the imine 3-ii. Acylation of 3-ii with an aroylhalide provides the enamine 3-iii. Cyclization of 3-iii is achieved using a palladium catalyst such as, for example, palladium acetate in the presence of an inorganic base such as, for example, potassium carbonate and a phosphorus ligand such as, for example, triphenyl phosphine. Removal of the $PG_2$ benzyl protecting group with, for example, sodium in liquid ammonia provides the intermediate 3-vi.

Compounds of formula 3-vi can be further elaborated through deprotection of $PG_1$ under suitable conditions such as TFA if $PG_1$ is Boc, followed by further substitution of the piperidine nitrogen to obtain compounds of formulae (I and Ic) as described in Scheme 1.

Alternatively, the lactam nitrogen can be first substituted with an appropriate halide of $R_9$ under basic conditions, such as NaH, followed by deprotection of $PG_1$ and coupling with a suitable electrophile under conditions described above to obtain compounds of formulae (I and Ic) where $R_9$ is alkyl.

Scheme 4 illustrates alternative conditions for the synthesis of compounds of formulae (I and Ia) in which W is —N($R_9$)—, n is 1, and $R_2$ and $R_3$ are hydrogen.

Scheme 4:

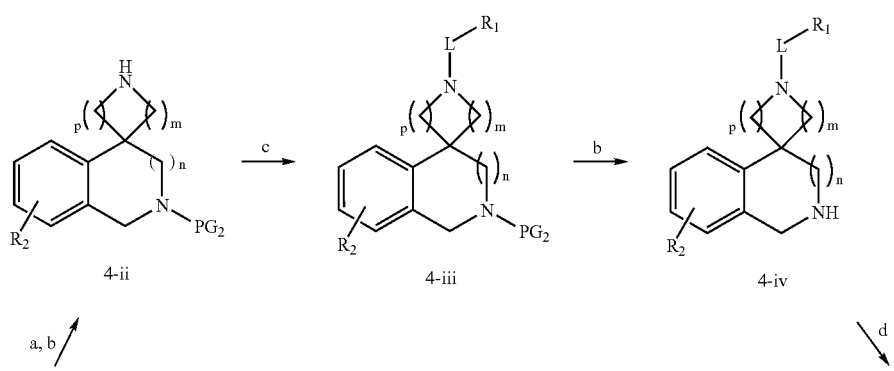

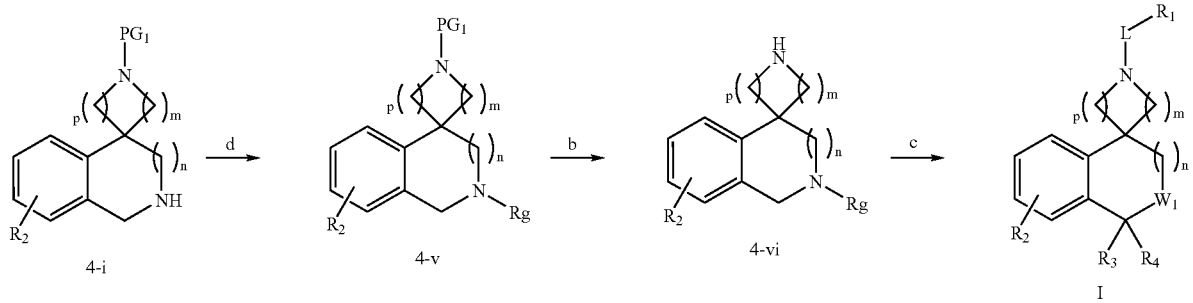

Amines of type 4-i in Scheme 4 may be prepared from methods known in the art and by using procedures analogous to those found in the following references: Berney, D. and Jauner, T., *Helvetica Chimica Acta* 1975, 59, 74; Chiavarelli, S. et al., *Gazzetta Chimica Italiana* 1960, 90, 189; CN1535967 "Preparation of spirocyclic template 1,2,3,4-tetrahydrospiro[isoquinoline-4,4'-piperidine] compounds". Refering to Scheme 4, in step a the 2-amino position is protected with $PG_2$ as previously described. Subsequently, in step b, removal of $PG_1$ is achieved as previously described, for example, with trifluoroacetic acid in methylene chloride at −10° C. when $PG_1$ is Boc. Transformation of 4-ii to compounds of formula 4-iii is achieved through reductive amination or alkylation as descibed in Scheme 1. Removal of the protecting group $PG_1$ and subsequent derivitization at the 2-nitrogen as previously described provides compounds of the invention. Alternatively, the sequences of deprotection and derivitization may be achieved as shown in Scheme I where 4-i is converted to 4-v (step d) followed by conversion to compounds of the invention with steps b and c as previously described.

Scheme 5 illustrates transformation of compounds of formula 5-i to compounds of formulae (I, Ia, Ib, Ic, and Id).

Scheme 5:

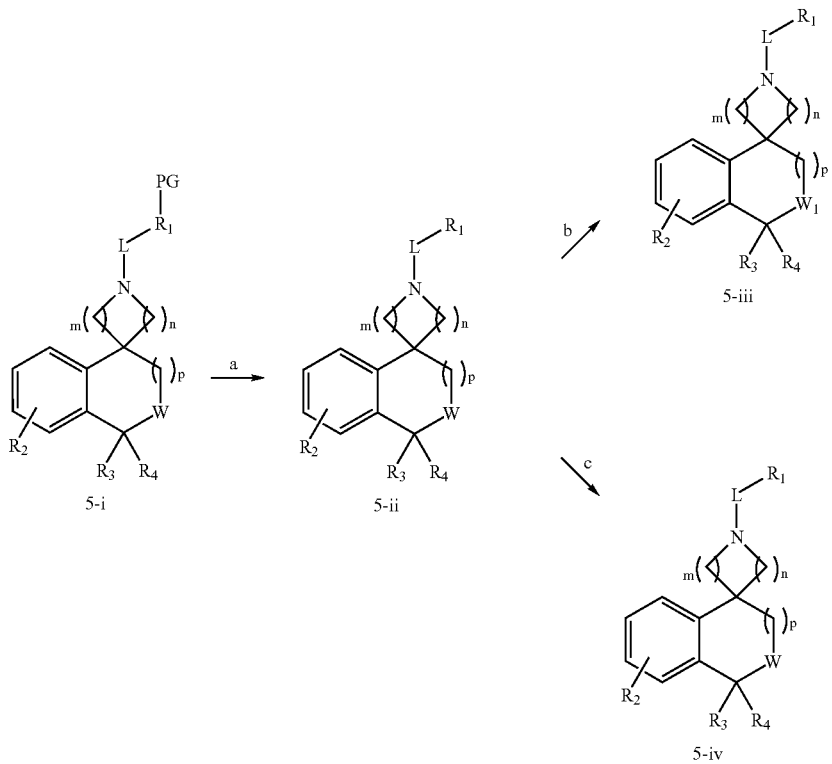

Referring to Scheme 5, compounds of formula 5-i contain an $R_1$ which is substituted with a protected functionality that may either be retained, deprotected and retained, or deprotected and further elaborated to produce additional compounds of formulae (I, Ia, Ib, Ic, and Id). Thus, removal of the protecting group PG in formula 5-i using methods described herein provides compounds of formula 5-ii. For example, if PG in $R_1$ is a ketal, hydrolysis with, for example, aqueous acetic acid leads to the corresponding 5-ii wherein $R_1$ contains a ketone which may be converted, for example, to the corresponding oxime or oxime ether under known conditions and as described in the examples (step b) to provide compounds of formula 5-iii wherein $R_1$ contains an oxime or oxime ether. As a further example, when PG of formula 5-i is N-PG, removal of the protecting group provides an amine which may be further transformed to alkyl, acyl, carbamoyl or sulfonyl derivatives using known conditions and as illustrated in the examples to give compounds of formula 5-iv (step c) wherein $R_1$ contains an amine alkyl, acyl, carbamoyl or sulfonyl derivative.

IV. Formulations Administrations and Uses

A. Pharmaceutically Acceptable Compositions

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\ alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formulae (I, Ia, Ib, Ic, and Id) are selective modulators of $M_1$, $M_2$ and $M_4$. More preferably, the compounds of formulae (I, Ia, Ib, Ic, and Id) are selective modulators of $M_1$ and/or $M_4$. Yet more preferably, certain compounds of formulae (I, Ia, Ib, Ic, and Id) are selective modulators of $M_1$. Or, preferably, certain compounds of formulae (I, Ia, Ib, Ic, and Id) are selective modulators of $M_4$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e., an agonist) or inhibits the activity of a muscarinic receptor.

The term "selective" as used herein means a measurably greater ability to modulate one muscarinic receptor subtype when compared to the other muscarinic receptor subtypes. E.g., the term "selective $M_4$ agonist" means a compound that has a measurably greater ability to act as an $M_4$ agonist when compared to that compound's agonist activity with the other muscarinic receptor subtype(s).

According to an alternative embodiment, the present invention provides a method of treating a muscarinic receptor mediated disease in a mammal, such as a human, including the step of administering to said mammal a composition comprising a compound of formulae (I, Ia, Ib, Ic, and Id), or an embodiment thereof as set forth herein.

According to another embodiment, the present invention provides a method of treating a disease mediated by a muscarinic receptor including the step of administering to said mammal a composition comprising a compound of formulae (I, Ia, Ib, Ic, and Id), or other embodiments thereof as set forth above. Preferably, said disease is mediated by $M_1$, or said disease is mediated by $M_4$.

According to yet another embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, sudden infant death syndrome, Parkinson's disease, peripheral disorders such as reduction of intra ocular pressure in Glaucoma and treatment of dry eyes and dry mouth including Sjögren's Syndrome, wherein said method comprises the step of contacting said patient with a compound according to the present invention.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradycardia, gastric acid secretion, asthma, or GI disturbances.

According to a preferred embodiment, the present invention is useful for treating or reducing the severity of psychosis, Alzheimer's disease, pain, or Parkinson's disease. All references cited within this document are incorporated herein by reference.

IV. Preparations and Examples

In order that the invention described therein may be more fully understood, the following examples are set forth. It should be understood that these examples are for illustrative purposes only and are not to be construed as limiting this invention in any manner.

Preparation A

Synthesis of ethyl 4-formylpiperidine-1-carboxylate

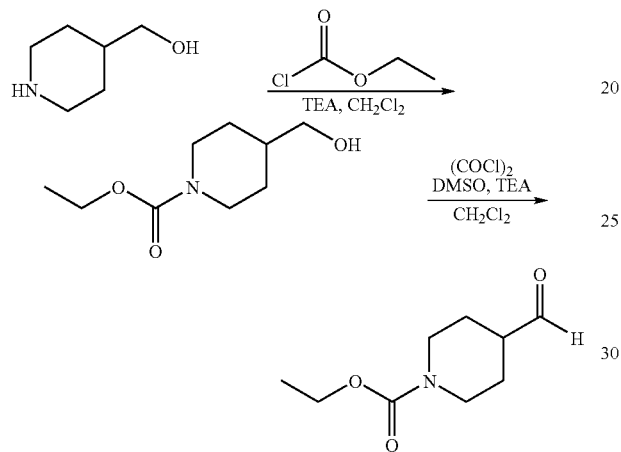

1.0 eq 4-piperidinemethanol (10.00 g, 86.8 mmol) was dissolved in dichloromethane (350 mL), cooled in an ice-$H_2O$ bath and treated dropwise with a solution of 1.05 eq ethyl chloroformate (9.89 g, 91.1 mmol) in dichloromethane (50 mL), followed by the dropwise addition of a solution of 1.0 eq triethylamine (8.78 g) in dichloromethane (50 mL). The reaction was stirred at ≈0° C. for 15 minutes, then at room temperature for 10 minutes. The reaction was diluted with dichloromethane (250 mL) and washed successively with (150 mL each) $H_2O$, 0.1 N HCl (aq) (×2), saturated brine, then dried ($Na_2SO_4$) and filtered. The filtrate was concentrated in vacuo to afford 15.60 g ethyl 4-(hydroxymethyl)-piperidine-1-carboxylate as a viscous, pale bluish-green oil. $^1$H-NMR (400 MHz, $CDCl_3$) δ 4.15 (br m, 2H), 4.09 (q, J=7.1 Hz, 2H), 3.46 (d, J=6.4 Hz, 2H), 2.72 (br t, J=12.4 Hz, 2H), 2.07 (s, 1H), 1.70 (m, 2H), 1.63 (m, 1H), 1.23 (t, J=7.2 Hz, 3H), 1.12 (m, 2H); LC/MS [M+H]$^+$ m/z 188.0, retention time 1.56 min (10-99% $CH_3CN$—$H_2O$ gradient, with 0.1% TFA, 5 min).

A solution of 1.2 eq oxalyl chloride (12.69 g, 0.10 mol) in dichloromethane (150 mL) was cooled to approximately −78° C. and treated dropwise, under nitrogen, with a solution of 2.4 eq anhydrous dimethylsulfoxide (15.63 g, 0.20 mol) in dichloromethane (50 mL). 15 minutes after the addition was complete, a solution of 1.0 eq ethyl 4-(hydroxymethyl)-piperidine-1-carboxylate (15.60 g, 83.3 mmol) in dichloromethane (50 mL) was added dropwise. 30 minutes after the addition was complete, a solution of 3.0 eq triethylamine (25.30 g, 0.25 mol) in dichloromethane (50 mL) was added dropwise and the reaction warmed to room temperature. The reaction was stirred at room temperature for 1 hour, then quenched with saturated sodium bicarbonate (500 mL). The layers were separated and the aqueous layer extracted once with dichloromethane (200 mL). The pooled organic layers were washed with $H_2O$ (3×100 mL), saturated sodium bicarbonate (1×100 mL) and saturated brine, then dried ($Na_2SO_4$) and filtered. The filtrate was concentrated in vacuo to afford 13.84 g ethyl 4-formylpiperidine-1-carboxylate as a viscous amber oil. $^1$H-NMR (400 MHz, $CDCl_3$) δ 9.64 (s, 1H), 4.10 (q, J=7.2 Hz, 2H), 4.00 (br m, 2H), 2.97 (m, 2H), 2.40 (m, 1H), 1.87 (br m, 2H), 1.54 (m, 2H), 1.23 (t, J=7.0 Hz, 3H).

Preparation B

Synthesis of ethyl 4-formyl-4-methylpiperidine-1-carboxylate

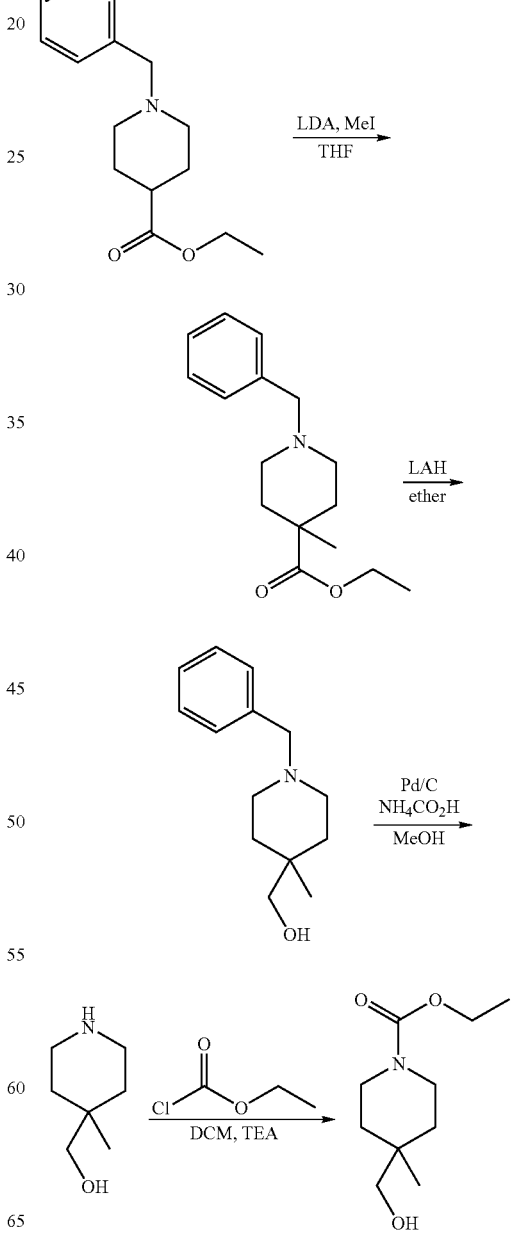

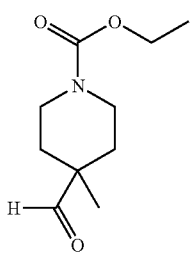

Diisopropylamine (3.14 mL; 22.23 mmol; 1.1 eq.) was dissolved in THF (60 mL) and cooled to −78° C. Butyl lithium (2.5 M in hexane; 8.89 mL; 22.23 mmol; 1.1 eq.) was then added and the solution was stirred for 30 minutes at −78° C. Ethyl 1-benzylpiperidine-4-carboxylate (5 g; 20.21 mmol; 1 eq.) was dissolved in THF (40 mL) and added to the LDA solution at −78° C. The solution was stirred at −78° C. for 30 minutes and iodomethane (1.32 mL; 21.22 mmol; 1.05 eq.) was added. The solution was slowly warmed to room temperature and stirred at room temperature for 1 hour. Water (100 mL) was then added to the reaction followed by EtOAc (50 mL). The layers were separated and the aqueous layer was extracted with EtOAc (2×50 mL). The combined organic layers were dried over $Na_2SO_4$, filtered, and concentrated under reduced pressure to afford the product (5.0 g) as an oil. The product was analytically pure and used without further purification. LC/MS m/z [M+H]$^+$ 262.0, Retention time 1.78 min. (10-99% $CH_3CN$—$H_2O$ gradient with 0.03% TFA, 5 min). $^1$H NMR (400 MHz, $CDCl_3$) δ 7.24-7.14 (m, 5H), 4.08 (q, J=7.1 Hz, 2H), 3.40 (s, 2H), 2.60-2.57 (m, 2H), 2.08-2.02 (m, 4H), 1.47-1.40 (m, 2H), 1.17 (t, J=7.1 Hz, 3H), 1.10 (s, 3H).

1-Benzyl-4-methylpiperidine-4-carboxylate (5.0 g; 19.15 mmol) was dissolved in $Et_2O$ (50 mL) and cooled to 0° C. $LiAlH_4$ (1.0 g; 26.3 mmol) was slowly added portion-wise to the solution. After the addition was complete, the solution was slowly warmed to room temperature and stirred for 1 h. The solution was then cooled to 0° C. and slowly quenched with 1N NaOH (6 mL). The resultant white precipitates were filtered and washed with EtOAc (100 mL). The combined organic layers were concentrated under reduced pressure to provide the product (3.9 g) as an oil that was used without further purification. LC/MS m/z [M+H] 220.0, retention time 0.64 min (10-99% $CH_3CN$—$H_2O$ gradient with 0.03% TFA, 5 min). $^1$H NMR (400 MHz, $CDCl_3$) δ 7.25-7.16 (m, 5H), 3.46 (s, 2H), 3.30 (d, J=3.9 Hz, 2H), 2.51-2.46 (m, 2H), 2.26-2.20 (m, 2H), 1.52-1.45 (m, 3H), 1.30-1.25 (m, 2H), 0.87 (s, 3H).

(1-benzyl-4-methylpiperidin-4-yl)methanol (3.9 g; 17.8 mmol) was dissolved in MeOH (50 mL) and $NH_4CO_2H$ (12.5 g; 178.0 mmol) was added. Pd/C (10% by weight, wet; 5.5 g) was then added and the system was flushed with nitrogen and then with hydrogen. The reaction was stirred at room temperature overnight (18 h) and then filtered through a pad of Celite. The solvent was removed under high vacuum to provide a solid that was a mixture of the amino alcohol and $NH_4CO_2H$. The crude product (2.4 g as a mixture with $NH_4COOH$) was used in the next step without further purification. LC/MS m/z [M+H]$^+$ 130.0, retention time 0.35 min (10-99% $CH_3CN$—$H_2O$ gradient with 0.03% TFA, 5 min). $^1$H-NMR (400 MHz, $CDCl_3$) δ 3.17 (s, 2H), 3.03-2.98 (m, 2H), 2.95-2.88 (m, 2H), 1.64-1.57 (m, 2H), 1.36-1.31 (m, 2H), 0.89 (s, 3H).

(4-methylpiperidin-4-yl)methanol (2.4 g, a mixture of the amino alcohol and $NH_4CO_2H$) was suspended in DCM (70 mL). $Et_3N$ (5 mL; 37.2 mmol) was then added followed by the drop-wise addition of ethyl chloroformate (1.05 mL, 13 mmol, 1.4 eq.). After 1 hour at room temperature, 1N HCl (70 mL) was added and the layers were separated. The aqueous layer was extracted with DCM (70 mL) and the combined organic layers were dried over $Na_2SO_4$, filtered, and concentrated under high vacuum. The product (1.7 g over 2 steps) is obtained analytically pure as an oil and used without further purification. LC/MS m/z [M+H]$^+$ 202.2, retention time 1.89 min. (10-99% $CH_3CN$—$H_2O$ gradient with 0.03% TFA, 5 min). $^1$H-NMR (400 MHz, DMSO-$d_6$) δ 4.05 (q, J=7.1 Hz, 2H), 3.66 (dt, J=13.6, 4.7 Hz, 2H), 3.32 (s, 2H), 3.11 (t, J=5.2 Hz, 1H), 3.11 (dd, J=23.9, 3.5 Hz, 1H), 1.44-1.37 (m, 3H), 1.26-1.22 (m, 2H), 1.19 (t, J=7.1 Hz, 3H), 0.93 (s, 3H).

To a 100 mL round bottom flask was added DCM (30 mL) and oxalyl chloride (0.88 mL; 10.13 mmol). The solution was cooled to −78° C. and treated with DMSO (1.19 mL; 16.88 mmol). The solution was stirred at −78° C. for 20 minutes and then treated with ethyl 4-(hydroxymethyl)-4-methylpiperidine-1-carboxylate (1.7 g; 8.44 mmol, dissolved in 10 mL of DCM). The solution was stirred for 30 minutes at −78° C. and then treated with $Et_3N$ (3.53 mL; 25.32 mmol). The solution was stirred at −78° C. for 20 min and then slowly warmed to room temperature and stirred at room temperature for an additional 2 h. The solution was then treated with saturated aqueous $NaHCO_3$ (50 mL), diluted with DCM (50 mL), and the layers were separated. The organic layer was washed with brine (50 mL), dried over $Na_2SO_4$, filtered, and concentrated under reduced pressure to afford 1.6 g of the product as an oil which was used without further purification. LC/MS m/z [M+H]$^+$ 200.0, retention time 2.23 minutes; (10-99% $CH_3CN$—$H_2O$ gradient with 0.03% TFA, 5 min). $^1$H-NMR (400 MHz, $CDCl_3$) δ 9.40 (s, 1H), 4.06 (q, J=7.1 Hz, 2H), 3.66 (dt, J=13.6, 4.7 Hz, 2H), 3.09 (dd, J=10.1, 3.5 Hz, 1H), 3.06 (dd, J=10.2, 3.4 Hz, 1H), 1.86 (dt, J=13.6, 4.4 Hz, 2H), 1.42-1.30 (m, 2H), 1.19 (t, J=7.1 Hz, 3H), 1.02 (s, 3H).

Preparation C

Synthesis of benzyl 3-oxo-8-azabicyclo[3.2.1]octane-8-carboxylate

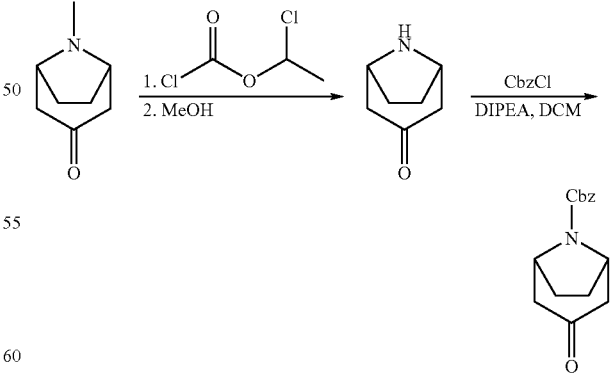

Tropinone (10.0 g; 71.84 mmol) was dissolved in DCE (60 mL) and treated dropwise with 1-chloroethyl chloroformate ACE-Cl (14.5 mL; 19.11 g; 133.7 mmol). The reaction was allowed to stir at room temperature overnight and was then diluted with $Et_2O$ (400 mL) and filtered. The filtrate was concentrated under reduced pressure to provide the crude chloroethyl carbamate. This compound was taken in MeOH (200 mL) and stirred at room temperature for 1 h, then concentrated under reduced pressure (at 55° C.) to provide the crude des-methyltropinone as the HCl salt (tan solid, 11.4 g, 98% yield). The crude material was recrystallized from acetonitrile to furnish the pure product as a white crystalline solid (5 g). ¹H-NMR (400 MHz, DMSO-d6) δ 10.00 (br s, 2H), 4.23 (s, 2H), 3.02 (dd, J=17.1, 4.3 Hz, 2H), 2.40 (d, J=16.7 Hz, 2H), 2.09 (m, 2H), 1.79 (dd, J=15.0, 6.9 Hz, 2H).

8-azabicyclo[3.2.1]octan-3-one (5.10 g; 31.55 mmol) was dissolved in CH₂Cl₂ (50 mL) and treated with benzyl chloroformate (4.29 mL; 5.11 g; 29.98 mmol) DIPEA (16.48 mL; 12.23 g; 94.66 mmol) was added drop-wise (exothermic reaction). The resulting clear solution was allowed to stir at room temperature for 30 min and was subsequently diluted with 100 mL CH₂Cl₂. The organic phase was washed with 1 N HCl (2×100 mL), dried on Na₂SO₄ and concentrated to provide the crude product (7.2 g). ¹H-NMR (400 MHz, CDCl₃) δ 7.38 (m, 5H), 5.22 (s, 2H), 4.62 (s, 2H), 2.67 (m, 2H), 2.38 (d, J=15.9 Hz, 2H), 2.12 (m, 2H), 1.71 (dd, J=15.0, 7.2 Hz, 2H).

Example 1 ethyl 4-(3-oxo-3H-spiro[isobenzofuran-1,4'-piperidine]-1'-yl)piperidine-1-carboxylate (Compound No. 314)

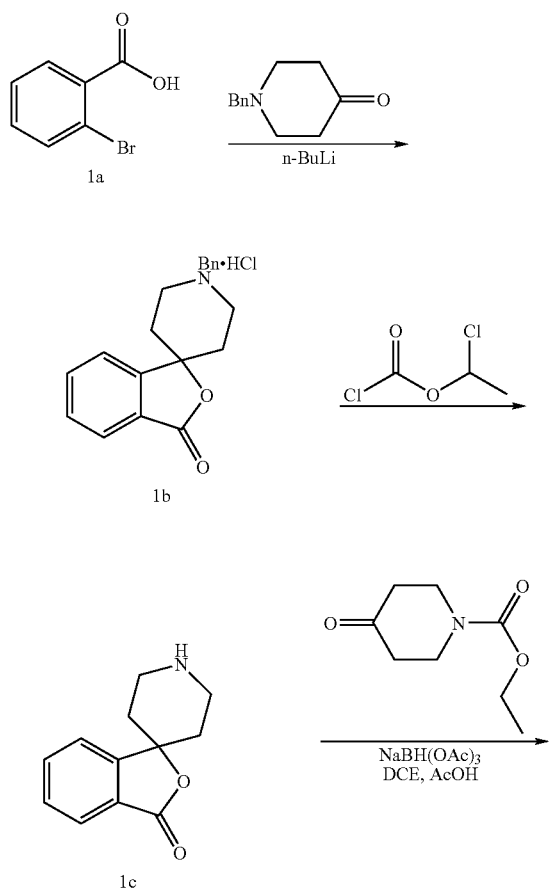

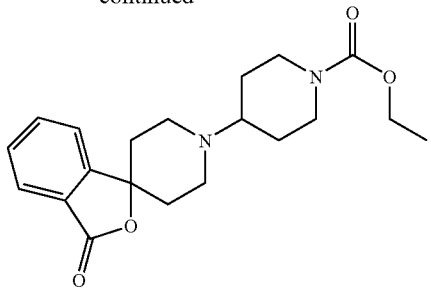

Compound No. 314

A solution of 2-bromobenzoic acid (20.12 g, 0.1 mol) in THF (200 mL) was treated dropwise with n-BuLi (2.5 M, 80 mL) at –78° C. The mixture was stirred at this temperature for 30 min, followed by dropwise addition of a solution of N-benzylpiperdine-4-one (26 g, 137 mmol) in THF (100 mL). The resulting mixture was stirred at –78° C. for 30 min, and was then allowed to warm to room temperature and stirred overnight. The reaction was quenched with water (100 mL) and the resulting mixture was washed with ether (100 mL). The aqueous layer was refluxed for 1 hr and then acidified to pH 2.5. The mixture was extracted with CHCl₃ (3×50 mL), the combined organic layers were washed with brine, dried over Na₂SO₄ and concentrated to dryness to obtain 1'-benzyl-3H-spiro[isobenzofuran-1,4'-piperidin]-3-one 1b (6 g).

To a solution of 1'-benzyl-3H-spiro[isobenzofuran-1,4'-piperidin]-3-one 1b (6 g, 20.4 mmol) in dichloromethane (30 mL) was added dropwise 1-chloroethyl chloroformate (2.9 g, 20.4 mmol). The mixture was stirred at 25° C. for 5 hr and then was concentrated to dryness under reduced pressure. The residue was dissolved in methanol and the mixture was heated to reflux for 30 min. The mixture was concentrated to dryness and ether was added. The precipitated solid was collected by filtration and washed with ether, dried in air to obtain 3H-spiro[isobenzofuran-1,4'-piperidin]-3-one 1c as its HCl salt (3.6 g). ¹H-NMR (400 MHz, DMSO-d₆) δ 9.16 (br, 2H), 7.86-7.81 (m, 2H), 7.63 (t, J=7.6 Hz, 1H), 7.56 (d, J=7.2 Hz, 1H), 3.39-3.42 (m, 2H), 3.11-3.14 (m, 2H), 2.47-2.48 (m, 2H), 1.85 (d, J=14.4 Hz, 2H). MS (ESI) m/z (M+H⁺): 203.24.

3H-spiro[isobenzofuran-1,4'-piperidin]-3-one hydrochloride 1c (2.7 g, 11.05 mmol) and ethyl 4-oxopiperidine-1-carboxylate (1.46 g, 13.26 mmol) were added to a 25-mL flask and dissolved in 5.0 mL anhydrous dichloroethane and treated with triethylamine (233 uL, 1.68 mmol) and glacial acetic acid (200 uL, 3.36 mmol) to produce a clear, light amber-colored solution. NaBH(OAc)₃ (4.68 g, 22.10 mmol) was then added in one portion. The flask was flushed with nitrogen, closed tightly, and allowed to stir for approximately 40 h. The reaction was diluted with dichloromethane (50 mL) and washed with 1.0 N NaOH (50 mL), 50% saturated sodium bicarbonate (50 mL), and brine (100 mL). The organic phase was dried over Na₂SO₄, filtered and concentrated to approximately 100 mL. Silicycle acid chloride resin was added (2.5 eq) followed by excess triethylamine, and the solution was stirred for 1 h, after which all residual starting amine had been removed. The resin was filtered and the organic phase treated as above to yield the free base as a clear oil. The oil was brought up in 1:1 ether/hexane and treated with 1.0 equivalents of ethereal HCl to yield an off-white solid after filtration and hexane wash (350 mg). The solid was brought up in minimal acetonitrile (1 mL) and crashed out using ether (15 mL) to yield a white solid, which was filtered, washed with ether, and dried under vacuum to yield 330 mg of ethyl 4-(3-oxo -3H-spiro[isobenzofuran-1,4'-piperidine]-1'-yl)piperidine-1-carboxylate hydrochloride as a white solid. LC/MS m/z [M+H]+ 359.2, retention time 1.63 min (10-99% CH₃CN—H2O gradient, with 0.05% TFA, 5 min). ¹H NMR (400 MHz, DMSO-d₆) δ 11.21 (s, 1H), 7.89 (d, J=7.6 Hz, 1H), 7.87 (dt, J=10.3, 3.8 Hz, 1H), 7.67 (dt, J=10.2, 3.8 Hz, 1H), 7.54 (d, J=7.6 Hz, 1H), 4.14 (d, J=12.5 Hz, 2H), 4.06 (q, J=7.1 Hz, 2H), 3.62 (d, J=11.1 Hz, 2H), 3.56-3.49 (m, 1H), 3.24 (q, J=11.2 Hz, 2H), 2.82 (dt, J=19.7, 7.2 Hz, 4H), 2.19 (d, J=11.4 Hz, 2H), 1.99 (d, J=14.4 Hz, 2H), 1.67 (q, J=12.2 Hz, 2H), 1.20 (t, J=7.1 Hz, 3H).

Example 2 ethyl 4-(2-benzyl-3-oxospiro[isoindoline-1,4'-piperidine]-1'-yl)piperidine-1-carboxylate (Compound No. 20)

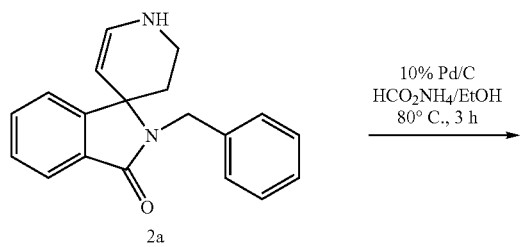

centrated to give a white solid. The solid was washed with ethyl acetate (4×25 mL) and the washings were concentrated to give 2-benzylspiro[isoindoline-1,4'-piperidin]-3-one 2b as a yellow oil (2.0 g, 99%). FIA m/z [M+H]+ 293.

Sodium triacetoxyborohydride (21 mg, 0.102 mmol) was added to a stirred solution of 2-benzylspiro[isoindoline-1,4'-piperidin]-3-one (20 mg, 0.068 mmol), ethyl 4-oxopiperidine-1-carboxylate (17 mg, 0.10 mmol) and titanium(IV) isopropoxide (0.06 mL, 0.205 mmol) in 1,2-dichloroethane (0.5 mL) at room temperature. The mixture was stirred at 35° C. for 24 h. A solution of acetonitrile/water (1:1, 5 mL) was added and the yellow precipitate filtered and the organic phase evaporated. The product was purified by preparative HPLC (5-70% CH₃CN—H₂O gradient, with 0.05% TFA, 15 min) to give ethyl 4-(2-benzyl-3-oxospiro[isoindoline-1,4'-piperidine]-1'-yl)piperidine-1-carboxylate as a TFA salt. LC/MS m/z [M+H]+ 448.0, retention time 2.5 min (10-90% CH₃CN—H₂O gradient, with 0.05% TFA, 5 min). ¹H-NMR (500 MHz, CD₃OD) δ 7.95 (d, 2H), 7.43 (t, 1H), 7.66 (t, 1H), 7.31 (d, H), 7.20 (m, 1H), 4.84 (br s, 2H), 4.33 (s, 2H), 4.14 (q, 2H), 3.62 (m, 2H), 3.59 (m, 3H), 2.90 (m, 2H), 2.60 (m, 2H), 2.20 (m, 2H), 1.72 (m, 4H), 1.26 (t, 3H).

Example 3

1'-(bicyclo[2.2.1]hept-5-en-2-ylmethyl)spiro[isoindoline-1,4'-piperidin]-3-one (Compound No. 267)

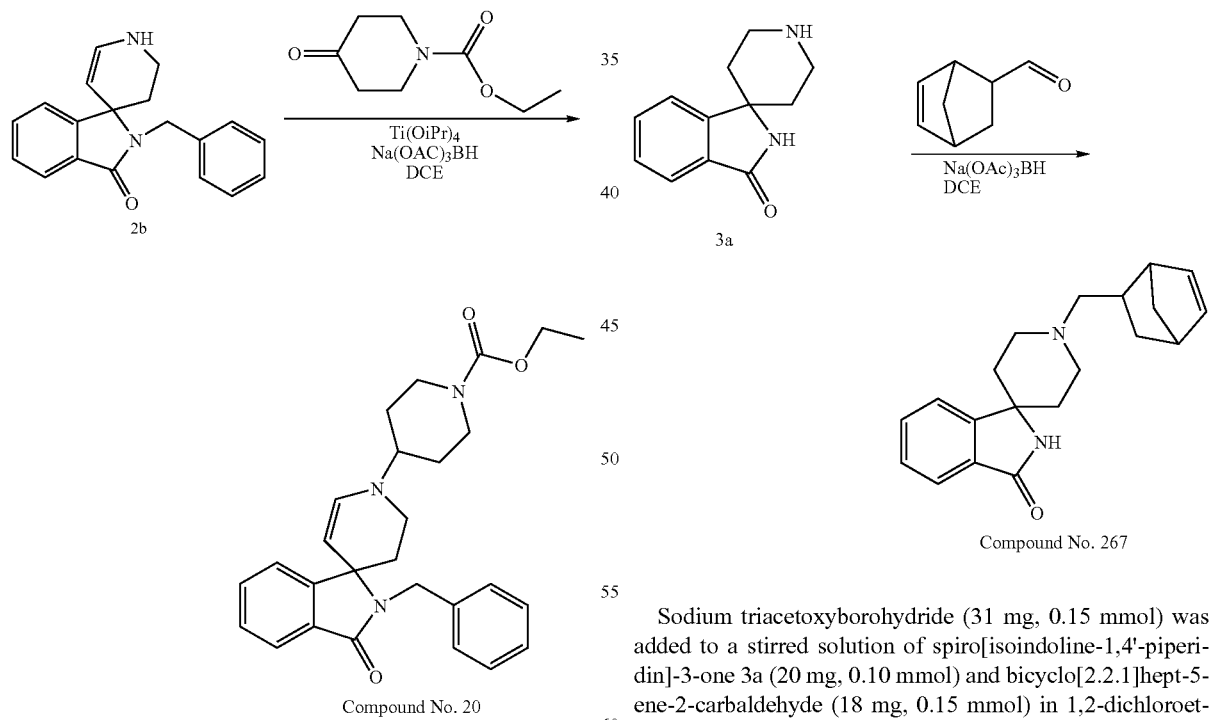

10% Palladium on carbon (1 g) was added to a stirred solution of 2-benzyl-2',3'-dihydro-1'H-spiro[isoindoline-1, 4'-pyridin]-3-one 2a (2 g, 6.9 mmol) and ammonium formate (8.7 g, 138 mmol) in ethanol (50 mL). The mixture was heated under reflux for 3 hr then cooled to room temperature. The solution was filtered through Celite and the filtrate was con- Sodium triacetoxyborohydride (31 mg, 0.15 mmol) was added to a stirred solution of spiro[isoindoline-1,4'-piperidin]-3-one 3a (20 mg, 0.10 mmol) and bicyclo[2.2.1]hept-5-ene-2-carbaldehyde (18 mg, 0.15 mmol) in 1,2-dichloroethane (1 mL) and the mixture was stirred at room temperature for 6 h. The solvent was removed under reduced pressure and the crude product was purified by preparative HPLC (5-70% CH₃CN—H₂O gradient with 0.05% TFA, 15 min) to give compound no. 267. LC/MS m/z [M+H]+ 309.0 retention time 1.7 min (10-90% CH₃CN—H₂O gradient, with 0.05% TFA, 5 min).

Example 4

(R)-tetrahydrofuran-3-yl 3-(2-(dimethylcarbamoyl)-2,3-dihydro-1H-spiro[isoquinoline-4,4'-piperidine]-1'-yl)-8-azabicyclo[3.2.1]octane-8-carboxylate (Compound No. 48)

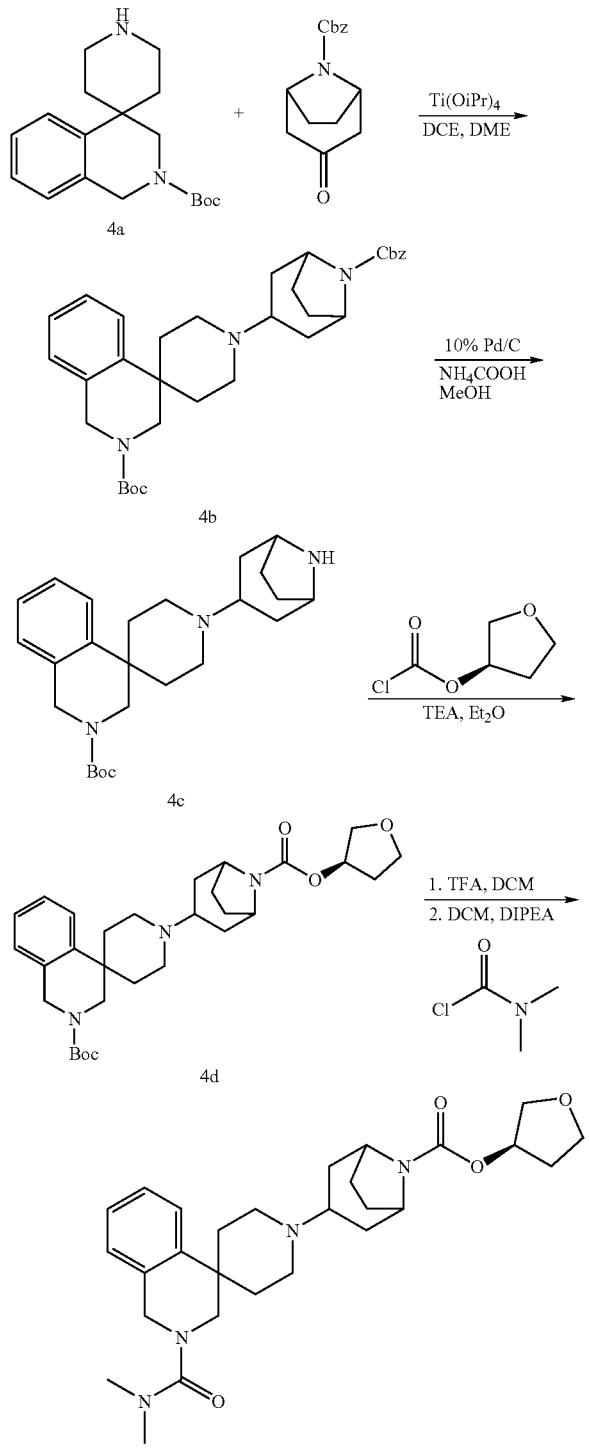

Compound No. 48 tert-Butyl 1H-spiro[isoquinoline-4,4'-piperidine]-2(3H)-carboxylate 4a (2.80 g, 8.263 mmol) and benzyl 3-oxo-8-azabicyclo[3.2.1]octane-8-carboxylate (2.014 g, 7.767 mmol) were dissolved in a mixture of DCE (10 mL) and DME (10 mL) and placed under a nitrogen atmosphere. Triethylamine (1.149 mL, 834.5 mg, 8.263 mmol) was added, followed by Ti(O$^i$Pr)$_4$ (7.2 mL, 6.9 g, 24.6 mmol) and the reaction was allowed to stir at room temperature for 60 h. The reaction mixture was diluted with 30 mL MeOH and cooled to −40° C. to −50° C. NaBH$_4$ (1.223 g, 33.051 mmol, 4.0 eq) was added portion-wise over 30 min and the reaction was allowed to stir at −40° C. until bubbling had subsided (approximately 3 h), was allowed to warm slowly back to room temperature and was stirred for 2 h. The sticky suspension was filtered through a pad of Celite, and the filter cake was washed with MeOH (2×30 mL) and Et$_2$O (3×50 mL). The filtrate was separated into the corresponding layers, and the aqueous layer was extracted with Et$_2$O (2×50 mL). The combined organic extracts were dried over Na$_2$SO$_4$ and concentrated to provide the crude product as a white foam. Unreacted starting material was converted to the corresponding ethyl carbamates by suspending the crude product in CH$_3$CN (30 mL) and treating sequentially with ethyl chloroformate (1 mL) and triethylamine (2 mL). After 10 min, the mixture was diluted with Et$_2$O (300 mL) and poured onto 1N aq HCl (300 mL). The biphasic suspension was filtered, and the precipitate was washed with HCl 1N (2×30 mL), H$_2$O (2×30 mL) and Et$_2$O (3×30 mL) and dried to provide tert-butyl 1'-(8-(benzyloxycarbonyl)-8-azabicyclo[3.2.1]octan-3-yl)-1H-spiro[isoquinoline-4,4'-piperidine]-2(3H)-carboxylate 4b as the hydrochloride salt (2.7 g, 56% yield). LC/MS m/z [M+H]$^+$ 546.4, retention time 2.92 min (10-99% CH$_3$CN—H$_2$O gradient, with 0.05% TFA, 5 min).

tert-Butyl 1'-(8-(benzyloxycarbonyl)-8-azabicyclo[3.2.1]octan-3-yl)-1H-spiro[isoquinoline-4,4'-piperidine]-2(3H)-carboxylate 4b (2.700 g, 4.638 mmol) was dissolved in methanol (30 mL) and treated with 10% wet Pd/C (2.7 g) and NH$_4$COOH (5.844 g, 92.756 mmol). The mixture was allowed to stir vigorously overnight under an empty balloon (for venting). LC/MS analysis shows complete conversion to the desired product. The reaction mixture was filtered through a pad of Celite under a nitrogen atmosphere, and the filter cake was rinsed with methanol (4×30 mL). The filtrate was concentrated to provide the crude product, which was taken up in a mixture of EtOAc (100 mL) and NaHCO$_3$ sat (100 mL). Some product stays undissolved in both layers. The biphasic mixture was filtered, and the precipitate was washed with H$_2$O (20 mL) and vacuum dried overnight to provide 1.01 g pure tert-butyl 1'-(8-azabicyclo[3.2.1]octan-3-yl)-1H-spiro[isoquinoline-4,4'-piperidine]-2(3H)-carboxylate 4c. The filtrate layers were separated, and the aqueous layer was extracted with Et$_2$O (100 mL) and CH$_2$Cl$_2$ (2×100 mL). The combined organic layers were dried on Na$_2$SO$_4$ and concentrated to provide additional product 4c (600 mg). LC/MS m/z [M+H]$^+$ 412.4, retention time 2.16 min (10-99% CH$_3$CN—H$_2$O gradient, with 0.05% TFA, 5 min).

tert-Butyl 1'-(8-azabicyclo[3.2.1]octan-3-yl)-1H-spiro[isoquinoline-4,4'-piperidine]-2(3H)-carboxylate 4c (205 mg, 0.5 mmol) was suspended in Et$_2$O (10 mL) and treated with the (R)-tetrahydrofuran-3-yl carbonochloridate (150 mg, 1 mmol) and triethylamine (0.21 mL, 1.5 mmol, 3 eq). The reaction was stirred at room temperature for 30 min and was then treated with 1N aq. HCl. The phases were separated, the aqueous phase was brought to a basic pH by adding solid KOH, and the resulting suspension was extracted with CH$_2$Cl$_2$ (3×10 mL). The combined organic extracts were dried over Na$_2$SO$_4$ and concentrated to provide crude tert-butyl 1'-(8-(((R)-tetrahydrofuran-3-yloxy)carbonyl)-8-azabicyclo[3.2.1]octan-3-yl)-1H-spiro[isoquinoline-4,4'-piperidine]-2(3H)-carboxylate 4d as a colorless, viscous oil (230 mg, 88% yield). LC/MS m/z [M+H]$^+$ 526.2, retention time 2.54 min (10-99% CH$_3$CN—H$_2$O gradient, with 0.05% TFA, 5 min.

tert-Butyl-1'-(8-(((R)-tetrahydrofuran-3-yloxy)carbonyl)-8-azabicyclo[3.2.1]octan -3-yl)-1H-spiro[isoquinoline-4,4'-piperidine]-2(3H)-carboxylate 4d (230 mg, 0.43 mmol, 1 eq) was dissolved in CH$_2$Cl$_2$ (10 mL) and treated with TFA (4 mL). The reaction was stirred at room temperature until complete consumption of the starting material was observed by LC/MS (approximately 1 h). The mixture was diluted with H$_2$O (50 mL) and brought to basic pH by addition of solid KOH. The aqueous phase was extracted with CH$_2$Cl$_2$ (2×50 mL) and Et$_2$O (50 mL), and the combined organic layers dried over Na$_2$SO$_4$ and concentrated to provide the crude (R)-tetrahydrofuran-3-yl 3-(2,3-dihydro-1H-spiro[isoquinoline-4,4'-piperidine]-1'-yl)-8-azabicyclo[3.2.1]octane-8-carboxylate (171 mg, 92% yield), which was used for the next step without further purification.

(R)-tetrahydrofuran-3-yl 3-(2,3-dihydro-1H-spiro[isoquinoline-4,4-piperidine]-1'-yl)-8-azabicyclo[3.2.1]octane-8-carboxylate (20 mg, 0.047 mmol) was dissolved in CH$_2$Cl$_2$ (1 mL) and treated with a solution of dimethylcarbamic chloride (20 mg, 0.13 mmol) in CH$_2$Cl$_2$ (100 µL). A solution of diisopropyl ethylamine (20 µL, 14.8 mg, 0.11 mmol) was added. The resulting mixture was allowed to stand at room temperature for 10 min and was then purified by LC/MS (10-99% CH$_3$CN—H$_2$O, with 0.03% TFA, 9 min) to provide (R)-tetrahydrofuran-3-yl 3-(2-(dimethylcarbamoyl)-2,3-dihydro-1H-spiro[isoquinoline-4,4'-piperidine]-1'-yl)-8-azabicyclo[3.2.1]octane-8-carboxylate. LC/MS m/z [M+H]$^+$ 497.4, retention time 2.15 min (10-99% CH$_3$CN—H$_2$O gradient, with 0.05% TFA, 5 min).

Example 5 ethyl 3-(2-acetyl-2,3-dihydro-1H-spiro[isoquinoline-4,4'-piperidine]-1'-yl)-8-azabicyclo[3.2.1]octane-8-carboxylate (Compound No. 197)

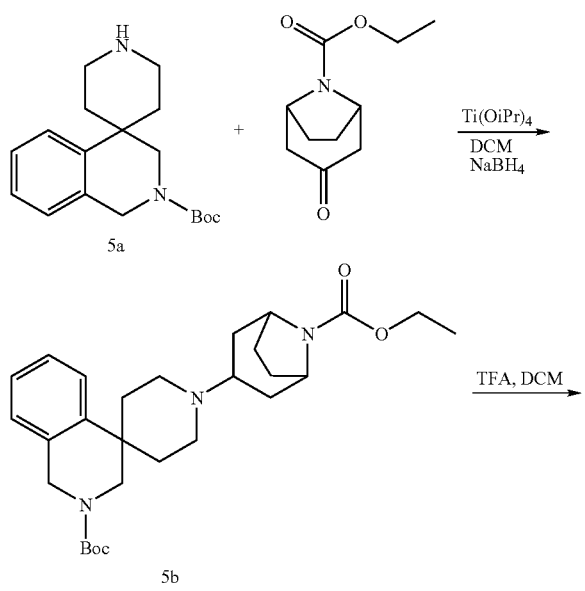

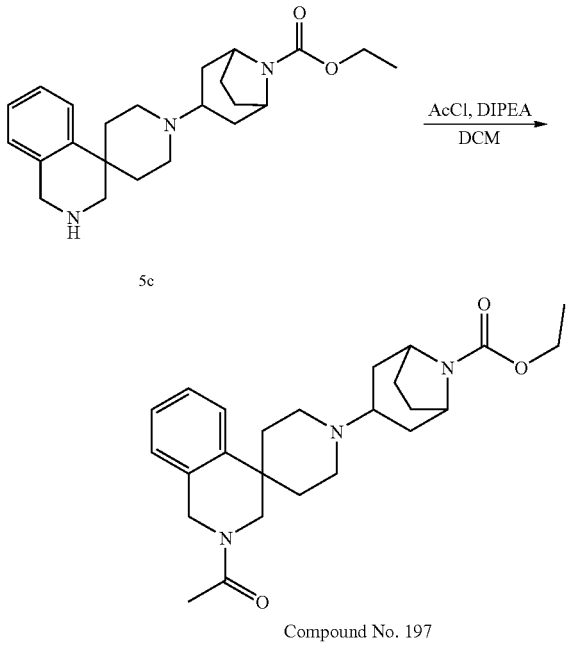

Compound No. 197 tert-Butyl 1H-spiro[isoquinoline-4,4'-piperidine]-2(3H)-carboxylate 5a (2.071 g, 6.11 mmol) and ethyl 3-oxo-8-azabicyclo[3.2.1]octane-8-carboxylate (1.51 g, 7.66 mmol) were dissolved in anhydrous dichloromethane (10 mL) in a 100-mL round-bottom flask and treated with triethylamine (618 mg, 6.11 mmol), followed by titanium tetraisopropoxide (5.21 g, 18.3 mmol). The reaction was stirred under nitrogen at room temperature for 21 h, then cooled in a dry ice/isopropanol bath to −40° C. and quenched with methanol (10 mL). The reaction was stirred for several minutes at the same temperature and treated in one portion with sodium borohydride (462 mg, 12.2 mmol). The reaction was stirred at −40° C. for 30 minutes, then warmed to room temperature. The reaction was then treated with 1 N NaOH (12 mL), diluted with methanol (50 mL) and stirred vigorously at room temperature for 10 minutes. The reaction was filtered through Celite and the solids rinsed with dichloromethane (4×25 mL). The filtrate was washed with H$_2$O, saturated brine, dried over Na$_2$SO$_4$ and filtered. The filtrate was concentrated under reduced pressure to afford 3.641 g tert-butyl 1'-(8-(ethoxycarbonyl)-8-azabicyclo[3.2.1]octan-3-yl)-1H-spiro[isoquinoline-4,4'-piperidine]-2(3H)-carboxylate 5b as a pale yellow oil. LC/MS m/z [M+H]$^+$ 484.3, retention time 2.32 min (10-99% CH$_3$CN—H$_2$O gradient, with 0.05% TFA, 5 min).

The crude tert-butyl 1'-(8-(ethoxycarbonyl)-8-azabicyclo[3.2.1]octan-3-yl)-1H -spiro[isoquinoline-4,4'-piperidine]-2(3H)-carboxylate 5b (3.641 g) was dissolved in dichloromethane (10 mL) and treated with trifluoroacetic acid (10 mL). The reaction was stirred at room temperature for 45 min, then concentrated under reduced pressure. The oil obtained was re-dissolved in acetonitrile, re-concentrated under reduced pressure, treated with 2 N NaOH (25 mL) and extracted with dichloromethane (2×50 mL). The combined extracts were washed with saturated NaHCO$_3$, saturated brine, dried over Na$_2$SO$_4$, and filtered. The filtrate was concentrated under reduced pressure to afford 2.55 g crude ethyl 3-(2,3-dihydro-1H-spiro[isoquinoline-4,4'-piperidine]-1'-yl)-8-azabicyclo[3.2.1]octane-8-carboxylate 5c as a pale yellow oil, which solidified upon standing overnight at room temperature. LC/MS m/z [M+H]$^+$ 384.2 retention time 1.34 min (10-99% CH$_3$CN—H$_2$O gradient, with 0.05% TFA, 5 min). $^1$H-NMR (400 MHz, CDCl$_3$) δ 7.60 (d, J=8.0 Hz, 1H), 7.29 (t, J=7.3 Hz, 1H), 7.19 (t, J=7.4 Hz, 1H), 7.07 (d, J=7.5 Hz, 1H), 6.06 (br s, 2H), 4.37 (br s, 2H), 4.25 (s, 2H), 4.12 (q, J=7.1 Hz, 2H), 3.47 (m, 3H), 3.24 (m, 2H), 2.93 (m, 2H), 2.53 (m, 2H), 1.96 (m, 8H), 1.71 (m, 2H), 1.26 (t, J=7.1 Hz, 3H).

Crude ethyl 3-(2,3-dihydro-1H-spiro[isoquinoline-4,4'-piperidine]-1'-yl)-8-azabicyclo[3.2.1]octane-8-carboxylate 5c (1.00 g, 2.6 mmol) was dissolved in anhydrous dichloromethane (12 mL), cooled in an ice/H$_2$O bath and treated dropwise with a solution of acetyl chloride (214 mg, 2.73 mmol) in anhydrous dichloromethane (2 mL). The reaction was then treated dropwise with a solution of 1.1 eq triethylamine (289 mg, 2.86 mmol) in anhydrous dichloromethane (2 mL) and stirred in the ice/H$_2$O bath for 30 min. The reaction was diluted with EtOAc (50 mL) and washed with 50% saturated NaHCO$_3$ (3×20 mL), saturated brine, dried over Na$_2$SO$_4$, and filtered. The filtrate was concentrated under reduced pressure to afford 1.063 g crude product as a pale yellow oil. The crude product was purified by reverse-phase HPLC (2-99% CH$_3$CN—H$_2$O gradient with 0.03% TFA, 15 min). The combined pure fractions were concentrated under reduced pressure and treated with 1 N NaOH (25 mL). The product was extracted with dichloromethane (2×50 mL) and the combined extracts washed with saturated brine, dried (Na$_2$SO$_4$) and filtered and concentrated. The free base was dissolved in anhydrous diethyl ether (~10 mL) and treated with 1.0 eq HCl (500 µL 2 N ethereal HCl). The suspension was cooled in an ice/H$_2$O bath, filtered, rinsed with Et$_2$O (3×10 mL) and dried to provide ethyl 3-(2-acetyl-2,3-dihydro-1H -spiro[isoquinoline-4,4'-piperidine]-1'-yl)-8-azabicyclo[3.2.1]octane-8-carboxylate. LC/MS m/z [M+H]$^+$ 426.2 retention time 1.89 min (10-99% CH$_3$CN—H$_2$O gradient, with 0.05% TFA, 5 min). $^1$H-NMR (400 MHz, DMSO-d$_6$) δ 10.88 (br s, 1H), 7.46 (d, J=7.5 Hz, 1H), 7.23 (m, 3H), 4.70 (s, 2H), 4.25 (br s, 2H), 4.05 (br q, 2H), 3.81 (s, 2H), 3.78 (m, 1H), 3.46 (m, 3H), 3.12 (br m, 2H), 2.46 (br m, 1H), 2.13 (s, 3H), 2.12 (br s, 2H), 1.87 (br m, 4H), 1.69 (br m, 4H), 1.21 (t, J=7.1 Hz, 3H).

Example 6

1-(1'-(4-(ethoxyimino)cyclohexyl)-1H-spiro[isoquinoline-4,4'-piperidine]-2(3H)-yl)ethanone (Compound No. 196)

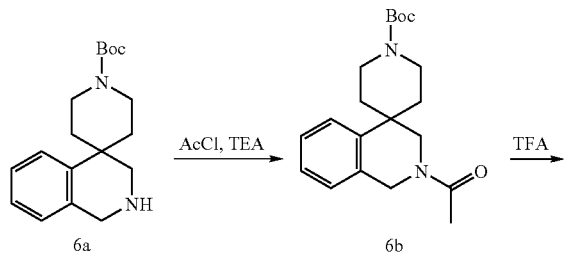

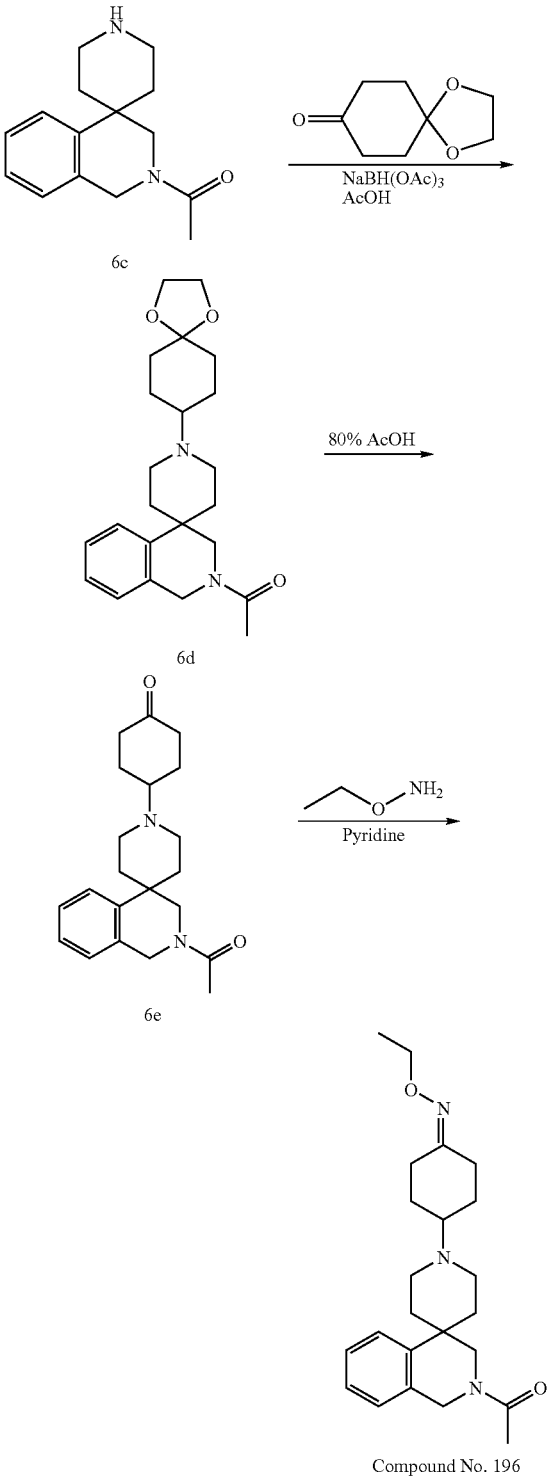

Compound No. 196 tert-Butyl 2,3-dihydro-1H-spiro[isoquinoline-4,4'-piperidine]-1'-carboxylate 6a (2.128 g, 6.28 mmol) was dissolved in anhydrous dichloromethane (30 mL), cooled in an ice-H$_2$O bath and treated dropwise with a solution of acetyl chloride (518 mg, 6.59 mmol) in anhydrous dichloromethane (5 mL). The reaction was then treated dropwise with a solution of triethylamine (1.335 g, 13.2 mmol) in anhydrous dichloromethane (5 mL). The reaction was stirred in the ice-H$_2$O bath for 15 minutes, then diluted with dichloromethane (100 mL), washed with H$_2$O, saturated NaHCO$_3$ (3×), saturated brine, dried (Na$_2$SO$_4$) and filtered. The filtrate was concentrated under reduced pressure to afford crude tert-butyl 2-acetyl-2,3-dihydro-1H-spiro[isoquinoline-4,4'-piperidine]-1'-carboxylate 6b as a colorless oil (2.732 g, quantitative yield). LC/MS m/z [M+H]$^+$ 345.2 retention time 2.98 min (10-99% CH$_3$CN—H$_2$O gradient, with 0.05% TFA, 5 min).

tert-Butyl 2-acetyl-2,3-dihydro-1H-spiro[isoquinoline-4,4'-piperidine]-1'-carboxylate 6b (2.732 g, 6.28 mmol) was dissolved in dichloromethane (20 mL), cooled in an ice-H$_2$O bath, slowly treated with ice-cold trifluoroacetic acid (20 mL) and stirred at ≈0° C. for 30 minutes. The reaction was concentrated under reduced pressure, re-dissolved in acetonitrile and re-concentrated. The oil obtained was cooled in an ice-H$_2$O bath, slowly treated with 1 N NaOH (50 mL) and extracted with dichloromethane (2×100 mL). The pooled extracts were washed with H$_2$O, saturated brine, dried (Na$_2$SO$_4$) and filtered. The filtrate was concentrated under reduced pressure and the resulting free base was dissolved in anhydrous diethyl ether (50 mL) and absolute ethanol (3 mL) and treated dropwise with a small excess of 1 N HCl in ether (6.5 mL). The suspension obtained was diluted with ether (30 mL) and stirred vigorously at room temperature for 10 minutes. The precipitate was filtered, rinsed with ether (2×10 mL) and hexanes (2×10 mL) and dried under reduced pressure to afford 1-(1H-spiro[isoquinoline-4,4'-piperidine]-2(3H)-yl)ethanone 6c as the corresponding HCl salt (1.640 g, 93% yield). LC/MS m/z [M+H]$^+$ 245.2 retention time 1.36 min (10-99% CH$_3$CN—H$_2$O gradient, with 0.05% TFA, 5 min).

1-(1H-spiro[isoquinoline-4,4'-piperidine]-2(3H)-yl)ethanone 6c (300 mg; 1.068 mmol) and 1,4-dioxaspiro[4.5]decan-8-one (250 mg; 1.6 mmol) were dissolved in DCE (5 mL) and treated with TEA (148 uL; 107 mg; 1.068 mmol.). After 10 minutes, NaBH(OAc)$_3$ (452 mg; 2.13 mmol) was added, followed by AcOH (61 uL; 64 mg; 1.06 mmol) and the mixture was allowed to stir at room temperature for 75 hrs. The reaction was quenched by adding MeOH (10 mL) and was allowed to stir for 24 hrs. The resulting suspension was diluted with DCM (30 mL) and NaOH 1N (10 mL) was added. The layers were separated, and the aqueous layer was extracted with DCM (3×30 mL). The combined organic extracts were dried on Na$_2$SO$_4$ and concentrated. The resulting oil was dissolved in Et$_2$O and treated with excess 1N HCl in ether (5 mL). The resulting suspension was fitered, and the precipitate was washed with ether (3×20 mL) and dried to provide the hydrochloride of 1-(1'-(1,4-dioxaspiro[4.5]decan-8-yl)-1H-spiro[isoquinoline-4,4'-piperidine]-2(3H)-yl) ethanone 6d (382 mg, 85% yield. LC/MS m/z [M+H]$^+$ 385.2 retention time 1.7 min (10-99% CH$_3$CN—H$_2$O gradient, with 0.05% TFA, 5 min).

1-(1'-(1,4-dioxaspiro[4.5]decan-8-yl)-1H-spiro[isoquinoline-4,4'-piperidine]-2(3H)-yl)ethanone 6d (350 mg; 0.83 mmol.) was dissolved in 80% aq. AcOH (20 mL) and the solution was refluxed overnight. The reaction mixture was diluted with water (20 mL), cooled on an ice bath and neutralized by addition of solid KOH. The resulting suspension was extracted with DCM (3×30 mL) and the combined organic extracts were dried on Na$_2$SO$_4$ and concentrated to provide the crude 4-(2-acetyl-2,3-dihydro-1H-spiro[isoquinoline-4,4'-piperidine]-1'-yl)cyclohexanone 6e (200 mg, 70% yield) as a white foam. LC/MS m/z [M+H]$^+$ 341.0 retention time 1.47 min (10-99% CH$_3$CN—H$_2$O gradient, with 0.05% TFA, 5 min).

4-(2-Acetyl-2,3-dihydro-1H-spiro[isoquinoline-4,4'-piperidine]-1'-yl)cyclohexanone 6e (100 mg; 0.29 mmol) was dissolved in pyridine (1 mL) and treated with O-ethyl hydroxyamine hydrochloride (34 mg; 0.35 mmol). The vial was sealed and heated to 60° C. for 1 hr. The solvent was evaporated under reduced pressure and the residue was dissolved in DMSO (2 mL) and purified by LC/MS (10-99% CH$_3$CN—H$_2$O gradient, with 0.05% TFA, 9 min) to provide 1-(1'-(4-(ethoxyimino)cyclohexyl)-1H-spiro[isoquinoline-4,4'-piperidine]-2(3H)-yl)ethanone. LC/MS m/z [M+H]$^+$ 384.4 retention time 1.80 min (10-99% CH$_3$CN—H$_2$O gradient, with 0.05% TFA, 5 min). $^1$H-NMR (400 MHz, CDCl$_3$) δ7.69 (d, J=7.8 Hz, 1H), 7.26 (t, J=7.3 Hz, 1H), 7.19-7.15 (m, 1H), 7.01 (d, J=7.5 Hz, 1H), 4.63 (s, 2H), 4.00 (q, J=7.0 Hz, 2H), 3.79 (dd, J=13.4, 18.1 Hz, 2H), 3.41 (d, J=13.0 Hz, 1H), 3.33 (d, J=9.3 Hz, 2H), 3.17 (m, 2H), 3.04-2.98 (m, 2H), 2.59-2.47 (m, 4H), 2.14 (s, 3H), 1.76-1.69 (m, 6H), 1.21-1.14 (t, J=7 Hz, 3H).

Example 7 ethyl 4-((2-acetyl-2,3-dihydro-1H-spiro[isoquinoline-4,4'-piperidine]-1'-yl)methyl)-4-methylpiperidine-1-carboxylate hydrochloride (Compound No. 103)

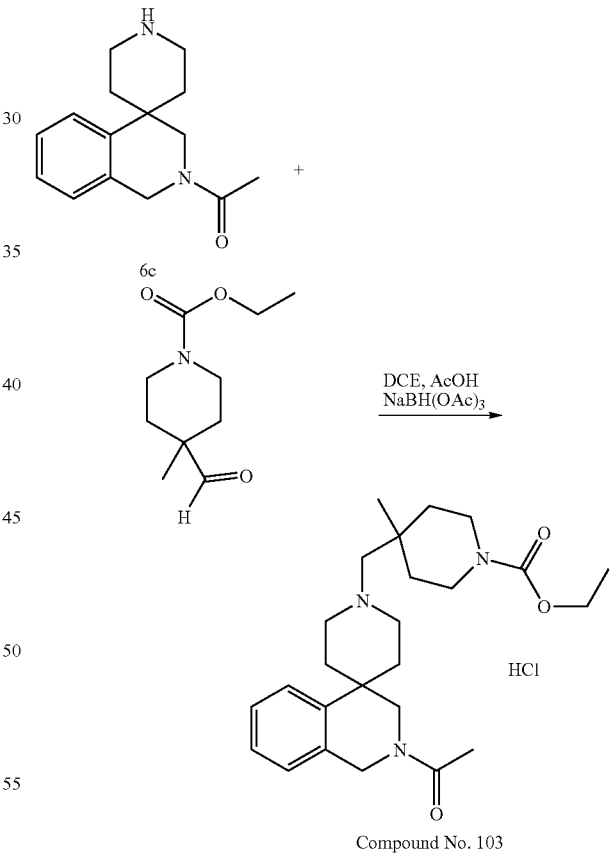

Compound No. 103

1-(1H-spiro[isoquinoline-4,4'-piperidine]-2(3H)-yl)ethanone 6c (free base, 200 mg, 0.82 mmol) was dissolved in 3 mL anhydrous dichloroethane in a scintillation vial followed by the addition of ethyl 4-formyl-4-methylpiperidine-1-carboxylate (245 mg, 1.23 mmol) and acetic acid (150 uL, 2.46 mmol). NaBH(OAc)$_3$ (260 mg, 1.23 mmol) was added in one portion and the reaction allowed to stir for 24 h. The reaction had progressed approximately 25-30%. 3.5 eq of additional aldehyde was added and the reactions stirred for 36 h (≈70% conversion to product). The reaction was quenched with 1.0 mL methanol, filtered, and purified by HPLC (5-99% CH$_3$CN—H$_2$O gradient, with 0.05% TFA, 5 min). The purified TFA salt was dissolved in 20 mL dichloromethane and washed with aqueous 1 N NaOH (1×5 mL), 50% saturated bicarb (1×5 mL), and saturated brine (1×5 mL). The organic layer was dried over Na$_2$SO$_4$, filtered, and the solvent removed in vacuo to yield the product as colorless oil. The free base was dissolved in 5 mL diethyl ether and cooled to 0° C. One equivalent of 1.0 N ethereal HCl was added to the rapidly stirring solution, resulting in the precipitation of the hydrochloride salt as a white solid. The suspension was allowed to stir for 30 min, filtered, and the precipitate was washed with ether (1×25 mL), hexanes (1×25 mL) and dried under vacuum to yield ethyl 4-((2-acetyl-2,3-dihydro-1H-spiro[isoquinoline -4,4'-piperidine]-1'-yl)methyl)-4-methylpiperidine-1-carboxylate hydrochloride as a white solid (100 mg, 26% yield). LC/MS m/z [M+H]$^+$ 428.0 retention time 1.97 min (10-99% CH$_3$CN—H$_2$O gradient, with 0.05% TFA, 5 min).

Example 8

1-(1'-(1-methylcyclohexyl)-1H-spiro[isoquinoline-4,4'-piperidine]-2(3H)-yl)ethanone (Compound No. 4)

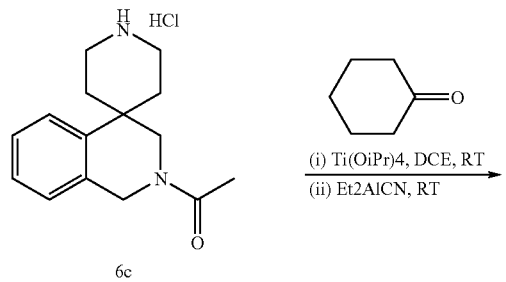

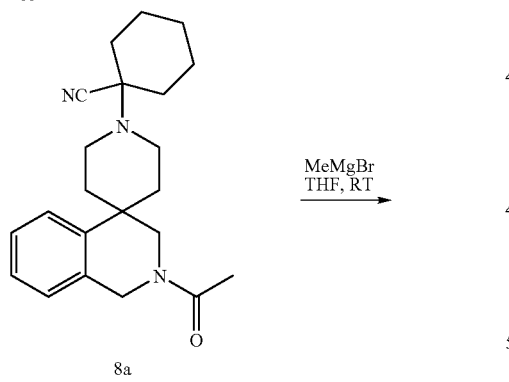

Compound No. 4

1-(1H-spiro[isoquinoline-4,4'-piperidine]-2(3H)-yl)ethanone 6c (140 mg, 0.50 mmol) and cyclohexanone (48 mg, 0.55 mmol) were combined in a scintillation vial and anhydrous 1,2-dichloroethane (1.0 mL) was added, followed by triethylamine (51 mg, 0.5 mmol) and titanium tetraisopropoxide (205 µL, 199 mg, 0.70 mmol). The vial was flushed with nitrogen and stirred at room temperature for ≈48 hours. The reaction was then concentrated under reduced pressure and treated with diethylaluminum cyanide (750 µL 1.0 M solution in toluene, 0.75 mmol). The vial was flushed with nitrogen and stirred at room temperature for 2 hours. The reaction mixture was diluted with ethyl acetate (5 mL), quenched with H$_2$O (1 mL) and stirred at room temperature for an additional 1 hour. The suspension obtained was centrifuged and the supernatants filtered and concentrated under reduced pressure. The crude 1-(2-acetyl-2,3-dihydro-1H-spiro[isoquinoline-4,4'-piperidine]-1'-yl)cyclohexanecarbonitrile intermediate 8a was taken to the next step without further purification.

The crude 1-(2-acetyl-2,3-dihydro-1H-spiro[isoquinoline-4,4'-piperidine]-1'-yl)cyclohexanecarbonitrile 8a was dissolved in anhydrous tetrahydrofuran (1.0 mL) and treated with methylmagnesium bromide (1.0 mL 1.0 M solution in butyl ether, 1.0 mmol). The vial was flushed with nitrogen and stirred at room temperature for 3 hours. The reaction was diluted with ethyl acetate (5.0 mL), quenched with saturated aqueous ammonium chloride (1.0 mL) and stirred overnight at room temperature. The layers were separated, the organic layer concentrated under reduced pressure and purified by reverse-phase HPLC (1-25% CH$_3$CN—H$_2$O gradient, with 0.05% TFA, 15 min) to provide 1-(1'-(1-methylcyclohexyl)-1H-spiro[isoquinoline-4,4'-piperidine]-2(3H)-yl)ethanone. LC/MS m/z [M+H]$^+$ 341.2 retention time 1.83 min (10-99% CH$_3$CN—H$_2$O gradient, with 0.05% TFA, 5 min).

Example 9 ethyl 4-(2-isopentyl-2,3-dihydro-1H-spiro[isoquinoline-4,4'-piperidine]-1'-yl)piperidine-1-carboxylate (Compound No. 313)

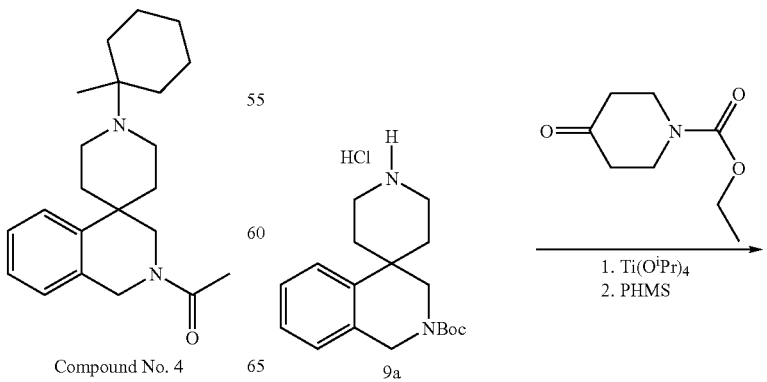

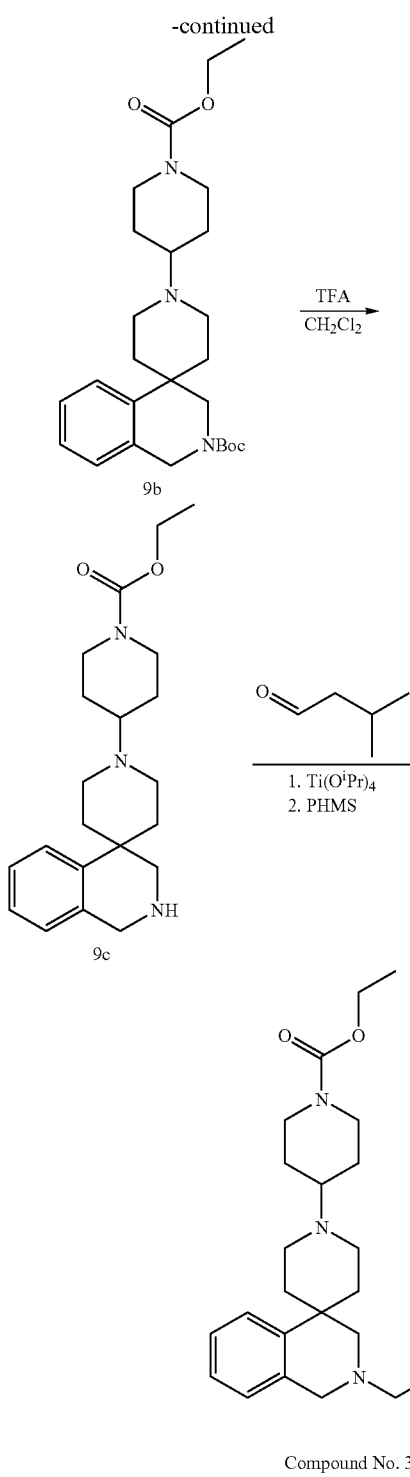

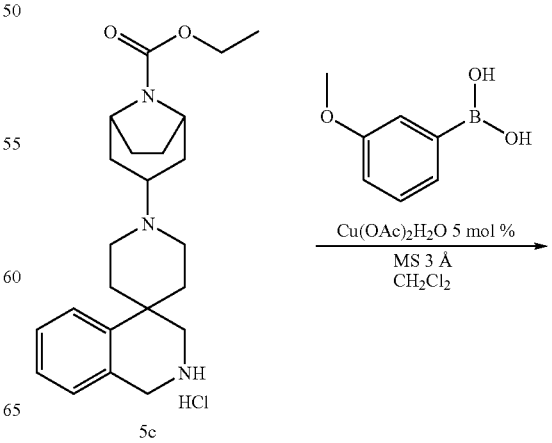

crude redissolved in CH$_2$Cl$_2$, adsorbed onto Celite and purified by silica gel chromatography eluting with 3-10% MeOH in CH$_2$Cl$_2$ with 2% NH$_4$OH to give tert-butyl 1'-(1-(ethoxycarbonyl)piperidin-4-yl)-1H-spiro[isoquinoline-4,4'-piperidine]-1-yl)-2(3H)-carboxylate 9b as a yellow solid (1.55 g, 58% yield). LC-MS m/z [M+H]$^+$ 458.31, retention time 2.26 min (10-90% CH$_3$CN—H$_2$O gradient, with 0.05% TFA, 5 min).

Tert-butyl 1'-(1-(ethoxycarbonyl)piperidin-4-yl)-1H-spiro[isoquinoline-4,4'-piperidine]-1-yl)-2(3H)-carboxylate 9b (0.63 g, 1.38 mmol) was dissolved in CH$_2$Cl$_2$ (5 mL) and TFA was added (5 mL). The reaction mixture was stirred at room temperature for 40 min. The solvent was removed in vacuo and azeotroped with CH$_2$Cl$_2$ (2×10 mL). The mixture was cooled to 0° C. and basified with 1N NaOH, followed by extraction with EtOAc (3×20 mL). The organics were combined, dried over Na$_2$SO$_4$, filtered and evaporated to give ethyl 4-(2,3-dihydro-1H-spiro[isoquinoline-4,4'-piperidine]-1-yl)piperidine-1-carboxylate 9c as a yellow oil (0.432 g, 88% yield). FIA m/z [M+H]$^+$ 358.3.

To a solution of 4-(2,3-dihydro-1H-spiro[isoquinoline-4,4'-piperidine]-1-yl)piperidine-1-carboxylate 9c (0.040 g, 0.112 mmol) in anhydrous THF (1 mL) was added titanium tetraisopropoxide (0.067 mL, 0.22 mmol) and the reaction was stirred at room temperature for 18 h. PHMS (20 uL, 0.33 mmol) was added and the reaction was stirred at room temperature for 2 d. MeOH (0.5 mL) was added and the reaction was allowed to stir at room temperature for 1 h. The solvents were removed in vacuo, and the compound purified by on an Agilent 1100 semi-prep HPLC (15-35% CH$_3$CN—H$_2$O gradient, with 0.1% TFA, 20 min) to give ethyl 4-(2-isopentyl-2,3-dihydro-1H-spiro[isoquinoline-4,4'-piperidine]-1'-yl)piperidine-1-carboxylate (compound no. 313) as an oil. LC-MS: m/z [M+H]$^+$ 428.6 retention time 1.65 min, (10-90% CH$_3$CN—H$_2$O gradient, with 0.05% TFA, 5 min). $^1$H-NMR (DMSO-d$_6$, 500 MHz) δ 9.58-9.22 (m, 2H), 7.46 (s, 2H), 7.39-7.22 (m, 2H), 4.62-4.50 (m, 1H), 4.40-4.27 (m, 1H), 4.19-3.99 (m, 5H), 3.5-3.03 (m, 8H), 2.93-2.76 (m, 2H), 2.39-2.25 (m, 2H), 2.18-2.00 (m, 3), 1.90-1.79 (m, 1H), 1.77-1.50 (m, 5H), 1.20 (t, 3H), 1.01-0.88 (m, 6H).

Example 10 ethyl 3-(2-(3-methoxyphenyl)-2,3-dihydro-1H-spiro[isoquinoline-4,4'-piperidine]-1'-yl)-8-azabicyclo[3.2.1]octane-8-carboxylate (Compound No. 141)

A suspension of tert-butyl-1H-spiro[isoquinoline-4,4'-piperidine]-2(3H)-carboxylate hydrochloride 9a (2.0 g, 5.9 mmol) 1-carbethoxy-4-piperidone (1.35 g, 8.9 mmol) and titanium tetraisopropoxide (3.5 mL, 11.7 mmol) in anhydrous THF (30 mL) was stirred at room temperature for 1 h. Poly(methylhydrosiloxane) (PHMS, 1.1 g, 18.3 mmol) was added and the reaction stirred at room temperature for 4 d. MeOH (5 mL) was added and the reaction was allowed to stir at room temperature for 1 h. The solvents were removed in vacuo, the

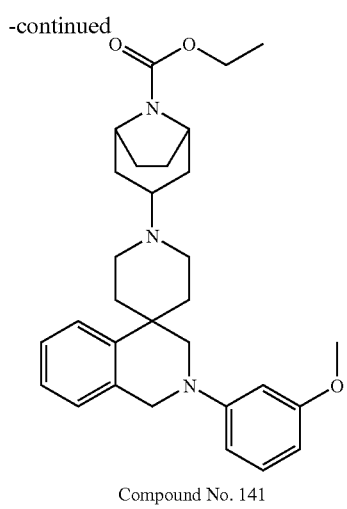

Compound No. 141

A suspension of 3-methoxyphenylboronic acid (30 mg, 0.2 mmol), Cu(OAc)₂H₂O (2 mg, 5 mol %), 3 Å molecular sieves (75 mg) in 1 mL of CH₂Cl₂ were stirred at room temperature for 5 min. Ethyl 3-(2,3-dihydro-1H-spiro[isoquinoline-4,4'-piperidine]-1'-yl)-8-azabicyclo[3.2.1]octane-8-carboxylate hydrochloride 5c (42 mg, 0.1 mmol) was added to the reaction and mixture was stirred at room temperature for 24 h. The reaction was diluted with methanol, filtered and subjected to reverse-phase HPLC purification (2-50% CH₃CN—H₂O gradient, with 0.05% TFA, 15 min) to give pure ethyl 3-(2-(3-methoxyphenyl)-2,3-dihydro -1H-spiro[isoquinoline-4,4'-piperidine]-1'-yl)-8-azabicyclo[3.2.1]octane-8-carboxylate. LC-MS: m/z [M+H]⁺ 490.0, retention time 2.61 min (10-90% CH₃CN—H₂O gradient, with 0.05% TFA, 5 min).

Example 11

[Ethyl 3-(2-(4-fluorophenylsulfonyl)-2,3-dihydro-1H-spiro -[isoquinoline-4,4'-piperidine]-1'-yl)-8-azabicyclo[3.2.1]-octane-8-carboxylate hydrochloride] (Compound No. 205)

[Ethyl 3-(2-(4-fluorophenylsulfonyl)-2,3-dihydro-1H-spiro-[isoquinoline4,4'-piperidine]-1'-yl)-8-azabicyclo [3.2.1]-octane-8-carboxylate hydrochloride] was synthesized using known methods and those described above. LC-MS: m/z [M+H]⁺ 542.4, Retention time 2.58 min (10-90% CH₃CN—H₂O gradient, with 0.05% TFA, 5 min). ¹H-NMR (400 MHz, DMSO-d₆) δ 11.09 (br s, 1H), 8.05 (m, 2H), 7.56 (m, 3H), 7.29 (t, J=7.5 Hz, 1H), 7.19 (m, 2H), 4.28 (m, 2H), 4.15 (s, 2H), 4.08 (m, 2H), 3.74 (m, 1H), 3.53 (m, 2H), 3.37 (m, 2H), 3.08 (m, 3H), 2.57 (m, 1H), 2.13 (m, 2H), 1.86 (m, 6H), 1.70 (m, 2H), 1.22 (t, J=7.1 Hz, 3H).

Example 12

[Ethyl 4-((2-acetyl-2,3-dihydro-1H-spiro[isoquinoline-4,4'-piperidine]-1'-yl)methyl)piperidine-1-carboxylate hydrochloride] (Compound No. 198)

[Ethyl 4-((2-acetyl-2,3-dihydro-1H-spiro[isoquinoline-4,4'-piperidine]-1'-yl)methyl)piperidine-1-carboxylate hydrochloride] was synthesized using known methods and those described above. LC-MS: m/z [M+H]⁺ 414.4, Retention time 1.94 min (10-90% CH₃CN—H₂O gradient, with 0.05% TFA, 5 min). ¹H-NMR (400 MHz, CDCl₃) δ 12.21 (br s, 1H), 7.76 (d, J=7.8 Hz, 1H), 7.33 (t, J=7.4 Hz, 1H), 7.25 (t, J=7.3 Hz, 1H), 7.08 (d, J=7.5 Hz, 1H), 4.71 (s, 2H), 4.22 (m, 2H), 4.12 (q, J=7.1 Hz, 2H), 3.89 (m, 2H), 3.52 (m, 2H), 3.13 (m, 4H), 2.91 (m, 2H), 2.79 (m, 2H), 2.21 (s, 3H), 2.16 (m, 2H), 1.68 (m, 2H), 1.32 (m, 3H), 1.26 (t, J=7.1 Hz, 3H).

Example 13

[Ethyl 3-(2-(3,5-dimethylisoxazol-4-ylcarbamoyl)-2,3-dihydro-1H -spiro[isoquinoline-4,4'-piperidine]-1'-yl)-8-azabicyclo[3.2.1]octane-8-carboxylate hydrochloride] (Compound No. 233)

[Ethyl 3-(2-(3,5-dimethylisoxazol-4-ylcarbamoyl)-2,3-dihydro-1H -spiro[isoquinoline-4,4'-piperidine]-1'-yl)-8-azabicyclo[3.2.1]octane-8-carboxylate hydrochloride] was synthesized using known methods and those described above. LC-MS: m/z [M+H]⁺ 522.5, Retention time 2.29 min (10-90% CH₃CN—H₂O gradient, with 0.05% TFA, 5 min). ¹H-NMR (400 MHz, DMSO-d₆) δ 10.44 (br s, 1H), 8.34 (s, 1H), 7.46 (d, J=7.5 Hz, 1H), 7.30 (t, J=7.6 Hz, 1H), 7.25 (t, J=7.4 Hz, 1H), 7.16 (d, J=7.4 Hz, 1H), 4.75 (s, 2H), 4.25 (m, 2H), 4.08 (q, J=7.0 Hz, 2H), 3.86 (m, 3H), 3.51 (m, 2H), 3.29 (m, 2H), 2.42 (m, 2H), 2.23 (s, 3H), 2.10 (m, 2H), 2.06 (s, 3H), 1.85 (m, 4H), 1.71 (m, 4H), 1.21 (t, J=7.1 Hz, 3H).

Example 14

[Propyl 4-(2-acetyl-2,3-dihydro-1H-spiro[isoquinoline-4,4'-piperidine]-1'-yl)piperidine-1-carboxylate hydrochloride] (Compound No. 129)

[Propyl 4-(2-acetyl-2,3-dihydro-1H-spiro[isoquinoline-4,4'-piperidine]-1'-yl)piperidine-1-carboxylate hydrochloride] was synthesized using known methods and those described above. LC-MS: m/z [M+H]⁺ 414.4, Retention time 1.87 min (10-90% CH₃CN—H₂O gradient, with 0.05% TFA, 5 min). ¹H-NMR (400 MHz, DMSO-d₆) δ 11.13 (br s, 1H), 7.52 (d, J=7.5 Hz, 1H), 7.24 (m, 3H), 4.72 (s, 2H), 4.13 (m, 2H), 3.97 (t, J=6.6 Hz, 2H), 3.82 (s, 2H), 3.45 (m, 3H), 3.19 (m, 2H), 2.83 (br s, 2H), 2.60 (m, 2H), 2.21 (m, 2H), 2.12 (s, 3H), 1.66 (m, 6H), 0.91 (t, J=7.4 Hz, 3H).

Example 15

[Ethyl 3-(2-(cyclopropanecarbonyl)-2,3-dihydro-1H-spiro[isoquinoline -4,4'-piperidine]-1'-yl)-8-azabicyclo-[3.2.1]octane-8-carboxylate hydrochloride] (Compound No. 224)

[Ethyl 3-(2-(cyclopropanecarbonyl)-2,3-dihydro-1H-spiro[isoquinoline-4,4'-piperidine]-1'-yl)-8-azabicyclo-[3.2.1]octane-8-carboxylate hydrochloride] was synthesized using known methods and those described above. LC-MS: m/z [M+H]⁺ 452.4, Retention time 2.05 min (10-90% CH₃CN—H₂O gradient, with 0.05% TFA, 5 min). ¹H-NMR (400 MHz, CDCl₃) δ 12.31 (br s, 1H), 7.74 (d, J=7.6 Hz, 1H), 7.32 (t, J=7.1 Hz, 1H), 7.25 (t, J=7.5 Hz, 1H), 7.11 (d, J=7.5 Hz, 1H), 4.93 (s, 2H), 4.47 (br s, 2H), 4.17 (q, J=7.1 Hz, 2H), 3.86 (m, 2H), 3.59 (m, 1H), 3.38 (m, 2H), 3.15 (m, 2H), 3.01 (m, 2H), 2.21 (m, 2H), 2.04 (m, 4H), 1.70 (m, 4H), 1.28 (t, J=7.1 Hz, 3H), 0.99 (m, 2H), 0.87 (m, 3H).

Example 16

[Ethyl 4-((2-benzoyl-2,3-dihydro-1H-spiro[isoquinoline-4,4'-piperidine]-1'-yl)methyl)piperidine-1-carboxylate hydrochloride] (Compound No. 147)

[Ethyl 4-((2-benzoyl-2,3-dihydro-1H-spiro[isoquinoline-4,4'-piperidine]-1'-yl)methyl)piperidine-1-carboxylate hydrochloride] was synthesized using known methods and those described above. LC-MS: m/z [M+H]$^+$ 476.2, Retention time 2.21 min (10-90% CH$_3$CN—H$_2$O gradient, with 0.05% TFA, 5 min). $^1$H-NMR (400 MHz, DMSO-d$_6$) δ 10.62 (br s, 1H), 7.61 (d, J=7.9 Hz, 1H), 7.47 (m, 5H), 7.29 (t, J=7.6 Hz, 1H), 7.17 (t, J=7.3 Hz, 1H), 7.02 (m, 1H), 4.64 (br s, 2H), 4.04 (q, J=7.1 Hz, 2H), 3.99 (m, 4H), 3.49 (m, 2H), 3.36 (m, 2H), 3.09 (m, 2H), 2.82 (m, 2H), 2.71 (m, 2H), 2.11 (m, 1H), 1.90 (m, 2H), 1.71 (m, 2H), 1.19 (t, J=7.1 Hz, 3H), 1.12 (m, 2H).

Example 17

Ethyl 4-(2-cycloheptyl-2,3-dihydro-1H-spiro[isoquinoline-4,4-piperidine]-1'-yl)piperidine-1-carboxylate (Compound No. 172)

Ethyl 4-(2-cycloheptyl-2,3-dihydro-1H-spiro[isoquinoline-4,4-piperidine]-1'-yl)piperidine-1-carboxylate was synthesized using known methods and those described above. LC-MS: m/z [M+H]$^+$ 453.3, Retention time 1.70 min (10-90% CH$_3$CN—H$_2$O gradient, with 0.05% TFA, 5 min). $^1$H-NMR (DMSO-d$_6$, 500 MHz) δ 9.66-9.22 (m, 1H), 9.16-8.97 (m, 1H), 7.52-7.41 (m, 2H), 7.39-7.30 (m, 1H), 7.29-7.20 (m, 1H), 4.61-4.45 (m, 1H), 4.39-4.26 (m, 1H), 4.21-4.00 (m, 4H), 3.94-3.82 (m, 1H), 3.75-3.04 (m, 8H), 2.94-2.75 (m, 4H), 2.40-2.31 (m, 1H), 2.25-1.99 (m, 5H), 1.95-1.70 (m, 5H), 1.66-1.42 (m, 8H), 1.20 (t, 3H).

Example 18

The examples and synthetic schemes described herein along with known methods are useful for producing additional compounds of the present invention, including the compounds in Table 2 below.

TABLE 2

Physical data for exemplary compounds.

| Compound No. | LC/MS M + 1 | LC/RT min | NMR |
|---|---|---|---|
| 1 | 386 | 1.74 | |
| 2 | 368.2 | 2.18 | |
| 3 | 533.2 | 2.31 | |
| 5 | 336.2 | 1.09 | |
| 6 | 414.5 | 2.28 | |
| 7 | 469.4 | 2.36 | |
| 8 | 470.2 | 2.35 | |
| 9 | 472.6 | 1.9 | |
| 10 | 454.5 | 2.55 | |
| 11 | 444.4 | 2.24 | |
| 12 | 488 | 2.86 | |
| 13 | 468.4 | 2.01 | |
| 14 | 496.2 | 2.5 | |
| 15 | 548.5 | 2.49 | |
| 16 | 477.4 | 2.17 | |
| 17 | 489.2 | 1.79 | |
| 18 | 538.4 | 2.6 | |
| 19 | 344.09 | 2.17 | |
| 21 | 353.5 | 2.06 | |
| 22 | 474.4 | 2.09 | |
| 23 | 460.2 | 1.95 | |
| 24 | 532.2 | 2.34 | |
| 25 | 517.4 | 2.31 | |
| 26 | 231.1 | 1.2 | DMSO-d6: 8.05(d, 1H), 7.73(d, 1H), 7.64(t, 1H), 7.57(t, 1H), 3.49(m, 2H), 3.42(q, 2H), 2.41(m, 2H), 1.59(m, 2H), 1.21(t, 3H) |
| 27 | 482 | 2.41 | |
| 28 | 359.4 | 1.9 | CD3OD: 8.06(d, 1H), 7.84(d, 1H), 7.67(t, 1H), 7.62(t, 1H), 3.81(m, 2H), 3.54(m, 3H), 3.42(m, 2H), 2.59-2.71(m, 6H), 1.32(t, 3H) |
| 29 | 592.4 | 2.8 | |
| 30 | 524.6 | 2.5 | |
| 31 | 339.1 | 1.92 | |
| 32 | 442.4 | 1.92 | |
| 33 | 494.4 | 2.18 | |
| 34 | 528.2 | 2.19 | |
| 35 | 341.5 | 2.09 | |
| 36 | 483.2 | 2.28 | |
| 37 | 366.2 | 1.81 | |
| 38 | 493.4 | 2.04 | |
| 39 | 497.4 | 2.14 | |
| 40 | 336.4 | 1.65 | |
| 41 | 316.2 | 1.87 | |
| 42 | 480 | 1.78 | CD3OD: 7.94(d, 2H), 7.74(t, 1H), 7.66(t, 1H), 7.43-7.49(m, 5H), 7.31(d, 4H), 7.20(m, 1H), 4.85(brs, 2H), 3.60-3.85(m, 5H), 2.55(m, 2H), 1.75(brm, 9H) |
| 43 | 508.4 | 2.6 | |
| 44 | 512.4 | 2.45 | |
| 45 | 456 | 1.81 | |
| 46 | 453.3 | 2.29 | |
| 47 | 532.2 | 2.35 | |
| 49 | 480.2 | 2.35 | |
| 50 | 372.2 | 1.6 | |
| 51 | 491.4 | 2.32 | |
| 52 | 389 | 1.9 | CD3OD: 8.08(d, 1H), 7.94(m, 1H), 7.73(t, 1H), 7.67(t, 1H), 7.31(m, 4H), 7.25(m, 1H), 4.83(s, 2H), 3.73(m, 2H), 3.57(m, 2H), 3.18(d, 2H), 2.64(m, 2H), 1.66-1.86(m, 8H), 1.23-1.37(m, 3H), 1.08(m, 2H) |
| 53 | 457 | 2.17 | |

TABLE 2-continued

Physical data for exemplary compounds.

| Compound No. | LC/MS M + 1 | LC/RT min | NMR |
|---|---|---|---|
| 54 | 299.3 | 1.7 | CD3OD: 7.79(d, 1H), 7.70(t, 1H), 7.56(t, 2H), 3.77(m, 2H), 3.23(m, 2H), 3.06(d, 2H), 2.60(m, 2H), 1.79-1.88(m, 7H), 1.10-1.40(m, 6H) |
| 55 | 482.4 | 2.21 | |
| 56 | 458.4 | 2.39 | |
| 57 | 344 | 2.14 | |
| 58 | 342.8 | 1.76 | |
| 59 | 407.4 | 2.09 | |
| 60 | 386.3 | 1.6 | DMSO-d6: 8.03(d, 1H), 7.74(d, 1H), 7.64(t, 1H), 7.58(t, 1H), 4.16(m, 2H), 4.06(q, 2H), 3.43-3.83(m, 5H), 3.43(q, 2H), 2.85(m, 2H), 2.19(m, 2H), 1.62-1.70(m, 4H), 1.20(m, 6H) |
| 61 | 483.2 | 2.25 | |
| 62 | 451.3 | 1.5 | |
| 63 | 428 | 2.02 | |
| 64 | 520.4 | 2.5 | |
| 65 | 379.4 | 2.21 | |
| 66 | 365.4 | 1.96 | |
| 67 | 608.2 | 2.8 | |
| 68 | 399.2 | 1.94 | |
| 69 | 558.2 | 2.55 | |
| 70 | 450.2 | 2.06 | |
| 71 | 506.4 | 2.33 | |
| 72 | 510.4 | 2.52 | |
| 73 | 486.4 | 2.09 | |
| 74 | 400 | 1.78 | |
| 75 | 399 | 1.9 | CD3OD: 8.06(d, 1H), 7.94(m, 1H), 7.73(t, 1H), 7.65(m, 1H), 7.23-7.33(m, 5H), 6.30(m, 1H), 6.04(m, 1H), 4.83(s, 2H), 3.76(m, 2H), 3.54(, 2H), 3.15(m, 1H), 2.90-3.00(m, 3H), 2.60(m, 3H), 2.9(m, 1H), 1.67(m, 2H), 1.52(m, 1H), 1.37(m, 1H), 0.75(m, 1H) |
| 76 | 455.2 | 2.03 | |
| 77 | 490.4 | 2.31 | |
| 78 | 301.2 | 1.39 | |
| 79 | 494.4 | 2.18 | |
| 80 | 532.2 | 2.58 | |
| 81 | 488.4 | 2.38 | |
| 82 | 496 | 2.81 | |
| 83 | 419.2 | 2.26 | |
| 84 | 496.2 | 1.89 | |
| 85 | 245.2 | 1.36 | |
| 86 | 522.4 | 2.56 | |
| 87 | 454.6 | 1.7 | |
| 88 | 414.4 | 2.13 | |
| 89 | 303.2 | 1.49 | |
| 90 | 456.4 | 2.03 | |
| 91 | 443.2 | 2 | |
| 92 | 622.4 | 2.57 | |
| 93 | 385.2 | 1.72 | |
| 94 | 367.2 | 2.21 | |
| 95 | 524.4 | 2.48 | |
| 96 | 516.2 | 2.19 | |
| 97 | 470.4 | 1.93 | |
| 98 | 342.4 | 1.54 | |
| 99 | 470.2 | 2.3 | |
| 100 | 393.2 | 2.28 | |
| 101 | 353.2 | 1.98 | |
| 102 | 478.2 | 2.43 | |
| 104 | 443.4 | 2.01 | |
| 105 | 393.2 | 1.97 | |
| 106 | 457.2 | 2.13 | |
| 107 | 383.2 | 1.99 | |
| 108 | 542.4 | 2.02 | |
| 109 | 469.4 | 2.08 | |
| 110 | 455.2 | 2.07 | |
| 111 | 481.2 | 2.18 | |
| 112 | 496.4 | 2.66 | |
| 113 | 528.3 | 2.04 | |
| 114 | 510 | 2.95 | |
| 115 | 353.2 | 1.95 | |
| 116 | 377.2 | 1.97 | |
| 117 | 509.4 | 2.07 | |
| 118 | 393.2 | 1.95 | |
| 119 | 516.2 | 2.6 | |
| 120 | 430.4 | 2.09 | |
| 121 | 365 | 1.98 | |
| 122 | 442.2 | 2.32 | |
| 123 | 454.6 | 1.6 | |
| 124 | 482.2 | 2.25 | |
| 125 | 505.2 | 2.53 | |
| 126 | 494.4 | 2.2 | |
| 127 | 483.2 | 2.28 | |
| 128 | 430.2 | 2.09 | |
| 130 | 377 | 1.93 | CD3OD: 8.10(d, 1H), 7.95(d, 1H), 7.74(t, 1H), 7.67(d, 1H), 7.31(d, 4H), 7.24(m, 1H), 4.83(s, 2H), 3.75(m, 2H), 3.59(m, 2H), 2.54(m, 2H), 1.69(m, 4H), 1.01(s, 9H) |
| 131 | 517.2 | 2.53 | |
| 132 | 521.4 | 2.41 | |
| 133 | 386.2 | 1.86 | |
| 134 | 331.17 | 1.7 | CD3OD: 7.90(d, 1H), 7.68(t, 1H), 7.56(m, 2H), 3.77(m, 2H), 3.25(m, 3H), 2.55-2.70(m, 6H), 2.07(m, 2H), 1.74-1.83(m, 4H), 1.45(m, 3H) |
| 135 | 367.2 | 2.06 | |
| 136 | 496 | 2.83 | |
| 137 | 379.2 | 2.1 | |
| 138 | 528.2 | 2.19 | |
| 139 | 324.8 | 1.68 | |
| 140 | 412.2 | 1.95 | |
| 142 | 355 | 1.84 | |
| 143 | 498.6 | 2.1 | |
| 144 | 377.2 | 1.86 | |

TABLE 2-continued

Physical data for exemplary compounds.

| Compound No. | LC/MS M + 1 | LC/RT min | NMR |
|---|---|---|---|
| 145 | 387.1 | 2.16 | |
| 146 | 494.4 | 2.27 | |
| 148 | 484.4 | 2.48 | |
| 149 | 506.3 | 2.28 | |
| 150 | 365 | 1.98 | |
| 151 | 463.3 | 2.25 | |
| 152 | 369 | 1.94 | |
| 153 | 341.2 | 1.49 | |
| 154 | 476.2 | 2.34 | |
| 155 | 531.4 | 2.44 | |
| 156 | 436.4 | 1.9 | |
| 157 | 500.2 | 2.38 | |
| 158 | 430.4 | 1.92 | |
| 159 | 478 | 2.71 | |
| 160 | 339 | 1.83 | |
| 161 | 428.2 | 2.03 | |
| 162 | 482.4 | 2.4 | |
| 163 | 483.4 | 2.31 | |
| 164 | 470.4 | 2.39 | |
| 165 | 468.2 | 2.26 | |
| 166 | 444.4 | 2.23 | |
| 167 | 448.5 | 1.6 | |
| 168 | 429.5 | 2.23 | |
| 169 | 492 | 2.85 | |
| 170 | 379.2 | 2.11 | |
| 171 | 510.2 | 2.03 | |
| 173 | 442.4 | 2.11 | |
| 174 | 474 | 2.76 | |
| 175 | 500.2 | 2.4 | |
| 176 | 465.2 | 2.07 | |
| 177 | 428.2 | 2.15 | |
| 178 | 482.5 | 2.78 | |
| 179 | 510.5 | 2.07 | |
| 180 | 302.2 | 1.72 | |
| 181 | 504.2 | 2.11 | |
| 182 | 343.2 | 1.79 | |
| 183 | 472.2 | 2.19 | |
| 184 | 442.2 | 2.15 | |
| 185 | 428.5 | 2.39 | |
| 186 | 458.4 | 2.41 | |
| 187 | 315.2 | 1.56 | |
| 188 | 393 | 1.93 | |
| 189 | 496.4 | 2.68 | |
| 190 | 498.6 | 2.21 | |
| 191 | 391 | 2.33 | |
| 192 | 395.2 | 2.08 | |
| 193 | 494.4 | 2.46 | |
| 194 | 508.4 | 2.73 | |
| 195 | 512.4 | 2.39 | |
| 199 | 353.2 | 1.86 | |
| 200 | 602.2 | 2.34 | |
| 201 | 462.2 | 2.06 | |
| 202 | 456.2 | 2.29 | |
| 203 | 523.4 | 2.03 | |
| 204 | 429 | 1.91 | |
| 206 | 456.4 | 2.38 | |
| 207 | 444.2 | 1.82 | |
| 208 | 440.6 | 2.1 | |
| 209 | 468.5 | 2.43 | |
| 210 | 548.2 | 2.21 | |
| 211 | 469.3 | 2.24 | |
| 212 | 524.4 | 2.48 | |
| 213 | 493.4 | 2.26 | |
| 214 | 467.4 | 2.07 | |
| 215 | 329.2 | 1.57 | |
| 216 | 400 | 2.1 | |
| 217 | 375.2 | 2.26 | |
| 218 | 538.4 | 2.49 | |
| 219 | 506.4 | 2.15 | |
| 220 | 538.5 | 2.65 | |
| 221 | 462.2 | 2.13 | |
| 222 | 504.2 | 2.11 | |
| 223 | 532.2 | 2.41 | |
| 225 | 454.5 | 2.34 | |
| 226 | 554.4 | 2.53 | |
| 227 | 387 | 1.77 | CD3OD: 8.08(d, 1H), 7.94(m, 1H), 7.73(t, 1H), 7.67(t, 1H), 7.31(m, 4H), 7.20(m, 1H), 7.92(d, 1H), 7.76(d, 1H), 3.74(m, 3H), 3.60(m, 2H), 2.64-2.73(m, 3H), 2.39(m, 1H), 2.15(m, 1H), 1.40-1.70(m, 7H), 1.45(m, 1H), 1.25(m, 1H) |
| 228 | 534.2 | 2.58 | |
| 229 | 442.5 | 2.52 | |
| 230 | 393.2 | 2.11 | |
| 231 | 558.2 | 2.67 | |
| 232 | 440.4 | 1.97 | |
| 234 | 512.4 | 2.4 | |
| 235 | 520.2 | 2.4 | |
| 236 | 489.4 | 1.97 | |
| 237 | 484.4 | 2.18 | |
| 238 | 484.4 | 2.48 | |
| 239 | 361.2 | 2.23 | |
| 240 | 416.2 | 1.95 | |
| 241 | 505.2 | 2.51 | |
| 242 | 457.2 | 2.19 | |
| 243 | 456.4 | 1.8 | |
| 244 | 466.4 | 2.11 | |
| 245 | 600.2 | 2.91 | |
| 246 | 543.4 | 2.48 | |
| 247 | 353 | 1.95 | |
| 248 | 354.2 | 0.54 | |
| 249 | 521.2 | 2.31 | |
| 250 | 440.5 | 2.52 | |
| 251 | 592.4 | 2.78 | |
| 252 | 454 | 2.18 | |
| 253 | 558.2 | 2.67 | |
| 254 | 444.4 | 2.22 | |
| 255 | 491.2 | 2.22 | |
| 256 | 316.6 | 1.62 | |
| 257 | 455.2 | 2.05 | |
| 258 | 426.2 | 2.17 | |
| 259 | 466.2 | 2.38 | |
| 260 | 536.4 | 2.21 | |
| 261 | 481.5 | 2.38 | |
| 262 | 379 | 2.28 | |
| 263 | 484.4 | 2.49 | |
| 264 | 480.3 | 2.08 | |
| 265 | 440.4 | 2.21 | |
| 266 | 342.8 | 1.57 | |
| 268 | 345.2 | 1.69 | |
| 269 | 339.2 | 1.83 | |
| 270 | 442.2 | 2.13 | |
| 271 | 468.4 | 2.43 | |
| 272 | 520.2 | 2.36 | |
| 273 | 456.2 | 2.17 | |
| 274 | 336.2 | 1.25 | |
| 275 | 495.4 | 2.14 | |
| 276 | 393.2 | 1.96 | |
| 277 | 373 | 1.99 | |
| 278 | 353.1 | 2.13 | |
| 279 | 428.5 | 2.4 | |
| 280 | 327 | 1.66 | CD3OD: 8.07(d, 1H), 7.84(d, 1H), 7.70(t, 1H), 7.62(t, 1H), 3.81(m, 2H), |

TABLE 2-continued

Physical data for exemplary compounds.

| Compound No. | LC/MS M + 1 | LC/RT min | NMR |
|---|---|---|---|
| | | | 3.56(m, 4H), |
| | | | 3.24(d, 2H), |
| | | | 2.70(m, 2H), |
| | | | 1.73-1.91(m, 6H), |
| | | | 1.14-1.40(m, 5H), |
| | | | 1.12(m, 2H) |
| 281 | 336.2 | 2 | DMSO-d6: |
| | | | 8.20(d, 1H), |
| | | | 7.73(d, 1H), |
| | | | 7.64(t, 1H), |
| | | | 7.57(t, 1H), |
| | | | 6.30(m, 1H), |
| | | | 6.07(m, 1H), |
| | | | 3.65(m, 2H), |
| | | | 3.42(m, 2H), |
| | | | 2.50-3.25(m, 6H), |
| | | | 2.02(m, 1H), |
| | | | 1.63(m, 2H), |
| | | | 1.40(m, 1H), |
| | | | 1.31(m, 1H), |
| | | | 0.72(m, 1H) |
| 282 | 512.4 | 2.5 | |
| 283 | 469.2 | 2.15 | |
| 284 | 454.2 | 2.24 | |
| 285 | 507.3 | 2.12 | |
| 286 | 400.2 | 2.01 | |
| 287 | 400.4 | 1.9 | |
| 288 | 443.4 | 2.06 | |
| 289 | 468.4 | 2.29 | |
| 290 | 484.4 | 2.18 | |
| 291 | 440.4 | 2.08 | |
| 292 | 581.2 | 2.33 | |
| 293 | 492.2 | 2.16 | |
| 294 | 327.2 | 1.99 | |
| 295 | 440.3 | 2.38 | |
| 296 | 443.4 | 1.99 | |
| 297 | 351.2 | 1.84 | |
| 298 | 353.1 | 2.03 | |
| 299 | 489.2 | 1.71 | |
| 300 | 476.2 | 2.36 | |
| 301 | 370 | 1.61 | |
| 302 | 442.4 | 1.92 | |
| 303 | 504.2 | 2.55 | |
| 304 | 533.2 | 2.29 | |
| 305 | 507.2 | 2.07 | |
| 306 | 454.2 | 2.2 | |
| 307 | 496 | 2.73 | |
| 308 | 485.4 | 2.18 | |
| 309 | 458.4 | 2.35 | |
| 310 | 456.4 | 2.38 | |
| 311 | 436.4 | 2 | |
| 312 | 371.2 | 1.92 | |
| 315 | 470.4 | 2.39 | |
| 316 | 530.2 | 2.46 | |
| 317 | 469.4 | 2.35 | |
| 318 | 479.2 | 2.09 | |
| 319 | 466.4 | 2.28 | |
| 320 | 400 | 2.1 | |
| 321 | 495.2 | 2.3 | |
| 322 | 360 | 1.81 | |
| 323 | 305.3 | 1.6 | CD3OD: |
| | | | 7.80(m, 1H), |
| | | | 7.69(t, 1H), |
| | | | 7.57(t, 2H), |
| | | | 3.80(m, 2H), |
| | | | 3.35(m, 4H), |
| | | | 2.85(m, 1H), |
| | | | 2.53(m, 2H), |
| | | | 2.11(s, 3H), |
| | | | 2.04(m, 2H), 1.83(m, 2H), 1.38(d, 3H) |
| 324 | 542.4 | 2.57 | |
| 325 | 384.2 | 1.05 | |
| 326 | 369.2 | 2.46 | |
| 327 | 481.2 | 2.4 | |
| 328 | 484.5 | 2.35 | |
| 329 | 468.4 | 2.12 | |
| 330 | 477.2 | 2 | |
| 331 | 367.2 | 2.01 | |
| 332 | 542.4 | 2.5 | |
| 333 | 454.2 | 2.13 | |
| 334 | 350.2 | 1.74 | |
| 335 | 379.2 | 1.78 | |
| 336 | 509.4 | 1.94 | |
| 337 | 516.4 | 2.43 | |
| 338 | 466.2 | 2.4 | |
| 339 | 538.2 | 2.6 | |
| 340 | 577.5 | 2.62 | |
| 341 | 399.2 | 2.17 | |
| 342 | 496.4 | 2.42 | |
| 343 | 520.4 | 2.37 | |
| 344 | 495.2 | 2.32 | |
| 345 | 530.4 | 2.53 | |
| 346 | 287.3 | 1.7 | CD3OD: |
| | | | 7.90(d, 1H), |
| | | | 7.68(t, 1H), |
| | | | 7.56(m, 2H), |
| | | | 3.79(m, 2H), |
| | | | 3.23(m, 4H), |
| | | | 2.54(m, 2H), |
| | | | 1.82(m, 2H), |
| | | | 1.73(m, 2H), |
| | | | 1.02(s, 9H) |
| 347 | 389 | 1.9 | CD3OD: |
| | | | 7.95(d, 1H), |
| | | | 7.89(m, 1H), |
| | | | 7.74(t, 1H), |
| | | | 7.67(t, 1H), |
| | | | 7.30(m, 4H), |
| | | | 7.25(m, 1H), |
| | | | 4.83(s, 2H), |
| | | | 3.68(m, 2H), |
| | | | 3.50-3.60(m, 3H), |
| | | | 2.59(m, 2H), |
| | | | 2.15(m, 2H), |
| | | | 1.86(m, 4H), |
| | | | 1.60-1.73(m, 8H) |
| 348 | 452.2 | 2.26 | |
| 349 | 341 | 1.92 | |
| 350 | 469.4 | 2.18 | |
| 351 | 548.2 | 2.19 | |
| 352 | 287.3 | 1.3 | |
| 353 | 504.2 | 2.58 | |
| 354 | 468.4 | 2.01 | |
| 355 | 549.4 | 2.49 | |
| 356 | 479.2 | 2.22 | |
| 357 | 440.4 | 2.24 | |
| 358 | 509.4 | 2.39 | |

Example 19

Assays for Detecting and Measuring Modulation Properties of Compounds

Functional Mobilization of Intracellular Calcium to Determine Muscarinic Receptor Activity:

CHO cells expressing muscarinic receptors ($M_1$ to $M_5$) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat# 12430-054), containing 25 mM Hepes and supplemented with Fetal Bovine Serum (Hyclone, cat# SH30071.03), 0.1 mM of MEM non-essential amino acids (GIBCO, Cat# 11140-050), 1 mM MEM Sodium Pyruvate (GIBCO Cat# 11360-070) and 100 units/ml of Penicillin G and 100 μg/ml of Streptomycin (GIBCO Cat# 15140-122). The recombinant muscarinic receptor cell lines are grown under antibiotic pressure with media containing 25 μg/ml zeocin and 500 μg/ml G418 (M1-CHO), 4 μg/ml puromycin, 50 μg/ml zeocin and 2.5 μg/ml blasticidin (M2 and M4-CHO) or 50 μg/ml zeocin and 4 μg/ml puromycin (M3 and M5-CHO).

Cells are harvested at 80-90% confluence using Versene (GIBCO Cat# 15040-066), collected by centrifugation and seeded 18-24 hrs prior to running the calcium assay at a density of 5,000-10,000 cells/well in back-walled, clear-bottomed 384-well plates (BD Biocoat, poly-D-lysine, Cat#356663). The day of the experiment, the cells are washed with a plate washer (Bioteck Instruments, ELX 405) using bath1 buffer (140-mM NaCl, 4.5-mM KCl, 2-mM $CaCl_2$, 1-mM $MgCl_2$, 10-mM Hepes-Na, 10-mM Glucose, pH 7.4, with NaOH) containing 1 mM Probenecid. Next, the calcium dye Fluo-3 (25 μl/well of Fluo-3 AM at 4 μM, Molecular Probes F-1241, in Bath 1 buffer containing 1 mM Probenecid) is added to the 25 μl of Bath 1 remaining in each well after the plate wash and the dye is loaded at 37° C. in the tissue culture incubator for 60-90 min. The fluorescent dye is removed using the plate washer with Bath 1 containing 1 mM Probenecid, leaving 25 μl/well of this solution after the wash. Alternatively, cells can be loaded with the calcium indicator from Molecular Devices (Calcium 3 Assay Reagents, Cat # R7181) adding 5 μl of a 5× solution dye in Bath 1 containing 1 mM Probenecid (10 ml per dye flask cat# R7182 to generate a solution 20×) to 20 μl of the same buffer. After loading for 60 min, the experiment can be run without having to remove the dye.

Compounds are prepared at a 2× fold concentration in a 96-well plate (round bottom, Costar Corning cat# 3656), by reconstituting the pre-spotted compounds in bath 1 containing 1 mM probenecid. The final concentration DMSO is 0.5%, and the amount of DMSO is normalized across the assay plate. To determine an agonist action of the compounds on muscarinic receptors, the reconstituted compounds are added (25 μl compound/well) to the cell assay plate (containing 25 μl/well) using the multi-channel robotic system of the FLIPR 3 Instrument (Molecular Devices, Sunnyvale, Calif.). To determine a functional inhibitory action of the compounds on muscarinic receptors, the reconstituted compounds are added (25 μl compound/well) to the assay plate and pre-incubated for 15 min prior to adding 25 μl of Carbachol at 3× the EC80 for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family ($M_1$ to $M_5$ cells). Compounds were also screened for activity on other proteins such as other GPCRs and ion channels to determine selectivity on $M_4$ receptors.

The compounds of the present invention were found to modulate the $M_1$ and/or $M_4$ muscarinic receptors selectively over the other receptor types.

Examples of activities and efficacies of the muscarinic compounds of formulae (I, Ia, Ib, Ic and Id) on modulating $M_1$ and $M_4$ receptors are shown below in Table 3. The compound activity for the $M_1$ and $M_4$ is illustrated with "+++" if activity was measured to be less than 1.0 μM, "++" if activity was measured to be from 1.0 μM to 5.0 μM, "+" if activity was measured to be greater than 5.0 μM, and "−" if no data was available. The efficacy for $M_1$, $M_4$ modulation is illustrated with "+++" if efficacy was calculated to be greater than 100%, "++" if efficacy was calculated to be from 100% to 25%, "+" if efficacy was calculated to be less than 25%, and "−" if no data was available. 100% efficacy is the maximum response obtained using Carbachol as a control.

TABLE 3

Compound activities and efficacies for modulating $M_1$, $M_2$, $M_3$ and $M_4$ receptors.

| Compound No. | $M_1$ Activity | $M_4$ Activity | $M_1$ Efficacy | $M_4$ Efficacy |
|---|---|---|---|---|
| 1 | ++ | ++ | ++ | + |
| 2 | + | + | + | + |
| 3 | +++ | +++ | ++ | ++ |
| 4 | ++ | +++ | ++ | ++ |
| 5 | + | + | + | + |
| 6 | +++ | +++ | ++ | ++ |
| 7 | +++ | +++ | ++ | ++ |
| 8 | +++ | +++ | ++ | ++ |
| 9 | +++ | +++ | ++ | ++ |
| 10 | +++ | ++ | ++ | + |
| 11 | +++ | +++ | ++ | ++ |
| 12 | +++ | +++ | ++ | ++ |
| 13 | +++ | +++ | ++ | ++ |
| 14 | +++ | +++ | ++ | ++ |
| 15 | +++ | +++ | ++ | ++ |
| 16 | +++ | +++ | ++ | ++ |
| 17 | +++ | +++ | ++ | ++ |
| 18 | +++ | +++ | ++ | ++ |
| 19 | ++ | ++ | ++ | + |
| 20 | ++ | + | ++ | + |
| 21 | + | + | ++ | ++ |
| 22 | +++ | +++ | ++ | ++ |
| 23 | +++ | +++ | ++ | ++ |
| 24 | +++ | +++ | ++ | ++ |
| 25 | +++ | +++ | ++ | ++ |
| 26 | − | − | − | − |
| 27 | +++ | +++ | ++ | ++ |
| 28 | − | − | − | − |
| 29 | +++ | +++ | ++ | ++ |
| 30 | +++ | +++ | ++ | ++ |
| 31 | + | + | ++ | ++ |
| 32 | +++ | +++ | ++ | ++ |
| 33 | +++ | +++ | ++ | ++ |
| 34 | +++ | +++ | ++ | ++ |
| 35 | + | ++ | + | + |
| 36 | +++ | +++ | ++ | ++ |
| 37 | + | + | ++ | + |
| 38 | +++ | +++ | ++ | ++ |
| 39 | +++ | +++ | ++ | ++ |
| 40 | + | + | + | + |
| 41 | + | + | ++ | + |
| 42 | + | + | + | + |
| 43 | +++ | +++ | ++ | + |
| 44 | +++ | +++ | ++ | ++ |
| 45 | + | + | + | + |
| 46 | +++ | +++ | ++ | ++ |
| 47 | +++ | +++ | ++ | ++ |
| 48 | +++ | +++ | ++ | ++ |
| 49 | +++ | +++ | ++ | ++ |
| 50 | + | + | + | + |
| 51 | +++ | +++ | ++ | ++ |
| 52 | + | + | ++ | + |
| 53 | +++ | +++ | ++ | ++ |
| 54 | + | + | + | ++ |
| 55 | +++ | +++ | ++ | ++ |
| 56 | +++ | +++ | ++ | ++ |
| 57 | ++ | + | ++ | + |
| 58 | + | + | + | + |
| 59 | + | + | + | + |
| 60 | − | − | − | − |
| 61 | +++ | +++ | ++ | ++ |
| 62 | +++ | +++ | ++ | ++ |
| 63 | +++ | +++ | ++ | ++ |
| 64 | +++ | +++ | ++ | ++ |

TABLE 3-continued

Compound activities and efficacies for modulating $M_1$, $M_2$, $M_3$ and $M_4$ receptors.

| Compound No. | $M_1$ Activity | $M_4$ Activity | $M_1$ Efficacy | $M_4$ Efficacy |
|---|---|---|---|---|
| 65 | + | + | ++ | ++ |
| 66 | + | + | + | + |
| 67 | ++ | +++ | ++ | ++ |
| 68 | +++ | +++ | ++ | ++ |
| 69 | +++ | +++ | ++ | ++ |
| 70 | +++ | +++ | ++ | ++ |
| 71 | +++ | + | ++ | + |
| 72 | +++ | +++ | ++ | ++ |
| 73 | +++ | +++ | ++ | ++ |
| 74 | +++ | +++ | ++ | ++ |
| 75 | + | + | ++ | + |
| 76 | +++ | +++ | ++ | ++ |
| 77 | +++ | +++ | ++ | ++ |
| 78 | + | + | ++ | ++ |
| 79 | +++ | +++ | ++ | ++ |
| 80 | +++ | +++ | ++ | ++ |
| 81 | +++ | +++ | ++ | ++ |
| 82 | +++ | +++ | ++ | ++ |
| 83 | +++ | + | ++ | ++ |
| 84 | +++ | +++ | ++ | + |
| 85 | − | − | − | − |
| 86 | +++ | +++ | ++ | +++ |
| 87 | ++ | ++ | ++ | + |
| 88 | +++ | +++ | ++ | ++ |
| 89 | + | + | + | + |
| 90 | +++ | +++ | ++ | ++ |
| 91 | +++ | +++ | ++ | ++ |
| 92 | ++ | ++ | ++ | ++ |
| 93 | + | + | ++ | + |
| 94 | ++ | +++ | ++ | ++ |
| 95 | +++ | +++ | ++ | ++ |
| 96 | +++ | +++ | ++ | ++ |
| 97 | +++ | +++ | ++ | ++ |
| 98 | + | + | + | + |
| 99 | +++ | +++ | ++ | ++ |
| 100 | + | + | + | + |
| 101 | + | + | + | + |
| 102 | +++ | +++ | ++ | ++ |
| 103 | +++ | +++ | ++ | ++ |
| 104 | +++ | +++ | ++ | ++ |
| 105 | + | + | + | + |
| 106 | +++ | +++ | ++ | ++ |
| 107 | + | + | + | + |
| 108 | +++ | +++ | ++ | ++ |
| 109 | +++ | +++ | ++ | ++ |
| 110 | +++ | +++ | ++ | ++ |
| 111 | +++ | +++ | ++ | ++ |
| 112 | +++ | +++ | ++ | ++ |
| 113 | +++ | +++ | ++ | ++ |
| 114 | ++ | +++ | +++ | ++ |
| 115 | + | + | + | + |
| 116 | + | + | + | + |
| 117 | +++ | +++ | ++ | ++ |
| 118 | + | + | + | + |
| 119 | +++ | +++ | ++ | ++ |
| 120 | +++ | +++ | ++ | ++ |
| 121 | + | + | + | + |
| 122 | +++ | +++ | ++ | ++ |
| 123 | +++ | +++ | ++ | ++ |
| 124 | +++ | +++ | ++ | ++ |
| 125 | +++ | +++ | ++ | ++ |
| 126 | +++ | +++ | ++ | ++ |
| 127 | +++ | +++ | ++ | ++ |
| 128 | +++ | +++ | ++ | ++ |
| 129 | +++ | +++ | ++ | ++ |
| 130 | ++ | + | ++ | + |
| 131 | +++ | +++ | ++ | ++ |
| 132 | +++ | +++ | ++ | ++ |
| 133 | +++ | +++ | ++ | ++ |
| 134 | + | + | + | + |
| 135 | ++ | +++ | ++ | ++ |
| 136 | +++ | +++ | +++ | ++ |
| 137 | + | + | + | + |
| 138 | +++ | +++ | ++ | ++ |
| 139 | + | + | + | + |
| 140 | +++ | +++ | ++ | ++ |
| 141 | +++ | +++ | ++ | ++ |
| 142 | + | + | + | + |
| 143 | +++ | +++ | ++ | ++ |
| 144 | + | + | ++ | + |
| 145 | +++ | +++ | ++ | ++ |
| 146 | +++ | +++ | ++ | ++ |
| 147 | +++ | +++ | ++ | ++ |
| 148 | +++ | +++ | ++ | ++ |
| 149 | + | +++ | + | ++ |
| 150 | + | + | + | + |
| 151 | +++ | +++ | ++ | ++ |
| 152 | + | ++ | + | ++ |
| 153 | + | ++ | ++ | ++ |
| 154 | +++ | +++ | ++ | ++ |
| 155 | +++ | +++ | ++ | ++ |
| 156 | +++ | +++ | ++ | ++ |
| 157 | +++ | +++ | ++ | ++ |
| 158 | +++ | +++ | ++ | ++ |
| 159 | +++ | +++ | +++ | ++ |
| 160 | ++ | ++ | ++ | ++ |
| 161 | ++ | +++ | ++ | + |
| 162 | +++ | +++ | ++ | ++ |
| 163 | +++ | +++ | ++ | ++ |
| 164 | +++ | +++ | ++ | ++ |
| 165 | +++ | +++ | ++ | ++ |
| 166 | +++ | +++ | ++ | ++ |
| 167 | ++ | +++ | ++ | + |
| 168 | +++ | +++ | ++ | ++ |
| 169 | +++ | +++ | +++ | ++ |
| 170 | +++ | +++ | ++ | ++ |
| 171 | +++ | +++ | ++ | ++ |
| 172 | ++ | ++ | ++ | ++ |
| 173 | +++ | +++ | ++ | ++ |
| 174 | +++ | +++ | +++ | ++ |
| 175 | +++ | +++ | ++ | ++ |
| 176 | +++ | +++ | ++ | ++ |
| 177 | +++ | + | ++ | + |
| 178 | +++ | + | ++ | + |
| 179 | +++ | +++ | ++ | ++ |
| 180 | + | + | ++ | ++ |
| 181 | +++ | +++ | ++ | ++ |
| 182 | + | + | + | + |
| 183 | +++ | +++ | ++ | ++ |
| 184 | +++ | +++ | ++ | ++ |
| 185 | +++ | +++ | ++ | ++ |
| 186 | +++ | +++ | ++ | ++ |
| 187 | + | + | + | + |
| 188 | + | + | + | + |
| 189 | +++ | +++ | ++ | ++ |
| 190 | +++ | +++ | ++ | ++ |
| 191 | + | + | + | + |
| 192 | + | + | ++ | ++ |
| 193 | +++ | +++ | ++ | + |
| 194 | +++ | +++ | ++ | ++ |
| 195 | +++ | +++ | ++ | ++ |
| 196 | +++ | +++ | ++ | ++ |
| 197 | +++ | +++ | ++ | ++ |
| 198 | +++ | +++ | ++ | ++ |
| 199 | + | + | + | ++ |
| 200 | +++ | +++ | ++ | ++ |
| 201 | +++ | +++ | ++ | ++ |
| 202 | +++ | +++ | ++ | ++ |
| 203 | +++ | +++ | ++ | ++ |
| 204 | +++ | +++ | ++ | ++ |
| 205 | +++ | +++ | ++ | ++ |
| 206 | +++ | +++ | ++ | ++ |
| 207 | + | ++ | ++ | ++ |
| 208 | +++ | +++ | ++ | ++ |
| 209 | +++ | +++ | ++ | ++ |
| 210 | +++ | +++ | ++ | ++ |

TABLE 3-continued

Compound activities and efficacies for modulating $M_1$, $M_2$, $M_3$ and $M_4$ receptors.

| Compound No. | $M_1$ Activity | $M_4$ Activity | $M_1$ Efficacy | $M_4$ Efficacy |
|---|---|---|---|---|
| 211 | +++ | + | ++ | + |
| 212 | +++ | +++ | ++ | ++ |
| 213 | +++ | +++ | ++ | ++ |
| 214 | +++ | +++ | ++ | ++ |
| 215 | ++ | + | ++ | ++ |
| 216 | +++ | +++ | ++ | ++ |
| 217 | + | + | + | + |
| 218 | +++ | +++ | ++ | ++ |
| 219 | +++ | +++ | ++ | ++ |
| 220 | +++ | +++ | ++ | ++ |
| 221 | +++ | +++ | ++ | ++ |
| 222 | +++ | +++ | ++ | ++ |
| 223 | +++ | +++ | ++ | ++ |
| 224 | +++ | +++ | ++ | ++ |
| 225 | +++ | +++ | ++ | ++ |
| 226 | +++ | +++ | ++ | ++ |
| 227 | + | + | + | + |
| 228 | +++ | +++ | ++ | ++ |
| 229 | +++ | +++ | ++ | ++ |
| 230 | +++ | ++ | ++ | ++ |
| 231 | +++ | +++ | ++ | ++ |
| 232 | +++ | +++ | ++ | ++ |
| 233 | +++ | +++ | ++ | ++ |
| 234 | +++ | +++ | ++ | ++ |
| 235 | +++ | +++ | ++ | ++ |
| 236 | +++ | +++ | ++ | ++ |
| 237 | +++ | +++ | ++ | ++ |
| 238 | +++ | +++ | ++ | ++ |
| 239 | − | − | − | − |
| 240 | +++ | +++ | ++ | ++ |
| 241 | +++ | +++ | ++ | ++ |
| 242 | +++ | + | ++ | + |
| 243 | + | + | + | + |
| 244 | +++ | +++ | ++ | ++ |
| 245 | ++ | ++ | ++ | ++ |
| 246 | +++ | +++ | ++ | +++ |
| 247 | + | + | + | + |
| 248 | − | − | − | − |
| 249 | +++ | +++ | ++ | ++ |
| 250 | +++ | +++ | ++ | ++ |
| 251 | +++ | +++ | ++ | ++ |
| 252 | + | + | + | + |
| 253 | +++ | +++ | ++ | ++ |
| 254 | +++ | +++ | ++ | ++ |
| 255 | +++ | +++ | ++ | ++ |
| 256 | + | + | + | + |
| 257 | +++ | +++ | ++ | ++ |
| 258 | +++ | +++ | ++ | ++ |
| 259 | +++ | +++ | ++ | ++ |
| 260 | +++ | +++ | ++ | ++ |
| 261 | +++ | +++ | ++ | ++ |
| 262 | + | + | + | + |
| 263 | +++ | +++ | ++ | ++ |
| 264 | +++ | +++ | ++ | ++ |
| 265 | +++ | +++ | ++ | ++ |
| 266 | + | + | + | + |
| 267 | ++ | ++ | ++ | ++ |
| 268 | ++ | ++ | ++ | ++ |
| 269 | ++ | ++ | ++ | ++ |
| 270 | +++ | +++ | ++ | ++ |
| 271 | +++ | +++ | ++ | ++ |
| 272 | +++ | +++ | ++ | ++ |
| 273 | +++ | +++ | ++ | ++ |
| 274 | + | + | + | + |
| 275 | +++ | +++ | ++ | ++ |
| 276 | ++ | ++ | ++ | ++ |
| 277 | +++ | +++ | ++ | ++ |
| 278 | ++ | +++ | ++ | ++ |
| 279 | +++ | +++ | ++ | ++ |
| 280 | − | − | − | − |
| 281 | − | − | − | − |
| 282 | +++ | +++ | ++ | ++ |
| 283 | +++ | +++ | ++ | ++ |
| 284 | +++ | +++ | ++ | ++ |
| 285 | +++ | +++ | ++ | ++ |
| 286 | +++ | +++ | ++ | ++ |
| 287 | + | + | + | + |
| 288 | +++ | +++ | ++ | ++ |
| 289 | +++ | +++ | ++ | ++ |
| 290 | +++ | +++ | ++ | ++ |
| 291 | + | + | + | + |
| 292 | +++ | +++ | ++ | ++ |
| 293 | +++ | +++ | ++ | ++ |
| 294 | +++ | +++ | ++ | ++ |
| 295 | ++ | ++ | ++ | + |
| 296 | +++ | +++ | ++ | ++ |
| 297 | + | + | + | + |
| 298 | +++ | +++ | ++ | ++ |
| 299 | +++ | +++ | ++ | + |
| 300 | +++ | +++ | ++ | ++ |
| 301 | + | + | + | + |
| 302 | +++ | +++ | ++ | ++ |
| 303 | +++ | +++ | ++ | ++ |
| 304 | +++ | +++ | ++ | ++ |
| 305 | +++ | +++ | ++ | ++ |
| 306 | +++ | +++ | ++ | ++ |
| 307 | +++ | +++ | ++ | ++ |
| 308 | +++ | +++ | ++ | ++ |
| 309 | +++ | +++ | ++ | ++ |
| 310 | +++ | +++ | ++ | ++ |
| 311 | +++ | +++ | ++ | ++ |
| 312 | + | + | + | + |
| 313 | +++ | +++ | +++ | ++ |
| 314 | +++ | +++ | ++ | ++ |
| 315 | +++ | +++ | ++ | ++ |
| 316 | +++ | +++ | ++ | ++ |
| 317 | +++ | +++ | ++ | ++ |
| 318 | +++ | +++ | ++ | ++ |
| 319 | +++ | +++ | ++ | ++ |
| 320 | +++ | +++ | ++ | ++ |
| 321 | +++ | +++ | ++ | ++ |
| 322 | + | + | + | + |
| 323 | + | + | + | + |
| 324 | +++ | +++ | ++ | ++ |
| 325 | − | − | − | − |
| 326 | +++ | +++ | ++ | ++ |
| 327 | +++ | +++ | ++ | ++ |
| 328 | +++ | +++ | ++ | ++ |
| 329 | +++ | +++ | ++ | ++ |
| 330 | +++ | +++ | ++ | ++ |
| 331 | + | + | + | + |
| 332 | +++ | +++ | ++ | ++ |
| 333 | +++ | +++ | ++ | ++ |
| 334 | + | + | + | + |
| 335 | + | + | + | + |
| 336 | +++ | +++ | ++ | ++ |
| 337 | +++ | +++ | ++ | ++ |
| 338 | +++ | +++ | ++ | ++ |
| 339 | +++ | +++ | ++ | ++ |
| 340 | +++ | +++ | ++ | ++ |
| 341 | +++ | +++ | ++ | ++ |
| 342 | +++ | +++ | ++ | ++ |
| 343 | +++ | +++ | ++ | ++ |
| 344 | +++ | +++ | ++ | ++ |
| 345 | +++ | +++ | ++ | ++ |
| 346 | ++ | ++ | ++ | ++ |
| 347 | + | + | ++ | + |
| 348 | +++ | +++ | ++ | ++ |
| 349 | +++ | +++ | ++ | ++ |
| 350 | +++ | +++ | ++ | ++ |
| 351 | +++ | +++ | ++ | ++ |
| 352 | + | + | + | + |
| 353 | +++ | +++ | ++ | ++ |
| 354 | +++ | +++ | ++ | ++ |
| 355 | +++ | +++ | ++ | ++ |
| 356 | +++ | +++ | ++ | ++ |

TABLE 3-continued

Compound activities and efficacies for modulating
$M_1$, $M_2$, $M_3$ and $M_4$ receptors.

| Compound No. | $M_1$ Activity | $M_4$ Activity | $M_1$ Efficacy | $M_4$ Efficacy |
|---|---|---|---|---|
| 357 | +++ | +++ | ++ | ++ |
| 358 | +++ | +++ | ++ | ++ |

VIII. Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula Ia:

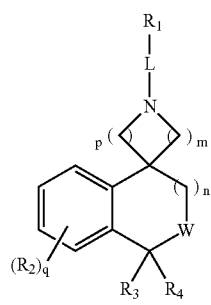

Ia or a pharmaceutically acceptable salt thereof, wherein:
$R^1$ is a bicyclic cycloaliphatic optionally substituted with 1-3 of halo, hydroxy, or optionally substituted aliphatic, optionally substituted alkoxy, optionally substituted alkoxycarbonyl, or combinations thereof;
bridged bicyclic cycloaliphatic optionally substituted with 1-3 of halo, hydroxy, or optionally substituted aliphatic, optionally substituted alkoxy, optionally substituted alkoxycarbonyl, or combinations thereof; or
heterocycloaliphatic optionally substituted with 1-3 of $R_5$;
Each $R_5$, is independently =O or -$Z^A R_6$, wherein each $Z^A$ is independently a bond or an optionally substituted branched or straight $C_{1-4}$ aliphatic chain wherein up to two carbon units of $Z^A$ are optionally and independently replaced by —CO—, —CS—, —CONR$^A$—, —CONR$^A$NR$^A$—, —CO$_2$—, —OCO—, —NR$^A$CO$_2$—, —O—, —NR$^A$CONR$^A$—, —OCONR$^A$—, —NR$^A$NR$^A$—, —NR$^A$CO—, —S—, —SO—, —SO$_2$—, —NR$^A$—, —SO$_2$NR$^A$—, —NR$^A$SO$_2$—, or —NR$^A$SO$_2$NR$^A$—;
$R_6$ is independently $R^A$, halo, —OH, —NH$_2$, —NO$_2$, —CN, =NR$^A$, =NOR$^A$, or —OCF$_3$;
Each $R^A$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl;
Each $R_2$ is independently -$Z^B R_7$, wherein each $Z^B$ is independently a bond or an optionally substituted branched or straight $C_{1-4}$ aliphatic chain wherein up to two carbon units of $Z^B$ are optionally and independently replaced by —CO—, —CS—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —SO—, —SO$_2$—, —NR$^B$—, —SO$_2$NR$^B$—, —NR$^B$SO$_2$— or —NR$^B$SO$_2$NR$^B$—;
Each $R_7$ is independently $R^B$, halo, —OH, —CN, —NH$_2$, —NO$_2$, or —OCF$_3$;
Each $R^B$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl;
Each $R_3$ and $R_4$ is independently -$Z^C R_8$, wherein each $Z^C$ is independently a bond or an optionally substituted branched or straight $C_{1-4}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —SO—, —SO$_2$—, —NR$^C$—, —SO$_2$NR$^C$—, —NR$^C$SO$_2$—, or —NR$^C$SO$_2$NR$^C$—;
$R_3$ and $R_4$, together form an oxo group;
Each $R_8$ is independently $R^C$, halo, —OH, —CN, or —OCF$_3$;
Each $R^C$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl;
W is —NR$_9$—;
$R_9$ is -$Z^D R_{10}$, wherein each $Z^D$ is independently a bond or an optionally substituted branched or straight $C_{1-4}$ aliphatic chain wherein up to two carbon units of $Z^D$ are optionally and independently replaced by —CO—, —CS—, —CONR$^D$—, —CONR$^D$NR$^D$—, —CO$_2$—, —OCO—, —NR$^D$CO$_2$—, —O—, —NR$^D$CONR$^D$—, —OCONR$^D$—, —NR$^D$NR$^D$—, —NR$^D$CO—, —S—, —SO—, —SO$_2$—, —NR$^D$—, —SO$_2$NR$^D$—, —NR$^D$SO$_2$—, or —NR$^D$SO$_2$NR$^D$—;
Each $R_{10}$ is independently $R^D$, halo, —OH, —CN, or —OCF$_3$;
Each $R^D$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl;
m is 0-3, p is 0-3, and m+p is 4;
n is 1;
q is 0-4; and
L is a bond or —CH$_2$—.

2. The compound of claim 1, wherein $R_1$ is a bicyclic cycloaliphatic optionally substituted with 1-3 of halo, hydroxy, or optionally substituted aliphatic, optionally substituted alkoxy, optionally substituted alkoxycarbonyl, or combinations thereof.

3. The compound of claim 2, wherein $R_1$ is a bridged bicyclic cycloaliphatic optionally substituted with 1-3 of halo, hydroxy, or optionally substituted aliphatic, optionally substituted alkoxy, optionally substituted alkoxycarbonyl, or combinations thereof.

4. The compound of claim 1, wherein $R_1$ is a heterocycloaliphatic optionally substituted with 1-3 of $R_5$.

5. The compound of claim 4, wherein $R_1$ is heterocycloaliphatic optionally substituted with 1-3 of halo, hydroxy, cyano, optionally substituted aliphatic, optionally substituted cycloaliphatic, optionally substituted heterocycloaliphatic, optionally substituted aryl, optionally substituted heteoraryl, optionally substituted alkoxycarbonyl, optionally substituted (cycloalkyl)oxycarbonyl, optionally substituted akylaminocarbonyl; optionally substituted (heterocycloalkyl)oxycarbonyl, optionally substituted arylcarbonyl, optionally substituted (alkoxy)alkoxycarbonyl, or combinations thereof.

6. The compound of claim 1, wherein W is —$NR_9$—, $R_9$ is -$Z^D R_{10}$, $Z^D$ is —C(O)—, —$SO_2$—, —C(O)$NR^D$—, —$SO_2 NR^D$—, —C(O)O—, or —OC(O)$NR^D$—; and $R_{10}$ is aliphatic, cycloaliphatic, heterocycloaliphatic, aryl, heteroaryl, or aryl, each of which is optionally substituted.

7. The compound of claim 6, wherein $R_{10}$ is aliphatic optionally substituted with 1-3 halo, hydroxy, cyano, aryl, cycloaliphatic, or combinations thereof.

8. The compound of claim 6, wherein $R_{10}$ is cycloaliphatic optionally substituted with 1-3 of halo, hydroxy, aliphatic, or combinations thereof.

9. The compound of claim 6, wherein $R_{10}$ is phenyl that is optionally substituted with 1-3 of halo, hydroxy, cyano, optionally substituted aliphatic, optionally substituted aryl, optionally substituted alkoxy, or combinations thereof.

10. The compound of claim 6, wherein $R_{10}$ is heteroaryl optionally substituted with 1-3 of halo, hydroxy, cyano, optionally substituted aliphatic, optionally substituted alkoxy, optionally substituted aryl, or combinations thereof.

11. A compound selected from

1

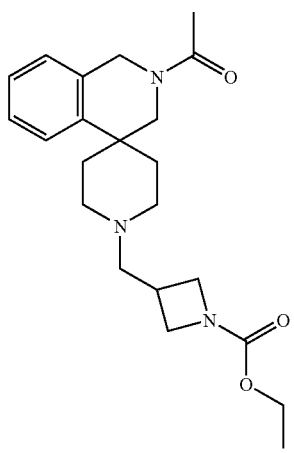

2

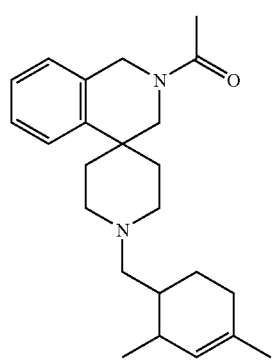

3

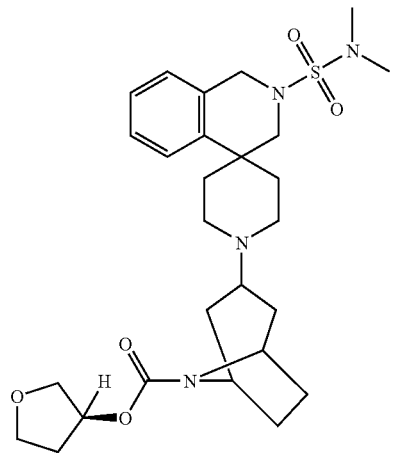

4

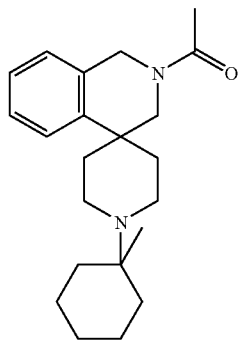

6

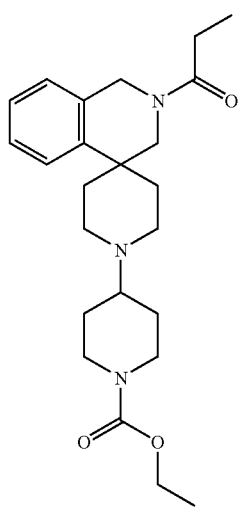

-continued
7
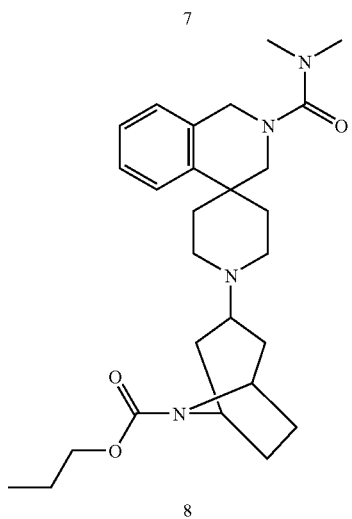
8
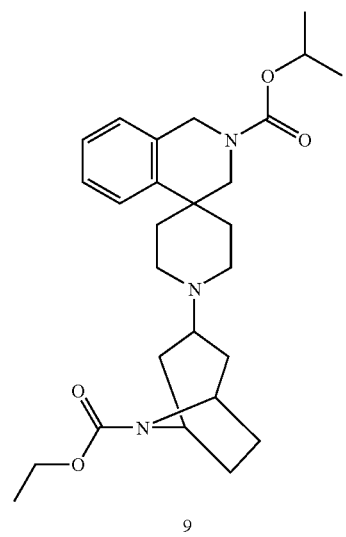
9
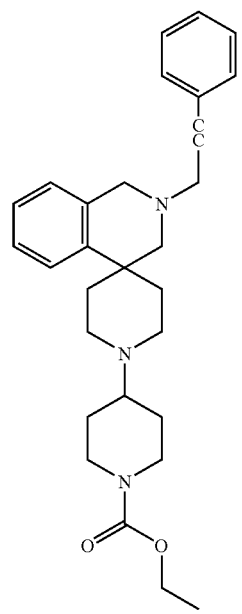
-continued
10
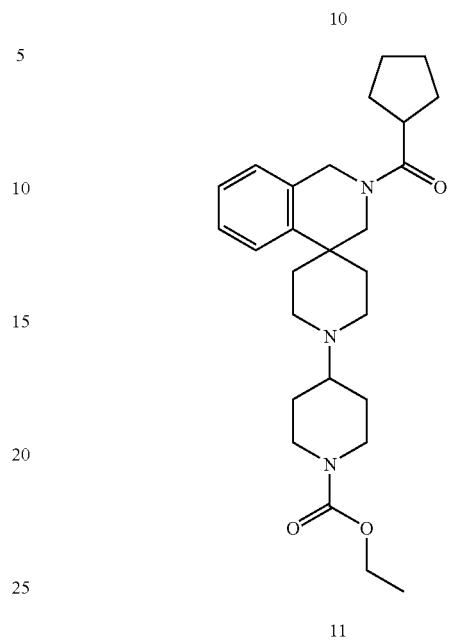
11
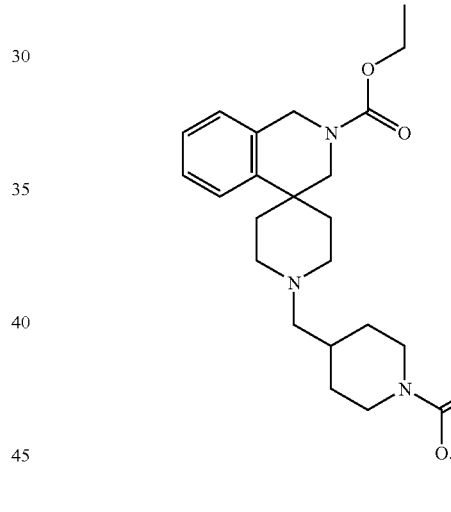
12
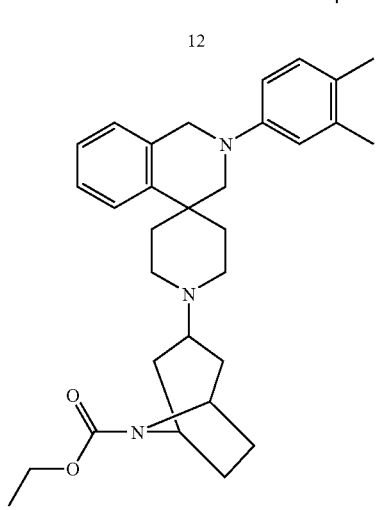

-continued
13
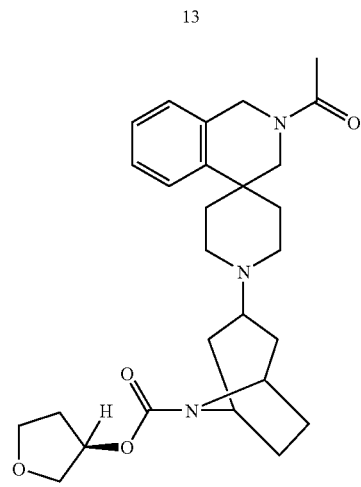
14
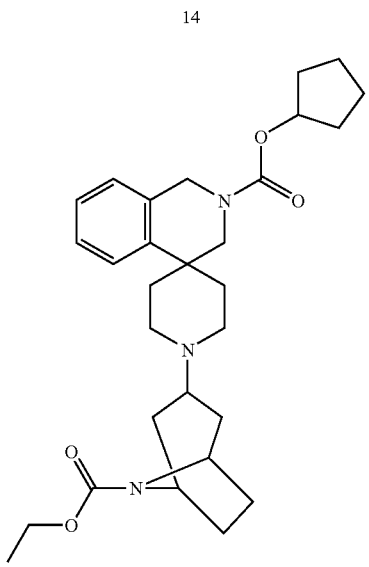
15
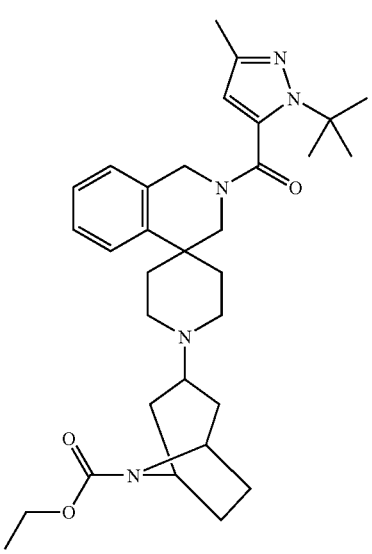
-continued
16
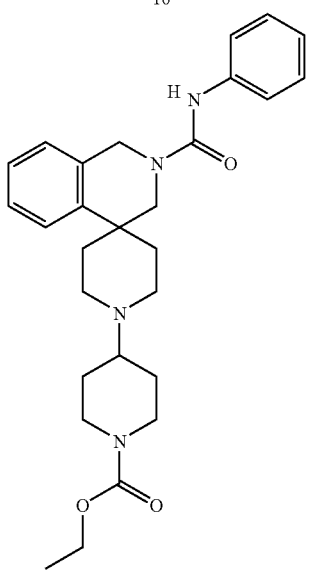
17
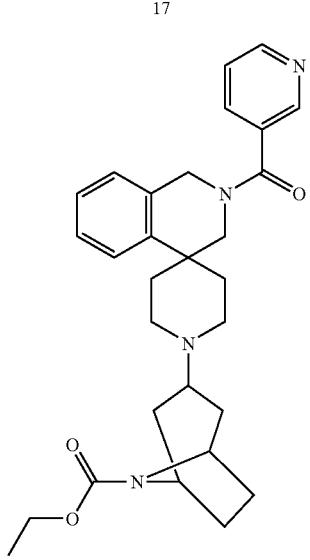
18
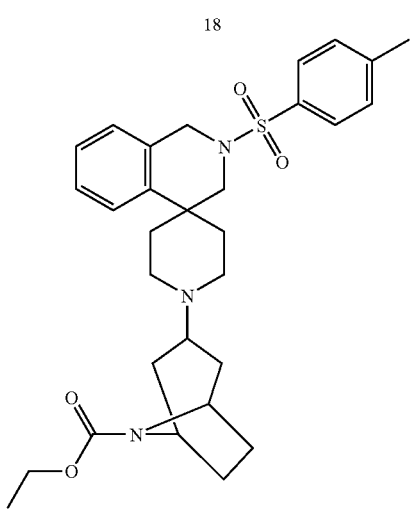

-continued
21
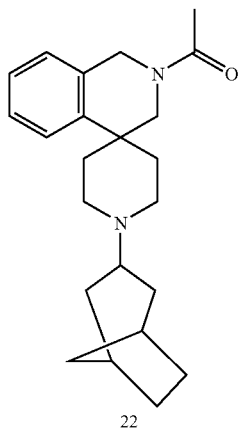
22
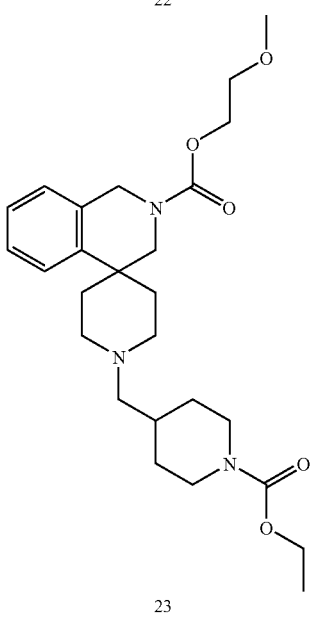
23
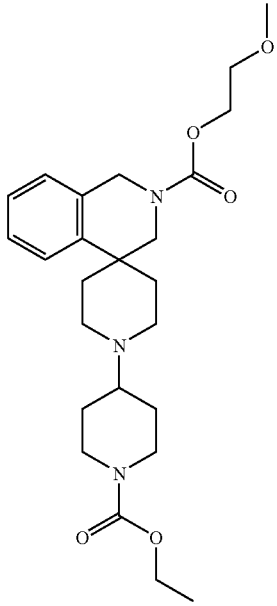
-continued
24
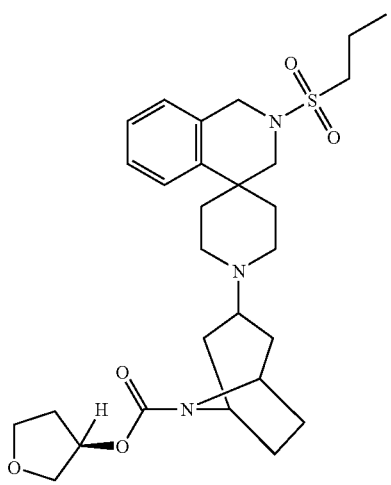
25
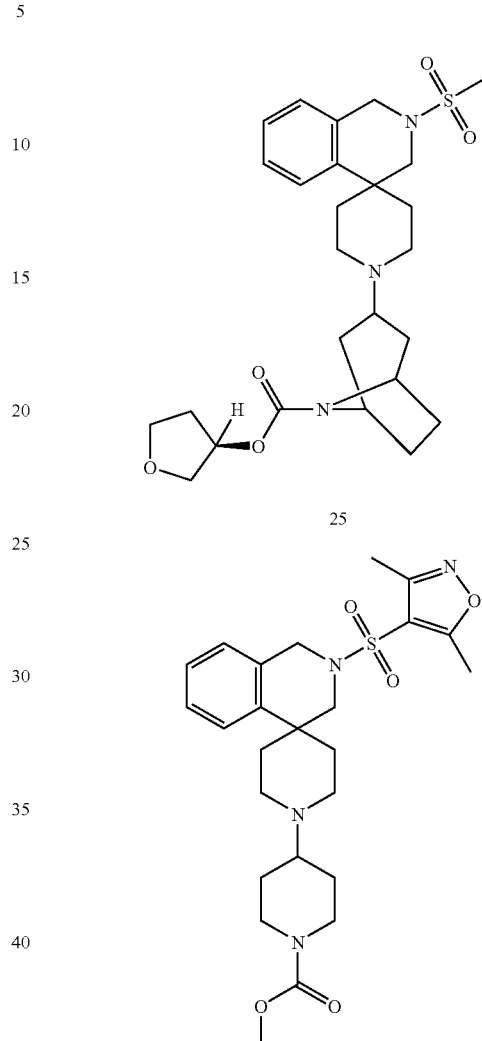
27
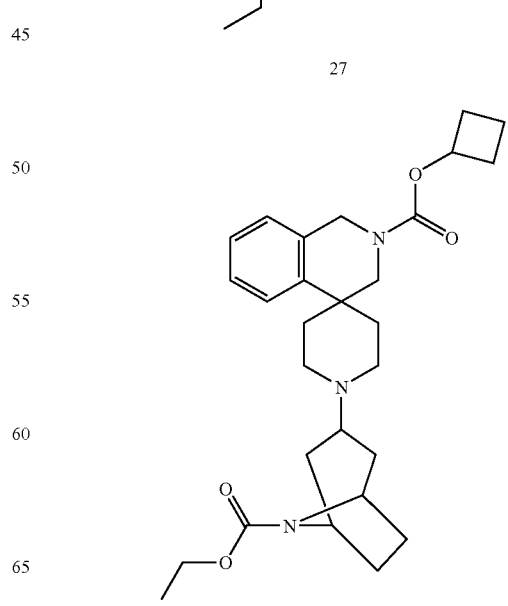

-continued
29
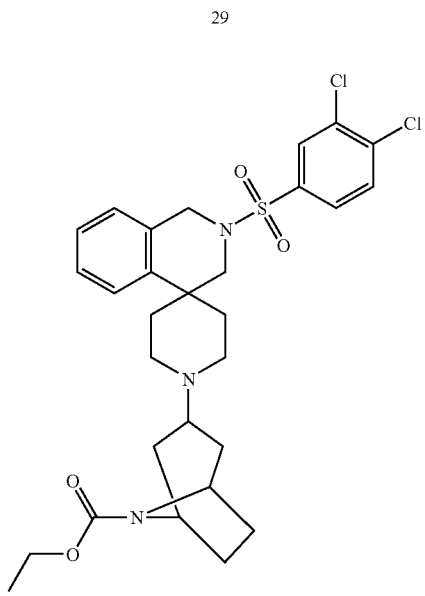
30
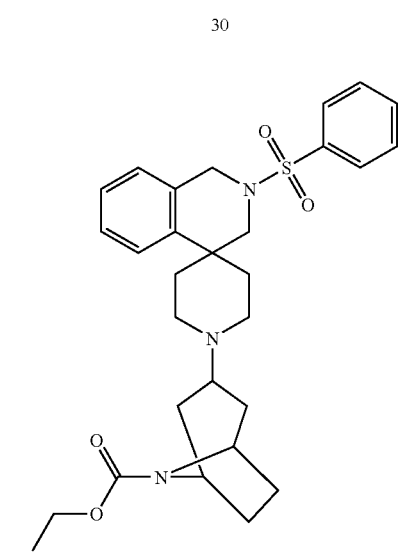
31
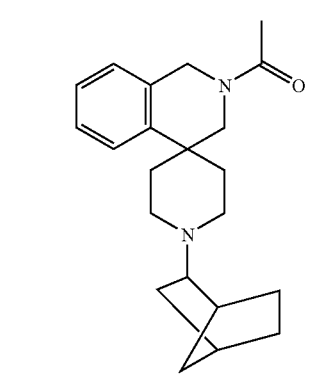
-continued
32
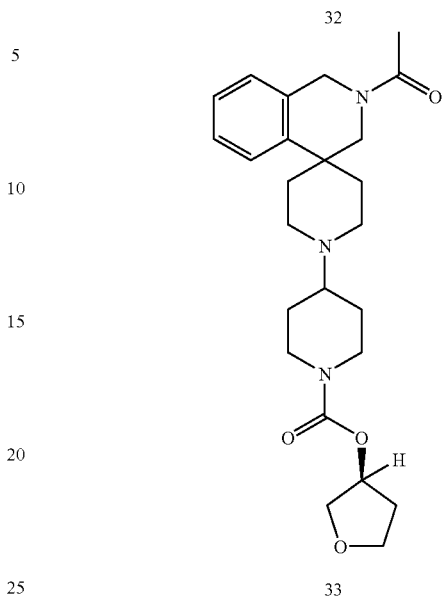
33
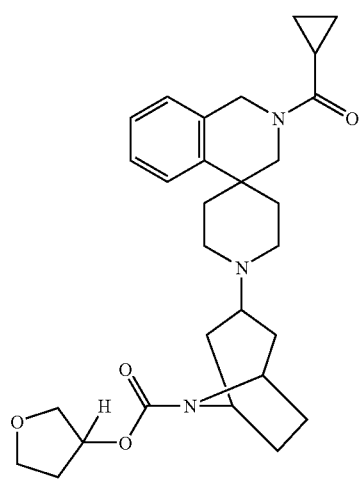
34
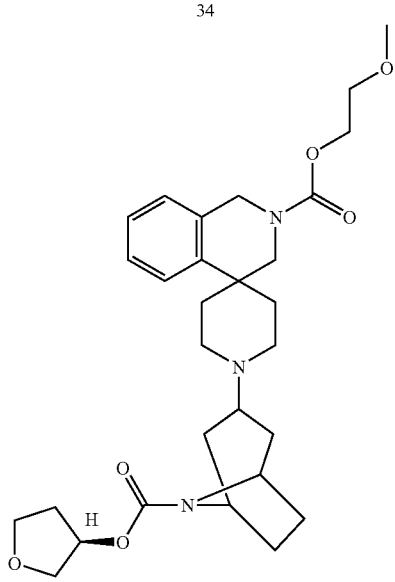

-continued
35
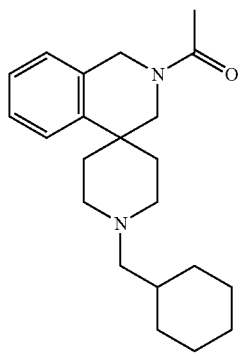
36
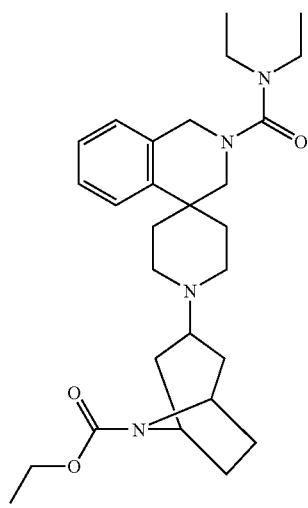
38
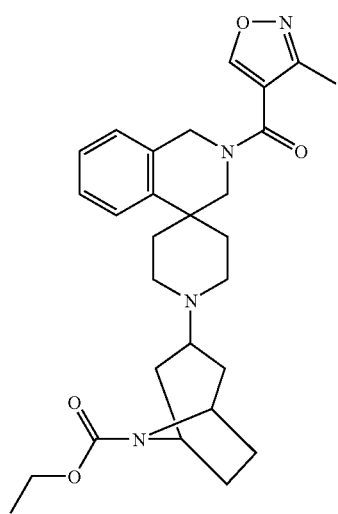
-continued
39
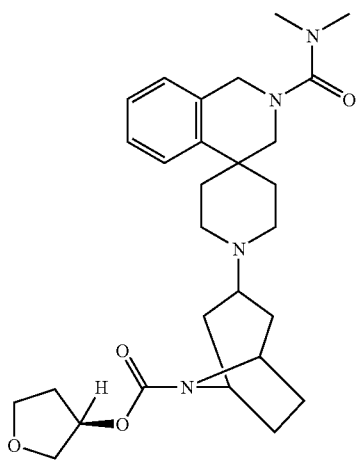
43
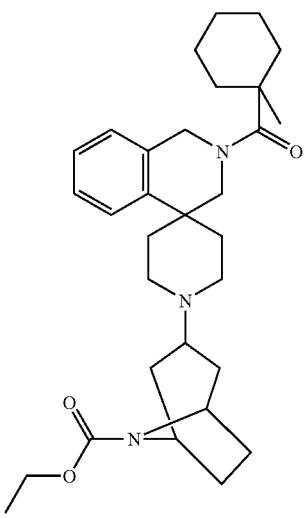
44
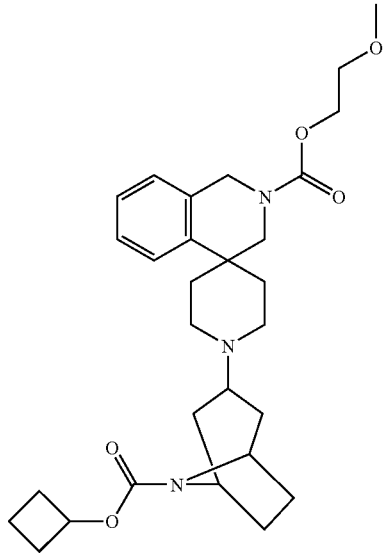

| 233 | 234 |
|---|---|
| -continued | -continued |
| 45 | 48 |
| 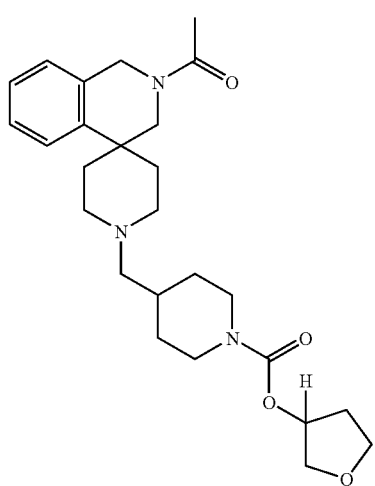 | 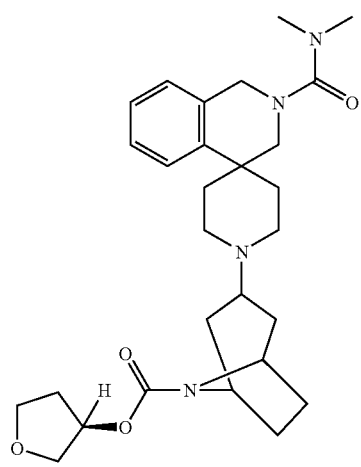 |
| 46 | 49 |
| 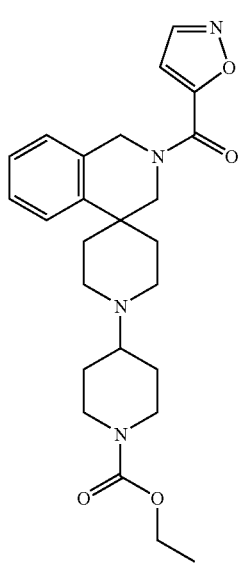 | 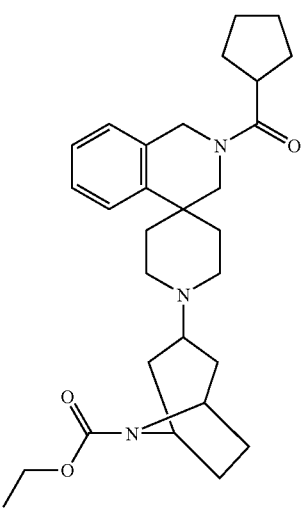 |
| 47 | 50 |
| 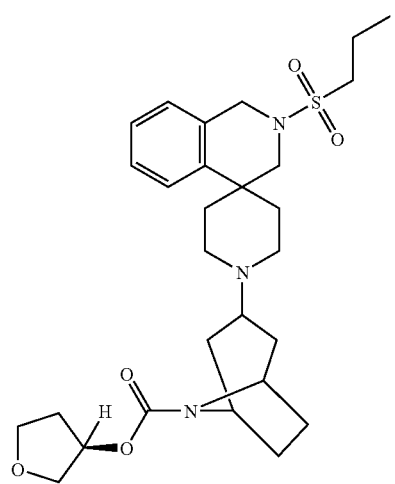 | 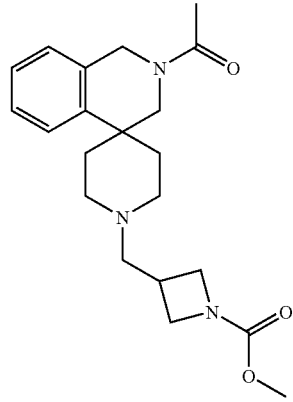 |

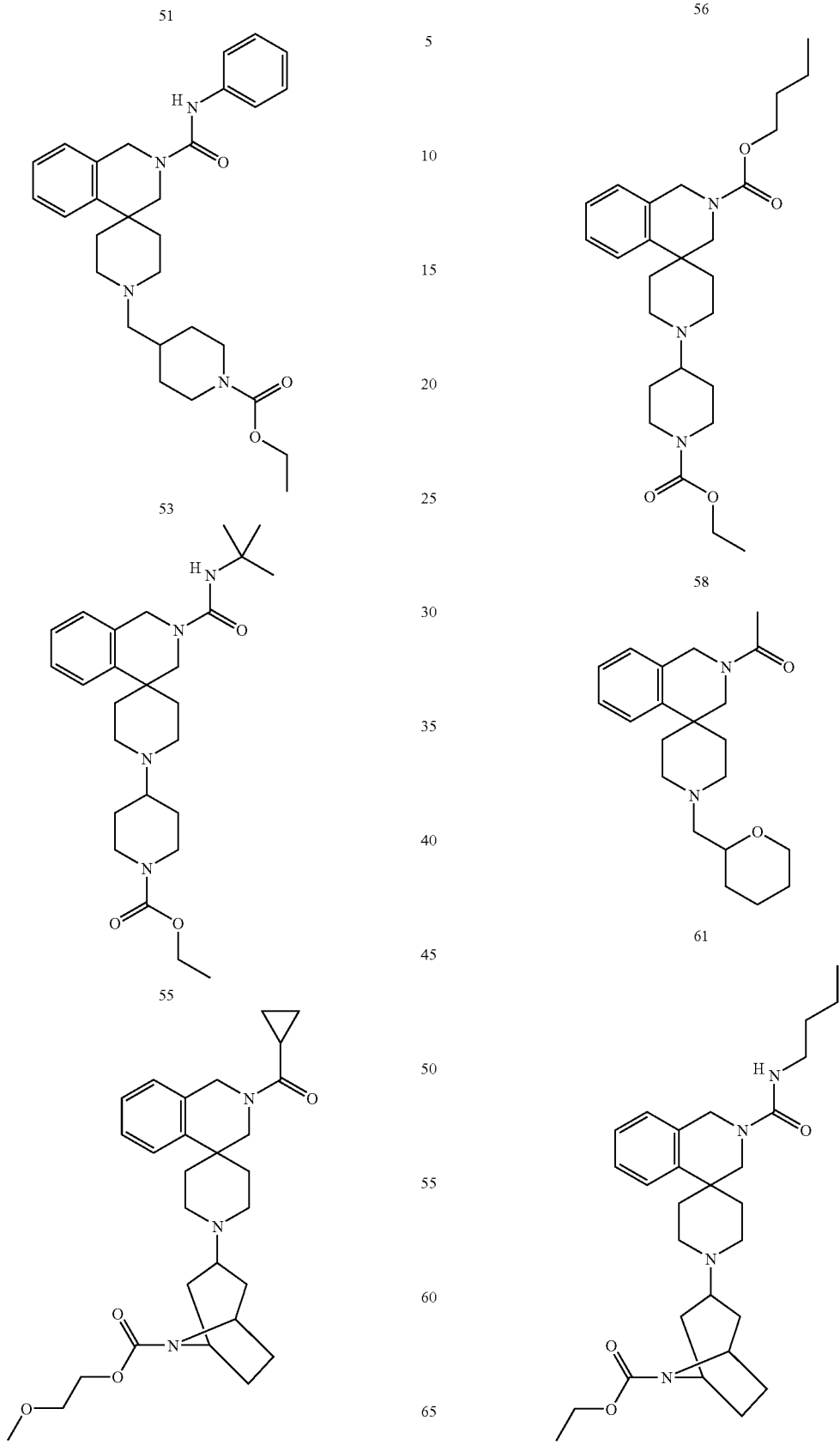

-continued
62
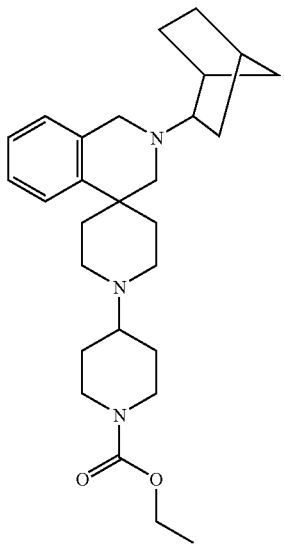
63
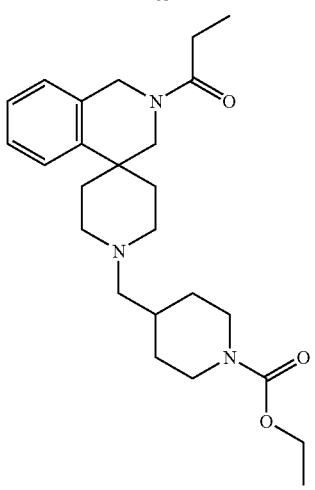
64
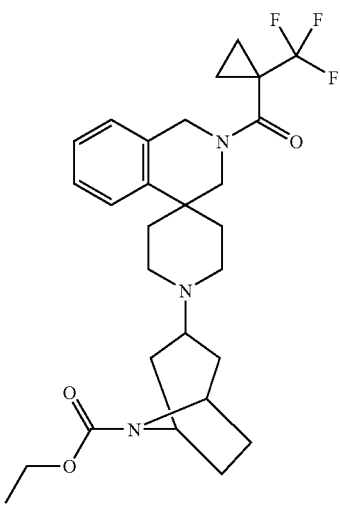
-continued
65
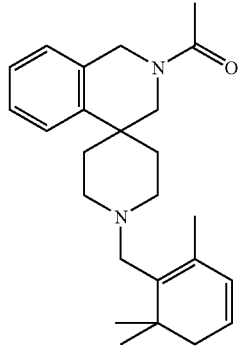
67
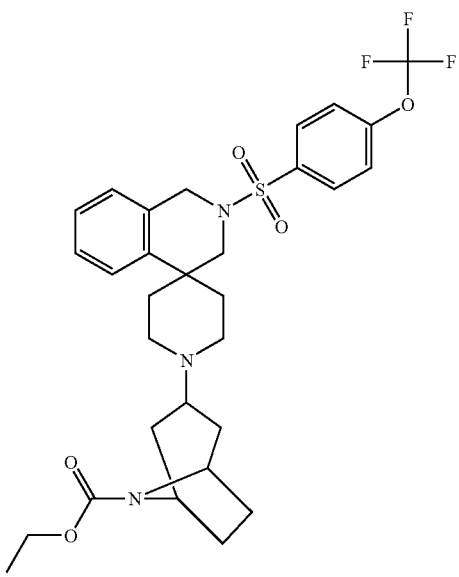
68
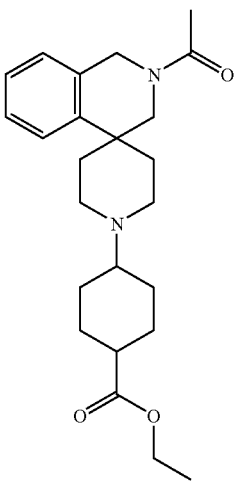

-continued
69
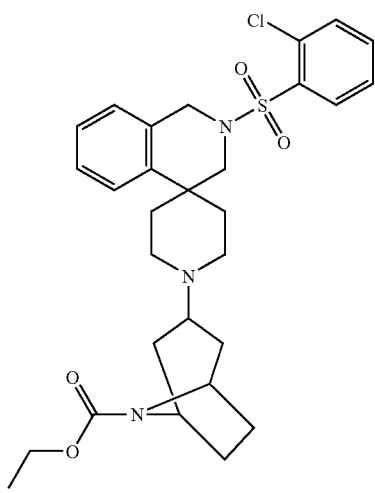
70
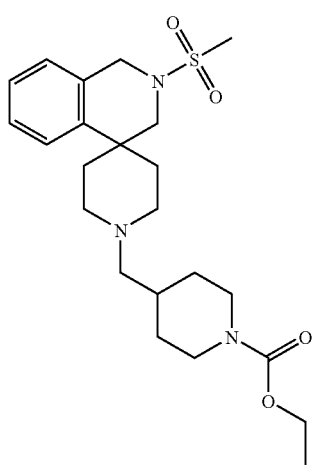
71
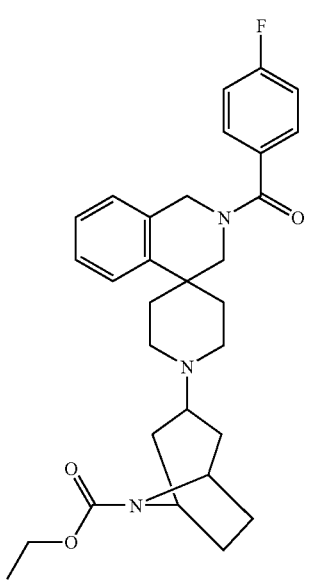
-continued
72
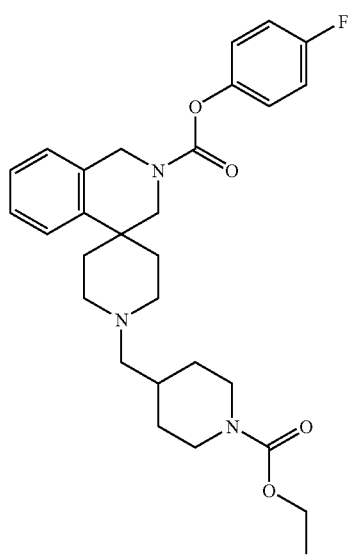
73
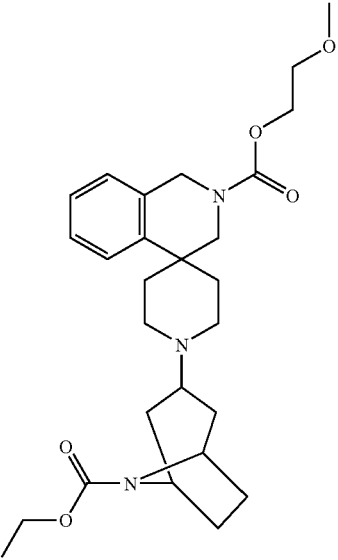
74
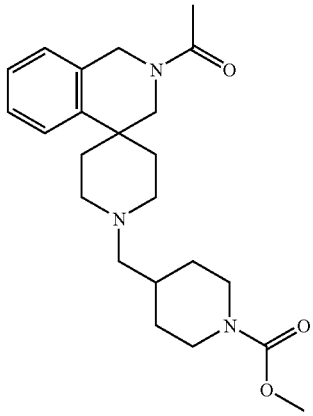

-continued
76
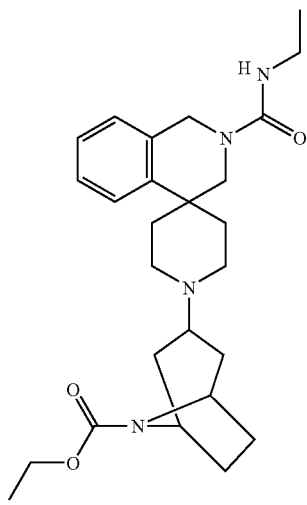
77
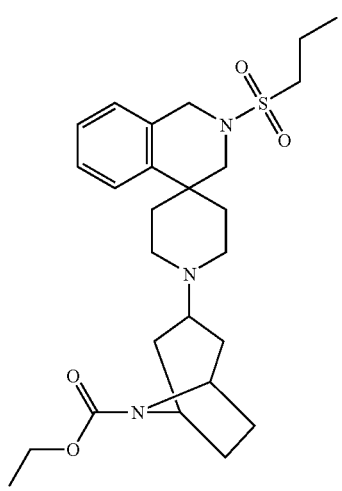
79
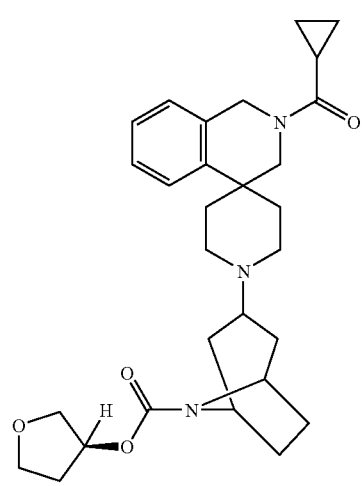
-continued
80
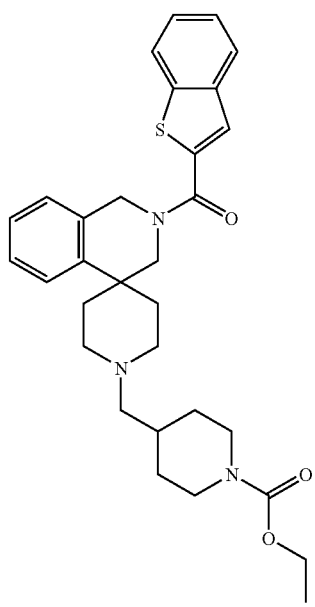
81
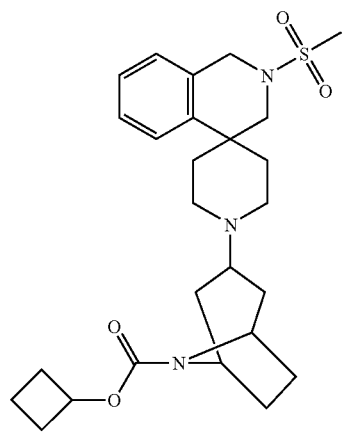
82
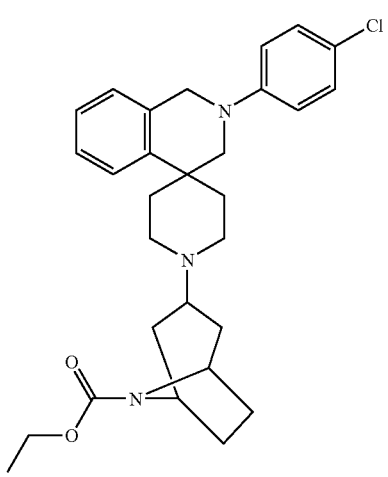

-continued
84
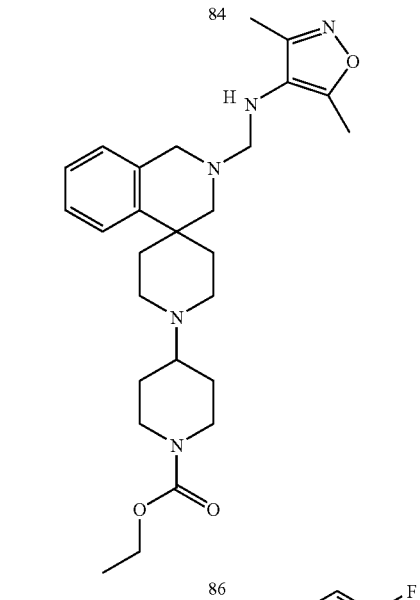
86
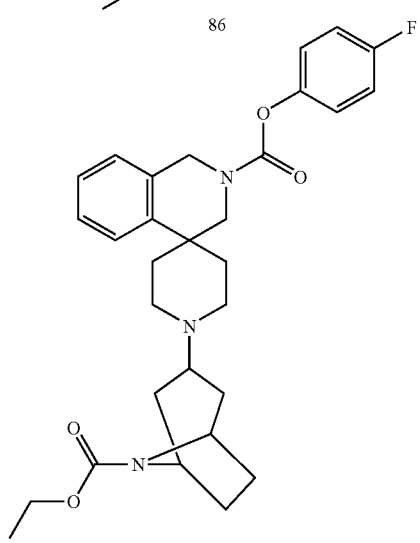
87
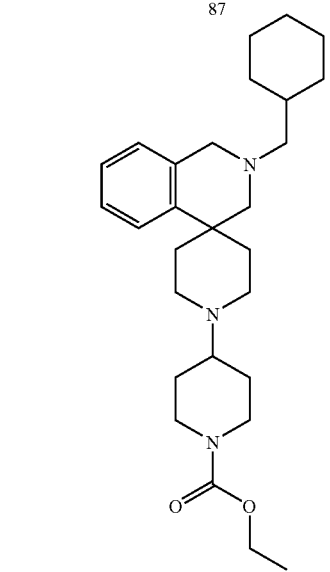
-continued
88
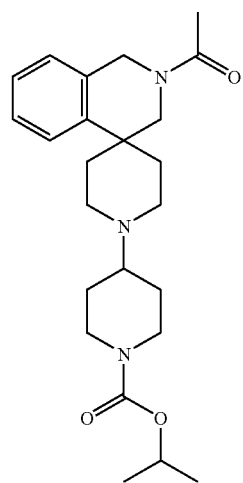
90
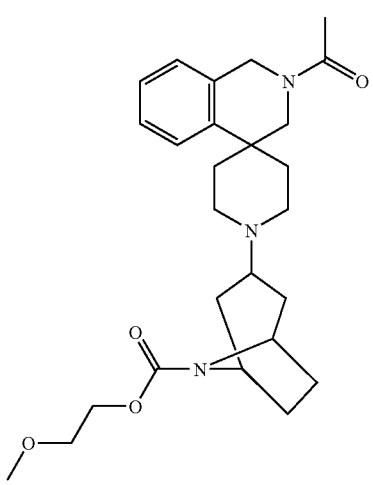
91
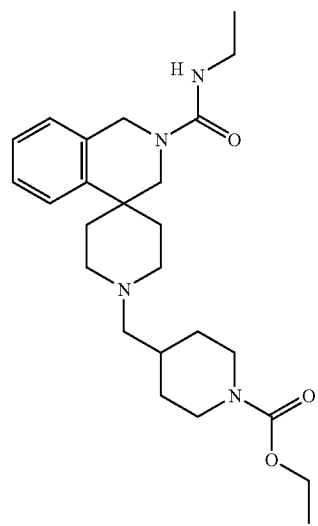

| 245 | 246 |
|---|---|
| -continued | -continued |
| 92 | 95 |
| 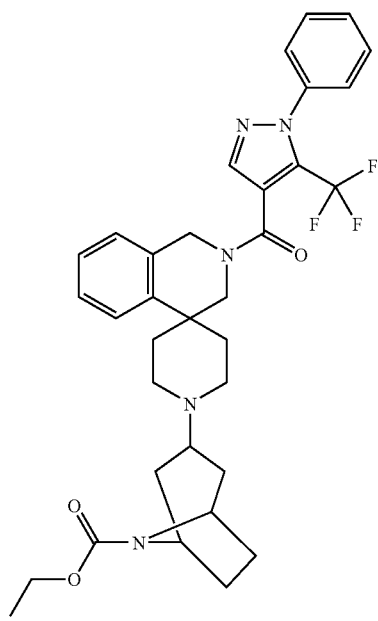 | 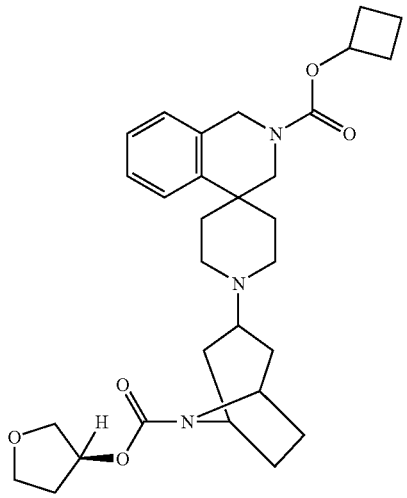 |
| 93 | 96 |
| 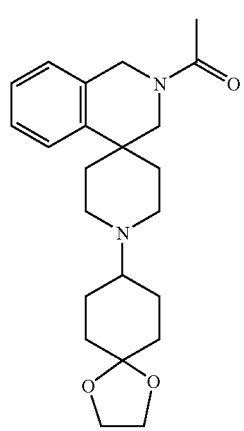 | 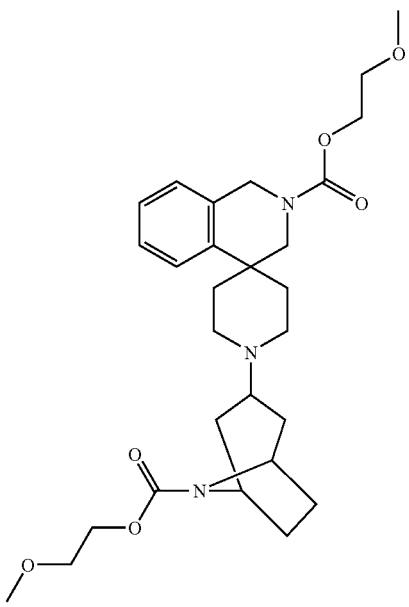 |
| 94 | 97 |
| 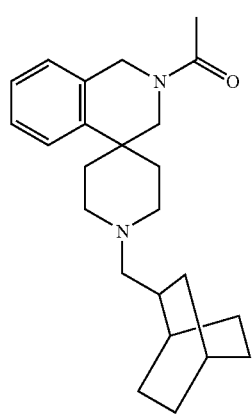 | 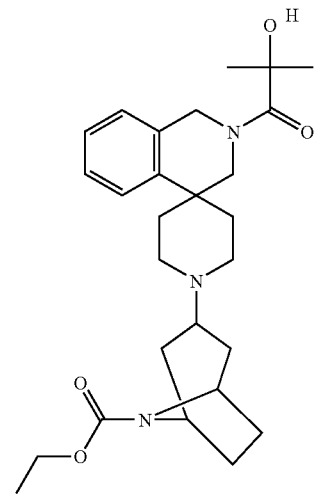 |

| 247 | 248 |
|---|---|
| -continued | -continued |
99
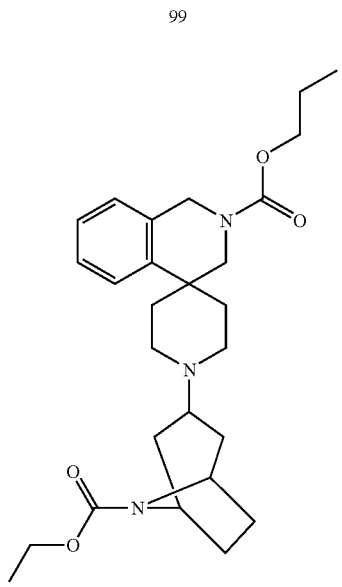
102
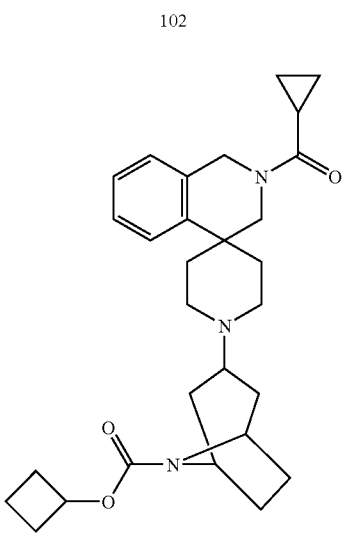
103
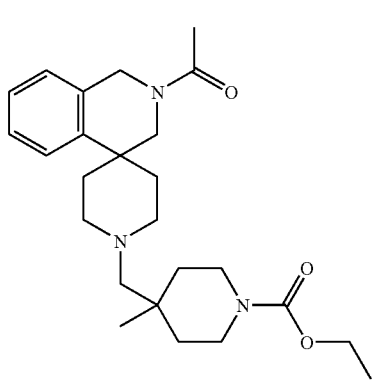
104
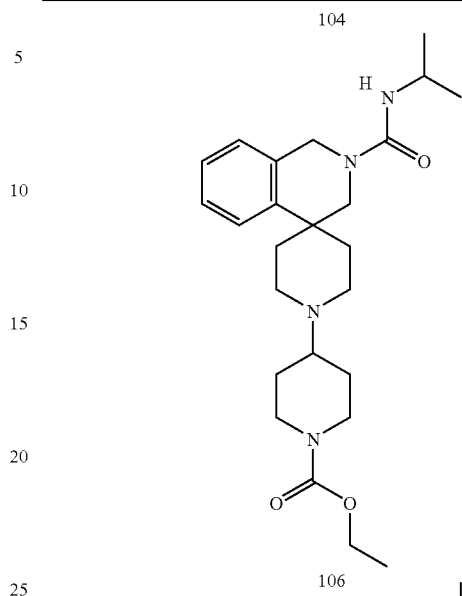
106
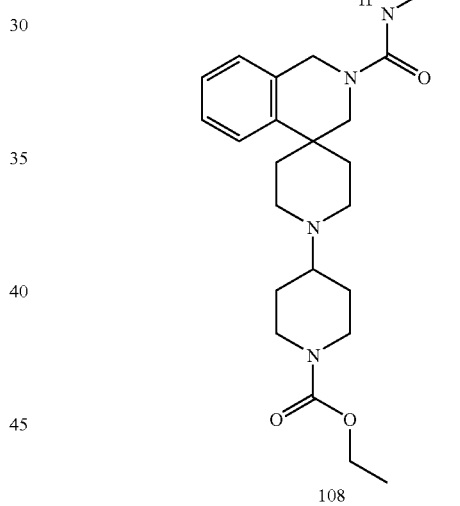
108
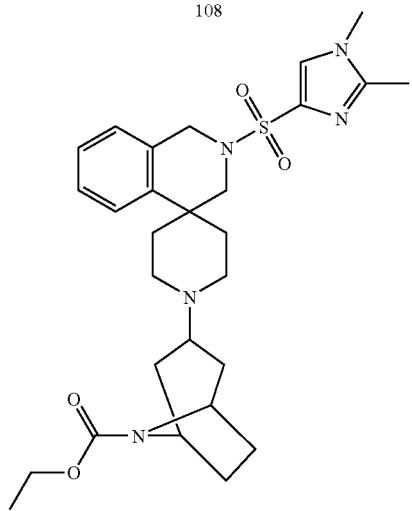

-continued
109
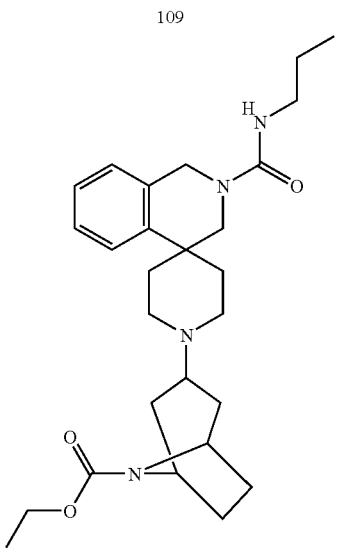
110
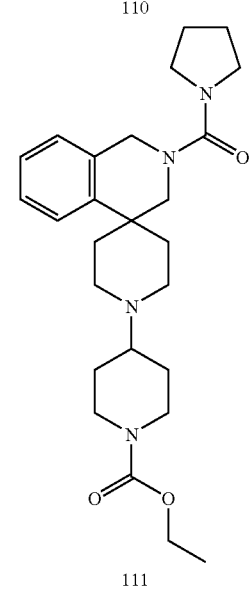
111
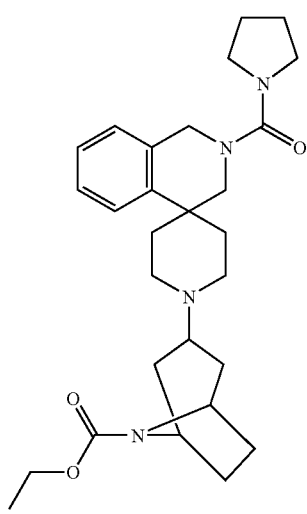
-continued
112
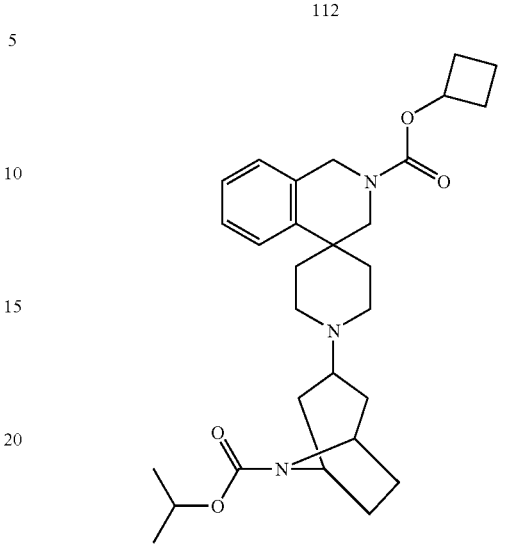
113
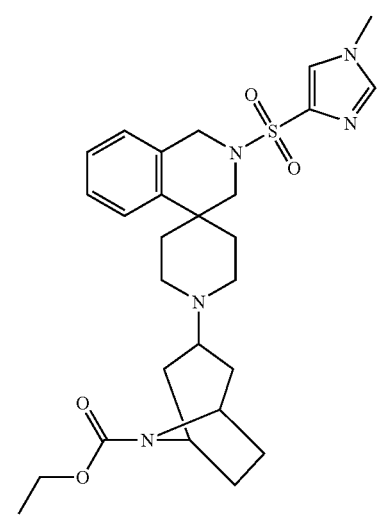
114
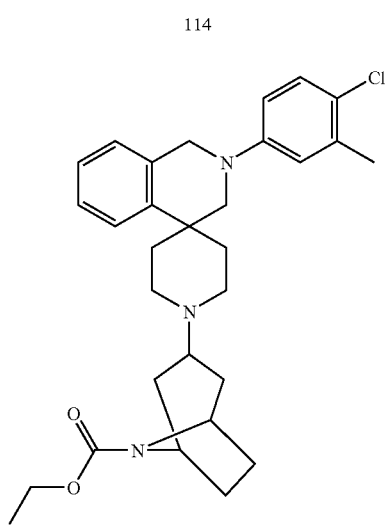

-continued
117
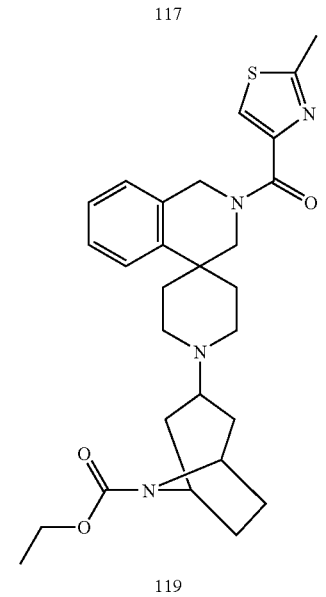
119
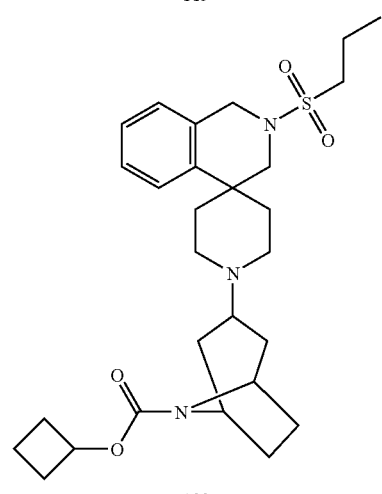
120
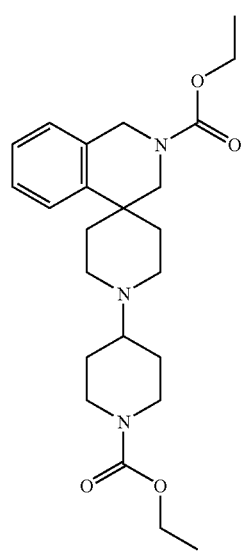
-continued
122
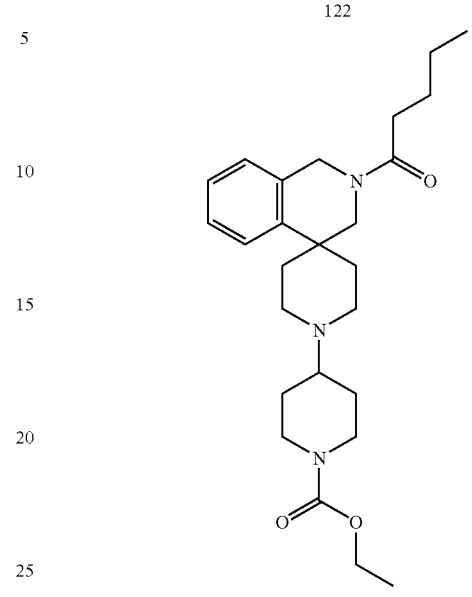
123
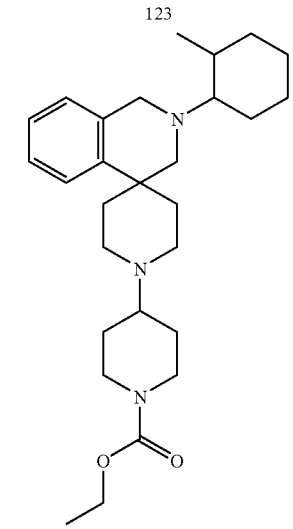
124
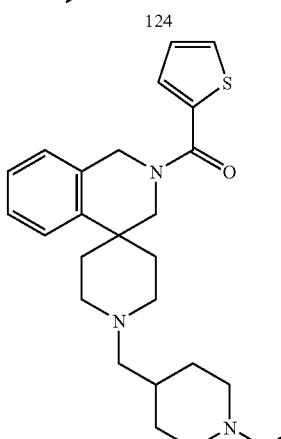

-continued
125
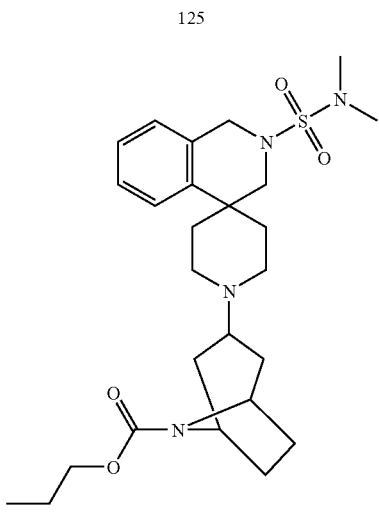
126
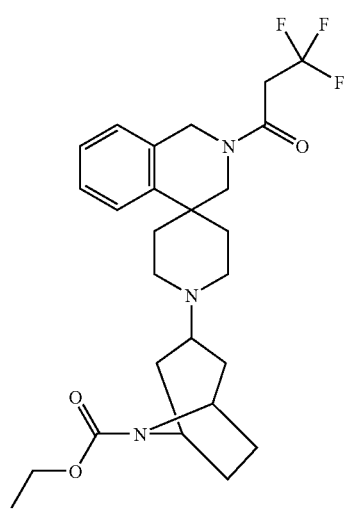
127
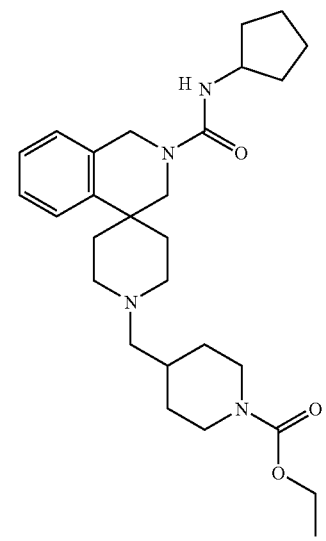
-continued
128
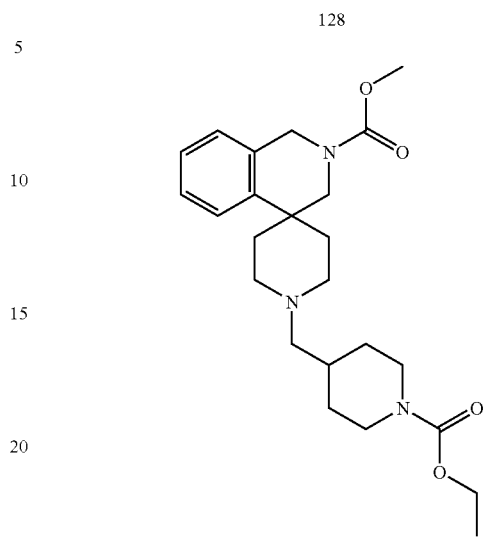
129
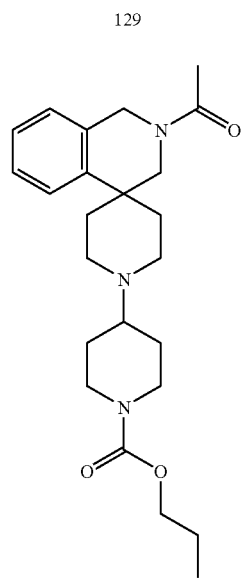
131
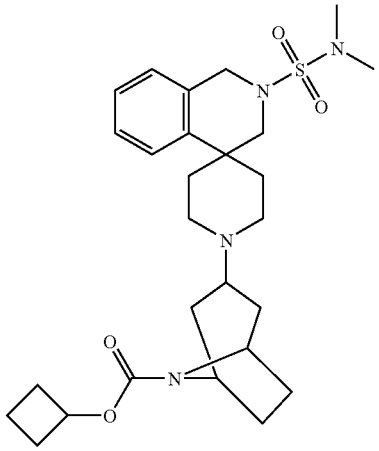

| 255 | 256 |
|---|---|
| -continued | -continued |
| 132 | 136 |
| 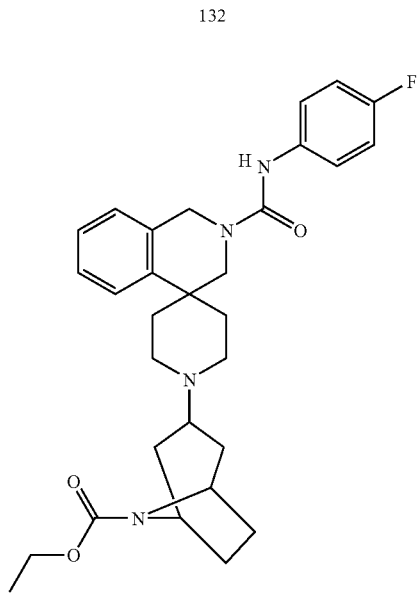 | 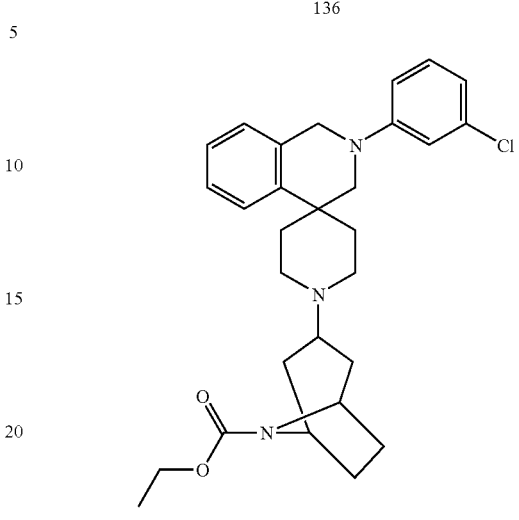 |
| 133 | 138 |
| 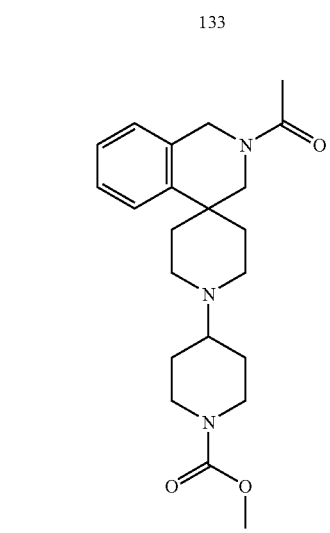 | 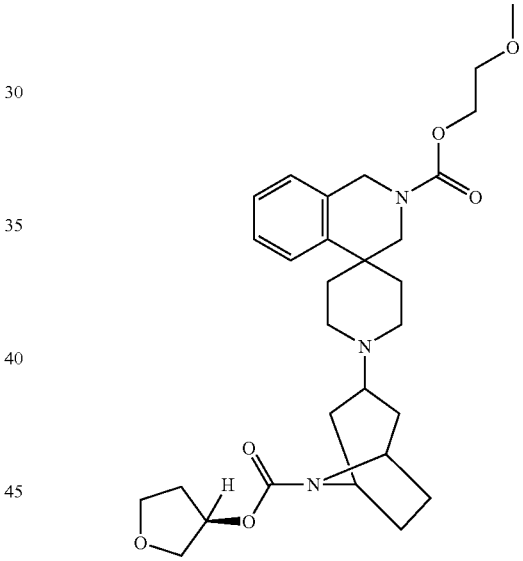 |
| 135 | 140 |
| 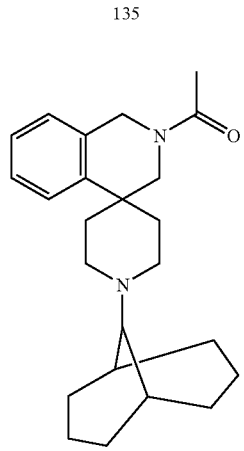 | 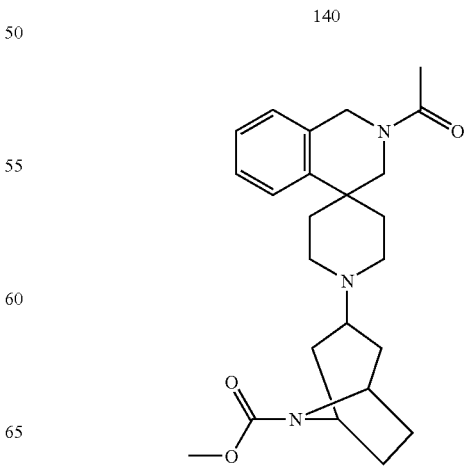 |

-continued
141
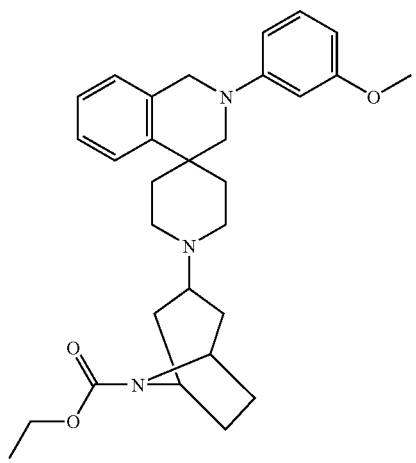
143
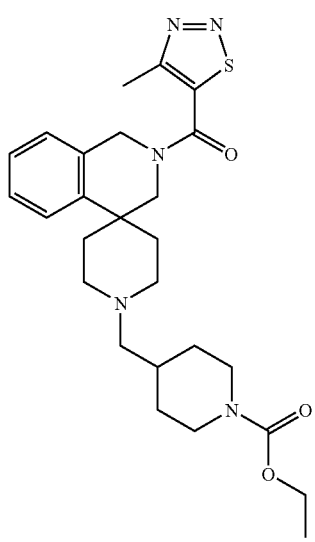
146
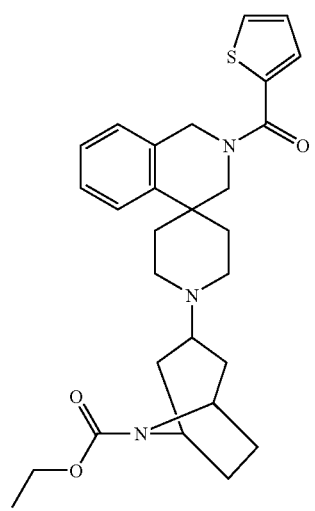
-continued
147
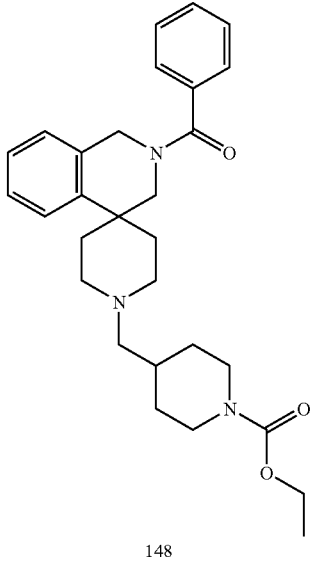
148
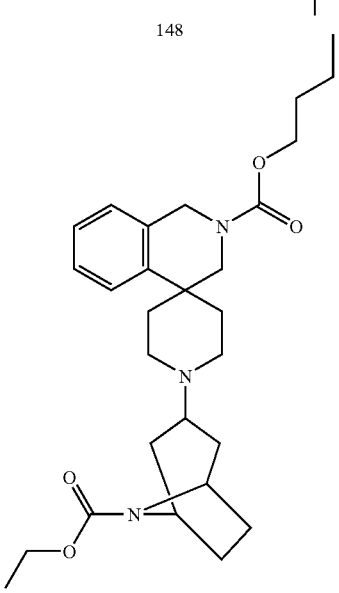
149
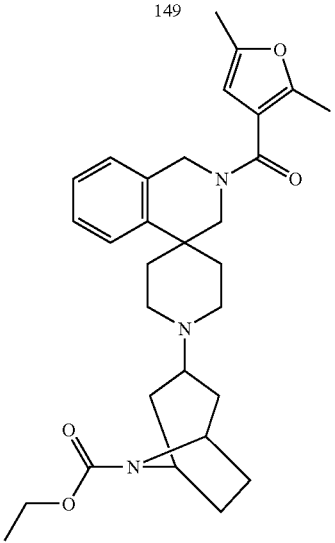

-continued
151
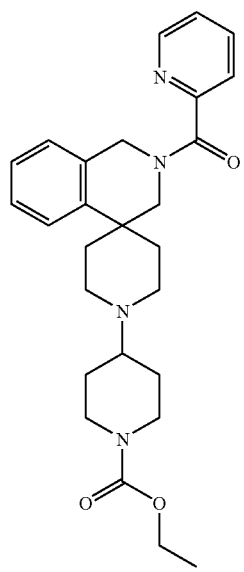
153
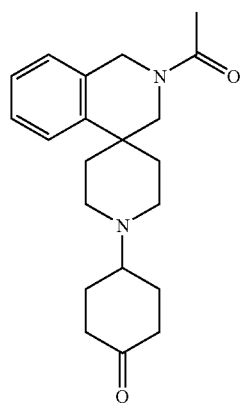
154
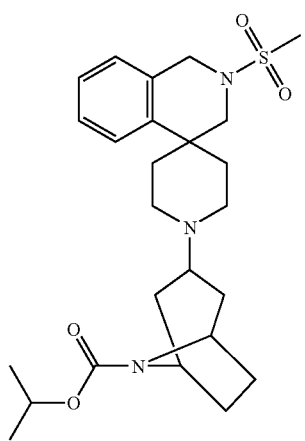
-continued
155
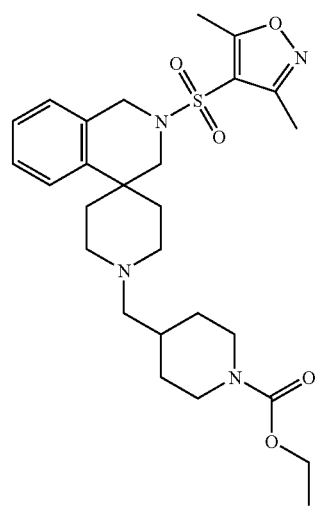
156
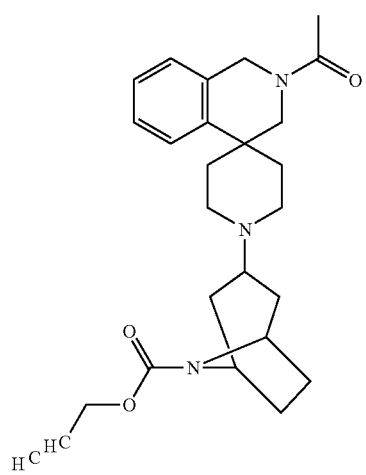
157
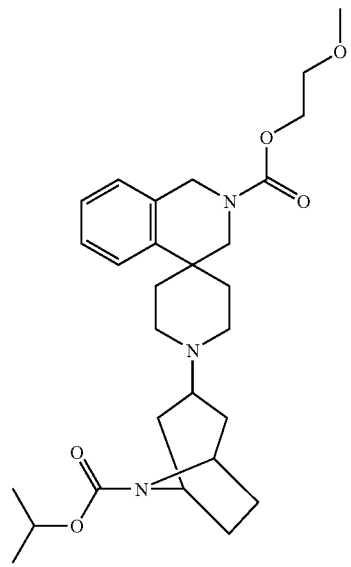

-continued
158
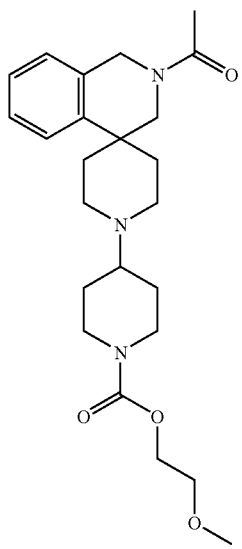
159
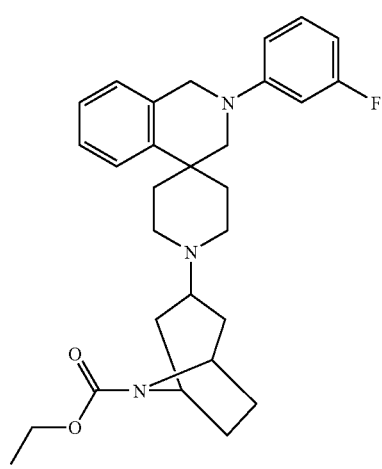
160
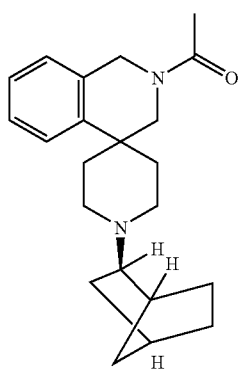
-continued
161
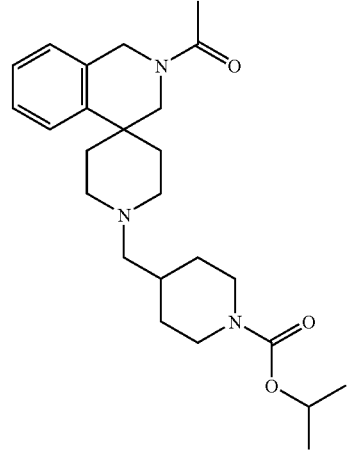
162
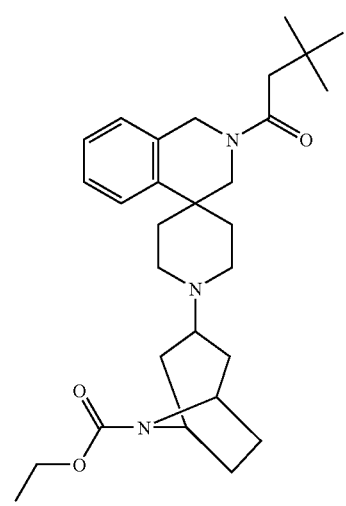
163
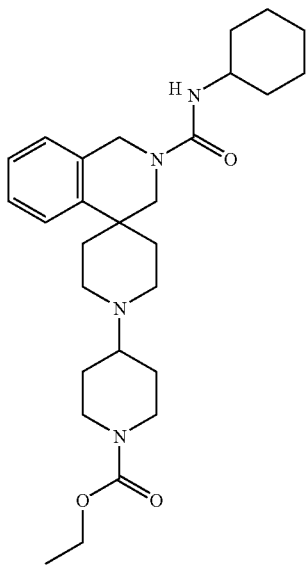

263
-continued
164
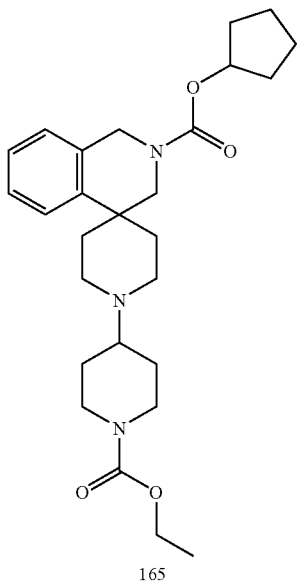
165
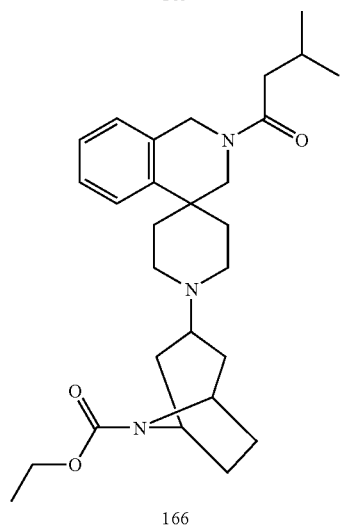
166
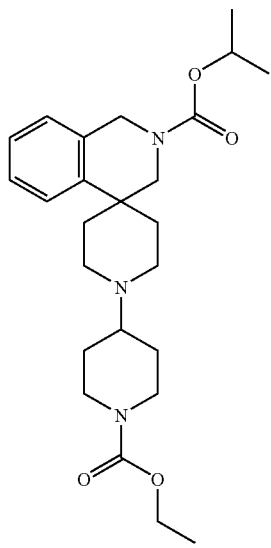
264
-continued
167
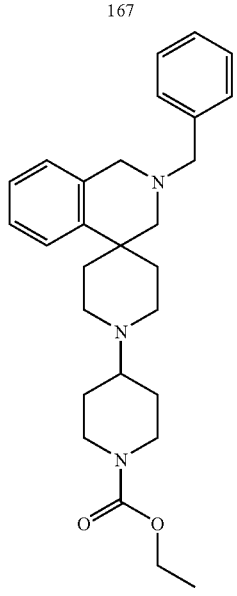
168
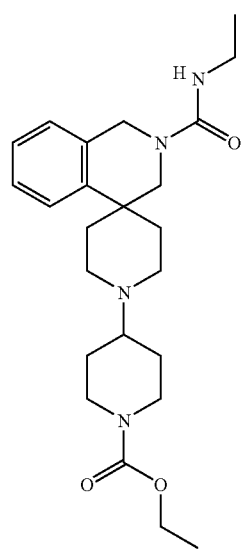
169
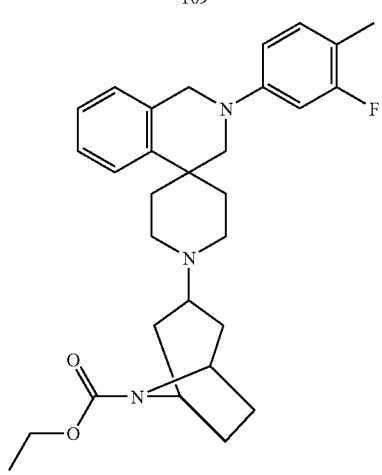

-continued
170
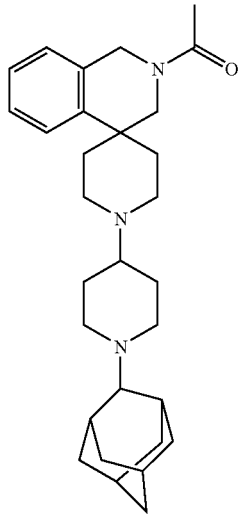
171
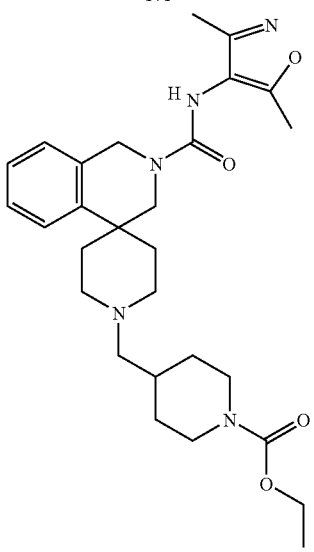
172
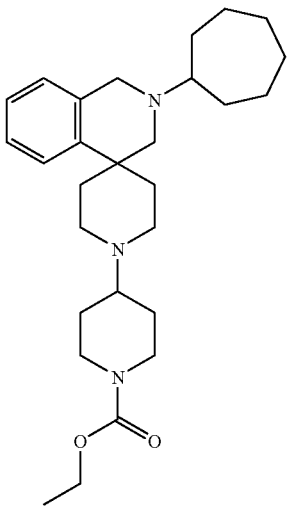
-continued
173
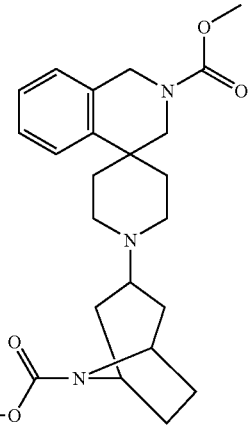
174
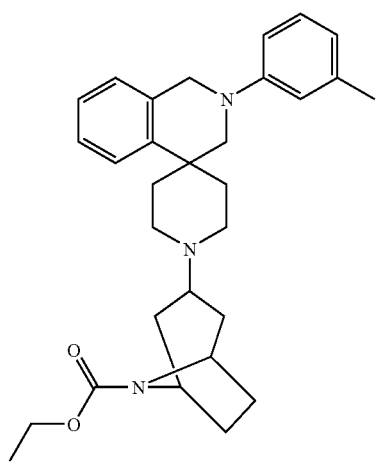
175
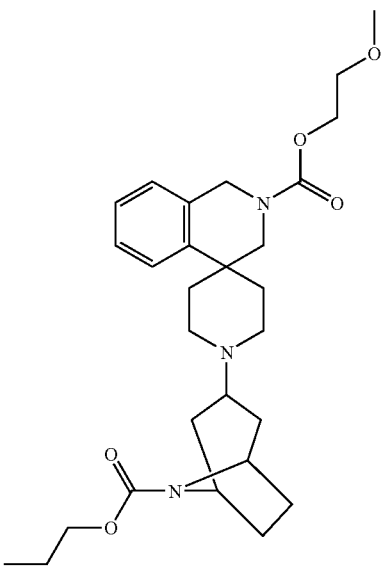

| 267 | 268 |
|---|---|
| -continued | -continued |
| 176 | 179 |
| 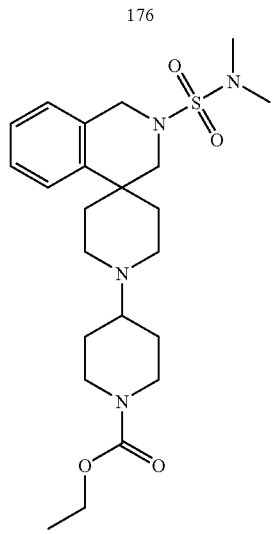 | 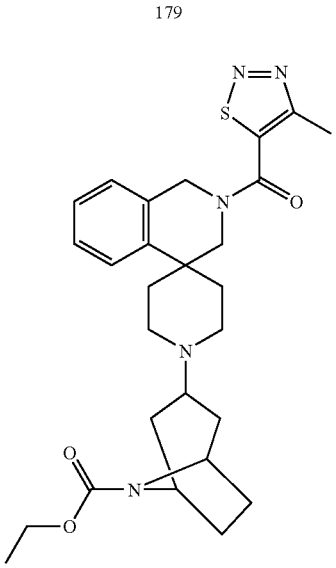 |
| 177 | 181 |
| 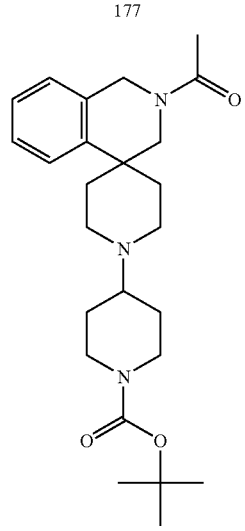 | 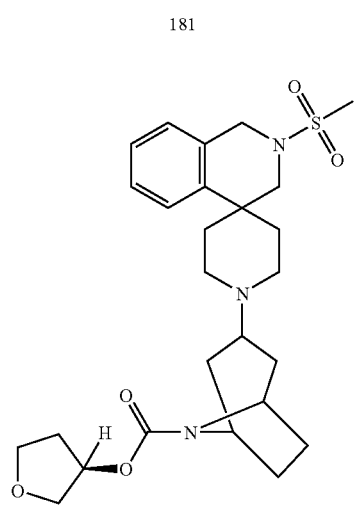 |
| 178 | 182 |
| 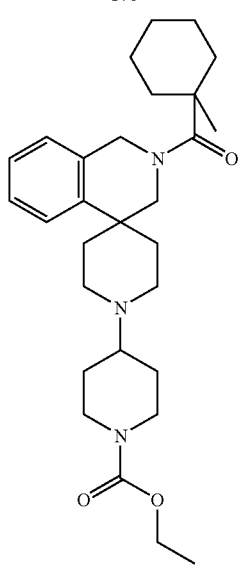 | 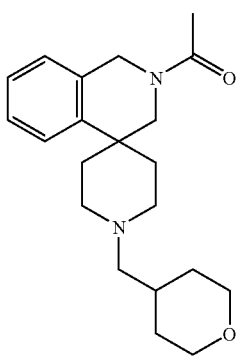 |

-continued
183
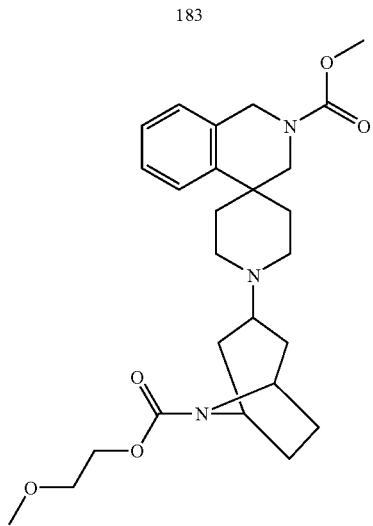
184
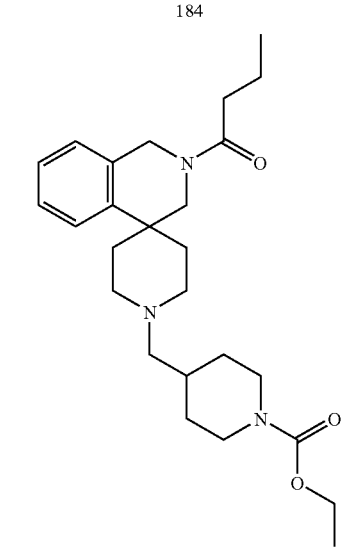
185
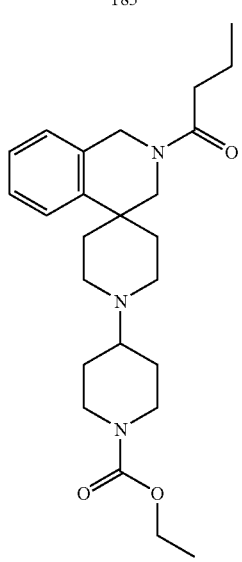
-continued
186
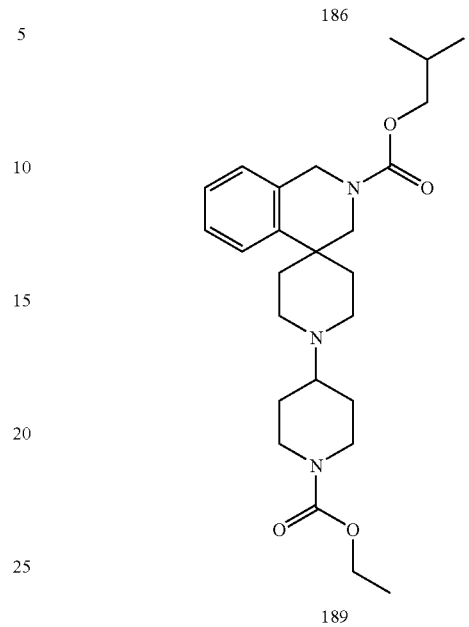
189
190
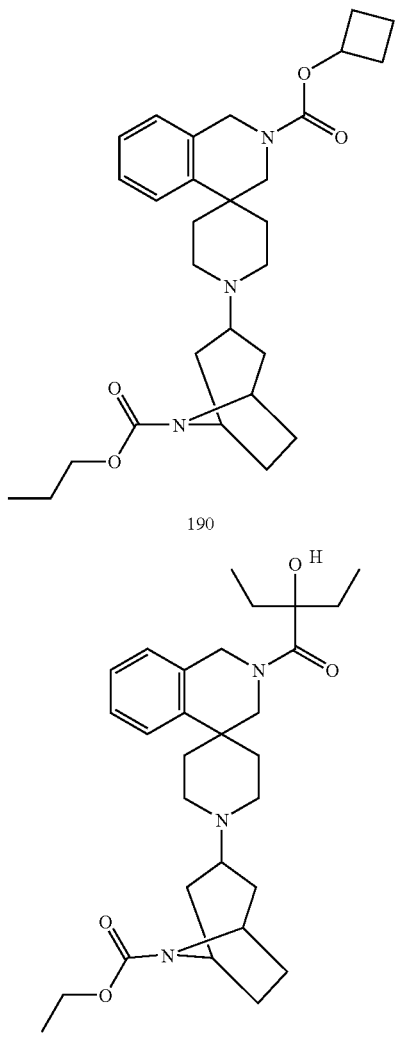

| 193 | 196 |
|---|---|
| 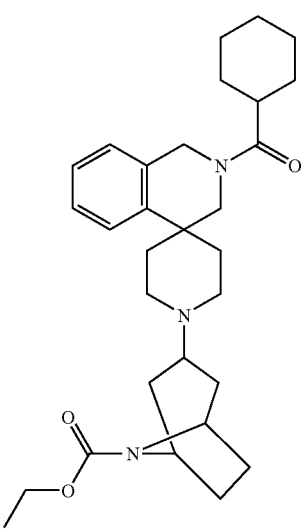 | 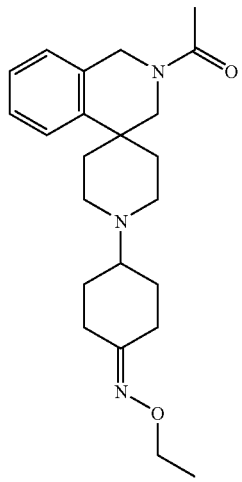 |
| 194 | 197 |
| 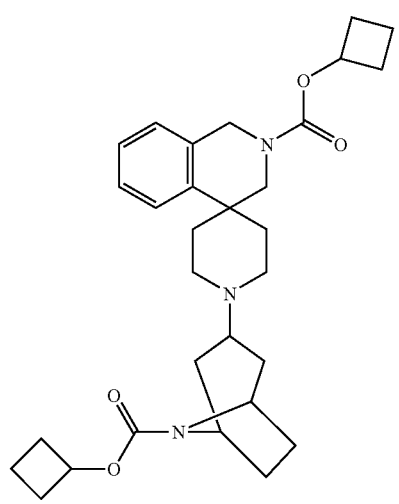 | 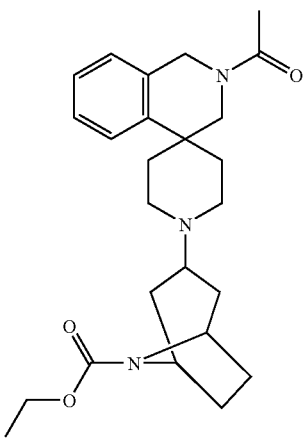 |
| 195 | 198 |
| 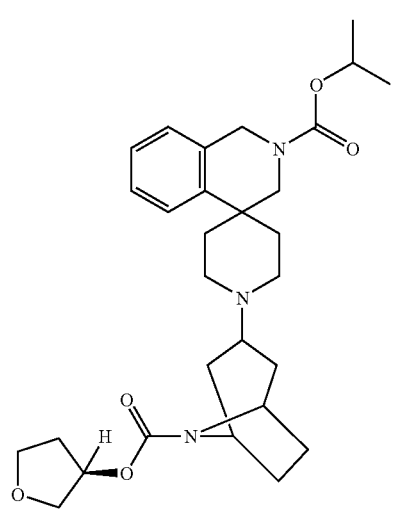 | 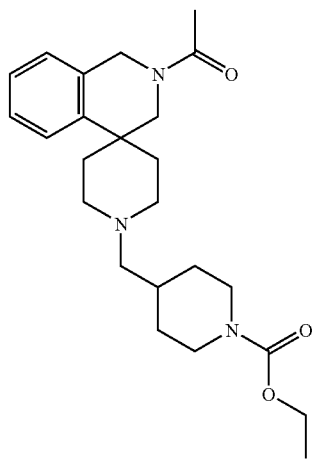 |

| 273 | 274 |
|---|---|
| -continued | -continued |
| 200 | 203 |
| 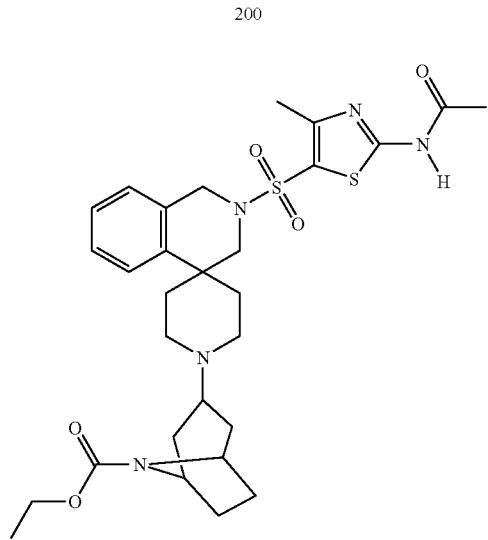 | 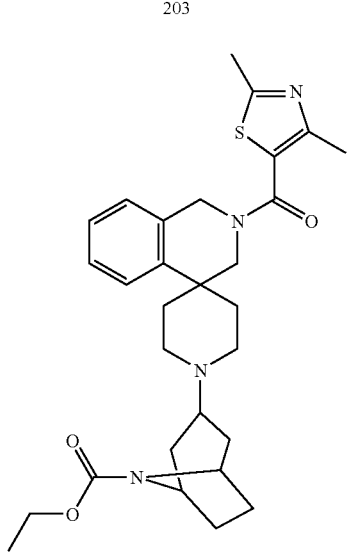 |
| 201 | 204 |
| 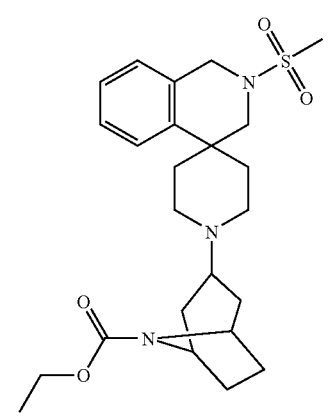 | 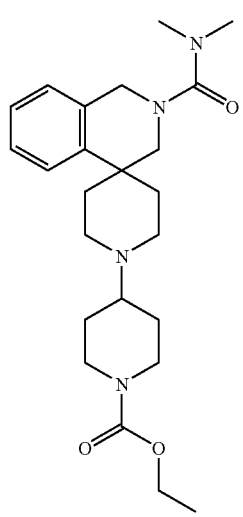 |
| 202 | 205 |
| 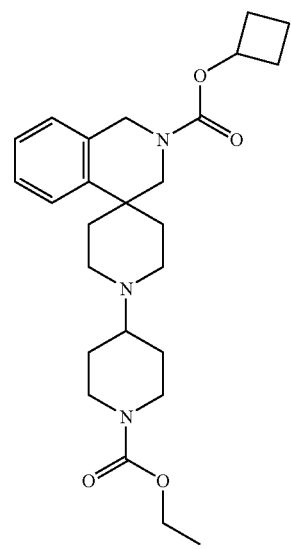 | |

-continued
206
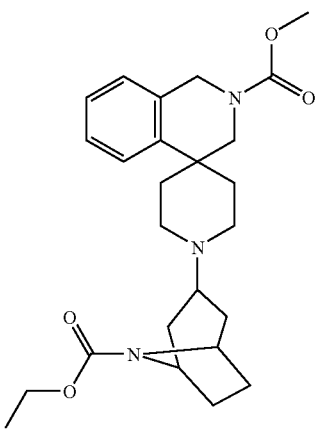
207
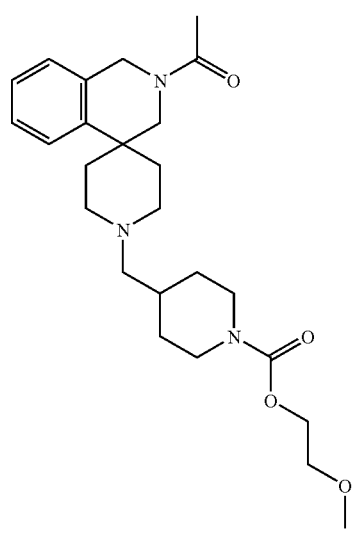
208
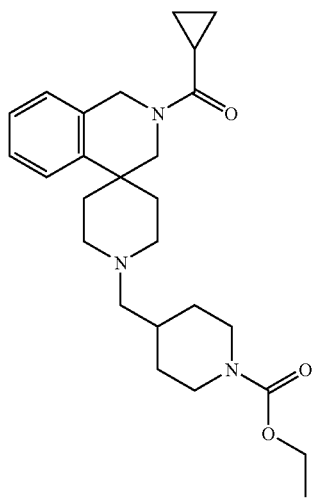
-continued
209
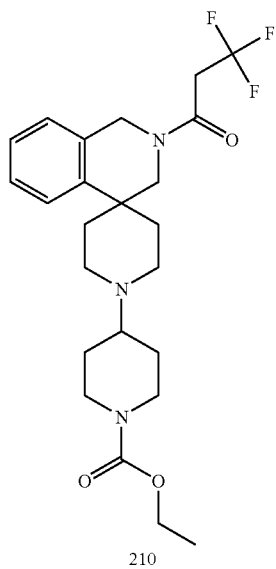
210
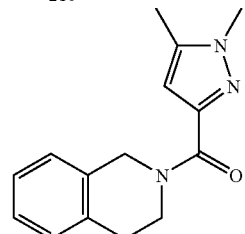
211
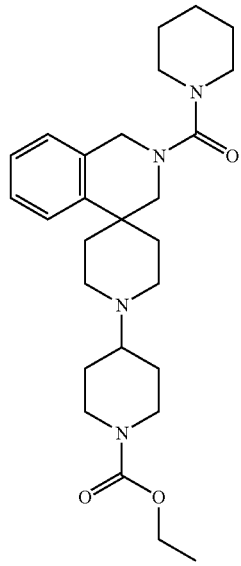

| 277 | 278 |
|---|---|
| -continued | -continued |
| 212 | 215 |
| 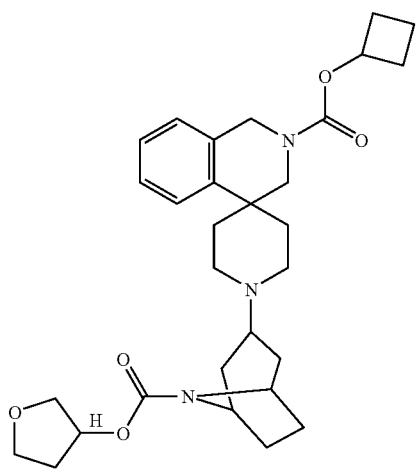 | 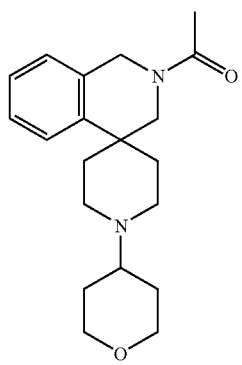 |
| 213 | 216 |
| 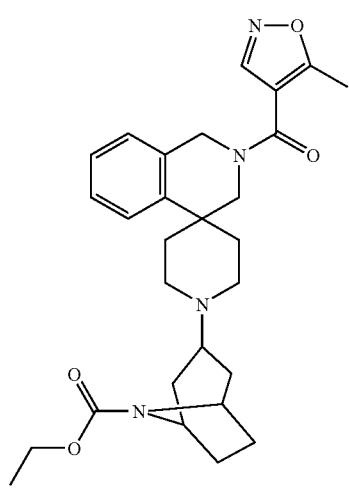 | 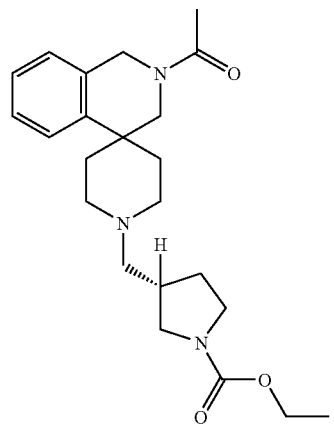 |
| 214 | 218 |
| 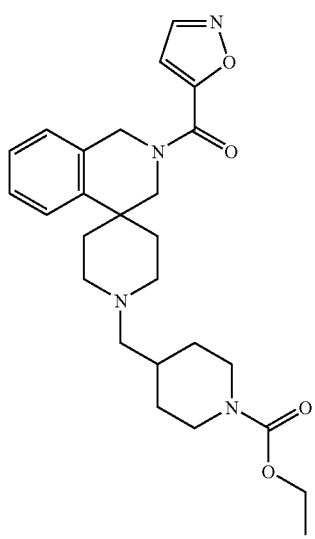 | 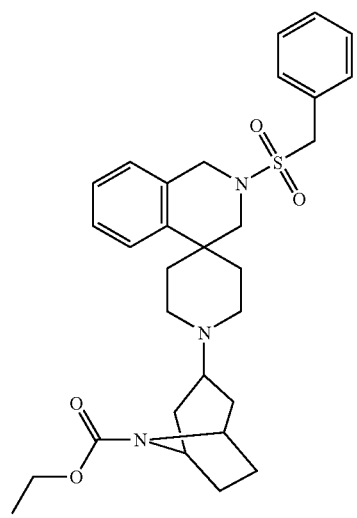 |

-continued
219
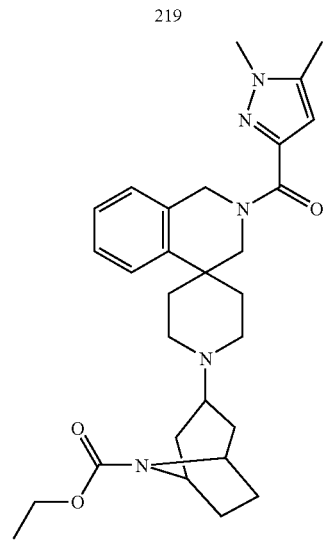
220
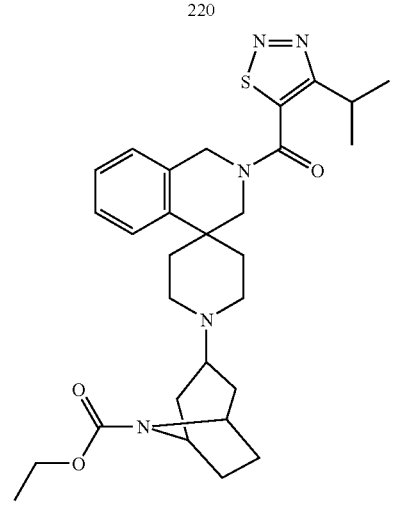
221
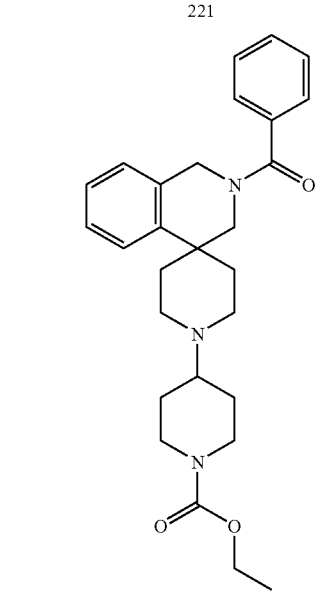
-continued
222
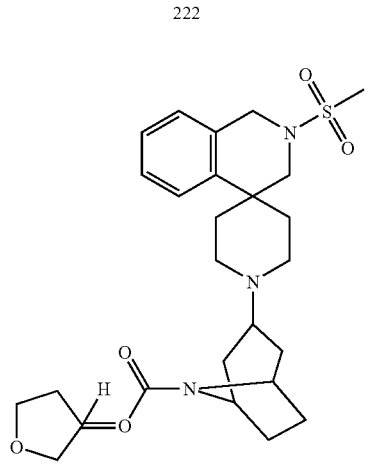
223
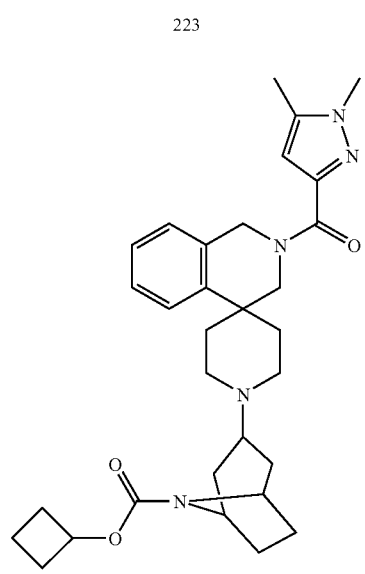
224
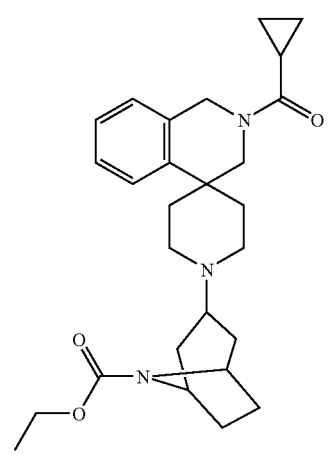

-continued
225
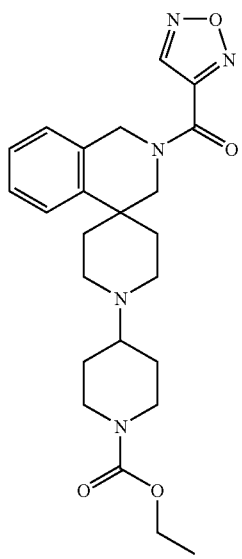
226
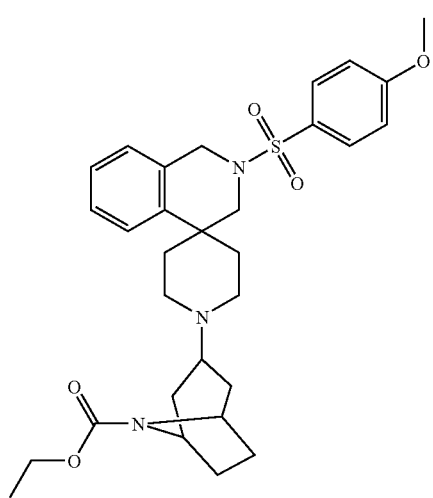
228
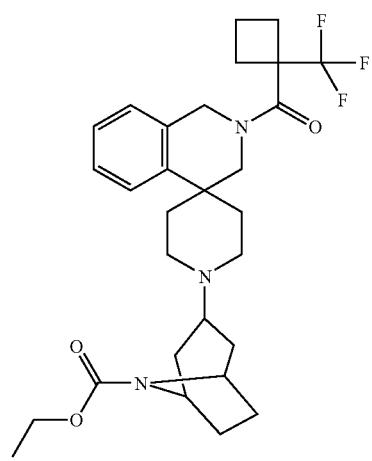
-continued
229
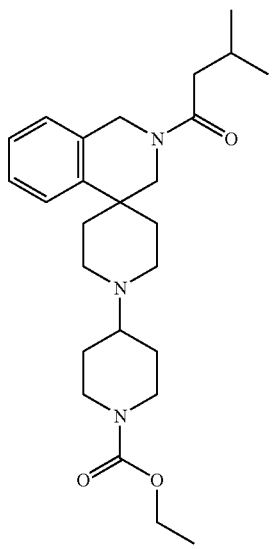
231
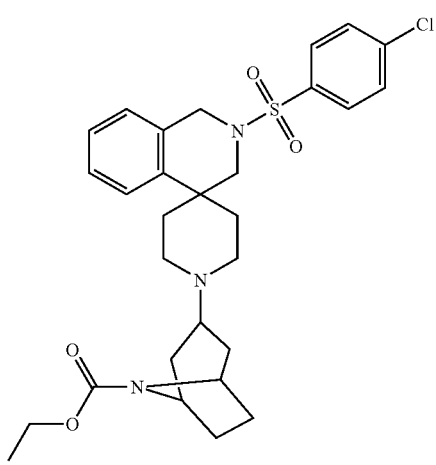
232
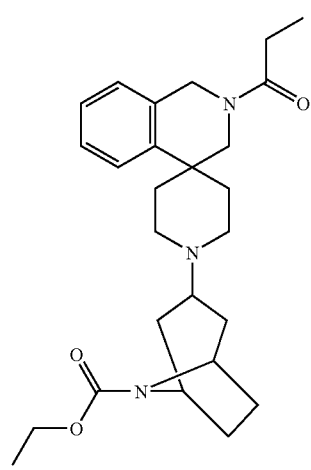

-continued
233
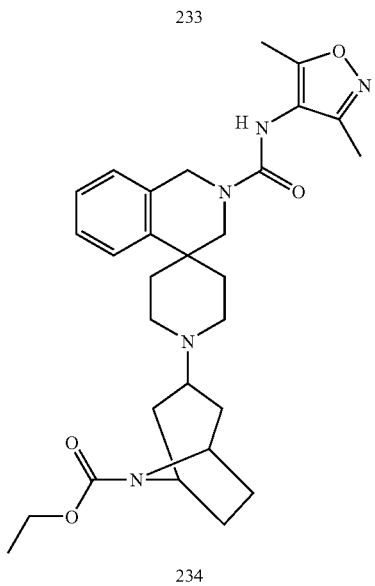
234
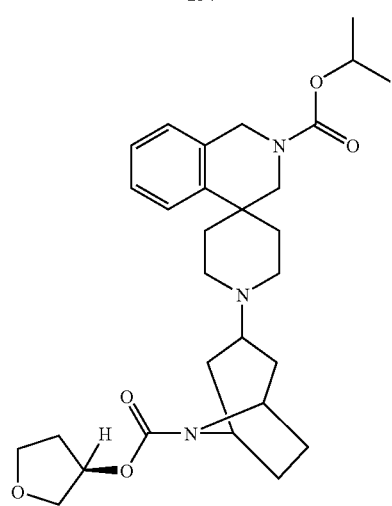
235
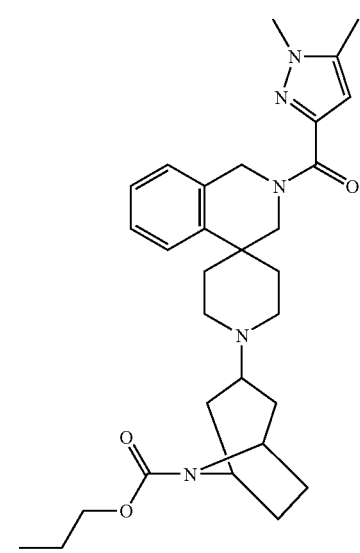
-continued
236
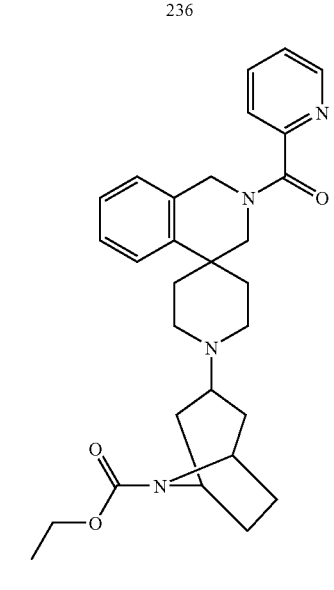
237
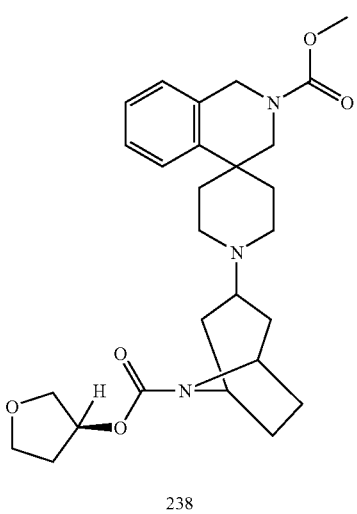
238
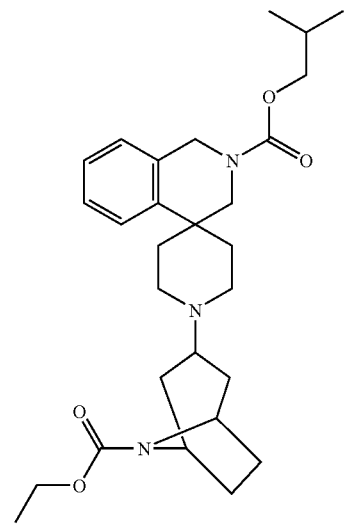

-continued
240
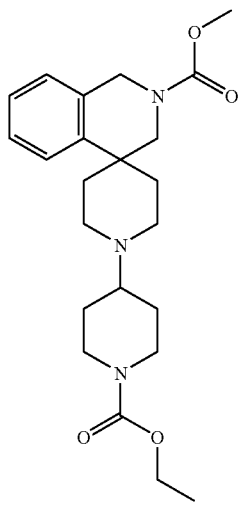
241
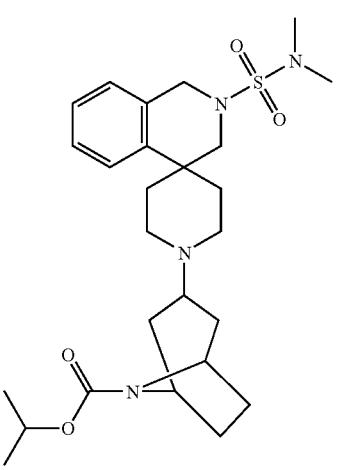
242
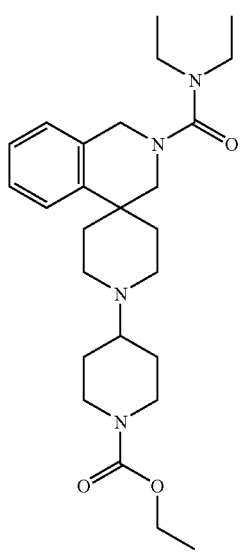
-continued
243
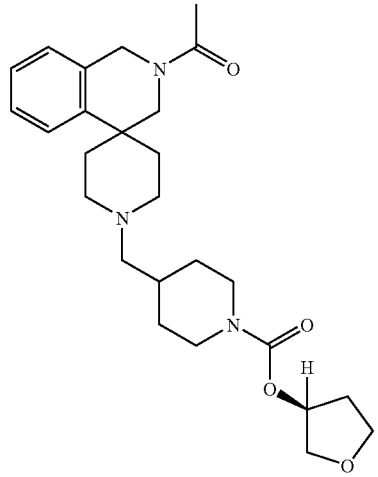
244
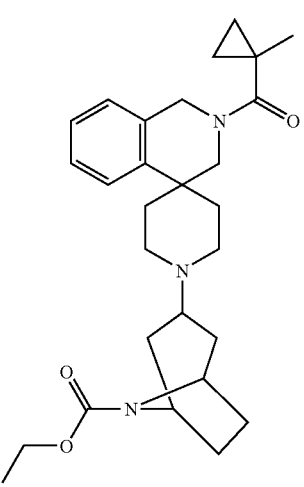
245
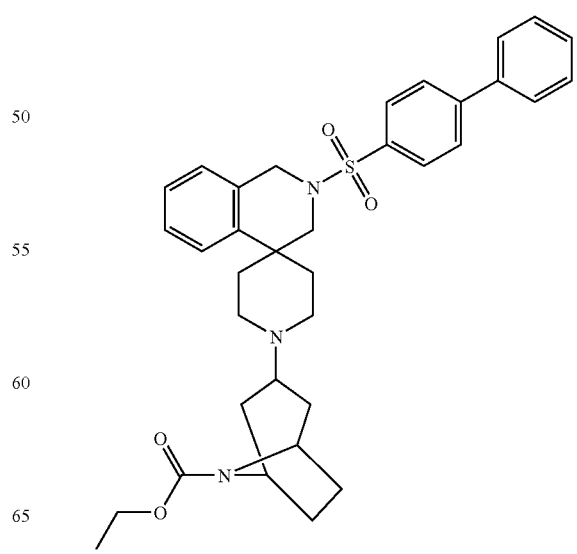

-continued
246
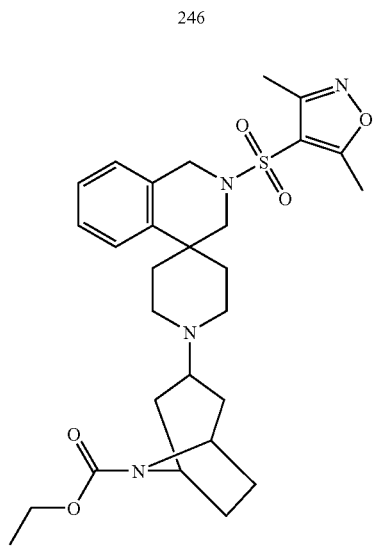
248
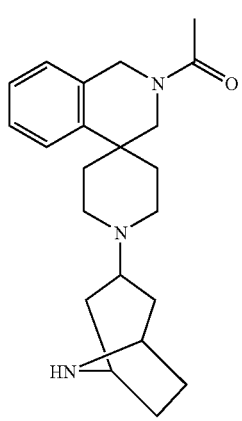
249
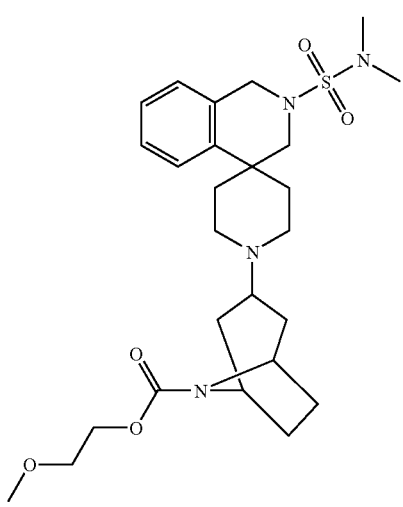
-continued
250
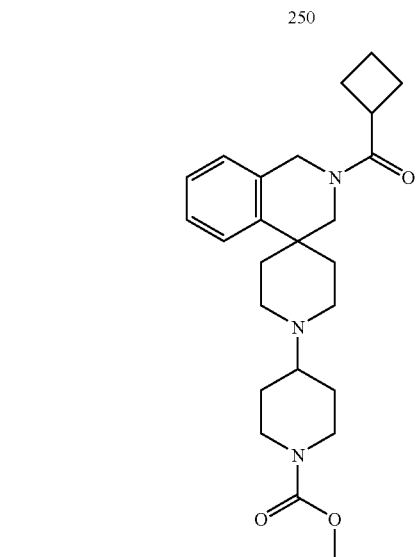
251
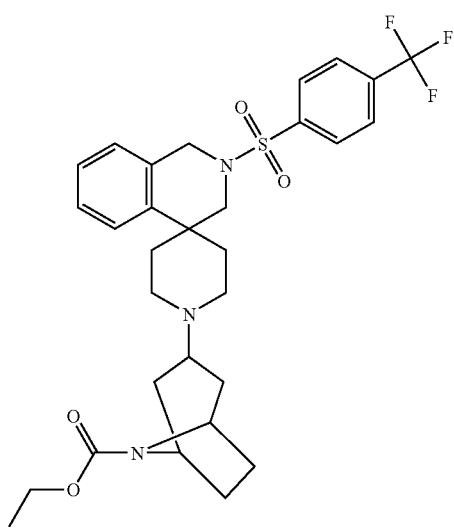
252
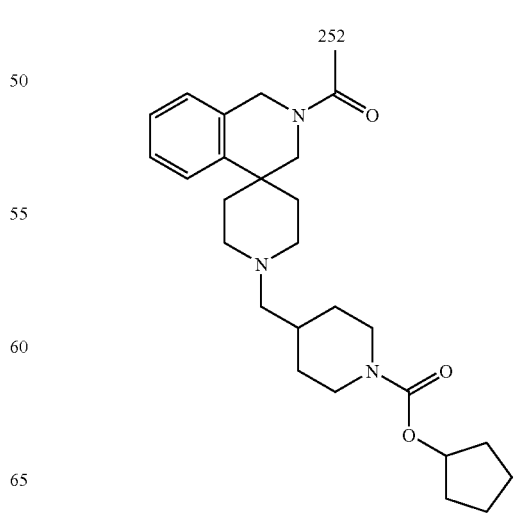

-continued
253
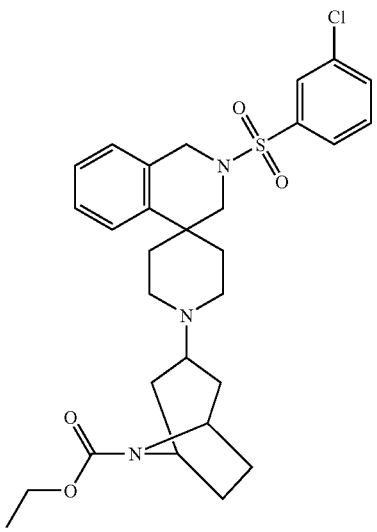
254
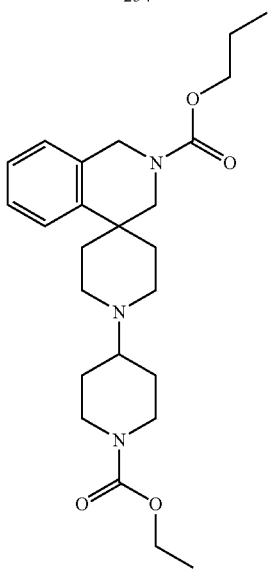
255
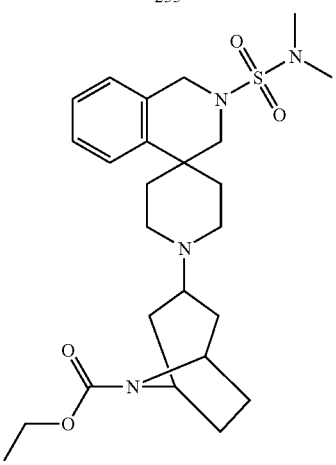
-continued
257
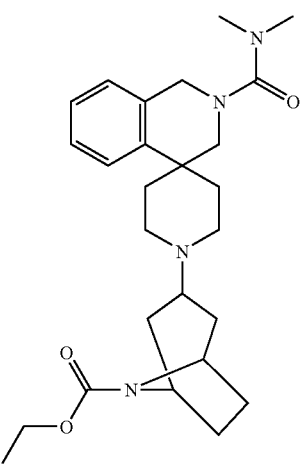
258
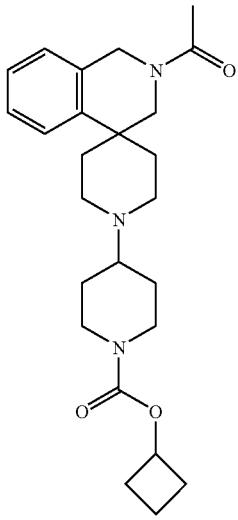
259
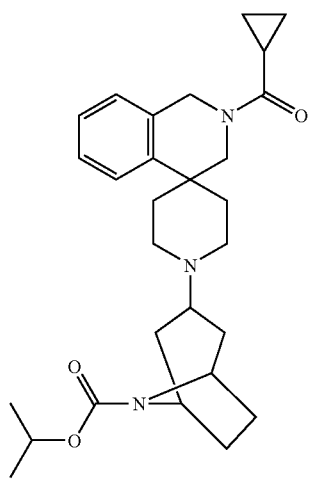

-continued
260
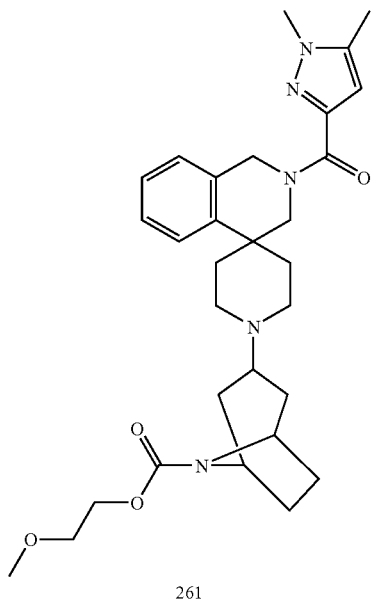
261
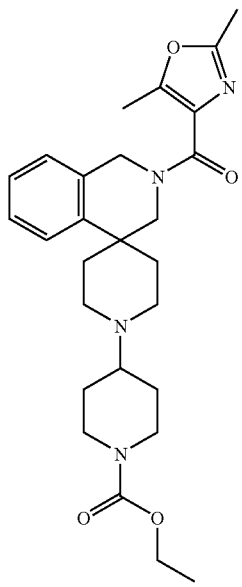
262
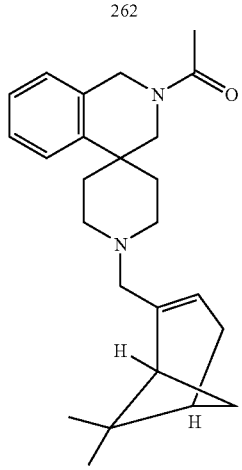
-continued
263
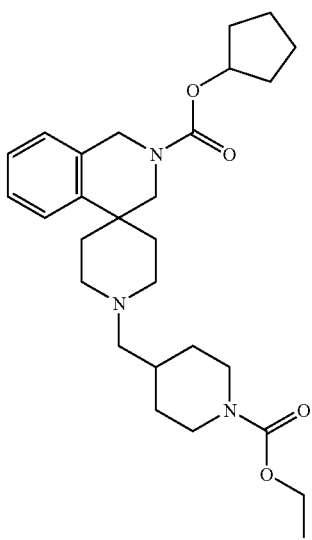
264
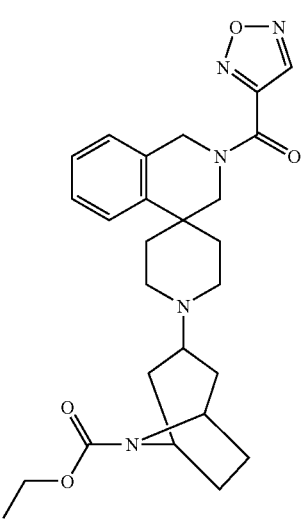
265
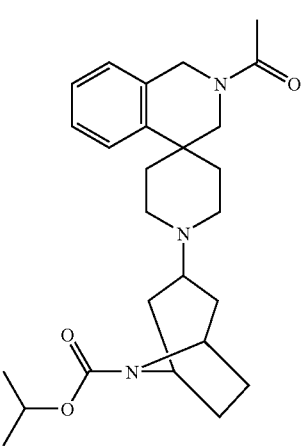

-continued
266
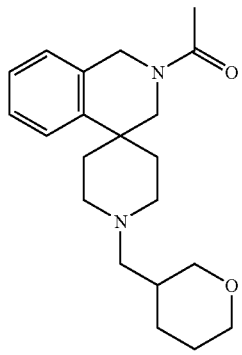
267
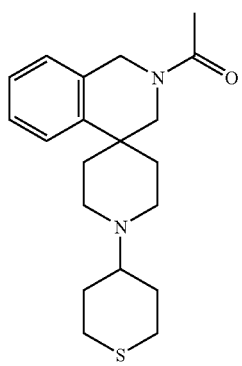
268
269
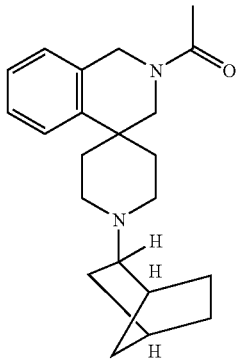
270
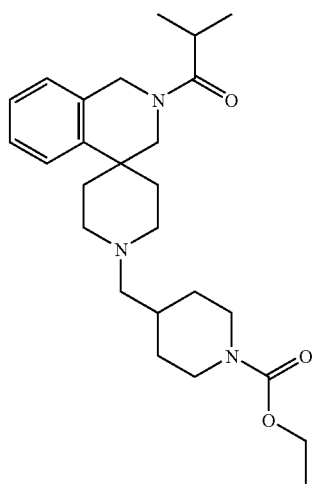
271
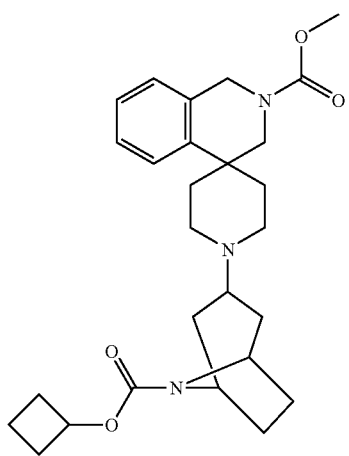

| 295 | 296 |
|---|---|
| -continued | -continued |
| 272 | 278 |
| 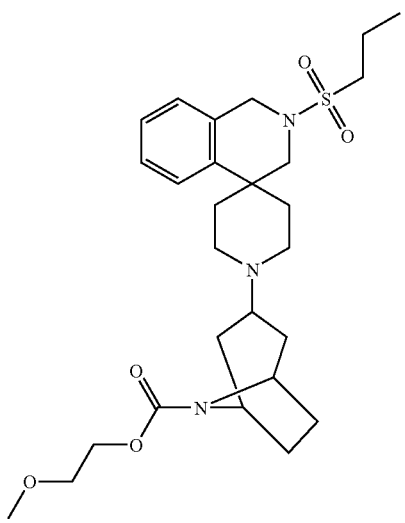 | 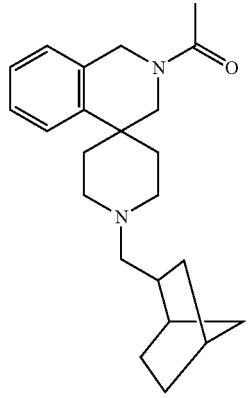 |
| 273 | 279 |
| 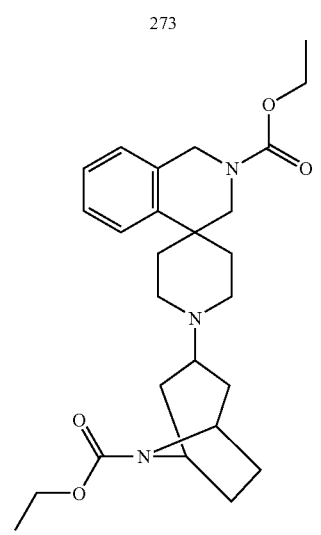 | 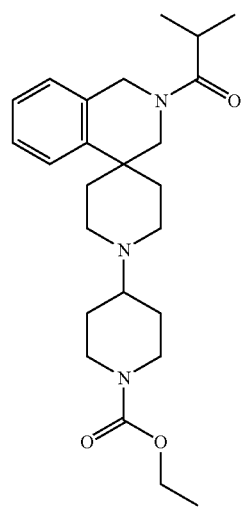 |
| 275 | 282 |
| 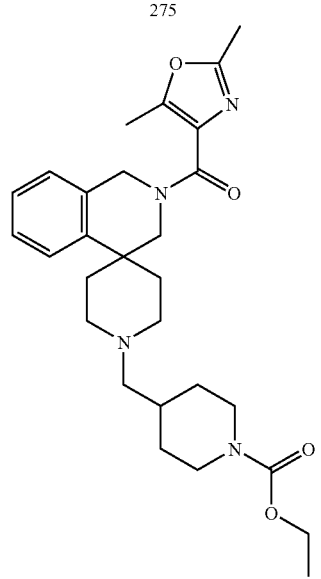 | 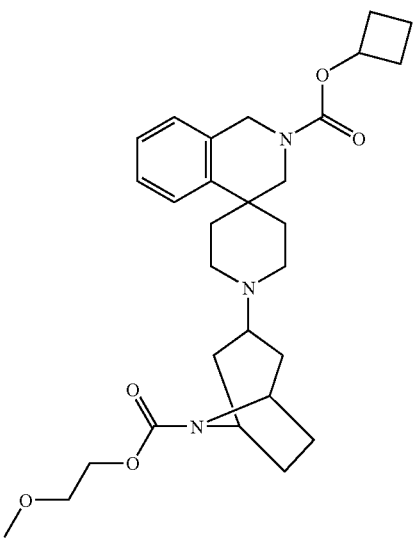 |

297
-continued
283
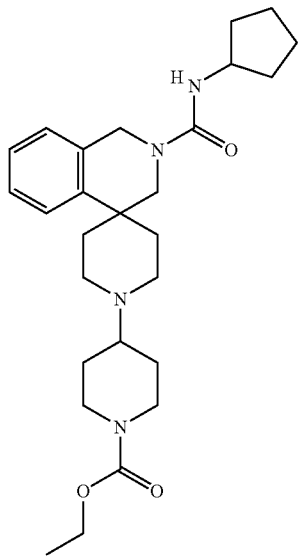
284
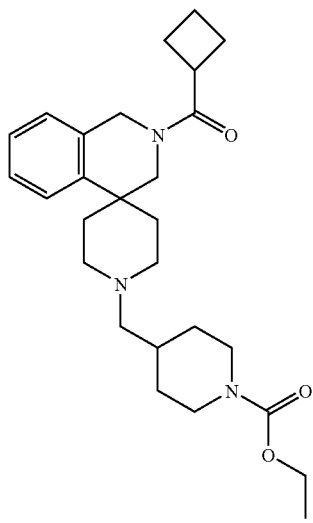
285
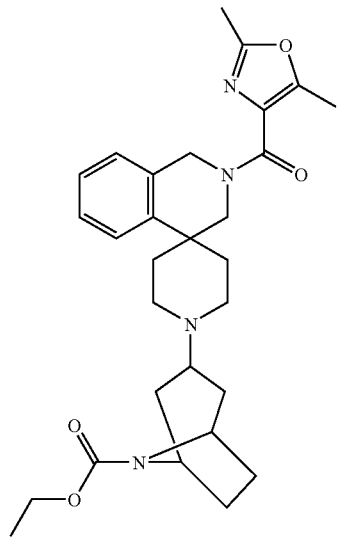
298
-continued
286
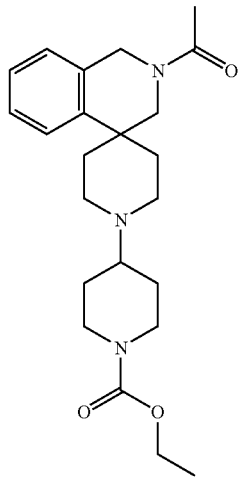
287
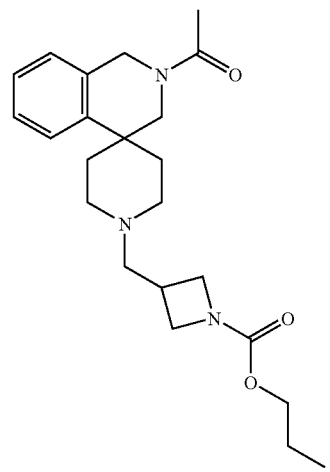
288
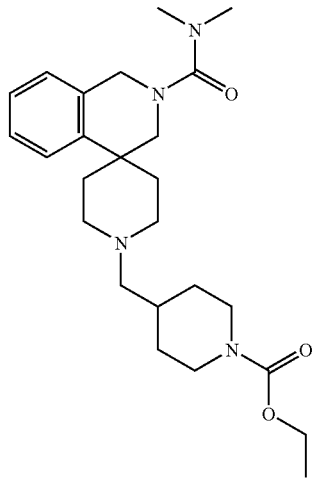

-continued
289
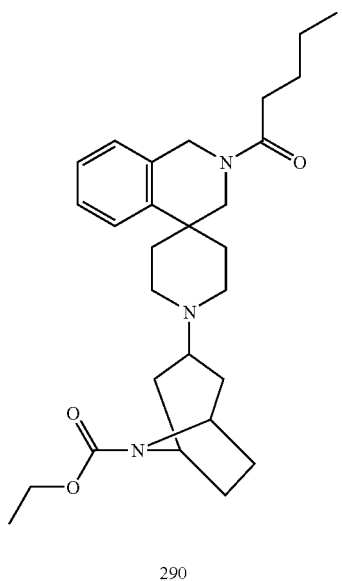
290
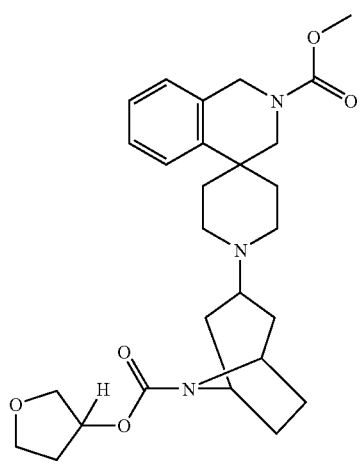
291
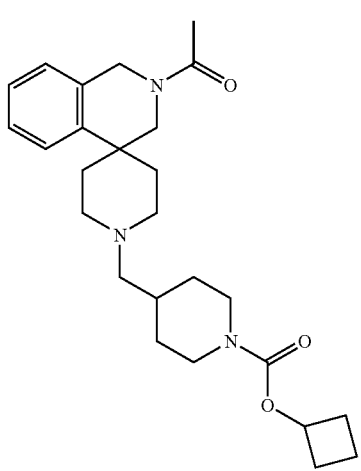
-continued
292
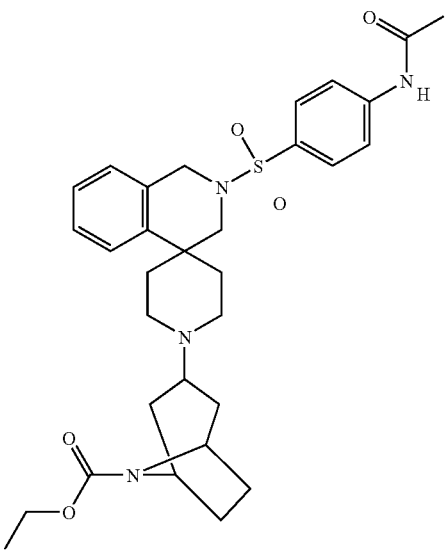
293
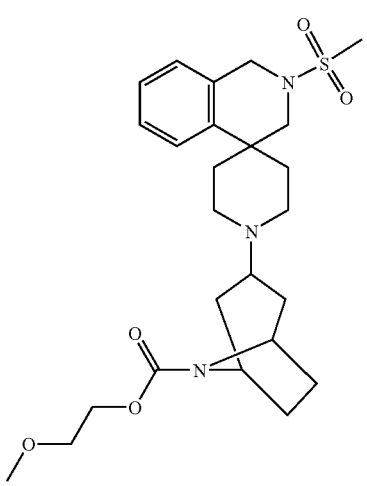
294

| 301 | 302 |
|---|---|
| -continued | -continued |
| 295 | 299 |
| 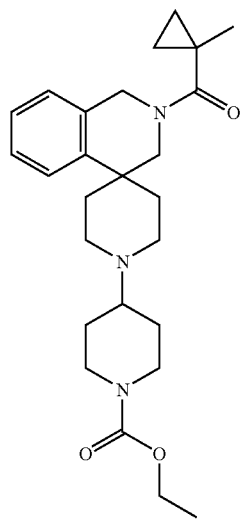 | 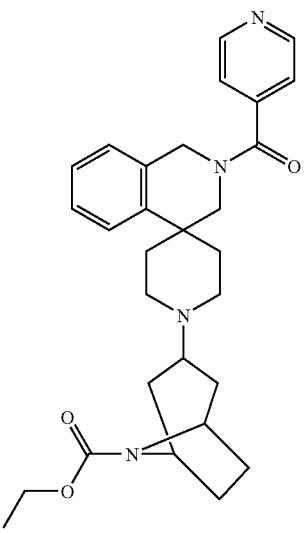 |
| 296 | 300 |
| 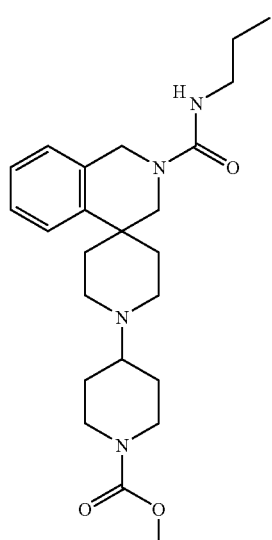 | 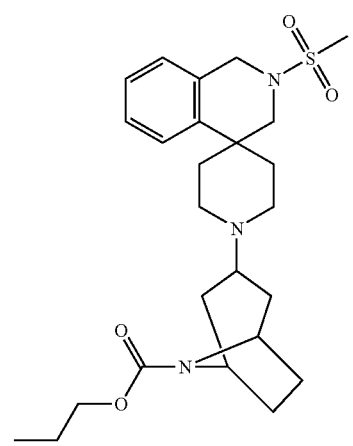 |
| 298 | 302 |
| 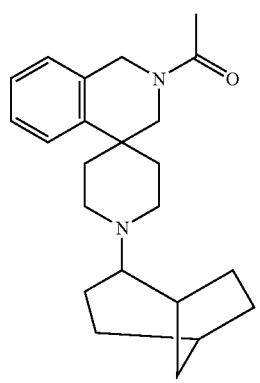 | 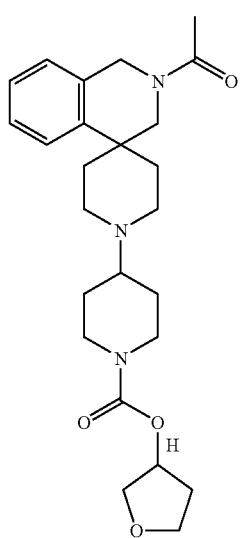 |

-continued
303
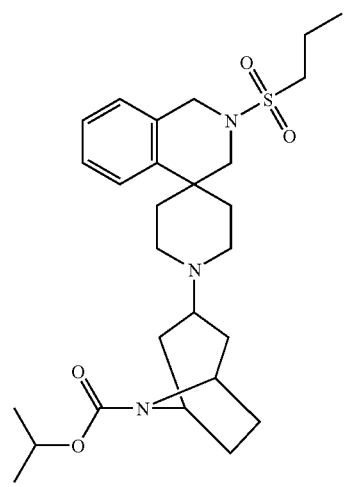
304
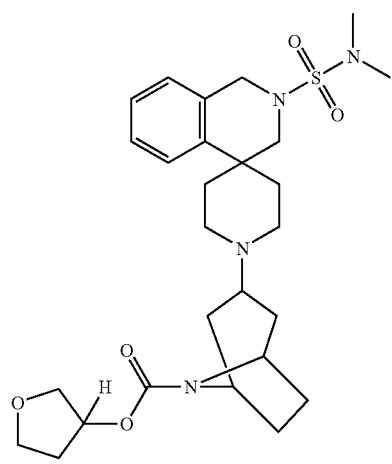
305
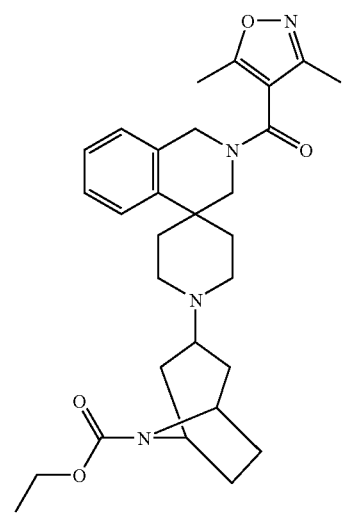
-continued
306
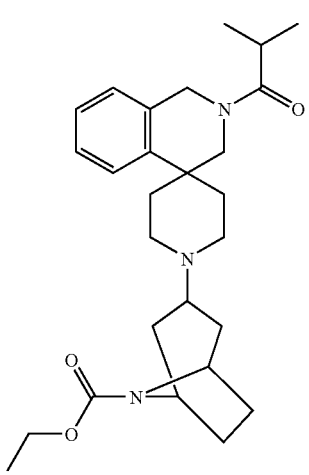
307
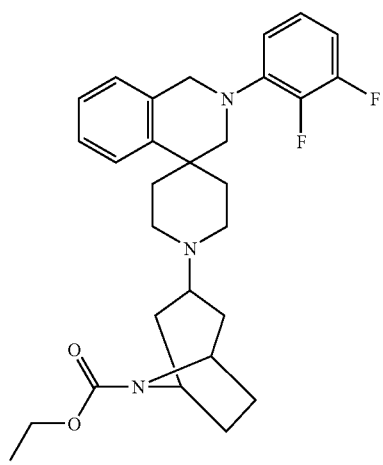
308
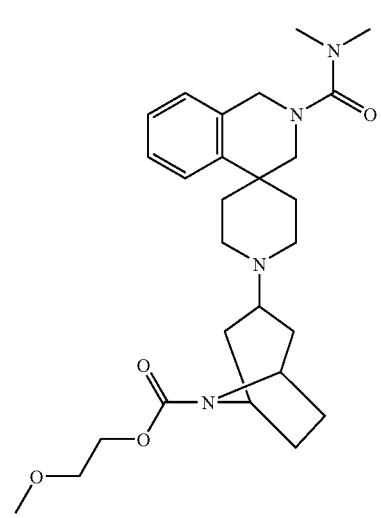

-continued
309
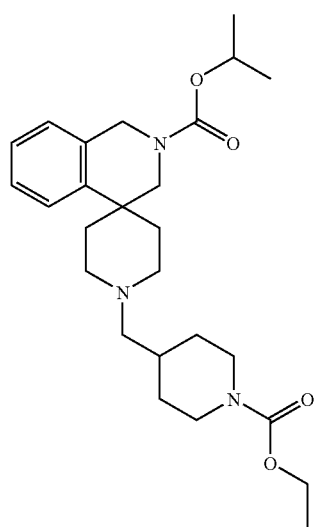
310
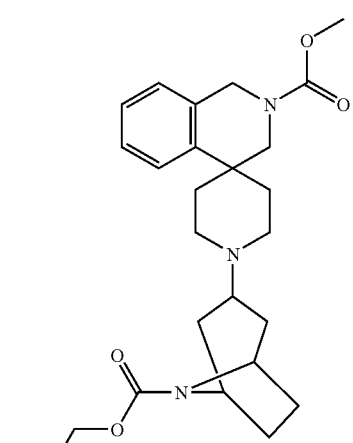
311
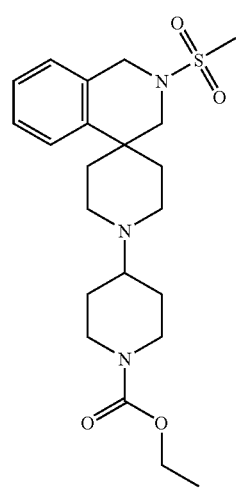
-continued
313
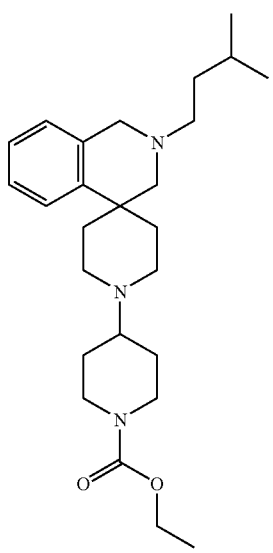
315
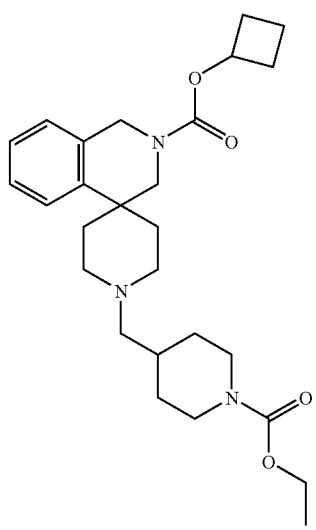
316
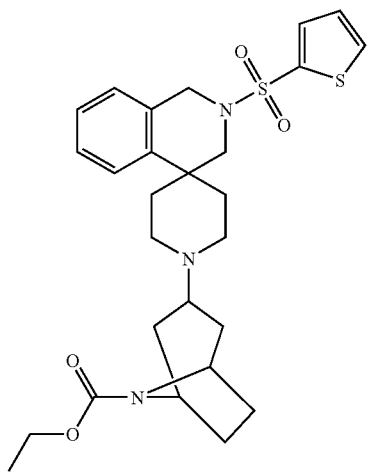

-continued
317
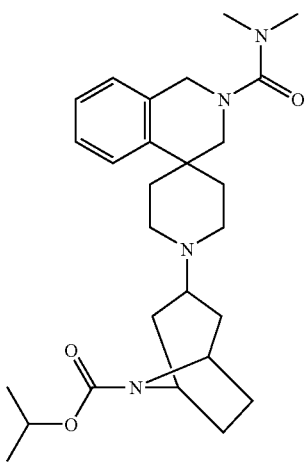
318
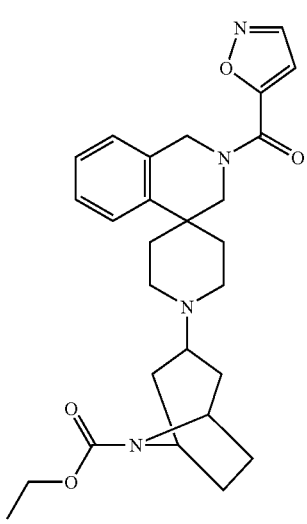
319
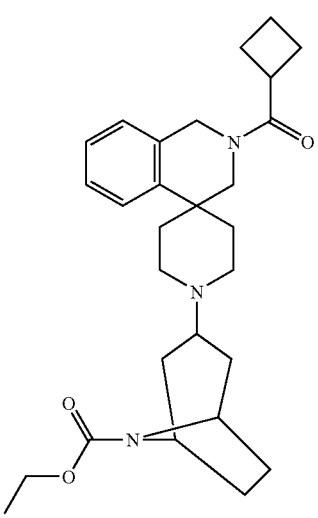
-continued
320
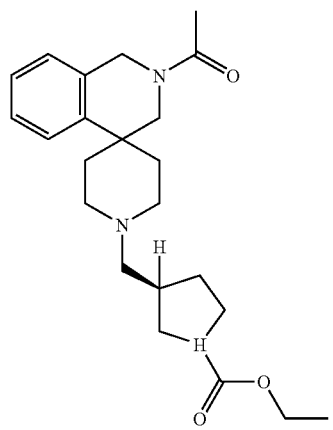
321
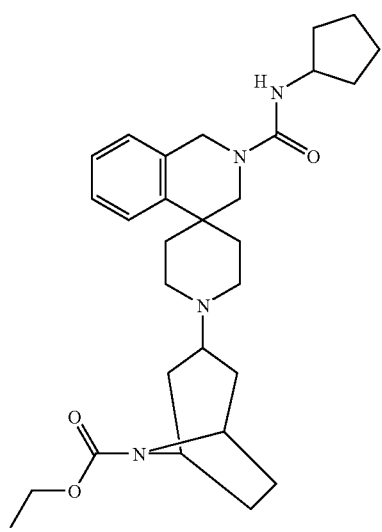
324
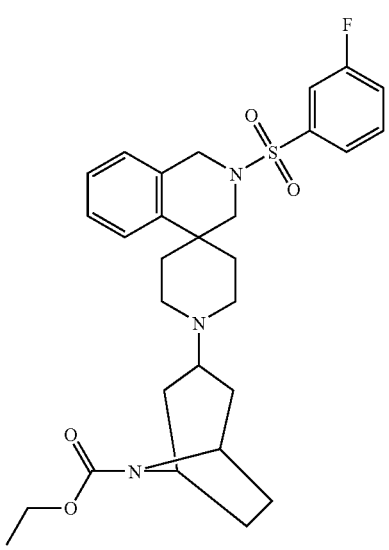

-continued
325
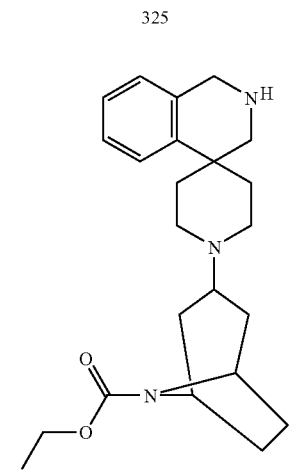
326
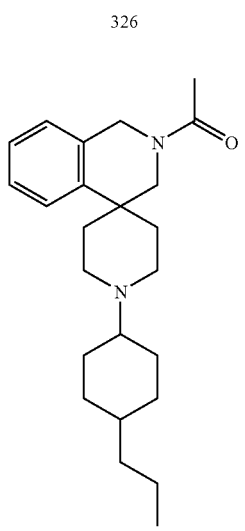
327
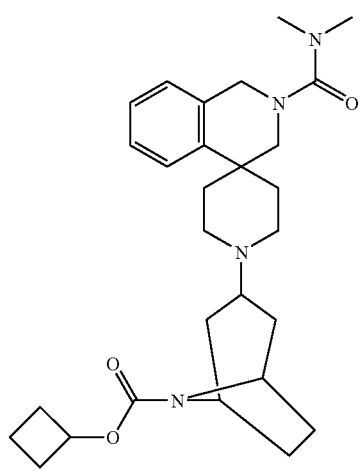
-continued
328
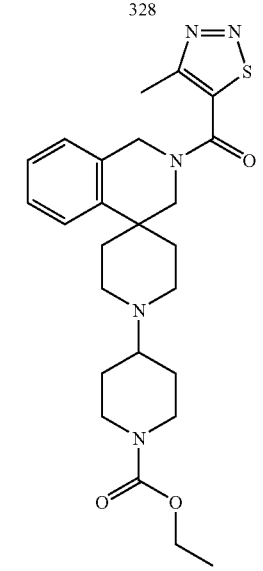
329
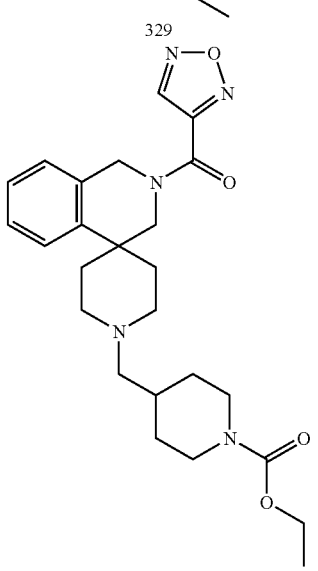
330
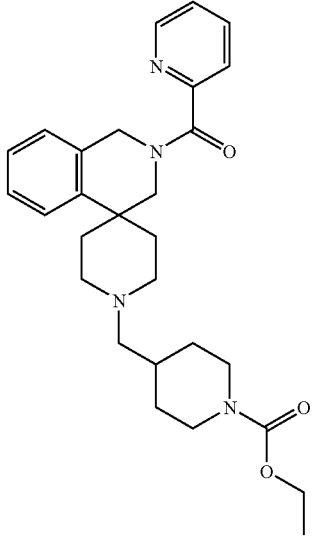

| 311 | 312 |
|---|---|
| 332 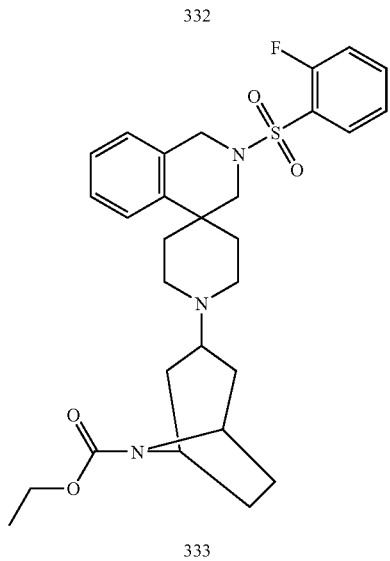 | 337 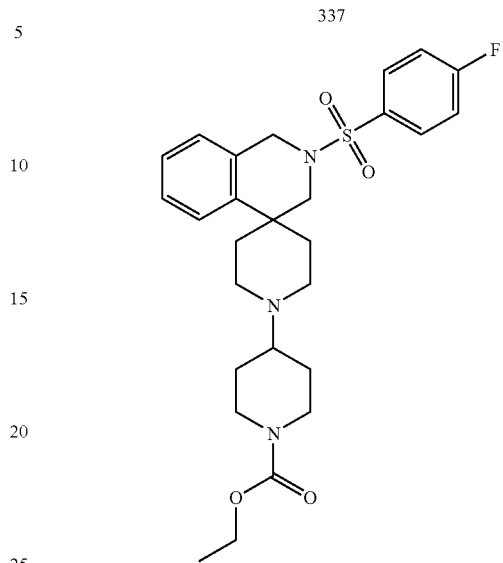 |
| 333 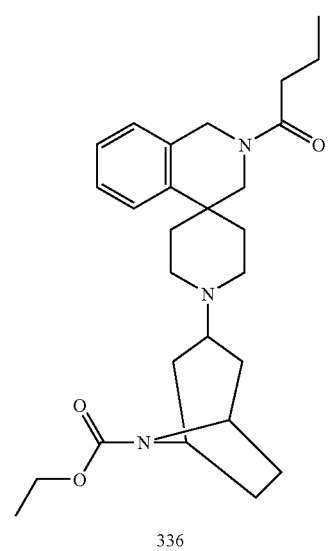 | 338 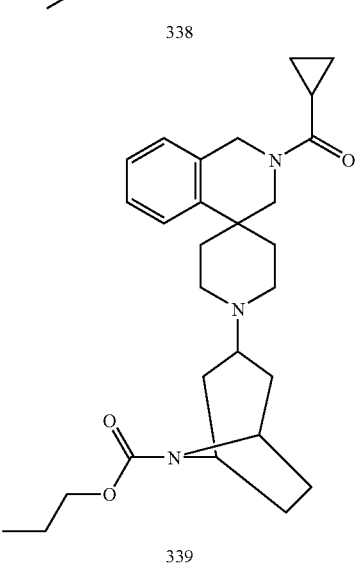 |
| 336 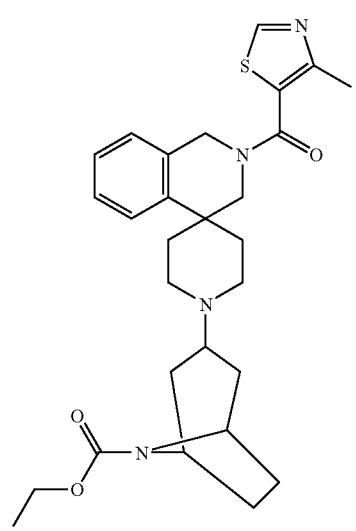 | 339 |

| 313 | 314 |
|---|---|
| -continued | -continued |
| 340 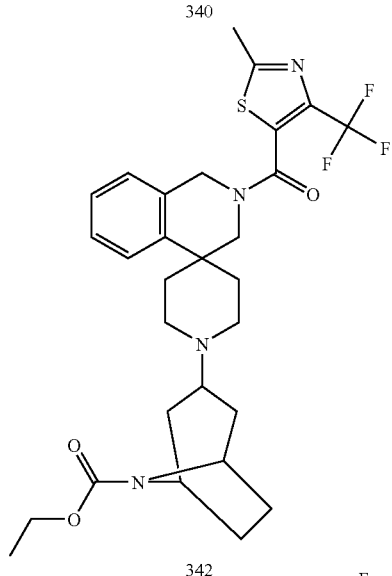 | 344 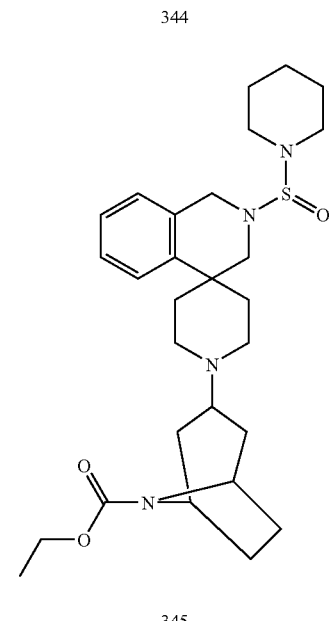 |
| 342 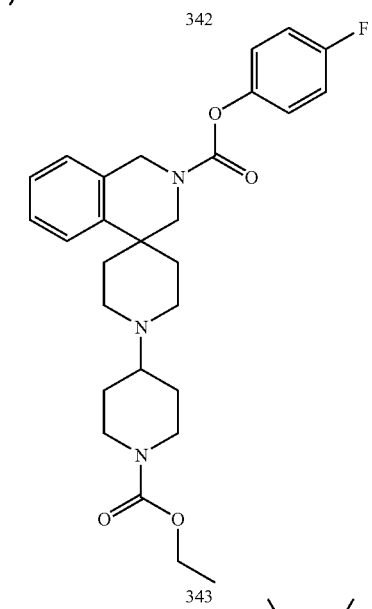 | 345 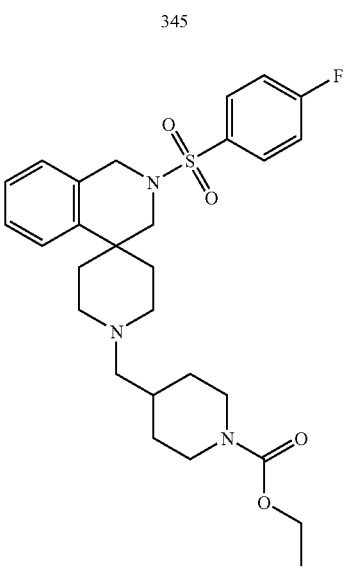 |
| 343 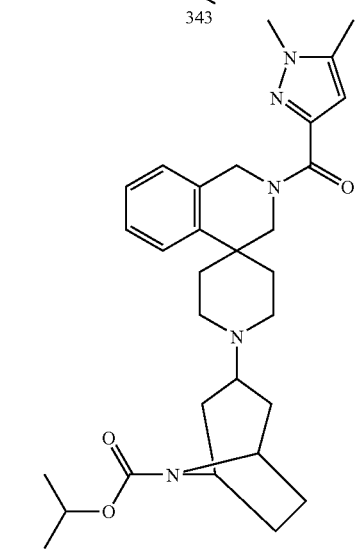 | 348 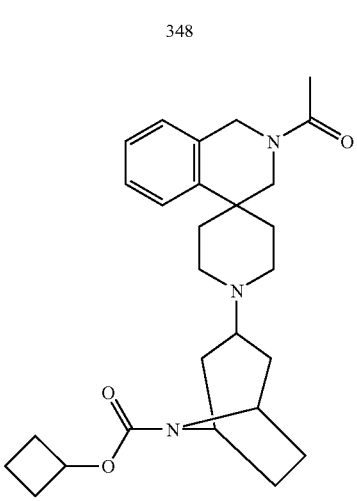 |

-continued
350
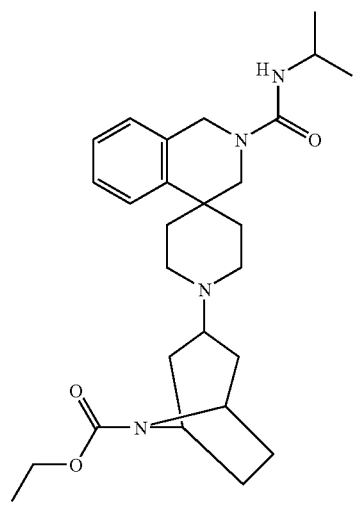
351
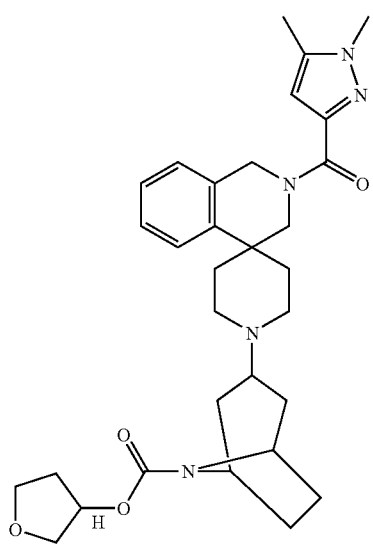
353
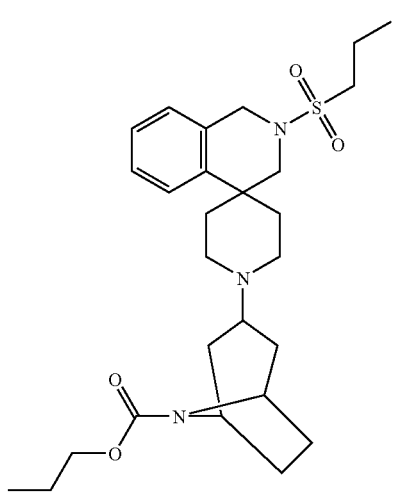
-continued
354
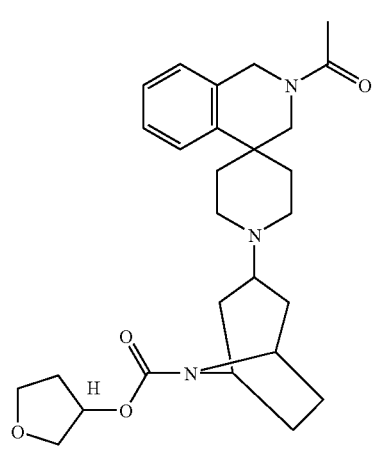
355
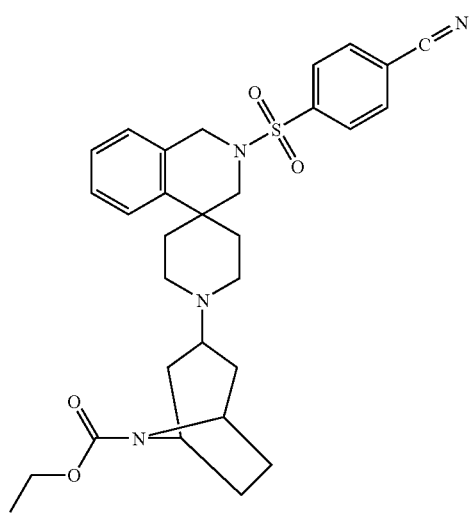
356
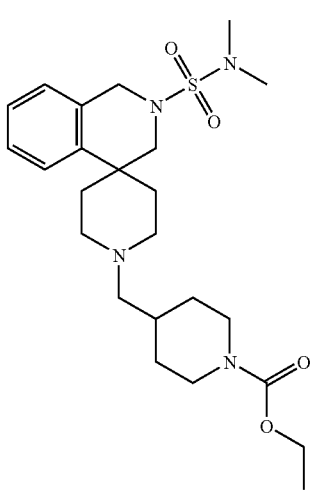

-continued
357
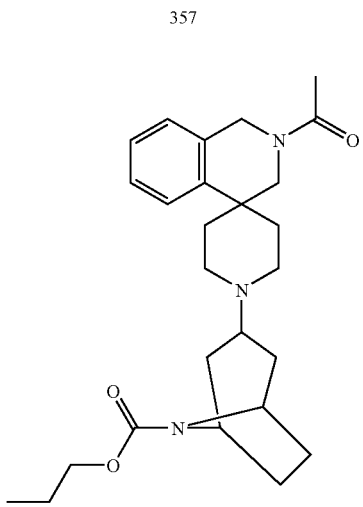
-continued
358
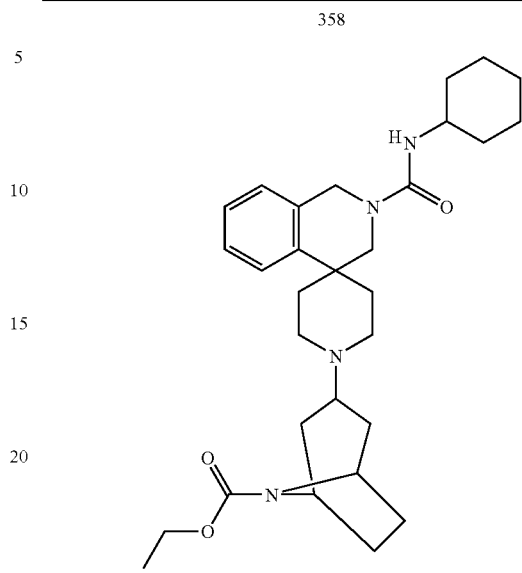
12. A pharmaceutical composition comprising a compound according to claim 1 and a pharmaceutical carrier.
* * * * *